(12) United States Patent
DeShong et al.

(10) Patent No.: US 10,711,043 B2
(45) Date of Patent: Jul. 14, 2020

(54) COMPOSITIONS AND VACCINES COMPRISING VESICLES AND METHODS OF USING THE SAME

(71) Applicants: University of Maryland, College Park, College Park, MD (US); University of Maryland, Baltimore, Baltimore, MD (US)

(72) Inventors: Philip R. DeShong, Silver Spring, MD (US); Lenea Stocker, Silver Spring, MD (US); Daniel C. Stein, Silver Spring, MD (US); Stefanie N. Vogel, Columbia, MD (US); Katharina Richard, Catonsville, MD (US)

(73) Assignees: University of Maryland, College Park, College Park, MD (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/030,506

(22) Filed: Jul. 9, 2018

(65) Prior Publication Data

US 2019/0016761 A1 Jan. 17, 2019

Related U.S. Application Data

(63) Continuation of application No. 14/295,306, filed on Jun. 3, 2014, now Pat. No. 10,017,545.

(60) Provisional application No. 61/830,435, filed on Jun. 3, 2013, provisional application No. 61/834,311, filed on Jun. 12, 2013, provisional application No. 61/916,654, filed on Dec. 16, 2013, provisional application No. 61/972,992, filed on Mar. 31, 2014.

(51) Int. Cl.
| | |
|---|---|
| *A61K 39/095* | (2006.01) |
| *A61K 39/02* | (2006.01) |
| *A61K 49/00* | (2006.01) |
| *C07K 14/195* | (2006.01) |
| *C07K 14/22* | (2006.01) |
| *A61K 39/39* | (2006.01) |
| *A61K 39/00* | (2006.01) |

(52) U.S. Cl.
CPC ........ *C07K 14/195* (2013.01); *A61K 39/0208* (2013.01); *A61K 39/095* (2013.01); *A61K 39/39* (2013.01); *C07K 14/22* (2013.01); *A61K 2039/55555* (2013.01)

(58) Field of Classification Search
CPC ......... A61K 49/00; A61K 39/00; A61K 39/02
USPC .................................. 424/9.2, 184.1, 234.1
See application file for complete search history.

(56) References Cited

U.S. PATENT DOCUMENTS

| | | | |
|---|---|---|---|
| 5,534,499 A | 7/1996 | Ansell | |
| 5,739,273 A | 4/1998 | Engelman et al. | |
| 6,531,131 B1 | 3/2003 | Gu et al. | |
| 2005/0106184 A1 | 5/2005 | Franks et al. | |
| 2007/0135651 A1 | 6/2007 | Dubois et al. | |

FOREIGN PATENT DOCUMENTS

WO WO2009/025777 2/2009

OTHER PUBLICATIONS

Allen, Theresa M., et al., "Therapeutic Opportunities for Targeted Liposomal Drug Delivery", Advanced Drug Delivery Reviews, 1996, vol. 21, pp. 117-133.
Mammen, Mathai, et al., "Polyvalent Interactions in Biological Systems: Implications for Design and Use of Multivalent Ligands and Inhibitors", Angew: Chem. Int. Ed., 1998, vol. 37, pp. 2754-2794.
John, Constance, M., "The Structural Basis for Pyocin Resistance in Neisseria gonorrhoeae Lipooligosaccharides", The Journal of Biological Chemistry, Oct. 15, 1991, vol. 266, vol. 29, pp. 19303-19311.
Danoff, Emily J., et al., "Surfactant Vesicles for High-Efficiency Capture and Separation of Charged Organic Solutes", Langmuir, 2007, vol. 23, No. 17, pp. 8965-8971.
Guo, Cai, X., et al., "Size Effect of Polydiacetylene Vesicles Functionalized with Glycolipids on Their Colorimetric Detection Ability", The Journal of Physical Chemistry B, 2005, vol. 109, No. 40, pp. 18765-18771.
Dubois, Michel, et al., "Colorimetric Method for Determination of Sugars and Related Substances", Analytical Chemistry, Mar. 1956, vol. 28, No. 3, pp. 350-356.
McKelvey, C.A., et al., "Templating Hollow Polymeric Spheres from Catanionic Equilibrium Vesicles: Synthesis and Characterization", Langmuir, 2000, vol. 16, No. 22, pp. 8285-8290.
Luzardo, Maria del Carmen, et al., "Aggregation Induced by Concanavalin A of Lipid Vesicles Containing Neoglycolipds", Colloids and Surfaces B, 2002, vol. 26, pp. 281-289.
Ishida, Akihiko, et al., "Fluorescein Chemiluminescence Method for Estimation of Membrane Permeability of Liposomes", Analytical Biochemistry, 2005, vol. 342, pp. 338-340.
Xiang, T.X., et al., "A Quantitative Model for the Dependence of Solute Permeability on Peptide and Cholesterol Content in Biomembranes", The Journal of Membrane Biology, 2000, vol. 177, pp. 137-148.
Wu, Li-Qun, et al., "Chitosan-Mediated and Spatially Selective Electrodeposition of Nanoscale Particles" Langmuir, 2005, vol. 21, No. 8, pp. 3641-3646.

(Continued)

*Primary Examiner* — Rodney P Swartz
(74) *Attorney, Agent, or Firm* — William C. Schrot; AuerbachSchrot LLC

(57) ABSTRACT

The disclosure relates to compositions, pharmaceutical compositions, vaccines, and methods of making and using the same. The compositions of the disclosure are useful to stimulate an antigen-specific immune response and, in some embodiments, a protective immune response in an animal after challenge to pathogens. The compositions of the disclosure are also useful for treatment and prevention of disease in a subject such as cancer.

5 Claims, 56 Drawing Sheets

Specification includes a Sequence Listing.

(56) References Cited

OTHER PUBLICATIONS

Miller, Ronald L., "Purification of Peanut (*Arachis hypogaea*) Agglutinin Isolectins by Chromatofocusing", Analytical Biochemistry, 1983, vol. 131, pp. 438-446.
Tondre, Christian, et al., "Properties of the Amphiphilic Films in Mixed Cationic/Anionic Vesicles: A Comprehensive View from a Literature Analysis", Advances in Colloid and Interface Science, 2001, vol. 93, pp. 115-134.
Safran, S.A., et al., "Theory of Spontaneous Vesicle Formation in Surfactant Mixtures", American Association for the Advancement of Science, Apr. 20, 1990, vol. 248, No. 4953, pp. 354-356.
Banerjee, Rahul, et al., "Crystal Structure of Peanut Lectin, a Protein with an Unusual Quaternary Structure", Proceedings of the National Academy of Sciences, USA, Jan. 1994, vol. 91, pp. 227-231.
Kuo, Jung-Hua Steven, et al., "Cytotoxicity Characterization of Catanionic Vesicles in RAW 264.7 Murine Macrophage-like Cells", Colloids and Surfaces B: Biointerfaces, 2005, vol. 41, pp. 189-196.
Okamoto, Kenji, et al., "Direct Observation of Wetting and Diffusion in the Hydrophobic Interior of Silica Nanotubes", Nano Letters, 2004, vol. 4, No. 2, pp. 233-239.
Lucas, Mark, et al., "ERK Activation Following Macrophage $Fc_iR$ Ligation Leads to Chromatin Modifications at the IL-10 Locus" The Journal of Immunology, 2005, vol. 175, pp. 469-477.
Lee, Jae-Ho, et al., "Vesicle-Biopolymer Gels: Networks of Surfactant Vesicles Connected by Associating Biopolymers", Langmuir, 2005, vol. 21, pp. 26-33.
Kaler, Eric W., et al., "Phase Behavior and Structures of Mixtures of Anionic and Cationic Surfactants", Journal of Physical Chemistry, 1992, vol. 96, No. 16, pp. 6698-6707.
Sundler, R., "Agglutination of Glycolipid-Phospholipid Vesicles by Concanavalin A: Evidence for Steric Modulation of Lectin Binding by Phospholipid Head Groups", Federation of European Biochemical Societies, May 1982, vol. 141, No. 1, pp. 11-13.
Cairo, Christopher W., et al., "Control of Multivalent Interactions by Binding Epitope Density", Journal of the American Chemical Society, 2002, vol. 124, No. 8, pp. 1615-1619.
Jayaraman, Karthik, et al., "Observing Capillarity in Hydrophobic Silica Nanotubes", Journal of the American Chemical Society, 2005, vol. 127, No. 49, pp. 17385-17392.
Sato, Yuko, et al., "Enhanced Uptake of Giant DNA in Cell-Sized Liposomes", Chemical Physics Letters, 2003, vol. 380, pp. 279-285.
Herrington, Kathleen L., et al., "Phase Behavior of Aqueous Mixtures of Dodecyltrimethylammonium Bromide (DTAB) and Sodium Dodecyl Sulfate (SDS)", The Journal of Physical Chemistry, 1993, vol. 97, No. 51, pp. 13792-13802.
Loris, Remy, et al., "Legume Lectin Structure", 1998, Biochimica et Biophysica Acta, 1998, pp. 9-36.
Bakowsky, Udo, et al., "Characterization of the Interactions Between Various Hexadecylmannoside-Phospholipid Model Membranes with the Lectin Concanavalin A", Physical Chemistry Chemical Physics, 2000, vol. 2, pp. 4609-4614.
Drickamer, Kurt et al., "Biology of Animal Lectins", Annual Review of Cell and Developmental Biology, 1993, vol. 9, pp. 237-264.
Abraham, Sheeta A., et al., "The Liposomal Formulation of Doxorubicin", Methods in Enzymology, 2005, vol. 391, pp. 71-97.
Goldstein, I.J., et al., "Protein-Carbohydrate Interaction. II. Inhibition Studies on the Interaction of Concanavalin A with Polysaccharides", Biochemistry, May 1965, vol. 4, No. 5, pp. 876-883.
Apel-Paz, Meirav, et al., "Impact of Membrane Cholesterol Content on the Resistance of Vesicles to Surfactant Attack", Langmuir, 2005, vol. 21, pp. 9843-9849.
Kaler, Eric W., et al., "Spontaneous Vesicle Formation in Aqueous Mixtures of Single-Tailed Surfactants", Sep. 22, 1989, vol. 245, No. 4924, pp. 1371-1374.
Wang, Xiang, et al., "Highly Efficient Capture and Long-Term Encapsulation of Dye by Catanionic Surfactant Vesicles", Langmuir, Jul. 18, 2006, vol. 22, No. 15, pp. 6461-6464.
Walker, Scott A., "Electrostatic Control of Spontaneous Vesicle Aggregation", Langmuir, 1997, vol. 13, pp. 5076-5081.
Renoncourt, Audrey, "Study of Supra-Aggregates in Catanionic Surfactant Systems", University of Regensburg, 2005, Doctoral Dissertation, pp. 1-160.

| Method | Protein (µg/mL) | Carbohydrate (µg/mL) |
|---|---|---|
| 1 | 333 | 38 |
| 2 | 309 | 62 |
| 3 | 408 | 56 |
| 4 | 346 | 44 |
| 5 | 341 | 26 |

FIG. 1

| Search against | Total No. Proteins | Unclassified | Subcellular component membrane | Membrane proteins (%) |
|---|---|---|---|---|
| *Neisseria* | 229 | 108 | 39 | 32.2 |
| *gonorrhoeae* | 138 | 62 | 29 | 38.16 |

FIG. 4

LOS F62Δ IgtD from *N. gonorrhoeae*

| | Carbohydrate (µg/mL) | % Incorporation |
|---|---|---|
| TRIAD Vaccine | 50 | 94 |

FIG. 14

|  | Inoculation | Antibody Titer | IgG:IgM |
|---|---|---|---|
| LOS/C-12 PADRE peptide functionalized vesicles | Initial | 1:1500 | 75:25 |
|  | Booster (2 weeks) | 1:2000 |  |
| LOS Vesicles (Control) | Initial | 1:100 | 0:100 |

LPS from *F. tularensis*

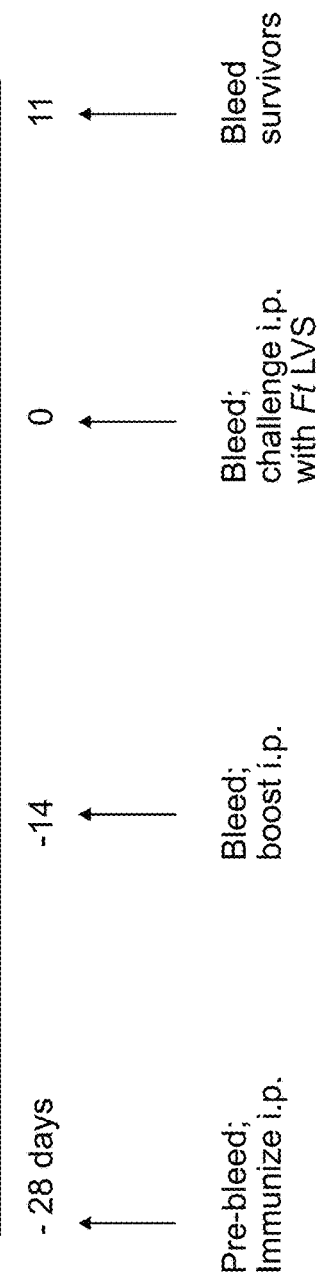
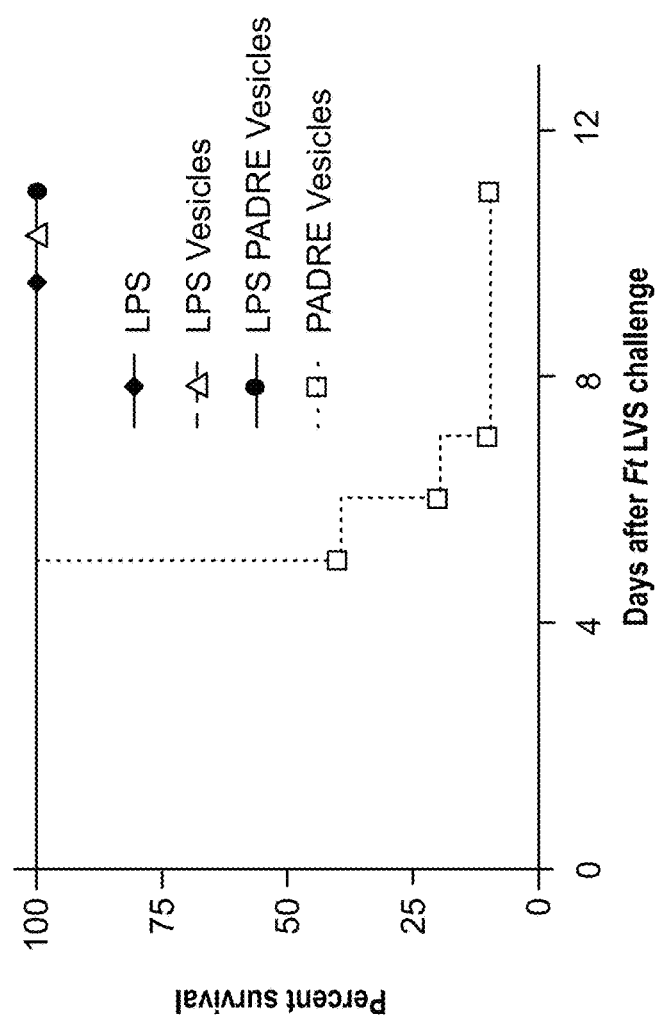
FIG. 20A
FIG. 20B

Experiment 1:
2 weeks rest
30.000 CFU/mouse

Experiment 2:
2 weeks rest
70.000 CFU/mouse

Experiment 3:
4 weeks rest
30,000 CFU/mouse

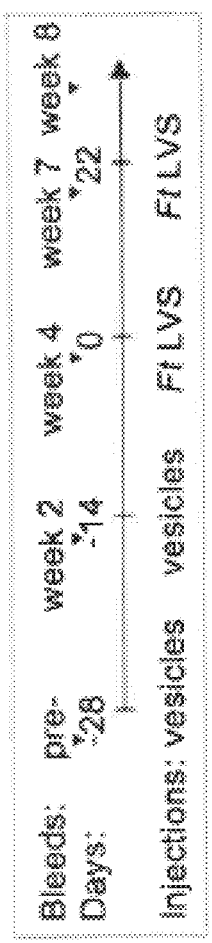
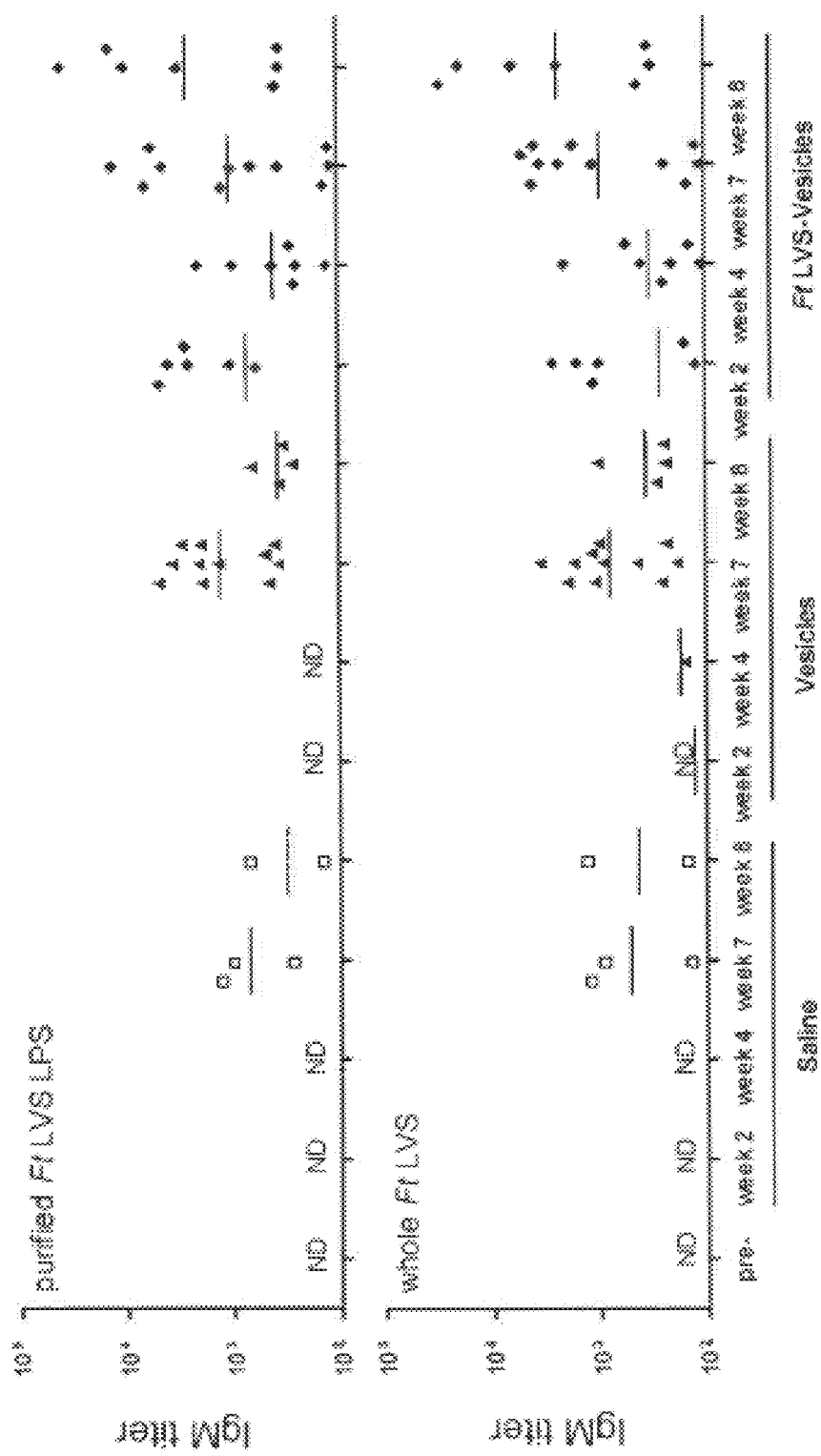
FIG. 22A
FIG. 22B

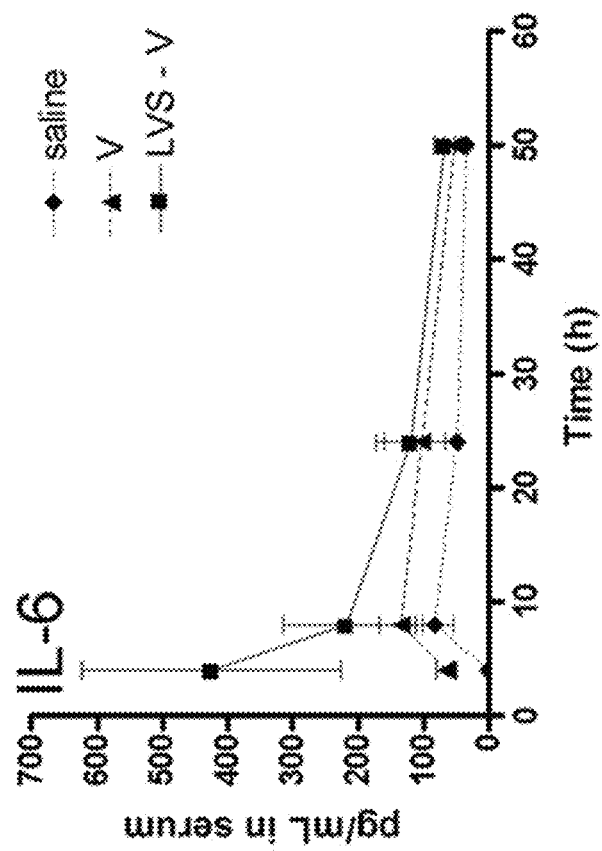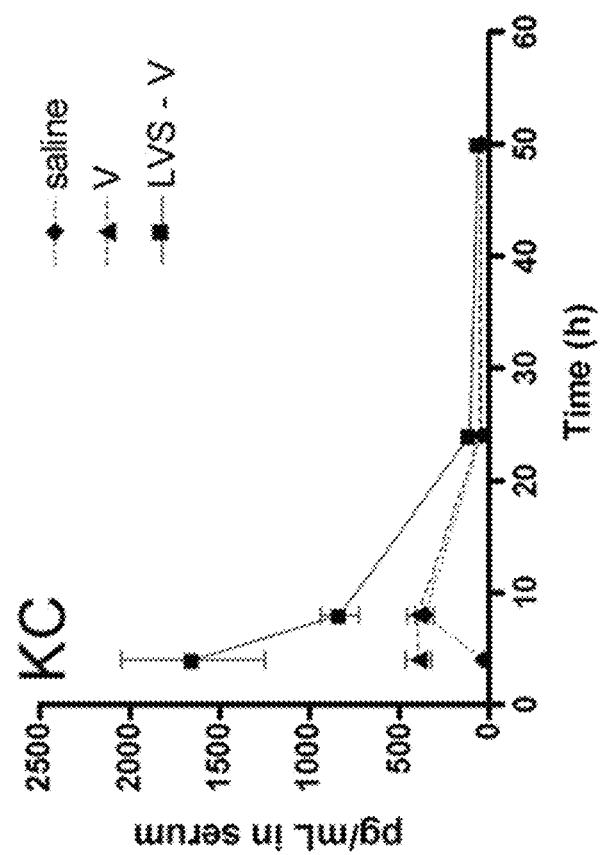
FIG. 24B

FIG. 28A  FIG. 28B

FIG. 29A  LVS-V, week 4 (pre-challenge)

FIG. 29B  LVS-V, week 8 (post-challenge)

FIG. 29C  Schu S4-V, week 7 (post-challenge)

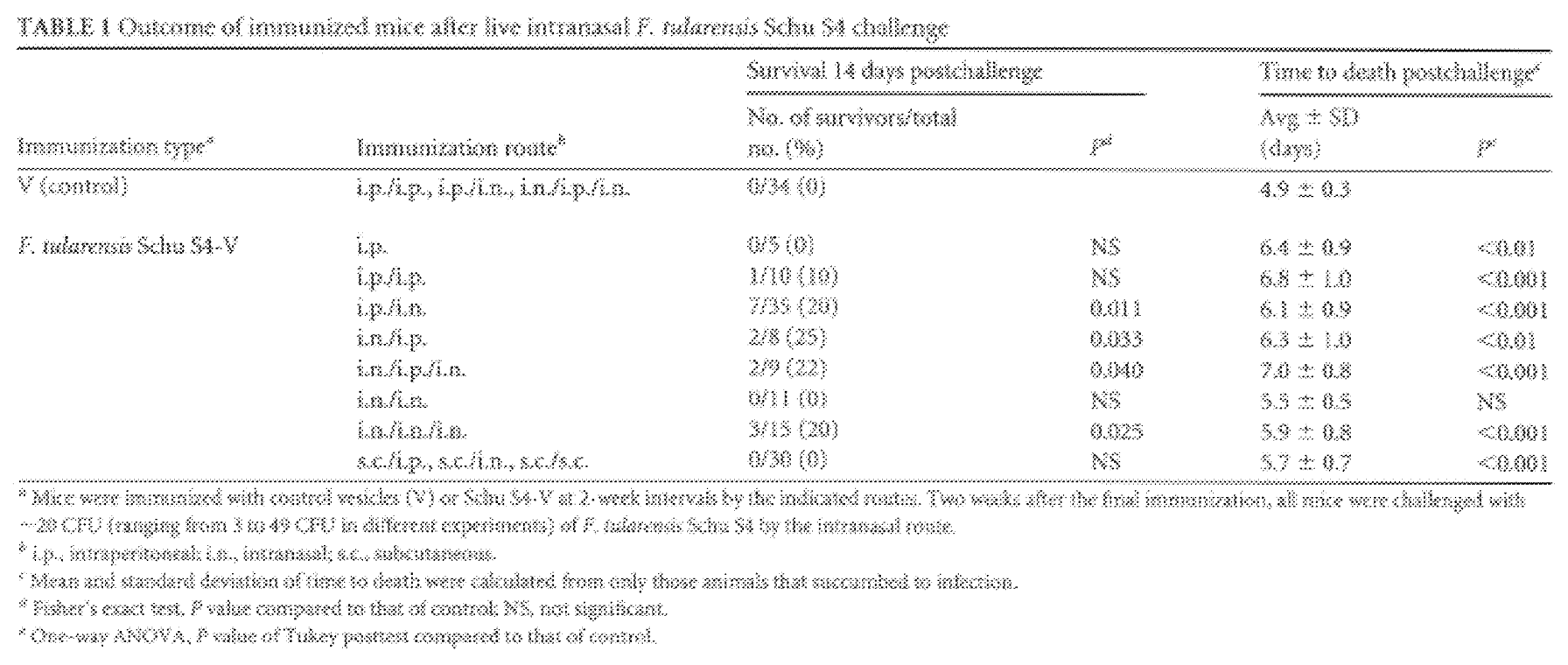

TABLE 1 Outcome of immunized mice after live intranasal F. tularensis Schu S4 challenge

| Immunization type[a] | Immunization route[b] | Survival 14 days postchallenge No. of survivors/total no. (%

| Initial Concentration | Concentration after SEC | |
|---|---|---|
| (µg/mL) | (µg/mL) | (µM) |
| 100 | 75 | 138 |
| 150 | 88 | 161 |
| 200 | 165 | 303 |
| 300 | 131 | 241 |

FIG. 34

$C_{12}$-Folate conjugate

Maytansine

Paclitaxel fluorescein derivative

| Extraction Method | Protein (µg/mL) | Carbohydrate (µg/mL) |
|---|---|---|
| *N. gonorrhoeae* 4 (original) | 346 | 44 |
| *N. gonorrhoeae* (4-I) | 402 | 335 |
| *N. gonorrhoeae* (4-II) | 294 | 446 |

FIG. 47

Outer Membrane Proteins FopA and Tul4 Are Detected by Immune Sera

COMPOSITIONS AND VACCINES COMPRISING VESICLES AND METHODS OF USING THE SAME

CROSS-REFERENCE TO RELATED APPLICATIONS

This application claims priority to U.S. Provisional Application Ser. No. 61/830,435, filed Jun. 3, 2013, and 61/834,311, filed Jun. 12, 2013, and 61/916,564 filed Dec. 16, 2013, and 61/972,992 filed Mar. 31, 2014, and U.S. patent application Ser. No. 14/295,306, filed Jun. 3, 2014, now U.S. Pat. No. 10,017,545, issued Jul. 10, 2018, each of which are incorporated herein by reference in their entireties.

GOVERNMENT SUPPORT

The invention was made with government support under CTS0608906 awarded by National Science Foundation and 5R01AI68888 & AI057168 awarded by the National Institutes of Health. The government may have certain rights in and to this invention.

TECHNOLOGY FIELD

The present invention relates generally to catanionic vesicles created by applying cationic and anionic surfactants to pathogenic bacteria, resulting in vesicles which display molecular components of the bacteria on their exterior surface. More specifically, the inventions relates to compositions and methods for the creation and administration of catanionic vesicles displaying molecular components of bacterial antigens for use as a vaccine.

BACKGROUND

In many types of bacteria, cell to cell recognition is a key feature of pathogen virulence. Accordingly, methods for the extraction and purification of carbohydrates and proteins from cellular membranes, followed by reconstitution of cellular components into stable hydrophobic matrices has been widely used. Due to the complexity of biological membranes, cell surface components are often arranged in artificial membranes such as liposomes.

Outer membrane proteins from bacteria have been incorporated into liposomes for vaccines and the immune response of the resulting liposome preparations is known in the art. Liposomal formulations of antigens have significant advantages in vaccine formulation over cell-based formulations since they avoid safety concerns that may arise from attenuated or killed pathogens. However, methods of liposomal formulations of cell surface components still have limitations as vehicles for displaying cell surface proteins and lipids in a stable membrane-like environment. First, since cell surface components typically reside in the hydrophobic bilayer, the solubilization and purification of these substances from the membrane often results in denaturation of the protein. Second, it is unclear that insertion of the purified protein into the membrane of a liposome results in the presentation of the protein in its 'natural' form, especially in the case of denatured components.

Finally, liposomal formulations are limited by the general physicochemical characteristics of the liposomes themselves. The production of liposomes requires either sonication or passage through a membrane, and these processes result in the addition of mechanical stress to the system that also may lead to denaturation of sensitive biological components. Liposomal formulations prepared by either sonication or membrane extrusion are very heterogeneous in size, with distributions ranging from 300 nm to 20 microns. Finally, liposomal formulations are difficult to maintain in long term storage because they often precipitate within days of creation due to their inherent thermodynamic instability, typically compounded by additional instability in biological media due to pH and ionic strength issues.

In addition to liposomal preparations, current methods of making multivalent vaccines against *Neisseria* involve removal of lipooligo and lipopolysaccharides (LOS and LPS respectively) specifically because of their toxicity and immunological problems. van der Waterbeemd et al., *Vaccine* 28 (2010) 4810-4816 discloses that outer membrane vesicles used as vaccines maintain a residual amount of LPS (only about 1%) but are needed to adjuvate the immune response. The removal of LPS, however, also depletes the amount of lipoprotein that exists in the vesicles and reduces immunogenicity.

In contrast to van der Waterbeemd et al., the present disclosure addresses the limitations of vaccine and composition delivery via liposomes by using artificial membrane components from catanionic surfactants that package pathogen antigens and antigens associated with hyperproliferative disease, such as cancer. The vesicles also protect membrane-bound antigens from degradation as well as cloak or reduce the toxicity caused by bacterial lipopolysaccharides and lipooligosaccharides.

*Francisella tularensis* is an immune-evasive coccobacillus that causes tularemia disease in humans and animals. *Francisella tularensis* is classified as a Tier 1 agent. To date, there is no vaccine for *Francisella tularensis* approved by the FDA. Limitations in *Francisella tularensis* vaccine development include the risk of reversion of live mutant strains and poor immunogenicity of killed bacteria. The present disclosure provides a multivalent vaccine from whole cell extract that can be used for treatment and/or prevention of bacterial infection while effectively adjuvating the immune response.

SUMMARY OF THE INVENTION

The disclosure relates to catanionic vesicles comprising LPS or LOS in therapeutically effective amounts. The disclosure also relates to catanionic vesicles and vaccines comprising catanionic vesicles that comprise *Francisella tularenis* components and/or antigens. In some embodiments, the disclosure relates to a methods of treating and/or preventing tularemia in a subject in need thereof by administering any of the disclosed vesicles, pharmaceutical compositions, or vaccines in a therapeutically effective amount to reduce or eliminate symptoms of tularemia or bacterial infection. The disclosure also relates to catanionic vesicles and vaccines comprising catanionic vesicles that comprise *Neisseria gonorrhoeae* components and/or antigens. In some embodiments, the disclosure relates to a methods of treating and/or preventing bacterial infection in a subject in need thereof by administering any of the disclosed vesicles, pharmaceutical compositions, or vaccines in a therapeutically effective amount to reduce or eliminate symptoms of the bacterial infection or bacterial infection in the subject.

In some embodiments, the disclosure relates to a methods of treating and/or preventing malignant cell growth in a subject in need thereof by administering any of the disclosed vesicles, pharmaceutical compositions, or vaccines in a therapeutically effective amount to reduce or eliminate symptoms of cancer or growth of malignant cells in the subject.

The present disclosure relates to a composition comprising a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of bacterial immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 15 micrograms per microliter of bacterial lipooligosaccharide (LOS) or lipopolysaccharide (LPS) optionally comprising one or a plurality of bacterial lipoproteins. In some embodiments, the at least one or plurality of bacterial immunogens is from a Gram-negative bacterial cell. In some embodiments, the at least one or plurality of bacterial immunogens is derived from cells that are from *Neisseria* or *Franicsiella*. In some embodiments, the at least one bacterial immunogen is from whole bacterial cell extract. In some embodiments, the one or plurality of bacterial immunogens comprise one or a combination of pilin, porA, porB, OPA, DnaK, Tul4, and FopA. In some embodiments, the one or plurality of bacterial immunogens comprises Pan HLA-DR reactive epitope (PADRE) individually or conjugated to one or a plurality of membrane-bound sugar molecules. In some embodiments, the catanionic surfactant vesicle is lyophilized or frozen.

The disclosure relates to a pharmaceutical composition comprising: a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of bacterial immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 1, 2, 3, 4, 5, 6, 7, 8, 9, 10, 11, 12, 13, 14, or 15 micrograms per microliter of bacterial lipooligosaccharide (LOS) or lipopolysaccharide (LPS) optionally comprising one or a plurality of bacterial lipoproteins and/outermembrance bacterial proteins; and a pharmaceutically acceptable carrier or excipient.

The disclosure relates to a vaccine or a pharmaceutical composition comprising: a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of bacterial immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 15 micrograms per microliter of bacterial lipooligosaccharide (LOS) or lipopolysaccharide (LPS) optionally comprising one or a plurality of bacterial lipoproteins; and a pharmaceutically acceptable carrier or excipient.

The disclosure relates to vaccine or a pharmaceutical composition comprising: a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of bacterial immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 15 micrograms per microliter of bacterial lipooligosaccharide (LOS) or lipopolysaccharide (LPS) optionally comprising one or a plurality of bacterial lipoproteins; a pharmaceutically acceptable carrier; and a nucleic acid molecule encoding one or a plurality of immunogens and or immunomodulating proteins, a protein adjuvant, a synthetic adjuvant, an attenuated bacterial cell, or a recombinant bacterial cell comprising a nucleic acid molecule encoding one or a plurality of immunogens and or immunomodulating proteins.

The disclosure relates to a method of treating and/or preventing a pathogen infection in a subject in need thereof, comprising: administering to the subject the pharmaceutical composition comprising: a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of pathogen immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 15 micrograms per microliter of bacterial lipooligosaccharide (LOS) or lipopolysaccharide (LPS) optionally comprising one or a plurality of bacterial lipoproteins or bacterial membrane-bound proteins; and a pharmaceutically acceptable carrier.

The disclosure relates to a method of immunizing a subject comprising: administering to a subject in need thereof a therapeutically effective amount of the vaccine or a pharmaceutical composition comprising: a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of bacterial immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 15 micrograms per microliter of bacterial lipooligosaccharide (LOS) or lipopolysaccharide (LPS) optionally comprising one or a plurality of bacterial lipoproteins; and a pharmaceutically acceptable carrier. In some embodiments, the effective amount is an amount effective to elicit an immune response. In some embodiments, the immune response is a protective, antigen-specific immune response after challenge of the subject with a pathogen.

The disclosure relates to a method of integrating a bacterial antigen into a vesicle, comprising:
(a) centrifuging bacterial cells;
(b) removing any bacterial growth medium;

(c) adding a weight/weight molar ratio of cationic surfactant and anionic surfactant in aqueous solution to the bacterial cells;

(d) stirring resulting mixture at room temperature for at least about 30 minutes; wherein the method does not comprise a step of purification prior to steps (a)-(d).

In some embodiments, the cationic surfactant and anionic surfactant are SDBS and CTAT, respectively, at a molar weight ratio of about 70:30 or about 30:70. In some embodiments, the vesicle, composition or vaccine comprises at least one or a plurality of bacterial antigens from Neisseria and/or Francisella. In some embodiments, methods comprise encapsulating at least one or a plurality of bacterial antigens from Neisseria and/or Francisella. In some embodiments, the aqueous solution or compositions comprise a marker or active agent. In some embodiments, the method further comprises filtering the vesicles through a size exclusion or ion chromatography column.

The disclosure relates to a method of creating a library of catanionic vesicles comprising:

(a) adding a weight/weight molar ratio of cationic surfactant and anionic surfactant in aqueous solution to a population of bacterial cells in pelleted form;

(b) stirring resulting mixture at room temperature for at least about 30 minutes; wherein the method does not comprise a step of purification prior to steps (a)-(b). In some embodiments, the cationic surfactant and anionic surfactant are SDBS and CTAT, respectively, at a molar weight ratio of about 70:30. In some embodiments, the bacterial cells comprise at least one or a plurality of bacterial antigens from Neisseria and/or Francisella. In some embodiments, the aqueous solution comprises one or more of a dye, a fluorescent protein, or a chemiluminescent agent.

The disclosure relates to a method of integrating a bacterial antigen into a vesicle, comprising:

(a) centrifuging bacterial cells;

(b) removing any bacterial growth medium;

(c) adding a weight/weight molar ratio of cationic surfactant and anionic surfactant in aqueous solution to the bacterial cells;

(d) stirring resulting mixture at room temperature for at least about 30 minutes;

wherein the method does not comprise a step of purification prior to steps (a)-(d), wherein the method further comprises filtering the vesicles through a size exclusion or ion chromatography column.

The disclosure relates to a method of manufacturing an antibody against an antigen comprising injecting into a subject the composition of comprising a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of bacterial immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 15 micrograms per microliter of bacterial lipooligosaccharide (LOS) or lipopolysaccharide (LPS) optionally comprising one or a plurality of bacterial lipoproteins and/or bacterial cell membrane proteins; and subsequently collecting its serum.

The disclosure relates to a method of reducing the immunological toxicity of a bacterial antigen comprising loading the bacterial antigen into a catanionic vesicle of comprising a catanionic surfactant vesicle; wherein the catanionic surfactant vesicle comprises a unilamellar bilayer comprising a mixture of oppositely charged single-tailed surfactants and one or a plurality of bacterial immunogens; wherein the at least one or plurality of bacterial immunogens comprise at least one membrane-bound sugar, polypeptide, functional fragment thereof, a combination thereof; and wherein the at least one sugar, polypeptide, functional fragment thereof, or combination thereof is positioned at least partially in the unilamellar bilayer; and wherein the catanionic surfactant vesicle comprises at least about 15 micrograms per microliter of bacterial lipooligosaccharide (LOS) or lipopolysaccharide (LPS) optionally comprising one or a plurality of bacterial lipoproteins.

BRIEF DESCRIPTION OF THE FIGURES

FIG. 1: Total protein and carbohydrate concentrations in vesicle extract samples determined by colorimetric BCA and carbohydrate assays. All five extraction methods yielded similar quantities of protein and carbohydrate by methods (1) solid surfactants added to the bacterial cell pellet followed by the addition of water, (2) SDBS solution added to the bacterial cell pellet followed by the addition of a CTAT solution (3) CTAT solution added to bacterial cell pellet followed by the addition of solid SDBS (4) SDBS solution added to bacterial cell pellet followed by the addition of solid CTAT (5) bare vesicles added to the bacterial cell pellet. BCA assay indicating the presence of protein in the different extraction methods.

FIG. 4: Proteomics data from GC/MS of vesicle extract samples.

FIG. 14: Average amount of carbohydrate in TRIAD vaccine from two batches. Carbohydrate determined by phenol/sulfuric acid colorimetric assay.

FIG. 16: Antibody titer results in mice inoculated with LOS and LOS/C12-PADRE functionalized surfactant vesicles; performed by a student in the Stein group (unpublished results).

FIG. 17: Chemical structure of one type of lipopolysaccharide (LPS) from F. tularensis.

FIG. 28: Serum samples from mice immunized with LVS-V or Schu S4-V and challenged with live homologous bacteria detect similar bands by Western analysis but also exhibit differences in their binding specificities. (A) Mice were immunized either with LVS-V by two i.p. injections and challenged i.p. with *F. tularensis* LVS as described in FIG. 21 or immunized with Schu S4-V by i.p. and i.n. routes and challenged i.n. with *F. tularensis* Schu S4. Serum samples harvested 3 weeks postchallenge (LVS serum, $1:10^6$; Schu S4 serum, $1:10^5$) were used to probe Western blots (4 to 20% gradient gel) of vesicles (V, LVS-V, and Schu S4-V), whole-lysed bacteria (LVS and Schu S4), and purified recombinant *F. tularensis* proteins (DnaK and Tul4). (B) The same membrane at a lower (1–s) exposure to show DnaK and Tul4 detected by Schu S4-V-immunized/Schu S4-challenged survivor serum. Similar results were seen in two separate experiments.

FIG. 29: Prominent *F. tularensis* epitopes detected in serum samples from vesicle-immunized mice are conserved across multiple strains of *F. tularensis*. *F. tularensis* from strains Schu S4, MA00-2987 (A1 strains), WY96-3418 (A2 strain), KY99-3387, OR96-0246, and LVS (B strains) were grown in enriched TSB and subjected to Western analysis (4 to 20% gradient gel) with the antisera used in FIGS. 26 and 28. (A) Sera from LVS-V-immunized mice before challenge. (B) Sera from LVS-V-immunized mice after live LVS challenge. (C) Sera from Schu S4-immunized mice after live Schu S4 challenge.

FIG. 30: Outcome of immunized mice after live intranasal *F. tularensis* Schu S4 challenge. a Mice were immunized with control vesicles (V) or Schu S4-V at 2-week intervals by the indicated routes. Two weeks after the final immunization, all mice were challenged with ~20 CFU (ranging from 3 to 49 CFU in different experiments) of *F. tularensis* Schu S4 by the intranasal route. b i.p., intraperitoneal; i.n., intranasal; s.c., subcutaneous. c Mean and standard deviation of time to death were calculated from only those animals that succumbed to infection. d Fisher's exact test, P value compared to that of control; NS, not significant. e One-way ANOVA, p value of Tukey posttest compared to that of control.

FIG. 34: Table 5.2. Amount of doxorubicin in vesicles from increasing concentrations.

FIG. 5.11. Fluorescently-labeled vesicles binding with cells.

FIG. 47: Table of protein content and sugar content of vesicles after using two disclosed techniques of vesicle encapsulation of bacterial antigens. In Method 4-I, 30 mg of CTAT, 71 mg SDBS, 6.9 mL of Millipore water, and 3 mL of cell suspension were mixed and then stirred for 15 minutes. The mixture was centrifuged for 1 hour and the supernatant was decanted. 1 mL of the sample of supernatant was purified on the column. In Method 4-II, 9.9 mL of preformed vesicles (1% SDBS rich), 3 mL cell suspension, and 5.91 mL of Millipore water were mixed and then stirred for 1 hour. The mixture was centrifuged for 1 hour and the supernatant was decanted. 1 mL of the sample of supernatant was purified on the column.

DETAILED DESCRIPTION OF ILLUSTRATIVE EMBODIMENTS

Figure 2:
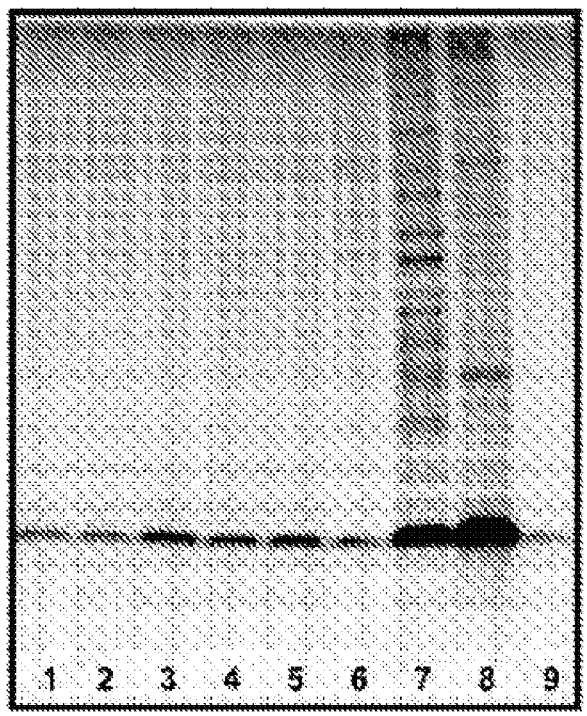
FIG. 2: Vesicle-containing fractions purified by gel filtration followed by silver staining. Lanes 1-6 and 9 were loaded with 1 μL, Lane 7 was loaded with 5 μL. and Lane 8 was loaded with 167 nL of sample and analyzed by SDS-polyacrylamide Tris-tricine 16.5% v/v gels followed by silver staining. Lanes 1-6 correspond to vesicle-containing fractions from prepared from extraction methods 1-6, respectively, and show similar protein patterns. Lane 7 shows the purified cell lysate disrupted by SDBS and purified by gel filtration. Lane 8 contains a very different protein pattern from resuspended GC cell pellet. Lane 9 contains purified LOS F62ΔlgtD as a standard.

Various terms relating to the methods and other aspects of the present invention are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "associated with" refers to the state of two or more entities which are linked by a direct or indirect covalent or non-covalent interaction. In some embodiments, an association is covalent. In some embodiments, a covalent association is mediated by a linker moiety. In some embodiments, an association is non-covalent (e.g. charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, etc.). For example, in some embodiments, an entity (e.g. targeting moiety or therapeutic agent to be delivered) may be covalently associated with a particle. In some embodiments, an entity (e.g. targeting moiety or therapeutic agent to be delivered) may be non-covalently associated with a particle, (e.g. the entity may be associated with the surface of, encapsulated within, surrounded by, and/or distributed throughout a vesicle or particle disclosed herein).

The term "anhydrous" is used throughout the specification to describe a form in which the purgative salts according to the present invention can be administered. Anhydrous formulations are those which essentially have excluded water from the formulations, except, in such instances where the salt is hydrated or otherwise complexed with small amount of water.

The term "salt" refers to acidic salts formed with inorganic and/or organic acids, as well as basic salts formed with inorganic and/or organic bases. Examples of these acids and bases are well known to those of ordinary skill in the art. Salts according to the present invention may be used in a variety of forms, for examples anhydrous or a hydrated crystalline form. In some embodiments, the salts may be those that are physiologically tolerated by a patient.

The term "soluble" or "water soluble" refers to an aqueous solubility that is higher than 1/10,000 (mg/mL). The solubility of a substance, or solute, is the maximum mass of that substances that can be dissolved completely in a specified mass of the solvent, such as water. "Practically insoluble" or "insoluble," on the other hand, refers to an aqueous solubility that is 1/10,000 (mg/mL) or less.

The terms "treating" and "to treat", mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with any condition. The treatment may be a pre-treatment as well as a treatment at the onset of symptoms.

"Effective amount" refers to an amount of a compound, material, or composition, as described herein effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art.

Sequence homology for nucleotides and amino acids may be determined using PASTA, BLAST and Gapped BLAST (Altschul et al., Nuc. Acids Res., 1997, 25, 3389, which is incorporated herein by reference in its entirety) and PAUP* 4.0b1 0 software (D. L. Swofford, Sinauer Associates, Massachusetts). "Percentage of similarity" is calculated using PAUP* 4.0b1 0 software (D. L. Swofford. Sinauer Associates, Massachusetts). The average similarity of the consensus sequence is calculated compared to all sequences in the phylogenic tree.

Briefly, the BLAST algorithm, which stands for Basic Local Alignment Search Tool is suitable for determining sequence similarity. Software for performing BLAST analyses is publicly available through the National Center for Biotechnology Information (ncbi.nlm.nih.gov). This algorithm involves first identifying high scoring sequence pair (HSPs) by identifying short words of length Win the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a protein such that when present in the cell of the individual, the coding sequence will be expressed.

As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment will typically comprise at least about 50 amino acids and more typically will comprise at least about 200 amino acids.

As used herein, the term "nucleic acid," in its broadest sense, refers to any compound and/or substance that can be incorporated into an oligonucleotide chain. As used herein, the terms "nucleic acid" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. The term "nucleic acid sequence" as used herein can refer to the nucleic acid material itself and is not restricted to the sequence information (e.g. the succession of letters chosen, for example, among the five base letters A, G, C, T, or U) that biochemically characterizes a specific nucleic acid, e.g., a DNA or RNA molecule. A nucleic acid sequence is presented in the 5' to 3' direction unless otherwise indicated. The term "nucleic acid segment" is used herein to refer to a nucleic acid sequence that is a portion of a longer nucleic acid sequence. In some embodiments, a "nucleic acid" or "polynucleotide" comprises natural nucleosides (e.g. adenosine, thymidine, guanosine, cytidine, uridine, deoxyadenosine, deoxythymidine, deoxyguanosine, and deoxycytidine): nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine. C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

As used herein, a "particle" refers to any entity having a diameter of less than 100 microns (µm). Typically, particles have a longest dimension (e.g. diameter) of 1000 nm or less. In some embodiments, particles have a diameter of 300 nm or less. In some embodiments, nanoparticles have a diameter of 200 nm or less. In some embodiments, nanoparticles have a diameter of 100 nm or less. In general, particles are greater in size than the renal excretion limit, but are small enough to avoid accumulation in the liver. In some embodiments, a population of particles may be relatively uniform in terms of size, shape, and/or composition. In general, inventive particles are biodegradable and/or biocompatible. Inventive particles can be solid or hollow and can comprise one or more layers. In some embodiments, particles are spheres, spheroids, flat, plate-shaped, cubes, cuboids, ovals, ellipses, cylinders, cones, or pyramids. In some embodiments, particles can be a matrix of polymers. In some embodiments, the matrix is cross-linked. In some embodiments, formation of the matrix involves a cross-linking step. In some embodiments, the matrix is not substantially cross-linked. In some embodiments, formation of the matrix does not involve a cross-linking step. In some embodiments, particles can be a non-polymeric particle (e.g. a metal particle, quantum dot, ceramic, inorganic material, bone, etc.). Components of the pharmaceutical compositions and vaccines disclosed herein may be particles or may be microparticles, nanoparticles, liposomes, and/or micelles. As used herein, the term "nanoparticle" refers to any particle having a diameter of less than 1000 nm.

As used herein, the term "subject" or "patient" refers to any organism to which a composition of this invention may be administered, e.g., for experimental, diagnostic, and/or therapeutic purposes. Typical subjects include animals (e.g., mammals such as mice, rats, rabbits, non-human primates, and humans) and/or plants. The term "subject" is used throughout the specification to describe an animal to whom treatment with the compositions according to the present invention is provided or administered. For treatment of those conditions which are specific for a specific subject, such as a human being or such as a mammal, the term "patient" may be interchangeably used. In some instances in the description of the present invention, the term "patient" will refer to human patients. In some embodiments, the subject may be a mammal to whom the present invention is provided or administered.

As used herein, the term "targeting moiety" refers to any moiety that binds to a component associated with a cell. Such a component is referred to as a "target" or a "marker." A targeting moiety may be a polypeptide, glycoprotein, nucleic acid, small molecule, carbohydrate, lipid, etc. In some embodiments, a targeting moiety is an antibody or characteristic portion thereof. In some embodiments, a targeting moiety is a receptor or characteristic portion thereof. In some embodiments, a targeting moiety is a ligand or characteristic portion thereof. In some embodiments, a targeting moiety is a nucleic acid targeting moiety (e.g. an aptamer) that binds to a cell type specific marker. In general, an aptamer is an oligonucleotide (e.g., DNA, RNA, or an analog or derivative thereof) that specifically binds to a particular target, such as a polypeptide. In some embodiments, a targeting moiety is a small molecule.

Compositions

Embodiments according to the disclosure include surfactant vesicles comprising mixtures of oppositely-charged single-tailed surfactants (commonly referred to as "catanionic" vesicles). Compositions of the disclosure comprise one or a plurality of vesicles comprising whole cell extract. In some embodiments, the catanionic vesicles comprised functionalized carbohydrate and/or peptide optionally fused with one or a plurality of linkers and/or peptides, nucleic acid molecules, or agent disclosed herein. A composition comprising a bacterial cell lysate fraction, a bacterial cell membrane-bound fraction, and a plurality of catanionic vesicles wherein the bacterial cell lysate components are encapsulated within said catanionic vesicles, an individual catanioic vesicle comprises a fraction of total bacterial cell lysate components and said plurality of catanionic vesicles collectively comprise total bacterial cell lysate components.

Single-tailed, anionic surfactant can include an amphipathic molecule having from about $C_6$ to about $C_{20}$ hydrocarbon tail region and a hydrophilic, polar head group. The head-group on the anionic surfactant can be, for example, sulfonate, sulfate, carboxylate, benzene sulfonate, or phosphate. The single-tailed, cationic surfactant can include an amphipathic molecule having a from about $C_6$ to about $C_{20}$ hydrocarbon tail region and a hydrophilic polar head group. The head group on the cationic surfactant can be, for example, a quaternary ammonium group, a sulfonium group, or a phosphonium group.

The size and curvature properties (shape) of catanionic vesicles formed according to embodiments of the invention can vary depending upon factors such as the length of the hydrocarbon tail regions of the constituent surfactants and the nature of the polar head groups. At a common 0.1% bioconjugate-to-surfactant ratio, the bioconjugate can have no observable effect on vesicle shape, size, or stability in aqueous media. In some embodiments, the bioconjugate-to-surfactant ratio in weight/weight is from about 0.1% to about 2%. In some embodiments, the bioconjugate-to-surfactant ratio weight/weight is from about 0.1% to about 3%. In some embodiments, the bioconjugate-to-surfactant weight/weight ratio is from about 0.1% to about 4%. In some embodiments, the bioconjugate-to-surfactant weight/weight ratio is from about 0.1% to about 5%. In some embodiments, the bioconjugate-to-surfactant weight/weight ratio is from about 0.1% to about 6%. In some embodiments, the bioconjugate-to-surfactant weight/weight ratio is from about 0.1% to about 7%. In some embodiments, the bioconjugate-to-surfactant weight/weight ratio is from about 0.1% to about 8%.

In some embodiments, the bioconjugate-to-surfactant weight/weight ratio is from about 0.1% to about 9%. In some embodiments, the bioconjugate-to-surfactant weight/weight ratio is from about 0.1% to about 10%. In some embodiments, the bioconjugate-to-surfactant weight/weight ratio is from about 0.1% to about 12%. In some embodiments, the bioconjugate-to-surfactant weight/weight ratio is from about 0.1% to about 15%. In some embodiments, the bioconjugate-to-surfactant weight/weight ratio is from about 1.0% to about 2%. In some embodiments, the bioconjugate-to-surfactant ratio weight/weight is from about 1.0% to about 3%. In some embodiments, the bioconjugate-to-surfactant ratio is from about 1.0% to about 4%. In some embodiments, the bioconjugate-to-surfactant ratio is from about 1.0% to about 5%. In some embodiments, the bioconjugate-to-surfactant ratio is from about 1.0% to about 6%. In some embodiments, the bioconjugate-to-surfactant ratio is from about 1.0% to about 7%. In some embodiments, the bioconjugate-to-surfactant ratio is from about 1.0% to about 8%. In some embodiments, the bioconjugate-to-surfactant ratio is from about 1.0% to about 9%. In some embodiments, the bioconjugate-to-surfactant ratio is from about 1.0% to about 10%. In some embodiments, the bioconjugate-to-surfactant ratio is from about 1.0% to about 12%. In some embodiments, the bioconjugate-to-surfactant ratio is from about 1.0% to about 15%.

In some embodiments, the bioconjugate-to-surfactant ratio weight/weight is from about 1.0% to about 3%. In some embodiments, the LPS or LOS-to-surfactant ratio is from about 1.0% to about 4%. In some embodiments, the LPS or LOS-to-surfactant ratio is from about 1.0% to about 5%. In some embodiments, the LPS or LOS-to-surfactant ratio is from about 1.0% to about 6%. In some embodiments, the LPS or LOS-to-surfactant ratio is from about 1.0% to about 7%. In some embodiments, the LPS or LOS-to-surfactant ratio is from about 1.0% to about 8%. In some embodiments, the LPS or LOS-to-surfactant ratio is from about 1.0% to about 9%. In some embodiments, the LPS or LOS-to-surfactant ratio is from about 1.0% to about 10%. In some embodiments, the LPS or LOS-to-surfactant ratio is from about 1.0% to about 12%. In some embodiments, the LPS or LOS-to-surfactant ratio is from about 1.0% to about 15%.

The bilayer can include cationic surfactant and anionic surfactant in a molar ratio in a range of from about 9:1 to about 1:9, excluding a molar ratio of about 1:1. For example, the bilayer can include cationic surfactant and anionic surfactant in a molar ratio of from about 9:1, 8:2, 7:3, 6:4, 5.5:4.5, 5.1:4.9, 4.9:5.1, 4.5:5.5, 4:6, 3:7, 2:8, and 1:9 to about 9:1, 8:2, 7:3, 6:4, 5.5:4.5, 5.1:4.9, 4.9:5.1, 4.5:5.5, 4:6, 3:7, 2:8, and 1:9. For example, the bilayer can include cationic surfactant and anionic surfactant in a molar ratio in a range of from about 6:4 to about 8:2, in a range of from about 6:4 to about 7:3, of about 6:4, in a range of from about 2:8 to about 4:6, in a range of from about 3:7 to about 4:6, and of about 4:6. The cationic surfactant and the anionic surfactant can have a concentration in the external aqueous environment of less than about 5 wt %. For example, the cationic surfactant and the anionic surfactant can have a concentration in the external aqueous environment of from about 0.0001 wt % to about 3 wt %, for example, of from about 0.5 wt % to about 2 wt %, for example, of about 1 wt %. The solute ion can be present in the aqueous environment at an external concentration, the solute ion can be present in the vesicle at a sequestration concentration, and the ratio of the sequestration concentration to the external concentration can be greater than 1, for example, greater than or equal to 5. For example, from about 20% to about 75% of the solute ion present in the aqueous environment and in the catanionic surfactant vesicle can be sequestered in the catanionic surfactant vesicle. The encapsulation efficiency of the solute ion in the vesicle can be at least about 2%, for example, at least about 3%, greater than about 7%, or at least about 10%, 20%, 30%, 40%, 50%, 60%, 70%, 75%, 80%, 90%, or 95%. The percentage of solute adsorbed on the bilayer can be at least about 0.5%, for example, at least about 1%, 2%, 5%, or 16%. The ratio of the percentage of solute adsorbed on the bilayer to the encapsulation efficiency can be at least about 10%, for example, greater than 25%, at least about 50%, at least about 75%, at least about 90%, or at least about 95%.

The release of solute ion from a catanionic vesicle according to the present invention can occur over a range of time such that the half-life time of the release is from about 2, 5, 10, 20, 30, 40, 50, 60, 70, 80, 85, 90, 100, 120, 150, 200, and 500 days to about 2, 5, 10, 20, 30, 40, 50, 60, 70, 80, 85, 90, 100, 120, 150, 200, and 500 days.

The diameter of vesicles according to the disclosure can be, for example from about 10 to about 250 nanometers, for example, from about 30 to about 150 nm. In some embodiments, the compositions, pharmaceutical compositions, and vaccines disclosed herein comprise a plurality of vesicles with a distribution of vesicles diameter from about 20 nm to about 200 nm. In some embodiments, the compositions, pharmaceutical compositions, and vaccines disclosed herein comprise a plurality of vesicles with a distribution of vesicles diameter from about 30 nm to about 200 nm. In some embodiments, the compositions, pharmaceutical compositions, and vaccines disclosed herein comprise a plurality of vesicles with a distribution of vesicles diameter from about 40 nm to about 200 nm. In some embodiments, the compositions, pharmaceutical compositions, and vaccines disclosed herein comprise a plurality of vesicles with a distribution of vesicles diameter from about 50 nm to about 200 nm. In some embodiments, the compositions, pharmaceutical compositions, and vaccines disclosed herein comprise a plurality of vesicles with a distribution of vesicles diameter from about 60 nm to about 200 nm. In some embodiments, the compositions, pharmaceutical compositions, and vaccines disclosed herein comprise a plurality of vesicles with a distribution of vesicles diameter from about 70 nm to about 200 nm. In some embodiments, the compositions, pharmaceutical compositions, and vaccines disclosed herein comprise a plurality of vesicles with a distribution of vesicles diameter from about 80 nm to about 200 nm. In some embodiments, the compositions, pharmaceutical compositions, and vaccines disclosed herein comprise a plurality of vesicles diameter from about 90 nm to about 200 nm. In some embodiments, the compositions, pharmaceutical compositions, and vaccines disclosed herein comprise a plurality of vesicles with a distribution of vesicles diameter from about 100 nm to about 200 nm. In some embodiments, the compositions, pharmaceutical compositions, and vaccines disclosed herein comprise a plurality of vesicles with a distribution of vesicles diameter from about 20 nm to about 100 nm. In some embodiments, the compositions, pharmaceutical compositions, and vaccines disclosed herein comprise a plurality of vesicles with a distribution of vesicles diameter from about 20 nm to about 150 nm.

In some embodiments, the catanionic vesicles or accompanying particles may optionally comprise one or more carbohydrates. The percent of carbohydrate in particles can range from 0% to 99% by weight, from 10% to 99% by weight, from 25% to 99% by weight, from 50% to 99% by weight, or from 75% to 99% by weight. In some embodiments, the percent of carbohydrate in particles can range from 0% to 75% by weight, from 0% to 50% by weight, from 0% to 25% by weight, or from 0% to 10% by weight. In some embodiments, the percent of carbohydrate in the vesicles or particles can be from about 0.05% to about 5.0% by weight, in some embodiments, the percent of carbohydrate in the vesicles or particles can be approximately 0.1%, approximately 0.2%, approximately 0.3%, approximately 0.4%, approximately 0.5%, approximately 0.6%, approximately 0.7%, approximately 0.8%, approximately 0.9%, or approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight. Carbohydrates may be natural or synthetic. A carbohydrate may be a derivatized natural carbohydrate. In certain embodiments, a carbohydrate is a monosaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a disaccharide, including but not limited to lactose, sucrose, maltose, trehalose, and cellobiose. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In certain embodiments, the carbohydrate is a sugar alcohol, including but not limited to mannitol, sorbitol, xylitol, erythritol, maltitol, and lactitol. In certain embodiments, the carbohydrate is a bacterial carbohydrate. In certain embodiments, the carbohydrate is a bacterial carbohydrate derived directly from the whole cell extract from which the catanionic vesicle is made. In certain embodiments, the carbohydrate is LOS or LPS. In certain embodiments, the carbohydrate is LOS or LPS and derived directly from the whole cell extract from which the catanionic vesicle is made.

In some embodiments, the catanionic vesicles, vaccines or accompanying particles may optionally comprise one or a plurality of bacterial lipoproteins. The lipoproteins may be any lipoprotein disclosed in Table 1 (identified by UniProt number and incorporated by reference in its entirety), either individually or in combination, and/or or antigenic fragments that 70%, 75%, 80%, 85%, 09%, 95%, 96%, 97%, 98%, or 99% homolgous to the lipoproteins identified by UniProt number. In some embodiments, the catanionic vesicles or accompanying particles may optionally comprise one or any combination of amino acids that are 70%, 75%, 80%, 85%, 09%, 95%, 96%, 97%, 98%, 99%, or 100% homolgous to SEQ ID NO:1 through SEQ ID NO:883. In some embodiments, the catanionic vesicles, vaccines or accompanying particles may optionally comprise one or a plurality of bacterial antigens identified by UniProt number in Table 1 and/or antigenic fragments that 70%, 75%, 80%, 85%, 09%, 95%, 96%, 97%, 98%, or 99% homolgous to the bacterial antigens identified by UniProt number in Table 1. In some embodiments, the catanionic vesicles, vaccines or accompanying particles may optionally comprise one or a plurality of *Francisella* lipoproteins or *Francisella* antigens. Examples of *Francisella* antigens of the present disclosure may be DnaK, Tul4, and those antigens disclosed in Example 4.

Vesicle size can be influenced by selecting the relative lengths of the hydrocarbon tail regions of the anionic and cationic surfactants. For example, large vesicles, e.g., vesicles of from 150 to 200 nanometers diameter, can be formed when there is disparity between the length of the hydrocarbon tail on the anionic surfactant and the hydrocarbon tail on the cationic surfactant. For example, large vesicles can be formed when a $C_{16}$ cationic surfactant solution is combined with a $C_8$ anionic surfactant solution. Smaller vesicles can be produced by using anionic and cationic surfactant species of which the lengths of the hydrocarbon tails are more closely matched. The permeability characteristics of vesicles according to the present invention can be influenced by the nature of the constituent surfactants, for example, the chain length of the hydrocarbon tail regions of the surfactants. Longer tail lengths on the surfactant molecules can decrease the permeability of the vesicles by increasing the thickness and hydrophobicity of the vesicle membrane (bilayer). The control of reagent and substrate permeation across vesicle membranes can be an important parameter, for example, when using the vesicles as microreactors.

Exemplary anionic, single-chain surface active agents include alkyl sulfates, alkyl sulfonates, alkyl benzene sulfonates, and saturated or unsaturated fatty acids and their salts. Moieties comprising the polar head group in the cationic surfactant can include, for example, quaternary ammonium, pyridinium, sulfonium, and/or phosphonium groups. For example, the polar head group can include trimethylammonium. Exemplary cationic, single-chain surface active agents include alkyl trimethylammonium halides, alkyl trimethylammonium tosylates, and N-alkyl pyridinium halides.

Alkyl sulfates can include sodium octyl sulfate, sodium decyl sulfate, sodium dodecyl sulfate, and sodium tetradecyl sulfate. Alkyl sulfonates can include sodium octyl sulfonate, sodium decyl sulfonate, and sodium dodecyl sulfonate. Alkyl benzene sulfonates can include sodium octyl benzene sulfonate, sodium decyl benzene sulfonate, and sodium dodecyl benzene sulfonate (SDBS). Fatty acid salts can include sodium octanoate, sodium decanoate, sodium dodecanoate, and the sodium salt of oleic acid.

Alkyl trimethylammonium halides can include octyl trimethylammonium bromide, decyl trimethylammonium bromide (DTAB), dodecyl trimethylammonium bromide, myristyl trimethylammonium bromide, and cetyl trimethylammonium bromide. Alkyl trimethylammonium tosylates can include octyl trimethylammonium tosylate, decyl trimethylammonium tosylate, dodecyl trimethylammonium tosylate, myristyl trimethylammonium tosylate, and cetyl trimethylammonium tosylate. For example, N-alkyl pyridinium halides can include decyl pyridinium chloride (DPC), dodecyl pyridinium chloride, cetyl pyridinium chloride, decyl pyridinium bromide, dodecyl pyridinium bromide, cetyl pyridinium bromide, decyl pyridinium iodide, dodecyl pyridinium iodide, cetyl pyridinium iodide.

Surfactants that can be used to form catanionic vesicles according to the present invention include, for example, sodium didoceyl sulfate (SDS), Dodecyltrimethylammonium chloride (DTAC), dodecyl(trimethyl)azanium bromide (DTAB), dodecyl-phosphatidylcholine (DPC), Decyl Dimethyl Amine Oxide (DDAO), dodecyldimethyl ammonium bromide (DDAB), sodium octylsulfate (SOS), dioctyl sulfosuccinate sodium salt (AOT), and cetyltrimethylammonium tosylate (CTAT). In some embodiments, the vesicles comprise bioconjugates, for example, glycoconjugates, such as alkylated carbohydrates. In some embodiments, these vesicles can sequester and separate charged biomolecules in solution. To add increased biofunctionality to these vesicles, or to target the delivery of sequestered molecules, these catanionic vesicles can be enhanced with the addition of one or more bioconjugates, both charged and non-ionic, in order to interact with natural or artificial carbohydrate and/or protein recognition systems. In some embodiments, these carbohydrate- and/or protein-functionalized vesicles present a protein and/or sugar moeity to an actual cell surface and facilitate multivalent interactions. The recognition process for a carbohydrate is fundamentally different than protein-protein or antibody-antigen interactions at cell surfaces in that carbohydrate recognition is a multivalent process. Because each binding event of a carbohydrate-mediated system involves weak interactions (H-bonding), then the receptors involved must establish multiple interactions to achieve high selectivity (Mammen, S. K. Choi and G. M. Whitesides, Angew. Chem. Int. Ed., 1998, 37, 2755-2794). Accordingly, the recognition of glycosyl residues on the cell surface requires clustering or a high density of surface receptors. It is this multivalent binding process of oligosaccharide-mediated recognition that can in certain cases be advantageous in comparison with recognition strategies associated with other biomolecules such as proteins or nucleic acids.

Aspects of the disclosure relate to a composition comprising: a catanionic surfactant vesicle; and at least one bacterial immunogen; wherein the catanionic surfactant vesicle comprises a unilamellar bilayer comprising a mixture of oppositely charged single-tailed surfactants; wherein the at least one bacterial immunogen comprises at least one membrane-bound sugar, a polypeptide, a functional fragment thereof, a combination thereof from the membrane of a bacterial cell wall; and wherein the at least one sugar, polypeptide, functional fragment thereof, or combination thereof is embedded at least partially in the bilayer; and wherein the catanionic surfactant vesicle comprises at least about 50 micrograms per microliter of bacterial oligosaccharide or polysaccharide.

The present disclosure also relates a composition comprising: a catanionic surfactant vesicle; and at least one bacterial immunogen; wherein the catanionic surfactant vesicle comprises a unilamellar bilayer comprising a mixture of oppositely charged single-tailed surfactants; wherein the at least one bacterial immunogen from the membrane of a bacterial cell wall comprises at least one membrane-bound sugar, polypeptide, functional fragment thereof, a combination thereof; and wherein the at least one sugar, polypeptide, functional fragment thereof, or combination thereof is positioned at least partially in the bilayer; and wherein the bacterial immunogen is chosen from one or a combination of: DnaK, Tul4, FopA. In some embodiments, the catanionic surfactant vesicle comprises a combination of DnaK and Tul4.

The present disclosure also relates a composition comprising: a catanionic surfactant vesicle; and at least one bacterial immunogen; wherein the catanionic surfactant vesicle comprises a unilamellar bilayer comprising a mixture of oppositely charged single-tailed surfactants; wherein the at least one bacterial immunogen from the membrane of a bacterial cell wall comprises at least one membrane-bound sugar, polypeptide, functional fragment thereof, a combination thereof; and wherein the at least one sugar, polypeptide, functional fragment thereof, or combination thereof is positioned at least partially in the bilayer.

In some embodiments, particles may optionally comprise one or more carbohydrates. The percent of carbohydrate in particles can range from 0% to 99% by weight, from 10% to 99% by weight, from 25% to 99% by weight, from 50% to 99% by weight, or from 75% to 99% by weight. In some embodiments, the percent of carbohydrate in particles can range from 0% to 75% by weight, from 0% to 50% by weight, from 0% to 25% by weight, or from 0% to 10% by weight. In some embodiments, the percent of carbohydrate in particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight. Carbohydrates may be natural or synthetic. A carbohydrate may be a derivatized natural carbohydrate. In certain embodiments, a carbohydrate is a monosaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a disaccharide, including but not limited to lactose, sucrose, maltose, trehalose, and cellobiose. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In certain embodiments, the carbohydrate is a sugar alcohol, including but not limited to mannitol, sorbitol, xylitol, erythritol, maltitol, and lactitol. In certain embodiments, a carbohydrate is LOS or LPS.

Aspects of the disclosure relate to pharmaceutical compositions comprising any one or plurality of vesicles disclosed herein and at least one pharmaceutically acceptable carrier or excipient. The present invention provides novel targeted particles comprising: a therapeutically effective amount of a particle, one or more targeting moieties (e.g. aptamers), and one or more therapeutic agents to be delivered; and one or more pharmaceutically acceptable excipients. In some embodiments, the present invention provides for pharmaceutical compositions comprising inventive targeted particles as described herein. Such pharmaceutical compositions may optionally comprise one or more additional therapeutically-active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to a vesicle disclosed herein and one or more therapeutic agents to be delivered.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

The formulations of the pharmaceutical compositions described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient(s), and/or any additional ingredients in a pharmaceutical composition of the invention will vary, depending upon the identity, size, and/or condition of the subject treated and further depending upon the route by which the composition is to be administered. By way of example, the composition may comprise between about 0.1% to about 99% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy,* 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,): natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary vaccine adjuvants include, but are not limited to, aluminium phosphate, aluminium hydroxide, calcium phosphate, monophosphoryl lipid A (MPL), Quil A/QS-21, inulin-derivatives, bacterial peptidoglycan, CpG-motif containing DNA, N-acetyl muramyl-L-alanyl-D-isoglutamine (MDP), trehalose dimycolate (TDM).

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus. Phenonip, methylparaben, Germall 115, Germaben 11, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsca cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the targeted particles of the invention are mixed with solubilizing agents such as Cremophor, alcohols, oils, modified oils, glycols, polysorbates, cyclodextrins, polymers, and combinations thereof. In some embodiments, the liquid dosage form is an aqueous solution or water. In some embodiments, the liquids dosage form heated and/or sterilized water.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the targeted particles of this invention with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a targeted particle of this invention may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

In some embodiments, the pharmaceutical compositions may further comprise one or a plurality of agents. According to the present invention, pharmaceutical compositions comprising any one or plurality of vesicles disclosed herein may be used for delivery of any agent, including, for example, therapeutic, diagnostic, and/or prophylactic agents. Exemplary agents to be delivered in accordance with the present invention include, but are not limited to, small molecules, organometallic compounds, nucleic acids, proteins (including multimeric proteins, protein complexes, etc.), peptides, lipids, carbohydrates, hormones, metals, radioactive elements and compounds, drugs, vaccines, immunological agents, etc., and/or combinations thereof.

In some embodiments, pharmaceutical compositions comprising any one or plurality of vesicles disclosed herein comprise less than 50% by weight, less than 40% by weight, less than 30% by weight, less than 20% by weight, less than 15% by weight, less than 10% by weight, less than 5% by weight, less than 1% by weight, or less than 0.5% by weight of the therapeutic agent to be delivered.

In some embodiments, the agent to be delivered may be a mixture of pharmaceutically active agents. For example, a local anesthetic may be delivered in combination with an anti-inflammatory agent such as a steroid. To give but another example, an antibiotic may be combined with an inhibitor of the enzyme commonly produced by bacteria to inactivate the antibiotic (e.g., penicillin and clavulanic acid).

In some embodiments, the agent to be delivered may be a mixture of anti-cancer agents. In some embodiments, inventive targeted particles are administered in combination with one or more of the anti-cancer agents described herein. To give but one example, in some embodiments, inventive compositions comprising an anti-cancer agent to be delivered are administered in combination with hormonal therapy. The growth of some types of tumors can be inhibited by providing or blocking certain hormones. For example, steroids (e.g. dexamethasone) can inhibit tumor growth or associated edema and may cause regression of lymph node malignancies. In some cases, prostate cancer is often sensitive to finasteride, an agent that blocks the peripheral conversion of testosterone to dihydrotestosterone. Breast cancer cells often highly express the estrogen and/or progesterone receptor. Inhibiting the production (e.g. with aromatase inhibitors) or function (e.g. with tamoxifen) of these hormones can often be used in breast cancer treatments. In some embodiments, gonadotropin-releasing hormone agonists (GnRH), such as goserelin possess a paradoxic negative feedback effect followed by inhibition of the release of follicle stimulating hormone (FSH) and leuteinizing hormone (LH), when given continuously.

In some embodiments, the agent to be delivered may be a mixture of Cas9 enzyme linked to an RNA molecule and a DNA template. Such a payload can be designed to repair single base pair mutations in genomic DNA of a subject.

In some embodiments, the agent to be delivered is a small molecule and/or organic compound with pharmaceutical activity. In some embodiments, the agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, .beta.-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitors of DNA, RNA, or protein synthesis, etc.

In certain embodiments, the therapeutic agent to be delivered is an anti-cancer agent (i.e. cytotoxic agents). Most anti-cancer agents can be divided in to the following categories: alkylating agents, antimetabolites, natural products, and hormones and antagonists. Anti-cancer agents typically affect cell division and/or DNA synthesis. However, some chemotherapeutic agents do not directly interfere with DNA. To give but one example, tyrosine kinase inhibitors (imatinib mesylate/Gleevec®) directly target a molecular abnormality in certain types of cancer (chronic myelogenous leukemia, gastrointestinal stromal tumors, etc.). Alkylating agents are so named because of their ability to add alkyl groups to many electronegative groups under conditions present in cells. Alkylating agents typically function by chemically modifying cellular DNA. Exemplary alkylating agents include nitrogen mustards (e.g. mechlorethamine, cyclophosphamide, ifosfamide, melphalan (1-sarcolysin), chlorambucil), ethylenimines and methylmelamines (e.g. altretamine (hexamethylmelamine; HMM), thiotepa (triethylene thiophosphoramide), triethylenemelamine (TEM)), alkyl sulfonates (e.g. busulfan), nitrosureas (e.g. carmustine (BCNU), lomustine (CCMU), semustine (methyl-CCNU), streptozocin (streptozotocin)), and triazenes (e.g. dacarbazine (DTIC; dimethyltriazenoimidazolecarboxamide)). Antimetabolites act by mimicking small molecule metabolites (e.g. folic acid, pyrimidines, and purines) in order to be incorporated into newly synthesized cellular DNA. Such agents also affect RNA synthesis. An exemplary folic acid analog is methotrexate (amethopterin). Exemplary pyrimidine analogs include fluorouracil (5-fluorouracil; 5-FU), floxuridine (fluorodeoxyuridine; FUdR), and cytarabine (cytosine arabinoside). Exemplary purine analogs include mercaptopurine (6-mercaptopurine; 6-MP), azathioprine, thioguanine (6-thioguanine: TG), fludarabine phosphate, pentostatin (2'-deoxycoformycin), cladribine (2-chlorodeoxyadenosine; 2-CdA), and erythrohydroxynonyladenine (EHNA). Natural small molecule products which can be used as anti-cancer agents include plant alkaloids and antibiotics. Plant alkaloids and terpenoids (e.g. vinca alkaloids, podophyllotoxin, taxanes, etc.) typically block cell division by preventing microtubule function. Vinca alkaloids (e.g. vincristine, vinblastine (VLB), vinorelbine, vindesine, etc.) bind to tubulin and inhibit assembly of tubulin into microtubules. Vinca alkaloids are derived from the Madagascar periwinkle, Catharanthus roseus (formerly known as Vinca rosea). Podophyllotoxin is a plant-derived compound used to produce two other cytostatic therapeutic agents, etoposide and teniposide, which prevent cells from entering the G1 and S phases of the cell cycle. Podophyllotoxin is primarily obtained from the American Mayapple (Podophyllum peltatum) and a Himalayan Mayapple (Podophyllum hexandrum). Taxanes (e.g. paclitaxel, docetaxel, etc.) are derived from the Yew Tree. Taxanes enhance stability of microtubules, preventing the separation of chromosomes during anaphase. Antibiotics which can be used as anti-cancer agents include dactinomycin (actinomycin D), daunorubicin (daunomycin; rubidomycin), doxorubicin, idarubicin, bleomycin, plicamycin (mithramycin), and mitomycin (mytomycin C).

Other small molecules which can be used as anti-cancer agents include platinum coordination complexes (e.g. cisplatin (cis-DDP), carboplatin), anthracenedione (e.g. mitoxantrone), substituted urea (e.g. hydroxyurea), methylhydrazine derivatives (e.g. procarbazine (N-methylhydrazine. MIH), and adrenocortical suppressants (e.g. mitotane (o,p'-DDD), aminoglutethimide).

Hormones which can be used as anti-cancer agents include adrenocorticosteroids (e.g. prednisone), aminoglutethimide, progestins (e.g. hydroxyprogesterone caproate, medroxyprogesterone acetate, megestrol acetate), estrogens (e.g. diethylstilbestrol, ethinyl estradiol), antiestrogen (e.g. tamoxifen), androgens (e.g. testosterone propionate, fluoxymesterone), antiandrogens (e.g. flutamide), and gonadotropin-releasing hormone analog (e.g. leuprolide).

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 µm to about 0.7 µm or from about 1 µm to about 6 µm. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 µm and at least 95% of the particles by number have a diameter less than 7 µm. Alternatively, at least 95% of the particles by weight have a diameter greater than 1 µm and at least 90% of the particles by number have a diameter less than 6 µm. Dry powder compositions may include a solid fine powder diluent such as sugar and are conveniently provided in a unit dose form.

Low boiling propellants generally include liquid propellants having a boiling point of below 65 degrees F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 µm to about 200 µm.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Vaccines

The present disclosure relates to pharmaceutical compositions comprising vaccines that comprise one or any combination of vesicles disclosed herein and a pharmaceutically acceptable carrier. Vesicles comprising any one or more glycoconjugates, glycolipids, lipids, sugars, DNA, RNA, proteins, and glycoproteins disclosed herein can comprise an antigen itself and/or an adjuvant. In some embodiments, the pharmaceutical composition is a vaccine designed to elicit an antigen-specific immune response against a pathogen or an antigen associated with a hyperproliferative disease, such as cancer. In some embodiments, the vaccine comprises a vesicle comprising an antigen derived from a Gram-negative bacterial cell. In some embodiments, the vaccine comprises an antigen derived directly from or extracted directly from a Gram-negative bacterial cell. In some embodiments, the Gram-negative bacterial cell is a *Francisella* or *Neisseria* bacterial cell. In some embodiments, the Gram-negative bacterial cell is derived from or is a *Francisella tularensis* bacterial cell. In some embodiments, the Gram-negative bacterial cell is derived from or is a *Neisseria gonorrhoeae* bacterial cell. In some embodiments, the Gram-negative bacterial cell is derived from or is a *Neisseria meningitidis* bacterial cell. In some embodiments, the Gram-negative bacterial cell is a *Pseudomonas* bacterial cell. In some embodiments, the Gram-negative bacterial cell is a *Pseudomonas aeruginosa* bacterial cell. The present disclosure relates to pharmaceutical compositions comprising vaccines that comprise one or any combination of vesicles disclosed herein and a pharmaceutically acceptable carrier for the treatment and or prevention of bacterial infection. In some embodiments, at least one antigen elicting the immune response is contained at least partially in the leaflet (or bilayer) of the vesicle.

Vaccines are disclosed which arise from a multi-phase strategy to enhance cellular immune responses induced by immunogens. The novel construct has been designed to elicit stronger and broader cellular immune responses than a corresponding codon optimized immunogens.

The vaccines are based upon proteins and genetic constructs that encode proteins with epitopes that make them particularly effective as immunogens against which bacterial antigens can be induced. Accordingly, vaccines may induce a therapeutic or prophylactic immune response. In some embodiments, the means to deliver the immunogen is a catanionic vesicle comprising a protein subunit, a composition comprising the catanionic vesicle and attenuated vaccine, killed vaccine, nucleic acid, or any of the components of adjuvants disclosed herein. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments, a vaccine is delivered to an individual to modulate the activity of the individual's immune system and thereby enhance the immune response against bacteria or an antigen. In some embodiments the bacteria or antigen from a bacterial cell is from or derived from at least one Gram-negative bacterial cell. Compositions and methods are provided which prophylactically and/or therapeutically immunize an individual against Gram-negative bacteria. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as *Streptococccus pnuemoniae, Haemophilus influenzae, Staphylococcus aureus, Streptococcus pyogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa. Salmonella typhi, Haemophilus parainfluenzae, Bordetella pertussis. Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever. Rift Valley fever, hepatitis A, B, C, D, and E virus, and the like: antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia tphi, Mycoplasma pneumoniae, Chlamydial psittaci, Chlamydial trachomatis. Plasmodium falciparum, Trypanosoma brucei, Entamoeba histolytica, Toxoplasma gondii. Trichomonas vaginalis, Schistosoma mansoni*, and the like. In some embodiments, the vaccine does not comprise a killed organism. In some embodiments, the vaccine does not comprise a killed organism that is a Gram-negative bacterial cell such as from the genus *Neisseria* or *Francisella*.

Compositions for delivery of catanionic vesicles that comprise at least one bacterial immunogen can comprise a genetic construct with a coding sequence operably linked to regulatory elements. Compositions may include a plasmid that encodes an immunogen, a recombinant vaccine comprising a nucleotide sequence that encodes the immunogen, a live attenuated pathogen that encodes a protein of the invention and/or includes a protein of the invention; a killed pathogen includes a protein of the invention; or a composition such as a catanionic vesicle or subunit vaccine that comprises a protein of the invention. The present invention further relates to injectable pharmaceutical compositions that comprise compositions disclosed herein.

In some embodiments, vaccines include any bacterial immunogen identified on Table 1 or functional fragments thereof. In some embodiments, antigenic fragment are those fragments SEQ ID NOs: 1 through 883. In some embodiments, vesicles, pharmaceutical compositions, and/or vaccines comprise any bacterial immunogen identified on Table 1 or antigenic fragments thereof. In some embodiments, vesicles, pharmaceutical compositions, and/or vaccines comprise any one or combination of: SEQ ID No: 1 through SEQ ID No: 883 disclosed or antigenic fragments thereof that are 70, 75, 80, 85, 90, 95, 96, 97, 98, 99% homologous to SEQ ID No: 1 through SEQ ID No: 883. In some embodiments, vesicles, pharmaceutical compositions, and/ or vaccines comprise a *Neisseria* antigen or antigenic fragments thereof that are 70, 75, 80, 85, 90, 95, 96, 97, 98, 99% homologous to a *Neisseria* antigen. *Neisseria* antigens can be found on Table 1 and any one or combination can be a component of the disclosed vesicles, pharmaceutical compositions, and/or vaccines. In some embodiments, the vaccine is a multivalent vaccine comprising a catanionic vesicle comprising whole cell extract with from about 1 µg to about 1 microgram of LPS or LOS and at least one or a plurality of lipoproteins and/or membrane-bound proteins taken from the whole cell extract from which the vesciles are formed.

Vaccines of the disclosure can comprise vesicles and one or a plurality of additional components that enhance an immune response stimulated by the vaccine. For instance vaccines of the present disclosure can comprise a nucleic acid molecule that encodes one or a plurality of immunomodulating proteins or antigens. In some embodiments, vaccines of the disclosure comprise proteins and genetic constructs that encode proteins with epitopes that make them particularly effective as immunogens against which bacterial immune responses can be induced. Accordingly, vaccines can be provided to induce a therapeutic or prophylactic immune response against a pathogen antigen or cancer-related antigen. In some embodiments, vaccines can be provided to induce a therapeutic or prophylactic immune response against a bacterial antigen such as a Gram-negative bacterial cell or Gram negative. In some embodiments, the means to deliver the immunogen is a vesicle comprising or in combination with a DNA vaccine, a recombinant vaccine, a protein subunit vaccine, a composition comprising the immunogen, a composition comprising a catanionic vesicle, an attenuated pathogen or a killed pathogen. In some embodiments, the vaccine comprises a combination selected from the groups consisting of: one or more DNA vaccines, one or more recombinant vaccines, one or more protein subunit vaccines, one or more compositions comprising the immunogen, one or more catanionic vesicles disclosed herein, one or more attenuated vaccines and one or more killed vaccines.

Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize subject.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

The present invention relates to compositions comprising improved attenuated live vaccines, improved killed vaccines and improved vaccines that use recombinant vectors to deliver foreign genes that encode antigens and well as subunit and glycoprotein vaccines in combination with a catanionic vesicle disclosed herein. Examples of attenuated live vaccines, those using recombinant vectors to deliver foreign antigens, subunit vaccines and glycoprotein vaccines are described in U.S. Pat. Nos. 4,510,245; 4,797,368; 4,722, 848; 4,790,987; 4,920,209; 5,017,487; 5,077,044; 5,110, 587; 5,112,749; 5,174,993; 5,223,424; 5,225,336; 5,240, 703; 5,242,829; 5,294,441; 5,294,548; 5,310,668; 5,387, 744; 5,389,368; 5,424,065; 5,451,499; 5,453,364; 5,462, 734; 5,470,734; 5,474,935; 5,482,713; 5,591,439; 5,643, 579; 5,650,309; 5,698,202; 5,955,088; 6,034,298; 6,042, 836; 6,156,319 and 6,589,529, which are each incorporated herein by reference in their entireties.

When taken up by a cell, a vesicle or vaccine of the present disclosure may fuse with a cell and distribute its payload. If the vaccine comprises a vesicle with a genetic construct, payload of the vesicle may remain present in the cell and stimulate an immune response, and, in the case of nucleic acid, may express as a functioning extra chromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to include on a given genetic construct, especially in the production of a genetic vaccine for mammals including humans, include but are not limited to promoters from Simian Virus 40 (SV 40), Mouse Mammary Tumor Virus (MMTV) promoter, Human Immunodeficiency Virus (MY) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV 40 polyadenylation signals and LTR polyadenylation signals. In particular, the SV 40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids such as pVAX from Invitrogen (San Diego, Calif.) contain the Epstein Barr virus origin of replication and nuclear antigen EBNA-1 coding region which produces high copy episomal replication without integration.

In some embodiments, vesicle(s) are delivered which include or comprise nucleotide sequences that encode protein, and, additionally, genes for proteins which further enhance the immune response against such target proteins. Examples of such genes are those which encode other cytokines and lymphokines such as alpha-interferon, gamma-interferon, platelet derived growth factor (PDGF), TNFa, TNF-~, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1a, MIP-lp, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DRS. KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAILR3, TRAIL-R4, RANK, RANK LIGAND, Ox40, Ox40 LIGAND, NKG2D, MICA, MICB, NKG2A. NKG2B, NKG2C, NKG2E, NKG2F, TAP1, TAP2 and functional fragments thereof.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In some embodiments, the compositions, pharmaceutical compositions, and vaccines disclosed herein comprise a vesicle with a targeting moiety. In some embodiments, vesicle can comprise a matrix of polymers. In some embodiments, a therapeutic agent to be delivered and/or targeting moiety can be associated with the surface of, encapsulated within, surrounded by, and/or dispersed throughout the bilayer of the vesicle.

In some embodiments, a polymeric matrix can comprise polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polyureas, polystyrenes, and/or polyamines. In some embodiments, a polymeric matrix may comprise poly(lactic-co-glycolic acid) (PLGA), polyethylene glycol (PEG), and/or copolymers thereof. In some embodiments, a polymeric matrix can comprise dendrimers, proteins, carbohydrates, and/or nucleic acids.

In some embodiments, the compositions, pharmaceutical compositions, and vaccines disclosed herein comprise a vesicle and a particle, such as a non-polymeric particles (e.g. metal particles, quantum dots, ceramics, inorganic materials, bone, etc.), which in combination stimulate the immune system to a magnitude sufficient to treat or prevent infection of a pathogen or a hyperproliferative disorder. In some embodiments, a therapeutic agent and/or targeting moiety can be covalently associated with a molecule in the vesicle. In some embodiments, a therapeutic agent and/or targeting moiety can be non-covalently associated with a non-polymeric particle or the vesicle disclosed herein. In some embodiments, a therapeutic agent and/or targeting moiety can be associated with the surface of, encapsulated within, surrounded by, and/or dispersed throughout a non-polymeric polymer or the vesicle(s) disclosed herein. In some embodiments, the vesicles and/or particles may optionally comprise one or more sugars, lipids, or release-retarding ingredients.

In certain embodiments, targeted particles in accordance with the present invention comprise a targeting moiety which specifically binds to one or more targets associated with an organ, tissue, cell, extracellular matrix, and/or intracellular compartment. As used herein, the terms "target" and "marker" can be used interchangeably.

A targeting moiety may be a nucleic acid (e.g. aptamer), polypeptide (e.g. antibody), glycoprotein, small molecule, carbohydrate, lipid, etc. For example, a targeting moiety can be an aptamer, which is generally an oligonucleotide (e.g., DNA. RNA, or an analog or derivative thereof) that binds to a particular target, such as a polypeptide. In general, the targeting function of the aptamer is based on the three-dimensional structure of the aptamer. In some embodiments, a targeting moiety is a polypeptide (e.g. an antibody that specifically recognizes a tumor marker).

In some embodiments, a target may be a marker that is exclusively or primarily associated with one or a few tissue types, with one or a few cell types, with one or a few diseases, and/or with one or a few developmental stages. In some embodiments, a target can comprise a protein (e.g. cell surface receptor, transmembrane protein, etc.), a carbohydrate (e.g. glycan moiety, glycocalyx, etc.), a lipid (e.g. steroid, phospholipid, etc.), and/or a nucleic acid (e.g. DNA, RNA, etc.)

In some embodiments, a target (i.e. marker) is a molecule that is present exclusively or in higher amounts on a neoplastic or malignant cell, e.g., a tumor antigen. In some embodiments, a marker is a prostate cancer marker. In certain embodiments, the prostate cancer marker is prostate specific membrane antigen (PSMA), a 100 kDa transmembrane glycoprotein that is expressed in most prostatic tissues, but is more highly expressed in prostatic cancer tissue than in normal tissue.

The present invention provides methods for designing novel targeting moieties. The present invention further provides methods for isolating or identifying novel targeting moieties from a mixture of candidate targeting moieties. Nucleic acid targeting moieties (e.g. aptamers) may be designed and/or identified using any available method, including SELEX and PICO, as described herein.

According to the present invention, any agents, including, for example, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered and the vesicles disclosed herein may comprise any one or combination of agents. Exemplary agents to be delivered in accordance with the present invention include, but are not limited to, small molecules (e.g. cytotoxic agents), nucleic acids (e.g. RNAi agents), proteins (e.g. antibodies), lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g. breast cancer).

In some embodiments, the agent to be delivered may be a mixture of pharmaceutically active agents. In some embodiments, the agent to be delivered may be a mixture of anti-cancer agents. In some embodiments, inventive targeted particles are administered in combination with one or more of the anti-cancer agents described herein.

In some embodiments, targeting moieties and/or therapeutic agents are covalently associated with a particle, and release and delivery of the therapeutic agent to a target site occurs by disrupting the association. In some embodiments, targeting moieties and/or therapeutic agents are not covalently associated with a particle. For example, particles may comprise a polymeric matrix, and therapeutic agents may be associated with the surface of, encapsulated within, and/or distributed throughout the polymeric matrix. Therapeutic agents can be released by diffusion, degradation of the particle, and/or combination thereof.

In some embodiments, the vaccine comprises a catanionic vesicle comprising whole bacterial cell extract and comprises LPS, LOS or other sugar molecule derived directly from the bacterial cell from which it is made. Further embodiments comprise one or a plurality of lipoproteins that derived directly from the bacterial cell from which the vesicle is made.

Methods

To increase the likelihood that molecules including glycolipids and cell membrane proteins are incorporated into vesicles during preparation, the disclosure relates to methods of extracting membrane-bound and/or cell wall-bound proteins and glycolipids directly from cells without a purification step by exposing surfactants and compositions comprising surfactants disclosed herein to whole cells or whole cell extract. The cells may be any cells including, for example, bacterial cells, mammalian cells, or insect cells. By forming spontaneous vesicles with whole cells, vesicles can capture membrane-bound forms of glycolipids and cell membrane proteins in the leaftlet of the vesicle and they capture solute and their respective cytosolic fractions in the lumens. By adjusting the exposure time of the vesicles to various components of the method steps, more or less membrane-bound glycolipids and cell membrane proteins can be loaded into the bilayer of the vesicles.

Aspects of the invention relate to methods of extracting membrane-bound fractions of cells at high loading efficiencies to increase the number or concentration of cytosolic or membrane-bound proteins loaded onto the vesicles. Aspects of the invention also relate to Some embodiments of the disclosure relate to a method of reducing or masking the immune response stimulated by a bacterial sugar molecule by exposing the bacterial sugar to any of the steps to formulate the vesicles disclosed herein.

The disclosure relates to a method of integrating, or loading, a bacterial antigen into a vesicle, comprising: (a) centrifuging a bacterial culture in a bacterial growth medium; (b) removing the bacterial growth medium; (c) adding a weight/weight molar ratio of cationic surfactant to anionic from about 80:20 and or 20:80 in aqueous solution to cellular debris; (d) stirring resulting mixture at room temperature for at least about 30 minutes; wherein the method does not comprise a step of purification prior to steps (a)-(d). In some embodiments, the aqueous solution is water. In some embodiments, the disclosure relates to a method of creating a vaccine containing bacterial antigen, comprising: of integrating, or loading, a bacterial antigen into a vesicle, comprising: (a) centrifuging a bacterial culture in a bacterial growth medium; (b) removing the bacterial growth medium; (c) adding a weight/weight molar ratio of cationic surfactant to anionic from about 80:20 and or 20:80 in about ten milliliters of water to bacterial culture; (d) stirring resulting mixture at room temperature for at least about 30 minutes; wherein the method does not comprise a step of purification prior to steps (a)-(d). In some embodiments, the aqueous solution is water. In some embodiments, the disclosure relates to a method of creating a vaccine containing bacterial antigen, comprising: of integrating, or loading, a bacterial antigen into a vesicle, comprising: (a) centrifuging a bacterial culture in a bacterial growth medium; (b) removing the bacterial growth medium; (c) adding a weight/weight molar ratio of cationic surfactant to anionic of about 30:70 CTAT:SDBS in about aqueous solution to bacterial culture; (d) stirring resulting mixture at room temperature for at least about 30 minutes; wherein the method does not comprise a step of purification prior to steps (a)-(d).

The disclosure provides a method of integrating a bacterial antigen into a vesicle, comprising: (a) centrifuging a bacterial culture in a bacterial growth medium; (b) removing the bacterial growth medium; (c) adding about 70 mg SDBS and in about 9.9 mL of aqueous solution to cellular debris; (d) stirring the mixture at room temperature for at least 30 minutes; (d) adding about 30 mg CTAT in solution to resulting mixture; and (e) stirring the mixture at room temperature for at least about 30 minutes.

The disclosure provides a method of integrating a bacterial antigen into a vesicle, comprising: (a) pelleting bacteria culture by centrifugation; (b) adding about 30 mg CTAT and about 9.9 mL H20 to cellular debris to form an aqueous mixture; (c) stirring the aqueous mixture at room temperature for at least about 30 minutes; (d) adding 70 mg SDBS in solution to the aqueous mixture; and (e) stirring the resulting mixture at room temperature for at least 30 minutes.

The disclosure provides a method of integrating a bacterial antigen into a vesicle, comprising:

(a) pelleting bacteria culture by centrifugation and removing any bacterial culture medium;

(b) adding about 70 mg SDBS and about 9.9 mL water to form an aqueous mixture;

(c) stirring the aqueous mixture at room temperature for at least about 30 minutes;

(d) adding about 30 mg of solid CTAT to the aqueous mixture; and (e) stirring the aqueous mixture at room temperature for at least about 30 minutes.

Aspects of the invention relate to a method of forming catanionic vesicles with a ratio of protein to carbohydrate in micrograms per mL from about 7 to about 8:1 comprising: (a) centrifuging bacterial cells; (b) removing any bacterial growth medium; (c) adding a weight/weight molar ratio of about 30:70 of cationic surfactant and anionic surfactant in aqueous solution to the bacterial cells; (d) stirring resulting mixture at room temperature for at least about 30 minutes; wherein the method does not comprise a step of purification prior to steps (a)-(d).

Aspects of the invention relate to a method of forming catanionic vesicles with a ratio of protein to carbohydrate in micrograms per mL from about 7 to about 8:1 comprising: (a) centrifuging bacterial cells; (b) removing any bacterial growth medium; (c) adding a weight/weight molar ratio of about 70:30 of cationic surfactant and anionic surfactant in aqueous solution to the bacterial cells; (d) stirring resulting mixture at room temperature for at least about 30 minutes; wherein the method does not comprise a step of purification prior to steps (a)-(d).

Aspects of the invention relate to a method of forming catanionic vesicles with a ratio of protein to carbohydrate in micrograms per mL from about 0.5 to about 1.5:1 comprising: (a) centrifuging bacterial cells; (b) removing any bacterial growth medium; (c) adding a weight/weight molar ratio of about 30:70 of cationic surfactant and anionic surfactant in aqueous solution to from about $10^6$ to about $10^9$ bacterial cells; (d) stirring resulting mixture at room temperature for at least about 15 minutes; wherein the method does not comprise a step of purification prior to steps (a)-(d).

Aspects of the invention relate to a method of forming catanionic vesicles with a ratio of protein to carbohydrate in micrograms per mL from about 0.5 to about 1.5:1 comprising: (a) centrifuging bacterial cells; (b) removing any bacterial growth medium; (c) adding a weight/weight molar ratio of about 70:30 of cationic surfactant and anionic surfactant in aqueous solution to from about $10^6$ to about $10^9$ bacterial cells; (d) stirring resulting mixture at room temperature for at least about 15 minutes; wherein the method does not comprise a step of purification prior to steps (a)-(d).

Aspects of the invention relate to a method of forming catanionic vesicles with a ratio of protein to carbohydrate in micrograms per mL of 1:from about 1 to about 1.5 comprising: (a) suspending from about $10^6$ to about $10^9$ bacterial cells in an aqueous solution comprising a volume/volume ratio of preformed catanionic vesicles of about 1% negatively charged surfactant and water of about 1 to about 2:1; (b) stirring the aqueous solution for about 1 hour; wherein the method does not comprise a step of purification prior to steps (a)-(b).

Aspects of the invention relate to a method of forming catanionic vesicles with a ratio of protein to carbohydrate in micrograms per mL of 1: from about 1 to about 1.5 comprising: (a) suspending from about $10^6$ to about $10^9$ bacterial cells in an aqueous solution comprising a volume/volume ratio of preformed catanionic vesicles of about 1% positively charged surfactant and water of about 1 to about 2:1; (b) stirring the aqueous solution for about 1 hour; wherein the method does not comprise a step of purification prior to steps (a)-(b).

Aspects of the invention relate to a method of forming catanionic vesicles with a ratio of protein to carbohydrate in micrograms per mL of 1:from about 1 to about 1.5 comprising: (a) suspending from about $10^6$ to about $10^9$ bacterial cells in an aqueous solution comprising a volume/volume ratio of preformed catanionic vesicles of about 1% SDBS and water of about 1 to about 2:1; (b) stirring the aqueous solution for about 1 hour; wherein the method does not comprise a step of purification prior to steps (a)-(b).

In any of the disclosed methods of making vesicles, the amount of bacterial cells used can be from about $10^6$ to about $10^9$ bacteria per mL of solution. In the case of centrifuged cells, one of ordinary skill in the art can take a density measurement to approximate the number of bacterial cells in a solution and add the appropriate volume with a known density to arrive at the number of cells. In any of the disclosed methods of making vesicles, the amount of bacterial cells used can be about $10^1$, about $10^2$, about $10^1$, about $10^4$, about $10^5$, about $10^6$, about $10^7$, to $10^8$, about $10^9$ bacteria per mL of culture medium. In any of the disclosed methods of making vesicles, the number of bacterial cells for each step can utilize from about 10 to about $10^{100}$ bacterial cells. In some embodiments, the above-mentioned methods do not comprise a step of purification or extraction of LPS or LOS prior to steps (a)-(b).

In some embodiments, the vesicles, compositions comprising vesicles, pharmaceutical compositions comprising vesicles, and in accordance with the present invention may be used to treat, alleviate, ameliorate, relieve, delay onset of, inhibit progression of, reduce severity of, and/or reduce incidence of one or more symptoms or features of a disease, disorder, and/or condition, such as tularemia. In some embodiments, inventive targeted particles may be used to treat cancer. In certain embodiments, inventive targeted particles may be used to treat prostate cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the disclosure, a method for the treatment of cancer (e.g. breast cancer) is provided. In some embodiments, the treatment of cancer comprises administering a therapeutically effective amount of inventive targeted particles to a subject in need thereof, in such amounts and for such time as is necessary to achieve the desired result. In certain embodiments of the present invention a "therapeutically effective amount" of a pharmaceutical composition comprising a catanionic vesicle disclosed herein is that amount effective for treating, alleviating, ameliorating, relieving, delaying onset of, inhibiting progression of, reducing severity of, and/or reducing incidence of one or more symptoms or features of cancer.

In one aspect of the invention, a method for administering inventive compositions to a subject suffering from cancer (e.g. prostate cancer) is provided. In some embodiments, such methods comprise administering a therapeutically effective amount of inventive targeted particles to a subject in such amounts and for such time as is necessary to achieve the desired result (i.e. treatment of cancer). In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e. a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer, patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In one aspect of the disclosure, a method of vaccinating a subject is provided. In some embodiments, the subject is in need of treatment or prevention for or from a particular pathogen infection, such as an infection with a Gram-negative bacteria, and the method comprises administering to the subject in need of treatment or prevention a therapeutically effective amount of the vaccine, pharmaceutical composition or composition disclosed herein. In one aspect of the disclosure, a method of stimulating an antigen-specific immune response in a subject is provided. In one aspect of the disclosure, a method of adjuvating an antigen-specific immune response in a subject is provided, by administering any one or plurality of compositions or pharmaceutical compositions disclosed herein in combination with a vaccine or other active agent.

In another aspect of the disclosure, a method of treating and/or preventing tularemia is provided by administering to a subject in need thereof any one or plurality of composition, vaccines or pharmaceutical compositions disclosed herein.

In another aspect of the disclosure, a method of treating and/or preventing gonorrhea is provided by administering to a subject in need thereof any one or plurality of composition, vaccines or pharmaceutical compositions disclosed herein.

In another aspect of the disclosure, a method of treating and/or preventing meningitis is provided by administering to a subject in need thereof any one or plurality of composition, vaccines or pharmaceutical compositions disclosed herein.

In another aspect of the disclosure, a method of treating and/or preventing a bacterial infection of Gram negative or Gram positive bacteria is provided by administering to a subject in need thereof any one or plurality of composition, vaccines or pharmaceutical compositions disclosed herein.

The present disclosure relates to a method of reducing the toxicity of a lipopolysaccharide or a lipooligosaccharide by exposing the lipopolysaccharide or a lipooligosaccharide of a bacterial cell to any of the methods disclosed herein.

In some embodiments, the disclosure relates to a method of manufacturing an antibody against an antigen comprising injecting any of the compositions disclosed herein into a subject and subsequently collecting its serum.

The present disclosure relates to a method of immunizing a subject by administration of any composition or vaccine disclosed herein. The vaccines of the invention can be administered via any route, including but not limited to intramuscular, intraperitoneal, intravenous, intranasally, and the like. Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. In some embodiments, the method comprises administering the composition or any of the compositions disclosed herein more than once, twice, or three times to elicit a protective antigen-specific immune response and maintain or boost antibody production. In some embodiments, the method include a dosing regimen with more than one mode of administration comprises. For instance, in the case of two different modes of administration, a method may include intranasal immunization followed by an intraperitoneal immunization or intraperitoneal immunization followed by intanasal immunization.

Kits

The present invention provides kits useful for carrying out various aspects of the invention. In some embodiments, a kit may include, for example, (i) any one or plurality of vesicles disclosed herein, optionally comprising a targeting moiety, and one or more particular therapeutic agents to be delivered; and (ii) instructions for administering the targeted particle to a subject in need thereof. In some embodiments, a kit may include, for example, (i) any one or plurality of vesicles and vaccines disclosed herein in a first container optionally comprising one or more particular therapeutic agents; and a syringe or other device to administer the vesicle or vaccine. In some embodiments, a kit may include instructions for administering the vaccine to a subject in need thereof. In some embodiments, a kit may be provided which includes materials useful for identifying and/or screening for novel targeting moieties. Such a kit may include, for example, (i) any one or plurality of vesicles disclosed herein, a library of targeting vesicles comprising any one or plurality of bacterial antigens, and one or more therapeutic agents to be delivered; (ii) a targeted particle or vesicle disclosed herein that may serve as a positive control; and (iii) a targeted particle or vesicle disclosed herein that may serve as a negative control.

TABLE 1

| UniProtA | | | |
|---|---|---|---|
| C | Desc | Peptide | SEQ ID NO: |
| Q5F905 | 30S ribosomal protein S1 | NAQGEIEVK | SEQ ID NO: 2 |
| Q5F905 | 30S ribosomal protein S1 | VGDFVTVTIESVENGFGETK | SEQ ID NO: 3 |
| Q5F905 | 30S ribosomal protein S1 | GGLTVMISSIR | SEQ ID NO: 4 |
| Q5F905 | 30S ribosomal protein S1 | AFLPGSLVDVRPVK | SEQ ID NO: 5 |
| Q5F905 | 30S ribosomal protein S1 | AFLPGSLVDVRPVKDTSHFEGK | SEQ ID NO: 6 |
| Q5F905 | 30S ribosomal protein S1 | RAVLEATLGEER | SEQ ID NO: 7 |
| Q5F905 | 30S ribosomal protein S1 | AVLEATLGEERK | SEQ ID NO: 8 |
| Q5F905 | 30S ribosomal protein S1 | KALLENLQEGSVIK | SEQ ID NO: 9 |
| Q5F905 | 30S ribosomal protein S1 | ALLENLQEGSVIK | SEQ ID NO: 10 |
| Q5F905 | 30S ribosotnal protein S1 | RVKHPSEVLEVGQEVEAK | SEQ ID NO: 11 |
| Q5F905 | 30S ribosomal protein S1 | VKHPSEVLEVGQEVEAK | SEQ ID NO: 12 |
| Q5F905 | 30S ribosomal protein S1 | QLGEDPWSGLTR | SEQ ID NO: 13 |

TABLE 1-continued

| UniProtAC | Desc | Peptide | SEQ ID NO: |
|---|---|---|---|
| Q5F905 | 30S ribosomal protein S1 | RYPQATR | SEQ ID NO: 14 |
| Q5F905 | 30S ribosomal protein S1 | QLEGDPFGNFISVNDKGSLVK | SEQ ID NO: 15 |
| Q5F905 | 30S ribosomal protein S1 | LKEGDEVEAVIVTVDRK | SEQ ID NO: 16 |
| Q5F905 | 30S ribosomal protein S1 | EALNSVNAAANANAGTTSLGDLLK | SEQ ID NO: 17 |
| Q5F9P8 | 5'-methylthioadenosine/S-adenosylhomocysteine nucleosidase | GQVPQLPAR | SEQ ID NO: 18 |
| Q5F9P8 | 5'-methyltlaioadenosine/S-adenosylhomocysteine nucleosidase | FASDGILIETAKR | SEQ ID NO: 19 |
| Q5FA17 | ABC transporter, periplasmic binding protein, iron related | GDQLAGQIKEEGSR | SEQ ID NO: 20 |
| Q5FA17 | ABC transporter, periplasmic binding protein, iron related | LEAPQVSATTVSEKEHATR | SEQ ID NO: 21 |
| Q5F7L8 | ABC transporter, periplasmic histidine-binding protein | VASNAEFAPFESLDSK | SEQ ID NO: 22 |
| Q5F7L8 | ABC transporter, periplasmic histidine-binding protein | GNVEGFDVDLMNAMAK | SEQ ID NO: 23 |
| Q5F7L8 | ABC transporter, periplasmic histidine-binding protein | AGNFKIEFK | SEQ ID NO: 24 |
| Q5F7L8 | ABC transporter, periplasmic histidine-binding protein | QSMDFSDPYFEITQVVLVPK | SEQ ID NO: 25 |
| Q5F7L8 | ABC transporter, periplasmic histidine-binding protein | VGVVTGHTGDFSVSK | SEQ ID NO: 26 |
| Q5F7L8 | ABC transporter, periplasmic histidine-binding protein | LLGNDNPK | SEQ ID NO: 27 |
| Q5F7L8 | ABC transporter, periplasmic histidine-binding protein | FENVPLIIK | SEQ ID NO: 28 |
| Q5F7L8 | ABC transporter, periplasmic histidine-bindingrotein | ELENGGLDSVVSDSAVIANYVK | SEQ ID NO: 29 |
| Q5F7L8 | ABC transporter, periplasmic histidine-binding protein | GMDFVTLPDFTTEHYGIAVR | SEQ ID NO: 30 |
| Q5F824 | Acetate kinase | LILVLNCGSSSLK | SEQ ID NO: 31 |
| Q5F824 | Acetate kit-lase | VVSGGELYNESILVDDEVIAGIEK | SEQ ID NO: 32 |
| Q5F824 | Acetate kinase | CIPLAPLHNPAHLLGIR | SEQ ID NO: 33 |
| Q5F824 | Acetate kinase | GLPNVVVFDTSFHQTMPEVAYK | SEQ ID NO: 34 |

TABLE 1-continued

| UniProtAC | Desc | Peptide | SEQ ID NO: |
|---|---|---|---|
| Q5F824 | Acetate kinase | YGAHGTSYR | SEQ ID NO: 35 |
| Q5F824 | Acetate kinase | FVADETAHFLGK | SEQ ID NO: 36 |
| Q5F824 | Acetate kinase | FVADETAHFLGKDKK | SEQ ID NO: 37 |
| Q5F824 | Acetate kinase | DTSMGLTPLEGLVMGTR | SEQ ID NO: 38 |
| Q5F824 | Acetate kinase | TIEEEAAKGHKGAK | SEQ ID NO: 39 |
| Q5F824 | Acetate kinase | FGNAGVITTADSK | SEQ ID NO: 40 |
| Q5F824 | Acetate kinase | AVAVVIPTNEELMIAHDTAR | SEQ ID NO: 41 |
| Q5F9Y5 | Acetyl-coenzyme A carboxylase carboxyl transferase subunit beta | CNHHNPLSAR | SEQ ID NO: 42 |
| Q5F9Y5 | Acetyl-coenzyme A carboxylase carboxyl transferase subunit beta | FIGGSMGSVVGER | SEQ ID NO: 43 |
| Q5F9Y5 | Acetyl-coenzyme A carboxylase carboxyl transferase subunit beta | TSAALHLLTEK | SEQ ID NO: 44 |
| Q5F7E7 | Aconitate hydratase 2 | AALGIPALPLNAQQTADLVELLK | SEQ ID NO: 45 |
| Q5F7E7 | Aconitate hydratase 2 | NPPAGEGEFLVELLAHR | SEQ ID NO: 46 |
| Q5F7E7 | Aconitate hydratase 2 | VKASFLAAVAEGSASSPLVSPK | SEQ ID NO: 47 |
| Q5F7E7 | Aconitate hydratase 2 | ASFLAAVAEGSASSPLVSPK | SEQ ID NO: 48 |
| Q5F7E7 | Aconitate hydratase 2 | AKVPEKITVTVFK | SEQ ID NO: 49 |
| Q5F7E7 | Aconitate hydratase 2 | DGITPDKPGEVGPIK | SEQ ID NO: 50 |
| Q5F7E7 | Aconitate hydratase 2 | DGITPDKPGEVGPIKLLEELK | SEQ ID NO: 51 |
| Q5F7E7 | Aconitate hydratase 2 | AKGHPVAYVGDVVGTGSSR | SEQ ID NO: 52 |
| Q5F7E7 | Aconitate hydratase 2 | GHPVAYVGDVVGTGSSR | SEQ ID NO: 53 |
| Q5F7E7 | Aconitate hydratase 2 | GHPVAYVGDVVGTGSSRK | SEQ ID NO: 54 |
| Q5F7E7 | Aconitate hydratase 2 | KSATNSVIWHTGEDIPFVPNKR | SEQ ID NO: 55 |
| Q5F7E7 | Aconitate hydratase 2 | SATNSVIWHTGEDIPFVPNKR | SEQ ID NO: 56 |
| Q5F7E7 | Aconitate hydratase 2 | IAPIFFNTQEDSGALPIEVDVSALK | SEQ ID NO: 57 |
| Q5F7E7 | Aconitate hydratase 2 | SQVLLDEVQAGGR | SEQ ID NO: 58 |

TABLE 1-continued

| UniProtA C | Desc | Peptide | SEQ ID NO: |
|---|---|---|---|
| Q5F7E7 | Aconitate hydratase 2 | ACGLPEGQGVRPGTYCEPR | SEQ ID NO: 59 |
| Q5F7E7 | Aconitate hydratase 2 | MTTVGSQDTTGPMTR | SEQ ID NO: 60 |
| Q5F7E7 | Aconitate hydratase 2 | THKELPAFISTR | SEQ ID NO: 61 |
| Q5F7E7 | Aconitate hydratase 2 | GGVSLRPGDGVIHSWLNR | SEQ ID NO: 62 |
| Q5F7E7 | Aconitate hydratase 2 | DLVNAIPLYAIK | SEQ ID NO: 63 |
| Q5F7E7 | Aconitate hydratase 2 | LNKEPIIEYMK | SEQ ID NO: 64 |
| Q5F7E7 | Aconitate hydratase 2 | LLEGKSDIPVR | SEQ ID NO: 65 |
| Q5F7E7 | Aconitate hydratase 2 | ELSDEGHYGVLGR | SEQ ID NO: 66 |
| Q5F7E7 | Aconitate hydratase 2 | EGATVMSTSTR | SEQ ID NO: 67 |
| Q5F7E7 | Aconitate hydratase 2 | NTFVYLGSAELAAICSK | SEQ ID NO: 68 |
| Q5F7E7 | Aconitate hydratase 2 | LGKIPTVEEYQANIGIINEQGDKIYR | SEQ ID NO: 69 |
| Q5F7E7 | Aconitate hydratase 2 | IPTVEEYQANIGIINEQGDKIYR | SEQ ID NO: 70 |
| Q5F7T9 | Alpha-2,3-sialyltransferase | NASDEHYTIFK | SEQ ID NO: 71 |
| Q5F7T9 | Alpha:-2,3-sialyltransferase | KMTYLPLFDASELKAGDETGGTVR | SEQ ID NO: 72 |
| Q5F7T9 | Alpha-2,3-sialyltransferase | ILLGSPDKEMKEISEK | SEQ ID NO: 73 |
| Q5F7T9 | Alpha-2,3-sialyltransferase | NFNIQYVAPHPR | SEQ ID NO: 74 |
| Q5F6Y6 | Aminotnethyltransferase | AFFRKLIANDVAK | SEQ ID NO: 75 |
| Q5F6Y6 | Aminomethyltransferase | ALQTAGVQPCGLGAR | SEQ ID NO: 76 |
| Q5F724 | Antibiotic resistance efflux pump component | AQVGGIIQK | SEQ ID NO: 77 |
| Q5F724 | Antibiotic resistance efflux pump component | AQVGGIIQKR | SEQ ID NO: 78 |
| Q5F724 | Antibiotic resistance efflux pump component | AGQPLYQIDSSTYEAGLESAR | SEQ ID NO: 79 |
| Q5F724 | Antibiotic resistance efflux pump component | AQLATAQATLAK | SEQ ID NO: 80 |
| Q5F724 | Antibiotic resistance efflux pump component | SAEAGVKAAQAAIK | SEQ ID NO: 81 |
| Q5F724 | Antibiotic resistance efflux pump component | SAGINLNR | SEQ ID NO: 82 |
| Q5F724 | Antibiotic resistance efflux pump component | SRITAPISGFIGQSK | SEQ ID NO: 83 |

TABLE 1-continued

| | UniProtA | | |
|---|---|---|---|
| C | Desc | Peptide | SEQ ID NO: |
| Q5F724 | Antibiotic resistance efflux pump component | ITAPISGFIGQSK | SEQ ID NO: 84 |
| Q5F724 | Antibiotic resistance efflux pump component | VSEGTLLNAGDTTVLATIR | SEQ ID NO: 85 |
| Q5F724 | Antibiotic resistance efflux pump component | QTNPMYVNVTSASEVMK | SEQ ID NO: 86 |
| Q5F724 | Antibiotic resistance efflux pump component | AAVSNDQNILMPGLYVR | SEQ ID NO: 87 |
| Q5F724 | Antibiotic resistance efflux pump component | VLMDQVAADNAFIVPQQAVTR | SEQ ID NO: 88 |
| Q5F724 | Antibiotic resistance efflux pump component | GAKDTVMIVNAQGGMEPR | SEQ ID NO: 89 |
| Q5F724 | Antibiotic resistance efflux pump component | EWAPSENQAAAPQAGVQTASEAKPASEAK | SEQ ID NO: 90 |
| Q5F725 | Antibiotic resistance efflux pump component | LSEVLSTLPATVQQYGVTVSK | SEQ ID NO: 91 |
| Q5F725 | Antibiotic resistance efflux pump component | ANTDGSNIYLKDVAK | SEQ ID NO: 92 |
| Q5F725 | Antibiotic resistance efflux pump component | TDATLAQVTQLAK | SEQ ID NO: 93 |
| Q5F725 | Antibiotic resistance efflux pump component | TASGSDAVAVAGK | SEQ ID NO: 94 |
| Q5F725 | Antibiotic resistance efflux pump component | ASGLFDPSTVR | SEQ ID NO: 95 |
| Q5F725 | Antibiotic resistance efflux pump component | AGGLEDSPQLK | SEQ ID NO: 96 |
| Q5F725 | Antibiotic resistance efflux pump component | AAAAAQGISFADIR | SEQ ID NO: 97 |
| Q5F725 | Antibiotic resistance efflux pump component | TALASALSSSYVSDFPNQGR | SEQ ID NO: 98 |
| Q5F725 | Antibiotic resistance efflux pump component | MQPADILNITVPNK | SEQ ID NO: 99 |
| Q5F725 | Antibiotic resistance efflux pump component | SGVAVPLSTIATVSWENGTEQSVR | SEQ ID NO: 100 |
| Q5F725 | Antibiotic resistance efflux pump component | LSASPATGVSTGQAMAAVQK | SEQ ID NO: 101 |
| Q5F725 | Antibiotic resistance efflux pump component | AGITGSDDKQY | SEQ ID NO: 102 |
| Q5F842 | Aspartokinase | YGGTSVGSPER | SEQ ID NO: 103 |
| Q5F842 | Aspartokinase | AAVTGIAFDKNQAR | SEQ ID NO: 104 |
| Q5FAH2 | Carbamoyl-phosphate synthase large chain | TPASFEPSIDYVVTK | SEQ ID NO: 105 |
| Q5FAH2 | Carbamoyl-phosphate synthase large chain | ELANPGPER | SEQ ID NO: 106 |
| Q5FAH2 | Carbamoyl-phosphate synthase large chain | VLNDLGLRQPPNR | SEQ ID NO: 107 |
| Q5FAH2 | Carbamoyl-phosphate synthase large chain | IAHNEEEALVK | SEQ ID NO: 108 |

TABLE 1-continued

| UniProtAC | Desc | Peptide | SEQ ID NO: |
|---|---|---|---|
| Q5FAH2 | Carbamoyl-phosphate synthase large chain | AEEIGYPLVVRPSYYLGGR | SEQ ID NO: 109 |
| Q5FAH2 | Carbamoyl-phosphate synthase large chain | VPQYTTTAGGEAMSEGAK | SEQ ID NO: 110 |
| Q5F6O1 | Catalase | TTSKCPVTHLTMNNGAPVADNQNSLTAGPR | SEQ ID NO: 111 |
| Q5F6O1 | Catalase | CPVTHLTMNNGAPVADNQNSLTAGPR | SEQ ID NO: 112 |
| Q5F6O1 | Catalase | GPLLTQDLWLNEK | SEQ ID NO: 113 |
| Q5F6O1 | Catalase | EVIPERR | SEQ ID NO: 114 |
| Q5F6O1 | Catalase | FTTVAGER | SEQ ID NO: 115 |
| Q5F6O1 | Catalase | LFNYADAQR | SEQ ID NO: 116 |
| Q5F6O1 | Catalase | QIPVNRPR | SEQ ID NO: 117 |
| Q5F6O1 | Catalase | ALFNLMNDAQK | SEQ ID NO: 118 |
| Q5F6O1 | Catalase | QALFDNTAAAMGDAPDFIK | SEQ ID NO: 119 |
| Q5F6O1 | Catalase | QALFDNTAAAMGDAPDFIKYR | SEQ ID NO: 120 |
| Q5F6O1 | Catalase | CDPAYGEGVAK | SEQ ID NO: 121 |
| Q5F6M2 | Cell division protein ftsA | ITHVTTGIAGNHIR | SEQ ID NO: 122 |
| Q5F6M2 | Cell division protein ftsA | VHIITGASTAVQNVQK | SEQ ID NO: 123 |
| Q5F6M3 | Cell division protein FtsZ | MEFVYDVAESAVSPAVIK | SEQ ID NO: 124 |
| Q5F6M3 | Cell division protein FtsZ | VIGLGGGGCNAINNMVANNVR | SEQ ID NO: 125 |
| Q5F6M3 | Cell division protein FtsZ | SVEFISANTDAQSLAK | SEQ ID NO: 126 |
| Q5F6M3 | Cell division protein FtsZ | RIQLGTNLTR | SEQ ID NO: 127 |
| Q5F6M3 | Cell division protein FtsZ | IQLGTNLTR | SEQ ID NO: 128 |
| Q5F6M3 | Cell division protein FtsZ | GLGAGANPDIGR | SEQ ID NO: 129 |
| Q5F6M3 | Cell division protein FtsZ | GIAMMGSGYAQGIDR | SEQ ID NO: 130 |
| Q5F6M3 | Cell division protein FtsZ | MATDQAISSPLLDDVTLDGAR | SEQ ID NO: 131 |
| Q5F6M3 | Cell division protein FtsZ | GVLVNITTAPGCLK | SEQ ID NO: 132 |
| Q5F6M3 | Cell division protein FtsZ | IVNQSAHPDLECK | SEQ ID NO: 133 |

TABLE 1-continued

| UniProtA | | | |
|---|---|---|---|
| C | Desc | Peptide | SEQ ID NO: |
| Q5F6M3 | Cell division protein FtsZ | ITIIATGLKEK | SEQ ID NO: 134 |
| Q5F6M3 | Cell division protein FtsZ | GAVDPTPAR | SEQ ID NO: 135 |
| Q5F6M3 | Cell division protein FtsZ | GAVDPTPAREVEAVAPSKQEQSHNVEGMIR | SEQ ID NO: 136 |
| Q5F6M3 | Cell division protein FtsZ | EVEAVAPSKQEQSHNVEGMIR | SEQ ID NO: 137 |
| Q5F9Z8 | Cell division protein ZipA | VRDQFGHSDKDALLNSK | SEQ ID NO: 138 |
| Q5F9Z8 | Cell division protein ZipA | TSHVRDGKPSGGPVMMPKPQPAVK | SEQ ID NO: 139 |
| Q5F9Z8 | Cell division protein ZipA | KPAKPQDSAMR | SEQ ID NO: 140 |
| Q5F9Z8 | Cell division protein ZipA | NLQEQDAVYIAK | SEQ ID NO: 141 |
| Q5F873 | Citrate synthase | SKSIKLNVPGR | SEQ ID NO: 142 |
| Q5F873 | Citrate synthase | SIKLNVPGR | SEQ ID NO: 143 |
| Q5F873 | Citrate synthase | AGLELPVLEASIGHDVVDIR | SEQ ID NO: 144 |
| Q5F873 | Citrate synthase | IFILHADHEQNASTSTVR | SEQ ID NO: 145 |
| Q5F873 | Citrate synthase | RDYVPAGER | SEQ ID NO: 146 |
| Q5F9Q2 | Cysteine synthase | MKIANSITELIGNTPLVK | SEQ ID NO: 147 |
| Q5F9Q2 | Cysteine synthase | IANSITELIGNTPLVK | SEQ ID NO: 148 |
| Q5F9Q2 | Cysteine synthase | GLKAEVAVK | SEQ ID NO: 149 |
| Q5F9Q2 | Cysteine synthase | TFGAELILTPAAEGMAGAIAK | SEQ ID NO: 150 |
| Q5F9Q2 | Cysteine synthase | AQSLVDAHPDTYFMPR | SEQ ID NO: 151 |
| Q5F9Q2 | Cysteine synthase | QFDNEANPEVHR | SEQ ID NO: 152 |
| Q5F9Q2 | Cysteine synthase | QFDNEANPEVHRK | SEQ ID NO: 153 |
| Q5F9Q2 | Cysteine synthase | GPHPIQGIGAGFIPTVLNTK | SEQ ID NO: 154 |
| Q5F9Q2 | Cysteine synthase | IYDSIAKVPNEAAFETAR | SEQ ID NO: 155 |
| Q5F9Q2 | Cysteine synthase | VPNEAAFETAR | SEQ ID NO: 156 |
| Q5F9Q2 | Cysteine synthase | EGILAGISSGAAVWSALQLAK | SEQ ID NO: 157 |
| Q5F9Q2 | Cysteine synthase | QPENEGKLIVVLLPSYGER | SEQ ID NO: 158 |

TABLE 1-continued

| UniProtAC | Desc | Peptide | SEQ ID NO: |
|---|---|---|---|
| Q5F9Q2 | Cysteine synthase | LIVLLPSYGER | SEQ ID NO: 159 |
| Q5F9K8 | Delta-aminolevulinic acid dehydratase | LGIPMLALFPVVTANK | SEQ ID NO: 160 |
| Q5F9K8 | Delta-aminolevulinic acid dehydratase | AQEAYNPEGLVPSTVR | SEQ ID NO: 161 |
| Q5F876 | Dihydrolipoyl dehydrogenase | SQYDVVVIGAGPGGYVAAIR | SEQ ID NO: 162 |
| Q5F876 | Dihydrolipoyl dehydrogenase | TNLPNVWAIGDVVR | SEQ ID NO: 163 |
| Q5F876 | Dihydrolipoyl dehydrogenase | ASDEGVAVAER | SEQ ID NO: 164 |
| Q5F8Y0 | DNA gyrase subunit A | IVGDVIGK | SEQ ID NO: 165 |
| Q5F8Y0 | DNA gyrase subunit A | IIDFVDILSKPER | SEQ ID NO: 166 |
| Q5F8Y0 | DNA gyrase subunit A | KNKGGQGSIAINTGER | SEQ ID NO: 167 |
| Q5F8Y0 | DNA gyrase subunit A | LINLDEGETLVSLER | SEQ ID NO: 168 |
| Q5F5M0 | DNA-binding competence protein 2 | VKGIGPAVLAK | SEQ ID NO: 169 |
| Q5G5M0 | DNA-binding competence protein 2 | LKDQASVGAPAPK | SEQ ID NO: 170 |
| Q5F696 | Enoyl-[acyl-carrier-protein] reductase [NADH] | EAFNTAHEISAYSLPALAK | SEQ ID NO: 171 |
| Q5G696 | Enoyl-[acyl-carrier-protein] reductase [NADH] | TLAASGIADFGK | SEQ ID NO: 172 |
| Q5F8I5 | Genome-derived *Neisseria* antigen 1220 | AMQAQITAER | SEQ ID NO: 173 |
| Q5F8I5 | Genome-derived *Neisseria* antigen 1220 | AMQAQITAEREK | SEQ ID NO: 174 |
| Q5F8I5 | Genome-derived *Neisseria* antigen 1220 | IAESEGRKIEQINLASGQR | SEQ ID NO: 175 |
| Q5F8I5 | Genome-derived *Neisseria* antigen 1220 | KIEQINLASGQR | SEQ ID NO: 176 |
| Q5F8I5 | Genome-derived *Neisseria* antigen 1220 | IEQINLASGQR | SEQ ID NO: 177 |
| Q5F8I5 | Genome-derived *Neisseria* antigen 1220 | EAEIQQSEGEAQAAVNASNAEK | SEQ ID NO: 178 |
| Q5F8I5 | Genome-derived *Neisseria* antigen 1220 | QIAAALQTQGGADAVNLK | SEQ ID NO: 179 |
| Q5F8I5 | Genome-derived *Neisseria* antigen 1220 | IAEQYVAAFNNLAK | SEQ ID NO: 180 |
| Q5F731 | Glutamate dehydrogenase | TDLNTLFANLK | SEQ ID NO: 181 |
| Q5F731 | Glutamate dehydrogenase | TDLNTLFANLKQR | SEQ ID NO: 182 |
| Q5F731 | Glutamate dehydrogenase | NPKYTQQSLLER | SEQ ID NO: 183 |

TABLE 1-continued

| UniProtAC | Desc | Peptide | SEQ ID NO: |
|---|---|---|---|
| Q5F731 | Glutamate dehydrogenase | YTQQSLLER | SEQ ID NO: 184 |
| Q5F731 | Glutamate dehydrogenase | FLAFEQVFK | SEQ ID NO: 185 |
| Q5F731 | Glutamate dehydrogenase | VLISGSGNVAQYAAEK | SEQ ID NO: 186 |
| Q5F731 | Glutamate dehydrogenase | ASNAGGVATSGLEMSQNAIR | SEQ ID NO: 187 |
| Q5F731 | Glutamate dehydrogenase | VGDKVNYVNGANIAGFVK | SEQ ID NO: 188 |
| Q5F6F9 | Glutamine synthetase | GGYAPVAPIDCGQDLR | SEQ ID NO: 189 |
| Q5F6F9 | Glutamine synthetase | FATLVKR | SEQ ID NO: 190 |
| Q5F6F9 | Glutamine synthetase | ALNAITNPSTNSYK | SEQ ID NO: 191 |
| Q5F6F9 | Glutamine synthetase | ALNAITNPSTNSYKR | SEQ ID NO: 192 |
| Q5F6F9 | Glutamine synthetase | LVPHFEAPTK | SEQ ID NO: 193 |
| Q5F6F9 | Glutamine synthetase | LVPHFEAPTKLAYSAK | SEQ ID NO: 194 |
| Q5F6F9 | Glutamine synthetase | SASIRIPSVNSSK | SEQ ID NO: 195 |
| Q5F7G1 | Glutathione synthetase | AADKVQTALK | SEQ ID NO: 196 |
| Q5F7G1 | Glutathione synthetase | FTAPTLVTTR | SEQ ID NO: 197 |
| Q5F7G1 | Glutathione synthetase | YIPEIVHGDKR | SEQ ID NO: 198 |
| Q5F7G1 | Glutathione synthetase | ILIIGGEVVPYALAR | SEQ ID NO: 199 |
| Q5F8H4 | Inosine-5'-monophosphate dehydrogenase | AYTFDDVLLVPAHSTVLPR | SEQ ID NO: 200 |
| Q5F8H4 | Inosine-5'-monophosphate dehydrogenase | EITLNLPLLSAAMDTVTEAR | SEQ ID NO: 201 |
| Q5F8H4 | Inosine-5'-monophosphate dehydrogenase | RHESGVVKDPVTVAPTTLIR | SEQ ID NO: 202 |
| Q5F8H4 | Inosine-5'-monophosphate dehydrogenase | HESGVVKDPVTVAPTTLIR | SEQ ID NO: 203 |
| Q5F8H4 | Inosine-5'-monophosphate dehydrogenase | TTEFPNANKDSEGR | SEQ ID NO: 204 |
| Q5F8H4 | Inosine-5'-monophosphate dehydrogenase | VGAAVGTGGDTDERVK | SEQ ID NO: 205 |
| Q5F8H4 | Inosine-5'-monophosphate dehydrogenase | IVAGVGVPQLTAIHNVAEALK | SEQ ID NO: 206 |
| Q5F809 | Lipid modified azurin protein*** | ACKEFTITLK | SEQ ID NO: 207 |
| Q5F809 | Lipid modified azurin protein | ASMGHNLVIAK | SEQ ID NO: 208 |

TABLE 1-continued

| UniProtAC | Desc | Peptide | SEQ ID NO: |
|---|---|---|---|
| Q5F809 | Lipid modified azurin protein | LIGGGEESSLTLDPAK | SEQ ID NO: 209 |
| Q5F809 | Lipid modified azurin protein | FACTFPGHGALMNGK | SEQ ID NO: 210 |
| Q5F809 | Lipid modified azurin protein | FACTFPGHGALMNGKVTLVD | SEQ ID NO: 211 |
| Q5F501 | Lipoprotein*** | DSAPAASAAAPSADNGAAK | SEQ ID NO: 212 |
| Q5F501 | Lipoprotein | DSAPAASAAAPSADNGAAKK | SEQ ID NO: 213 |
| Q5F501 | Lipoprotein | EIVFGTTVGDFGDMVK | SEQ ID NO: 214 |
| Q5F501 | Lipoprotein | EQIQAELEKK | SEQ ID NO: 215 |
| Q5F501 | Lipoprotein | EHNLDITEAFQVPTAPLGLYPGK | SEQ ID NO: 216 |
| Q5F501 | Lipoprotein | LKSLEEVKDGSTVSAPNDPSNFAR | SEQ ID NO: 217 |
| Q5F501 | Lipoprotein | SLEEVKDGSTVSAPNDPSNFAR | SEQ ID NO: 218 |
| Q5F501 | Lipoprotein | DGSTVSAPNDPSNFAR | SEQ ID NO: 219 |
| Q5F501 | Lipoprotein | ALVMLNELGWIK | SEQ ID NO: 220 |
| Q5F501 | Lipoprotein | LKDGINPLTASK | SEQ ID NO: 221 |
| Q5F501 | Lipoprotein | IVELEAAQLPR | SEQ ID NO: 222 |
| Q5F501 | Lipoprotein | LTEALFQEPSFAYVNWSAVK | SEQ ID NO: 223 |
| Q5F501 | Lipoprotein | TADKDSQWLKDVTEAYNSDAFK | SEQ ID NO: 224 |
| Q5F501 | Lipoprotein | RFEGYKYPAAWNEGAAK | SEQ ID NO: 225 |
| Q5F501 | Lipoprotein | FEGYKYPAAWNEGAAK | SEQ ID NO: 226 |
| Q5F5V7 | Major outer membrane protein porin P.IB | AGVQTYRSVEHTDGK | SEQ ID NO: 227 |
| Q5F5V7 | Major outer membrane protein porin P.IB | AGVQTYRSVEHTDGKVSK | SEQ ID NO: 228 |
| Q5F5V7 | Major outer membrane protein porin P.IB9 | AGVQTYRSVEHTDGKVSKVETGSEIADFGSK | SEQ ID NO: 229 |
| Q5F5V7 | Major outer membrane protein porin P.IB | SVEHTDGKVSK | SEQ ID NO: 230 |
| Q5F5V7 | Major outer membrane protein porin P.IB | SVEHTDGKVSKVETGSEIADFGSK | SEQ ID NO: 231 |
| Q5F5V7 | Major outer membrane protein porin P.IB | VSKVETGSEIADFGSK | SEQ ID NO: 232 |
| Q5F5V7 | Major outer membrane protein porin P.IB | VETGSEIADFGSK | SEQ ID NO: 233 |

TABLE 1-continued

| UniProtA C | Desc | Peptide | SEQ ID NO: |
|---|---|---|---|
| Q5F5V7 | Major outer membrane protein porin P.IB | IGFKGQEDLGNGLK | SEQ ID NO: 234 |
| Q5F5V7 | Major outer membrane protein porin P.IB | GQEDLGNGLK | SEQ ID NO: 235 |
| Q5F5V7 | Major outer membrane protein porin P.IB | AVWQLEQGASVAGTNTGWGNK | SEQ ID NO: 236 |
| Q5F5V7 | Major outer membrane protein porin P.IB | AVWQLEQGASVAGTNTGWGNKQSFVGLK | SEQ ID NO: 237 |
| Q5F5V7 | Major outer membrane protein porin P.IB | QSFVGLKGGFGTIR | SEQ ID NO: 238 |
| Q5F5V7 | Major outer membrane protein porin P.IB | AGSLNSPLK | SEQ ID NO: 239 |
| Q5F5V7 | Major outer membrane protein porin P.IB | FTGNVLEISGMAQR | SEQ ID NO: 240 |
| Q5F5V7 | Major outer membrane protein porin P.IB | YDSPEFAGFSGSVQYAPK | SEQ ID NO: 241 |
| Q5F5V7 | Major outer membrane protein porin P.IB | LVGGYDNNALYVSVAAQQQDAK | SEQ ID NO: 242 |
| Q5F5V7 | Major outer membrane protein porin P.IB | VSYAHGFK | SEQ ID NO: 243 |
| Q5F5V7 | Major outer membrane protein porin P.IB | GTVDSANHDNTYDQVVVGAEYDFSKR | SEQ ID NO: 244 |
| Q5F5V7 | Major outer membrane protein porin P.IB | RTSALVSAGWLQEGK | SEQ ID NO: 245 |
| Q5F5V7 | Major outer membrane protein porin P.IB | TSALVSAGWLQEGK | SEQ ID NO: 246 |
| Q5F5V7 | Major outer membrane protein porin P.IB | TSALVSAGWLQEGKGADK | SEQ ID NO: 247 |
| Q5F5V7 | Major outer membrane protein porin P.IB | TSALVSAGWLQEGKGADKIVSTASAVVLR | SEQ ID NO: 248 |
| Q5F5V7 | Major outer membrane protein porin P.IB | GADKIVSTASAVVLR | SEQ ID NO: 249 |
| Q5F5V7 | Major outer membrane protein porin P.IB | IVSTASAVVLR | SEQ ID NO: 250 |
| Q5F4X7 | Malonyl CoA-acyl carrier protein transacylase | TVEIKQPQIR | SEQ ID NO: 251 |
| Q5F4X7 | Malonyl CoA-acyl carrier protein transacylase | VIHNADVAAYDDAGK | SEQ ID NO: 252 |
| Q5F4X7 | Malonyl CoA-acyl carrier protein transacylase | IKDALVR | SEQ ID NO: 253 |
| Q5F726 | Multidrug efflux pump channel protein | NNLLPTLAANANGSR | SEQ ID NO: 254 |
| 5F726 | Multidrug efflux pump channel protein | AGVISAVALRQQEALIESAK | SEQ ID NO: 255 |
| Q5F726 | Multidrug efflux pump channel protein | NALATLINRPIPEDLPAGLPLDK | SEQ ID NO: 256 |
| Q5F726 | Multidrug efflux pump channel protein | LPAGLSSEVLLDRPDIR | SEQ ID NO: 257 |
| Q5F726 | Multidrug efflux pump channel protein | AAEHALKQANANIGAAR | SEQ ID NO: 258 |

TABLE 1-continued

| UniProtAC | Desc | Peptide | SEQ ID NO: |
|---|---|---|---|
| Q5F726 | Multidrug efflux pump channel protein | QANANIGAAR | SEQ ID NO: 259 |
| Q5F726 | Multidrug efflux pump channel protein | LTGSVGTGSVELGGLFK | SEQ ID NO: 260 |
| Q5F726 | Multidrug efflux pump channel protein | YKHGVSGALDLLDAER | SEQ ID NO: 261 |
| Q5F6N6 | Outer membrane opacity protein D | NKISTVSDYFR | SEQ ID NO: 262 |
| Q5F6N6 | Outer membrane opacity protein D | ISTVSDYFR | SEQ ID NO: 263 |
| Q5F6N6 | Outer membrane opacity protein D | VSVGYDFGGWR | SEQ ID NO: 264 |
| Q5F6N6 | Outer membrane opacity protein D | VAYGHVR | SEQ ID NO: 265 |
| Q5F5W8 | Outer membrane protein assembly factor BamA | TEPSTVFNYLPVK | SEQ ID NO: 266 |
| Q5F5W8 | Outer membrane protein assembly factor BamA | VGDTYNDTHGSAIIK | SEQ ID NO: 267 |
| Q5F5W8 | Outer membrane protein assembly factor BamA | GKLNIQITPK | SEQ ID NO: 268 |
| Q5F5W8 | Outer membrane protein assembly factor BamA | ILDTDIQTNEDKTR | SEQ ID NO: 269 |
| Q5F5W8 | Outer membrane protein assembly factor BamA | QQMTAVLGEIQNR | SEQ ID NO: 270 |
| Q5F5W8 | Outer membrane protein assembly factor BamA | IYVNEIHITGNNK | SEQ ID NO: 271 |
| Q5F5W8 | Outer membrane protein assembly factor BamA | TKEIPFFENFYGGGLGSVR | SEQ ID NO: 272 |
| Q5F9W0 | Outer membrane protein assembly factor BamD | GLVLFNEDQSFLNK | SEQ ID NO: 273 |
| Q5F9W0 | Outer membrane protein assembly factor BamD | GAYIAAANR | SEQ ID NO: 274 |
| Q5F5Y8 | Outer membrane protein assembly factor BamE | AVAALRPGMTKDQVLLLLGSPILR | SEQ ID NO: 275 |
| Q5F6I1 | Outer membrane protein PIII*** | NAYFDKASQGR | SEQ ID NO: 276 |
| Q5F6I1 | Outer membrane protein PIII | ASQGRVECGDAVAVPEPEPAPVAVVEQAPQYVDETISLSAK | SEQ ID NO: 277 |
| Q5F6I1 | Outer membrane protein PIII | TLFGFDKDSLR | SEQ ID NO: 278 |
| Q5F6I1 | Outer membrane protein PIII | TLFGFDKDSLRAEAQDNLK | SEQ ID NO: 279 |
| Q5F6I1 | Outer membrane protein PIII | DSLRAEAQDNLK | SEQ ID NO: 280 |
| Q5F6I1 | Outer membrane protein PIII | TNVQSVR | SEQ ID NO: 281 |
| Q5F6I1 | Outer membrane protein PIII | VEGHTDFMGSEK | SEQ ID NO: 282 |
| Q5F6I1 | Outer membrane protein PIII | VEGHTDFMGSEKYNQALSER | SEQ ID NO: 283 |

TABLE 1-continued

| | UniProtA | | |
|---|---|---|---|
| C | Desc | Peptide | SEQ ID NO: |
| Q5F6I1 | Outer membrane protein PIII | YNQALSER | SEQ ID NO: 284 |
| Q5F6I1 | Outer membrane protein PIII | RAYVVANNLVSNGVPASR | SEQ ID NO: 285 |
| Q5F6I1 | Outer membrane protein PIII | AYVVANNLVSNGVPASR | SEQ ID NO: 286 |
| Q5F6I1 | Outer membrane protein PIII | ISAVGLGESQAQMTQVCQAEVAK | SEQ ID NO: 287 |
| Q5F6I1 | Outer membrane protein PIII | EALIACIEPDR | SEQ ID NO: 288 |
| Q5F6I1 | Outer membrane protein PIII | EALIACIEPDRRVDVK | SEQ ID NO: 289 |
| Q5F6I1 | Outer membrane protein PIII | IRSIVTR | SEQ ID NO: 290 |
| Q5F7F3 | Peptidyl-prolyl cis-trans isomerase | SLKQMKEQGAEIDLK | SEQ ID NO: 291 |
| Q5F7F3 | Peptidyl-prolyl cis-trans isomerase | FLQEQQAK | SEQ ID NO: 292 |
| Q5F7F3 | Peptidyl-prolyl cis-trans isomerase | ANKEKGEAFLKENAAK | SEQ ID NO: 293 |
| Q5F7F3 | Peptidyl-prolyl cis-trans isomerase | ANKEKGEAFLKENAAKDGVK | SEQ ID NO: 294 |
| Q5F7F3 | Peptidyl-prolylcis-trans isotnerase | DGVKTTASGLQYK | SEQ ID NO: 295 |
| Q5F7F3 | Peptidyl-prolyl cis-trans isomerase | DGVKTTASGLQYKITK | SEQ ID NO: 296 |
| Q5F7F3 | Peptidyl-prolyl cis-trans isomerase | TTASGLQYK | SEQ ID NO: 297 |
| Q5F7F3 | Peptidyl-prolyl cis-trans isomerase | TTASGLQYKITK | SEQ ID NO: 298 |
| Q5F7F3 | Peptidyl-prolyl cis-trans isomerase | QGEGKQPTKDDIVTVEYEGR | SEQ ID NO: 299 |
| Q5F7F3 | Peptidyl-prolyl cis-trans isomerase | LIDGTVFDSSK | SEQ ID NO: 300 |
| Q5F7F3 | Peptidyl-prolyl cis-trans isomerase | ANGGPATFPLSQVIPGWTEGVR | SEQ ID NO: 301 |
| Q5F7F3 | Peptidyl-prolyl cis-trans isomerase | LLKEGGEATFYIPSNLAYREQAGEK | SEQ ID NO: 302 |
| Q5F7F3 | Peptidyl-prolyl cis-trans isomerase | EGGEATFYIPSNLAYR | SEQ ID NO: 303 |
| Q5F7F3 | Peptidyl-prolyl cis-trans isomerase | IGPNATLVFDVK | SEQ ID NO: 304 |
| Q5F7F3 | Peptidyl-prolyl cis-trans isomerase | IGAPENAPAKQPDQVDIK | SEQ ID NO: 305 |
| Q5F7F3 | Peptidyl-prolyl cis-trans isomerase | IGAPENAPAKQPDQVDIKK | SEQ ID NO: 306 |
| Q5F7F3 | Peptidyl-prolyl cis-trans isomerase | IGAPENAPAKQPDQVDIKKVN | SEQ ID NO: 307 |
| Q5F820 | Peptidyl-prolyl cis-trans isomerase | FKATVESVR | SEQ ID NO: 308 |

TABLE 1-continued

| UniProtA | | | |
|---|---|---|---|
| C | Desc | Peptide | SEQ ID NO: |
| Q5F9L7 | Peptidyl-prolyl cis-trans isomerase | TVVQDWGYAVFGK | SEQ ID NO: 309 |
| Q5F9L7 | Peptidyl-prolyl cis-trans isomerase | VVDGFDVVDAIESVSTKR | SEQ ID NO: 310 |
| Q5F668 | Phospho-2-dehydro-3-deoxyheptonate aldolase | ELLPPIAHLYELPISK | SEQ ID NO: 311 |
| Q5F668 | Phospho-2-dehydro-3-deoxyheptonate aldolase | EASGLVHR | SEQ ID NO: 312 |
| Q5FA34 | Phosphoenolpyruvate synthase | ADNYVIWFENLR | SEQ ID NO: 313 |
| Q5FA34 | Phosphoenolpyruvate synthase | NASLGEMISQLTEK | SEQ ID NO: 314 |
| Q5FA34 | Phosphoenolpyruvate synthase | VPGGFATTADAYR | SEQ ID NO: 315 |
| Q5FA34 | Phosphoenolpyruvate synthase | AFLAHNGLNER | SEQ ID NO: 316 |
| Q5FA34 | Phosphoenolpyruvate synthase | VHKGFEHDIVALSAGVQR | SEQ ID NO: 317 |
| Q5FA34 | Phosphoenolpyruvate synthase | GFEHDIVALSAGVQR | SEQ ID NO: 318 |
| Q5FA34 | Phosphoenolpyruvate synthase | MIFTDKAEAGK | SEQ ID NO: 319 |
| Q5FA34 | Phosphoenolpyruvate synthase | DGLDGKLYILQARPETVK | SEQ ID NO: 320 |
| Q5FA34 | Phosphoenolpyruvate synthase | LYILQARPETVK | SEQ ID NO: 321 |
| Q5FA34 | Phosphoenolpyruvate synthase | VRDEMGLTNVEIMIPFVR | SEQ ID NO: 322 |
| Q5FA34 | Phosphoenolpyruvate synthase | ALKENGLER | SEQ ID NO: 323 |
| Q5FAD1 | Pilin assembly protein | KAELLLNSSDKNTEQAAAPAAEQN | SEQ ID NO: 324 |
| Q5F693 | Pilus assembly protein | KITQEDITVFTR | SEQ ID NO: 325 |
| Q5F693 | Pilus assembly protein | AGLPLMQAFEIVAR | SEQ ID NO: 326 |
| Q5F693 | Pilus assembly protein | GQVEQGSSLSR | SEQ ID NO: 327 |
| Q5FAD0 | Pilus assembly protein | SIDAASLNNLRDELASIR | SEQ ID NO: 328 |
| Q5FAD0 | Pilus assembly protein | IAQSPENGGNPDGK | SEQ ID NO: 329 |
| Q5FAD0 | Pilus assembly protein | SSILNLSAIATTYQAK | SEQ ID NO: 330 |
| Q5FA67 | Pilus-associated protein | VQMYSASVSTYPGSSSSR | SEQ ID NO: 331 |
| Q5FA67 | Pilus-associated protein | KDIEGNDSDLAK | SEQ ID |
| Q5FAG7 | Pilus-associated protein | TQNGKYAAFLASGYAAK | SEQ ID NO: 333 |
| Q5FAG7 | Pilus-associated protein | YAAFLASGYAAK | SEQ ID NO: 334 |

TABLE 1-continued

| UniProtAC | Desc | Peptide | SEQ ID NO: |
|---|---|---|---|
| Q5FAG7 | Pilus-associated protein | TIFEGDKPITSAPAVSR | SEQ ID NO: 335 |
| Q5FAG7 | Pilus-associated protein | TVCPNGYVYDKPVNVR | SEQ ID NO: 336 |
| Q5F7F1 | Probable cytosol aminopeptidase | FSQAVFHSAHEAAVK | SEQ ID NO: 337 |
| Q5F7F1 | Probable cytosol aminopeptidase | VAEAQVYGQSLCR | SEQ ID NO: 338 |
| Q5F7F1 | Probable cytosol aminopeptidase | TAKAEAEKLGAHAK | SEQ ID NO: 339 |
| Q5F7F1 | Probable cytosol aminopeptidase | GATGRPVPLLMNYLR | SEQ ID NO: 340 |
| Q5FA43 | Protein translocase subunit SecD | QNITTLHNR | SEQ ID NO: 341 |
| Q5F8V3 | Pseudouridine synthase | QWRDGAAPSAKK | SEQ ID NO: 342 |
| Q5F8V3 | Pseudouridine synthase | GQFYELNPAEVANILK | SEQ ID NO: 343 |
| Q5F874 | Putative 2-oxoglutarate dehydrogenase, E1 component | IASVAGGADEAMLKK | SEQ ID NO: 344 |
| Q5F874 | Putative, 2-oxoglutarate dehydrogenase, E1 component | IQGVGAAQLDPLK | SEQ ID NO: 345 |
| Q5F874 | Putative 2-oxoglutarate dehydrogenase, E1 component | IQGVGAAQLDPLKR | SEQ ID NO: 346 |
| Q5F874 | Putative 2-oxoglutarate dehydrogenase, E1 component | NYFESVLSTPHYNADQK | SEQ ID NO: 347 |
| Q5F874 | Putative 2-oxoglutarate dehydrogenase, E1 component | ILKEMTAAETLER | SEQ ID NO: 348 |
| Q5F874 | Putative 2-oxoglutarate dehydrogenase, E1 component | STVHCTDIAK | SEQ ID NO: 349 |
| Q5F874 | Putative 2-oxoglutarate dehydrogenase, E1 component | EKIETGLPAADIER | SEQ ID NO: 350 |
| Q5F874 | Putative 2-oxoglutarate dehydrogenase, E1 component | LTEKFTAVPEGFALHPTAK | SEQ ID NO: 351 |
| Q5F874 | Putative 2-oxoglutarate dehydrogenase, E1 component | FTAVPEGFALHPTAK | SEQ ID NO: 352 |
| Q5F874 | Putative 2-oxoglutarate dehydrogenase, E1 component | QAIDWGMAETLAYASLLTK | SEQ ID NO: 353 |
| Q5F874 | Putative 2-oxoglutarate dehydrogenase, E1 component | VVLCAGQVYYDLEAGR | SEQ ID NO: 354 |
| Q5F874 | Putative 2-oxoglutarate dehydrogenase, E1 component | VEQLYPFPYDEVKAELAK | SEQ ID NO: 355 |

TABLE 1-continued

| UniProtA | | | |
|---|---|---|---|
| C | Desc | Peptide | SEQ ID NO: |
| Q5F874 | Putative 2-oxoglutarate dehydrogenase, E1 component | NQGAFYQIR | SEQ ID NO: 356 |
| Q5F874 | Putative 2-oxoglutarate dehydrogenase, E1 component | HRIEDVISEEQK | SEQ ID NO: 357 |
| Q5F4Y0 | Putative 3-oxoacyl-[acyl-carrier protein] reductase | IALVTGASR | SEQ ID NO: 358 |
| Q5F4Y0 | Putative 3-oxoacyl-[acyl-carrier protein] reductase | GIGAAIADTLAAAGAK | SEQ ID NO: 359 |
| Q5F4Y0 | Putative 3-oxoacyl-[acyl-carrier protein] reductase | IIGTATGESGAAAISK | SEQ ID NO: 360 |
| Q5F4Y0 | Putative 3-oxoacyl-[acyl-carrier protein] reductase | IIGTATGESGAAAISKR | SEQ ID NO: 361 |
| Q5F4Y0 | Putative 3-oxoacyl-[acyl-carrier protein] reductase | LAQWGGEGR | SEQ ID NO: 362 |
| Q5F4Y0 | Putative 3-oxoacyl-[acyl-carrier protein] reductase | VLNSAEPETVENLIADIEK | SEQ ID NO: 363 |
| Q5F4Y0 | Putative 3-oxoacyl-[acyl-carrier protein] reductase | TFGKLDILVNNAGITR | SEQ ID NO: 364 |
| Q5F4Y0 | Putative 3-oxoacyl-[acyl-carrier protein] reductase | LDILVNNAGITR | SEQ ID NO: 365 |
| Q5F4Y0 | Putative 3-oxoacyl-[acyl-carrier protein] reductase | ALPEETRQTFTAQTALGR | SEQ ID NO: 366 |
| Q5F4Y0 | Putative 3-oxoacyl-[acyl-carrier protein] reductase | FGDAQDIADAVLFLASDQAK | SEQ ID NO: 367 |
| Q5F4Y0 | Putative 3-oxoacyl-[acyl-carrier protein] reductase | YITGTLHVNGGMLMP | SEQ ID NO: 368 |
| Q5F6I5 | Putative ABC transporter, ATP-binding protein | LGNEVIEFVNVSK | SEQ ID NO: 369 |
| Q5F6I5 | Putative ABC transporter, ATP-binding protein | VPAGAIVGIIGPNGAGK | SEQ ID NO: 370 |
| Q5F6I5 | Putative ABC transporter, ATP-binding protein | DILQVGQFEIPAR | SEQ ID NO: 371 |
| Q5F9W7 | Putative ABC transporter, ATP-binding protein, amino acid | KGEVVVVCGPSGSGK | SEQ ID NO: 372 |
| Q5F9W7 | Putative ABC transporter, ATP-binding protein, amino acid | DAFPSQLSGGQQQR | SEQ ID NO: 373 |
| Q5F9W7 | Putative ABC transporter, ATP-binding protein, amino acid | AKQFLQQVMTH | SEQ ID NO: 374 |
| Q5F9M1 | Putative ABC transporter, periplasmic binding protein, amino acid | INNKGTVTVGTEGTYAPFTYHDKDGK | SEQ ID NO: 375 |
| Q5F9M1 | Putative ABC transporter, periplasmic binding protein, amino acid | INNKGTVTVGTEGTYAPFTYHDKDGKLTGYDVEVTR | SEQ ID NO: 376 |
| Q5F9M1 | Putative ABC transporter, periplasmic binding protein, amino acid | VEFKETQWDSMMAGLK | SEQ ID NO: 377 |
| Q5F9M1 | Putative ABC transporter, periplasmic binding protein, amino acid | AGRFDVVANQVGLTSPER | SEQ ID NO: 378 |

TABLE 1-continued

| | UniProtA | | |
|---|---|---|---|
| C | Desc | Peptide | SEQ ID NO: |
| Q5F9M1 | Putative ABC transporter, periplasmic binding protein, amino acid | FDVVANQVGLTSPER | SEQ ID NO: 379 |
| Q5F9M1 | Putative ABC transporter, periplasmic binding protein, amino acid | QATFDKSEPYSWSGAVLVAHNDSNIK | SEQ ID NO: 380 |
| Q5F9M1 | Putative ABC transporter, periplasmic binding protein, amino acid | SEPYSWSGAVLVAHNDSNIK | SEQ ID NO: 381 |
| Q5F9M1 | Putative ABC transporter, periplasmic binding protein, amino acid | TAQSLTSNYGEK | SEQ ID NO: 382 |
| Q5F9M1 | Putative ABC transporter, periplasmie binding protein, amino acid | AKAAGAQLVPVDGLAQSLTLIEQK | SEQ ID NO: 383 |
| Q5F9M1 | Putative ABC transporter, periplasmic binding protein, amino acid | AAGAQLVPVDGLAQSLTLIEQK | SEQ ID NO: 384 |
| Q5F9M1 | Putative ABC transporter, periplasmic binding protein, amino acid | AAGAQLVPVDGLAQSLTLIEQKR | SEQ ID NO: 385 |
| Q5F9M1 | Putative ABC transporter, periplasmic binding protein, amino acid | RADATLNDELAVLDYLK | SEQ ID NO: 386 |
| Q5F9M1 | Putative ABC transporter, periplasmic binding protein, amino acid | RADATLNDELAVLDYLKK | SEQ ID NO: 387 |
| Q5F9M1 | Putative ABC transporter, periplasmic binding-protein, amino acid | ADATLNDELAVLDYLK | SEQ ID NO: 388 |
| Q5F9M1 | Putative ABC transporter, periplasmic binding protein, amino acid | ADATLNDELAVLDYLKK | SEQ ID NO: 389 |
| Q5F9M1 | Putative ABC transporter, periplasmic binding-protein, amino acid | IVWSAPADEKVGSGLIVNK | SEQ ID NO: 390 |
| Q5F9M1 | Putative ABC transporter, periplasmic binding protein, amino acid | IVWSAPADEKVGSGLIVNKGNDEAVAK | SEQ ID NO: 391 |
| Q5F9M1 | Putative ABC transporter, periplasmic binding protein, amino acid | VGSGLIVNK | SEQ ID NO: 392 |
| Q5F9M1 | Putative ABC transporter, periplasmic binding protein, amino acid | VGSGLIVNKGNDEAVAK | SEQ ID NO: 393 |
| Q5F9M1 | Putative ABC transporter, periplasmic binding protein, amino acid | FSTAINELK | SEQ ID NO: 394 |
| Q5F9M1 | Putative ABC transporter, periplasmic binding protein, amino acid | FSTAINELKADGTLK | SEQ ID NO: 395 |
| Q5F9M1 | Putative ABC transporter, periplasmic binding protein, amino acid | FSTAINELKADGTLKK | SEQ ID NO: 396 |
| Q5F9M1 | Putative ABC transporter, periplasmic binding protein, amino acid | KLGEQFFGKDISVQ | SEQ ID NO: 397 |

TABLE 1-continued

| UniProtAC | Desc | Peptide | SEQ ID NO: |
|---|---|---|---|
| Q5F9M1 | Putative ABC transporter, periplasmic binding protein, amino acid | LGEQFFGKDISVQ | SEQ ID NO: 398 |
| Q5F6Q5 | Putative ABC transporter, periplasmic binding protein, polyamine | SGYDLVVPGIAFLPR | SEQ ID NO: 399 |
| Q5F6Q5 | Putative ABC transporter, periplasmic binding protein, polyamine | VNKDLIPNYKNIDPELLK | SEQ ID NO: 400 |
| Q5F6Q5 | Putative ABC transporter, periplasmic binding protein, polyamine | GSNPEDLKAAAEVLK | SEQ ID NO: 401 |
| Q5F6Q5 | Putative ABC transporter, periplasmic binding protein, polyamine | RFSPSIIDELAR | SEQ ID NO: 402 |
| Q5F6Q5 | Putative ABC transporter, periplasmic binding protein, polyamine | FSPSIIDELAR | SEQ ID NO: 403 |
| Q5F6Q5 | Putative ABC transporter, periplasmic binding protein, polyamine | ARSEEVKNNVGIEVLTPK | SEQ ID NO: 404 |
| Q5F6Q5 | Putative ABC transporter, periplastnic binding protein, polyamine | SEEVKNNVGIEVLTPK | SEQ ID NO: 405 |
| Q5F6Q5 | Putative ABC transporter, periplasmic binding protein, polyamine | YINYTLDPEIAAK | SEQ ID NO: 406 |
| Q5F6Q5 | Putative ABC transporter, periplasmic binding protein, polyamine | NGIAVTFAPASKPAR | SEQ ID NO: 407 |
| Q5F6Q5 | Putative ABC transporter, periplasmic binding protein, polyamine | EKMPAELVNTR | SEQ ID NO: 408 |
| Q5F6Q5 | Putative ABC transporter, periplasmic binding protein, polyamine | MPAELVNTR | SEQ ID NO: 409 |
| Q5F7C5 | Putative ABC transporter, periplasmic binding protein, polyamine | NGNFVTYAPSSKPAR | SEQ ID NO: 410 |
| Q5FA28 | Putative ABC transporter, periplasmic binding protein, polyamine | SGYDLTAPSIANVGR | SEQ ID NO: 411 |
| Q5FA28 | Putative ABC transporter, periplasmic binding protein, polyamine | AQIPHYGNIDKDLLK | SEQ ID NO: 412 |
| Q5FA28 | Putative ABC transporter, periplasmic binding protein, polyamine | TGVGVWVDSFMIPR | SEQ ID NO: 413 |
| Q5FA28 | Putative ABC transporter, periplasmic binding protein, polyamine | YIDYTLRPEVAAK | SEQ ID NO: 414 |
| Q5F8K8 | Putative ABC-transporter, ATP-binding protein | FAEYDGYTAEAR | SEQ ID NO: 415 |
| Q5F8K8 | Putative ABC-transporter, ATP-binding protein | LQELQEFVAR | SEQ ID NO: 416 |

TABLE 1-continued

UniProtAC

| C | Desc | Peptide | SEQ ID NO: |
|---|---|---|---|
| Q5F8K8 | Putative ABC-transporter, ATP-binding protein | LKQADKIKSEMVEVKPSTR | SEQ ID NO: 417 |
| Q5F8K8 | Putative ABC-transporter, ATP-binding protein | SEMVEVKPSTR | SEQ ID NO: 418 |
| Q5F8K8 | Putative ABC-transporter, ATP-binding protein | LAIIGPNGAGK | SEQ ID NO: 419 |
| Q5F8B6 | Putative ABC-type transporter, ATP-binding protein | SREDKIQTASAPK | SEQ ID NO: 420 |
| Q5F655 | Putative adenylosuccinate lyase | LLELTPAILYVGK | SEQ ID NO: 421 |
| Q5F655 | Putative adenylosuccinate lyase | LLELTPALYVGKAEALAK | SEQ ID NO: 422 |
| Q5F6V3 | Putative alcohol dehydrogenase | MKMQAVVVNK | SEQ ID NO: 423 |
| Q5F6V3 | Putative alcohol dehydrogenase | ETGADLVVNAAKEDAAK | SEQ ID NO: 424 |
| Q5F6V3 | Putative alcohol dehydrogenase | TGGAHAAVVTAVSAAAFNSAVNCVR | SEQ ID NO: 425 |
| Q5F6V3 | Putative alcohol dehydrogenase | VVAVGLPPESMDLSIPR | SEQ ID NO: 426 |
| Q5F6V3 | Putative alcohol dehydrogenase | LVLDGIEVVGSLVGTR | SEQ ID NO: 427 |
| Q5F6V3 | Putative alcohol dehydrogenase | LVLDGIEVVGSLVGTRK | SEQ ID NO: 428 |
| Q5F6V3 | Putative alcohol dehydrogenase | ALDEAPAIFQEMR | SEQ ID NO: 429 |
| Q5F8U5 | Putative aldehyde dehydrogenase | ILAAHAGANLKK | SEQ ID NO: 430 |
| Q5F758 | Putative amino acid aminotransferase | IVTVQTLGGSGALK | SEQ ID NO: 431 |
| Q5F6U0 | Putative aminopeptidase | LIEGINPSTFFK | SEQ ID NO: 432 |
| Q5F6U0 | Putative atninopeptidase | VVPVGTPTAEQKR | SEQ ID NO: 433 |
| Q5F6U0 | Putative aminopeptidase | RLEPLTEGAAK | SEQ ID NO: 434 |
| Q5FA72 | Putative aminopeptidase N | YLKDYQTPAYR | SEQ ID NO: 435 |
| Q5FA72 | Putative aminopeptidase N | LKNNVFELTIK | SEQ ID NO: 436 |
| Q5FA72 | Putative aminopeptidase N | RSDTLQQVQTALQHPK | SEQ ID NO: 437 |
| Q5FA72 | Putative aminopeptidase N | NVPHFHAQDGSGYR | SEQ ID NO: 438 |
| Q5F9D9 | Putative aminotransferases | TYHGSAMSIPVQR | SEQ ID NO: 439 |
| Q5F9D9 | Putative aminotransferases | AAIQVLPGR | SEQ ID NO: 440 |
| Q5F6R0 | Putative aspartyl-tRNA synthetase | LRYQVATGYR | SEQ ID NO: 441 |

TABLE 1-continued

| UniProtA | | | |
|---|---|---|---|
| C | Desc | Peptide | SEQ ID NO: |
| Q5F6R0 | Putative aspartyl-tRNA synthetase | VHPGEFFALPQSPQLFK | SEQ ID NO: 442 |
| Q5F6R0 | Putative aspartyl-tRNA synthetase | QVFKDALNVDLGDFPR | SEQ ID NO: 443 |
| Q5F6R0 | Putative aspartyl-tRNA synthetase | VVALRVPNGAK | SEQ ID NO: 444 |
| Q5F6R0 | Putative aspartyl-tRNA synthetase | VNDAGNLSNGEDSGLQSPIVK | SEQ ID NO: 445 |
| Q5F6R0 | Putative aspartyl-tRNA synthetase | YVAVHHPFTAPK | SEQ ID NO: 446 |
| Q5F6R0 | Putative aspartyl-tRNA synthetase | EGHEDLMVSDPANCLAR | SEQ ID NO: 447 |
| Q5F6R0 | Putative aspartyl-tRNA synthetase | FGFLLDNLK | SEQ ID NO: 448 |
| Q5F6R0 | Putative aspartyl-tRNA synthetase | FGAPPHGGLAFGLDR | SEQ ID NO: 449 |
| Q5F6R0 | Putative aspartyl-tRNA synthetase | LVTLMFGAESIRDVIAFPK | SEQ ID NO: 450 |
| Q5F6R0 | Putative aspartyl-tRNA synthetase | AQCLLTDAPNSVDDK | SEQ ID NO: 451 |
| Q5F6R0 | Putative aspartyl-tRNA synthetase | AQCLLTDAPNSVDDKQLR | SEQ ID NO: 452 |
| Q5FAG6 | Putative atpase | TLLDTVAVPNTAR | SEQ ID NO: 453 |
| Q5FAG6 | Putative atpase | LNVPLLGQLPLSLPVR | SEQ ID NO: 454 |
| Q5F916 | Putative ATP-dependent Clp protease | QKKVIGK | SEQ ID NO: 455 |
| Q5F8W0 | Putative ATP-dependent RNA helicase | GIDVPTITHVINYDLPK | SEQ ID NO: 456 |
| Q5F8W0 | Putative ATP-dependent RNA helicase | RGDHKPGKEGFGGK | SEQ ID NO: 457 |
| Q5FA80 | Putative ATP-dependent RNA helicase | ALAGHDLLAAAQTGTGK | SEQ ID NO: 458 |
| Q5FA80 | Putative ATP-dependent RNA helicase | YATASTSPAMHPVR | SEQ ID NO: 459 |
| Q5F697 | Putative branched-chain amino acid aminotranferase | IVLFRPTANIAR | SEQ ID NO: 460 |
| Q5F697 | Putative branched-chain amino acid aminotranferase | AADEIPDAPAALYLRPTLIGTDPVIGK | SEQ ID NO: 461 |
| Q5F697 | Putative branched-chain amino acid aminotranferase | AGSPSETALLYILASPVGDYFK | SEQ ID NO: 462 |
| Q5FAB9 | Putative carboxypeptidase, penicillin binding protein | RSDNLIAR | SEQ ID NO: 463 |
| Q5F932 | Putative carboxy-terminal processing protease | AVIVGTQSFGK | SEQ ID NO: 464 |
| Q5F8D2 | Putative cell-division protein | SPDVSQGQSVSDGTAVR | SEQ ID NO: 465 |

TABLE 1-continued

| UniProtAC | Desc | Peptide | SEQ ID NO: |
|---|---|---|---|
| Q5F8D2 | Putative cell-division protein | APHLLVAGTTGSGK | SEQ ID NO: 466 |
| Q5F4Z9 | Putative chromosome segregation protein | AAQIAGLSEIPAVIK | SEQ ID NO: 467 |
| Q5F4Z9 | Putative chromosome segregation protein | TISDETALAMGLIENLQR | SEQ ID NO: 468 |
| Q5F4Z9 | Putative chromosome segregation protein | LADEFGLTHETIAQAVGK | SEQ ID NO: 469 |
| Q5F4Z9 | Putative chromosome segregation protein | LLSLPESVQEMLYQR | SEQ ID NO: 470 |
| Q5F4Z9 | Putative chromosome segregation protein | ALLTLPVVEQLELAQK | SEQ ID NO: 471 |
| Q5F4Z9 | Putative chromosome segregation protein | SQAALQNKRPEPK | SEQ ID NO: 472 |
| Q5F7W9 | Putative ClpB protein | QRLQQHLNSLPK | SEQ ID NO: 473 |
| Q5F7W9 | Putative ClpB protein | VSGQGGEILPSR | SEQ ID NO: 474 |
| Q5F7W9 | Putative ClpB protein | EAGATEQNINAAIDAVR | SEQ ID NO: 475 |
| Q5F7W9 | Putative ClpB protein | TKNNPVLIGEPGVGK | SEQ ID NO: 476 |
| Q5F7W9 | Putative ClpB protein | LLVLDLAALIAGAK | SEQ ID NO: 477 |
| Q5F7W9 | Putative ClpB protein | VLVGEPSVEDTIAILR | SEQ ID NO: 478 |
| Q5F7W9 | Putative ClpB protein | FLPDKAIDLIDEAASR | SEQ ID NO: 479 |
| Q5F7W9 | Putative ClpB protein | AISDGAANIKK | SEQ ID NO: 480 |
| Q5F7W9 | Putative ClpB protein | IKIEQAKR | SEQ ID NO: 481 |
| Q5F7W9 | Putative ClpB protein | NNVGAEEIAEVVSR | SEQ ID NO: 482 |
| Q5F7W9 | Putative ClpB protein | SGLADPNKPYGSFLFLGPTGVGK | SEQ ID NO: 483 |
| Q5F7W9 | Putative ClpB protein | ALAGFLFDSEDHLIR | SEQ ID NO: 484 |
| Q5F7W9 | Putative ClpB protein | AIQSEIENPLAK | SEQ ID NO: 485 |
| Q5F9I4 | Putative cold shock protein | GFGFITPDEGGEDLFAHFSAINMEGFK | SEQ ID NO: 486 |
| Q5F9I4 | Putative cold shock protein | GFGFITPDEGGEDLFAHFSAINMEGFKTLK | SEQ ID NO: 487 |
| Q5F9I4 | Putative cold shock protein | VSFDVTTGPK | SEQ ID NO: 488 |
| Q5F9I4 | Putative cold shock protein | GKQAANIQAA | SEQ ID NO: 489 |
| Q5F759 | Putative cytochrome | IQPVGQLTMGDGIPVGER | SEQ ID NO: 490 |

TABLE 1-continued

| UniProtAC | Desc | Peptide | SEQ ID NO: |
|---|---|---|---|
| Q5F759 | Putative cytochrome | GGAADLTDQELKR | SEQ ID NO: 491 |
| Q5F759 | Putative cytochrome | AEDKGAAAPAVGVDGK | SEQ ID NO: 492 |
| Q5F759 | Putative cytochrome | AEDKGAAAPAVGVDGKK | SEQ ID NO: 493 |
| Q5F759 | Putative cytochrotne | HALEGFNAMPAK | SEQ ID NO: 494 |
| Q5FAC5 | Putative cytochrome | SGEANPKENPELGAK | SEQ ID NO: 495 |
| Q5FAC5 | Putative cytochrome | MSEEDLKAVANFIQGLR | SEQ ID NO: 496 |
| Q5F716 | Putative cytochrome c oxidase subunit | AATQPAPGVKPYNALQVAGR | SEQ ID NO: 497 |
| Q5F716 | Putative cytochrome c oxidase subunit | DVVPESNMPAFPWLAR | SEQ ID NO: 498 |
| Q5F716 | Putative cytochrome c oxidase subunit | NKVDVDATVANMK | SEQ ID NO: 499 |
| Q5F718 | Putative cytochrome c oxidase subunit | GGRGDLSDDEVK | SEQ ID NO: 500 |
| Q5F598 | Putative cytochrome C1 | LKDIGLTDEEIKK | SEQ ID NO: 501 |
| Q5F598 | Putative cytochrome C1 | WFGAAPPDLTLIAR | SEQ ID NO: 502 |
| Q5F598 | Putative cytochrome C1 | GQPVMVKDEHGEMKPK | SEQ ID NO: 503 |
| Q5F598 | Putative cytochrome C1 | LYWESTGLHSR | SEQ ID NO: 504 |
| Q5F940 | Putative dihydrolipoamide acetyltransferase component of pyruvate dehydrogenase complex | ELGVDLGQVK | SEQ ID NO: 505 |
| Q5F940 | Putative dihydrolipoamide acetyltransferase component of pyruvate dehydrogenase complex | FGNVEVKELSR | SEQ ID NO: 506 |
| Q5F940 | Putative dihydrolipoamide acetyltransferase component of pyruvate dehydrogenase complex | IKKISGQNLSR | SEQ ID NO: 507 |
| Q5F940 | Putative dihydrolipoamide acetyltransferase component of pyruvate dehydrogenase complex | ISGQNLSR | SEQ ID NO: 508 |
| Q5F940 | Putative dihydrolipoamide acetyltransferase component of pyruvate dehydrogenase complex | LSPLAFIIK | SEQ ID NO: 509 |
| Q5F940 | Putative dihydrolipoamide acetyltransferase component of pyruvate dehydrogenase complex | AFPEFNASLDGDNLVLK | SEQ ID NO: 510 |
| Q5F940 | Putative dihydrolipoamide acetyltransferase component of pyruvate dehydrogenase complex | NYFNIGFAADTPNGLVVPVIK | SEQ ID NO: 511 |

TABLE 1-continued

| UniProtA C | Desc | Peptide | SEQ ID NO: |
|---|---|---|---|
| Q5F940 | Putative dihydrolipoamide acetyltransferase component of pyruvate dehydrogenase complex | NYFNIGFAADTPNGLVVPVIKDVDQK | SEQ ID NO: 512 |
| Q5F940 | Putative dihydrolipoamide acetyltransferase component of pyruvate dehydrogenase complex | QISQELTELSK | SEQ ID NO: 513 |
| Q5F940 | Putative dihydrolipoamide acetyttransferase component of pyruvate dehydrogenase complex | QISQELTELSKK | SEQ ID NO: 514 |
| Q5F940 | Putative dihydrolipoamide ace tyltrans ferase component of pyruvate dehydrogenase complex | SQIKPVWNGKEFAPR | SEQ ID NO: 515 |
| Q5F940 | Putative dihydrolipoamide acetyltransferase component of pyruvate dehydrogenase complex | VIDGAAGMR | SEQ ID NO: 516 |
| Q5F940 | Putative dihydrolipoamide acetyltransferase component of pyruvate dehydrogenase complex | FTVFLANLLK | SEQ ID NO: 517 |
| Q5F866 | Putative dihydrolipoamide dehydrogenase | LLIAAAEAR | SEQ ID NO: 518 |
| Q5F866 | Putative dihydrolipoamide dehydrogenase | GVPVADPLTMQTSIPHIFIAGDASNQLPLLHEAADQGK | SEQ ID NO: 519 |
| Q5F942 | Putative dihydrolipoamide dehydrogenase | AEAAAAPAQEAPK | SEQ ID NO: 520 |
| Q5F942 | Putative dihydrolipoamide dehydrogenase | TLGGVCLNVGCIPSK | SEQ ID NO: 521 |
| Q5F942 | Putative dihydrolipoamide dehydrogenase | ALLHNAAVIDEVR | SEQ ID NO: 522 |
| Q5F942 | Putative dihydrolipoamide dehydrogenase | AYKDGVVSR | SEQ ID NO: 523 |
| Q5F942 | Putative dihydrolipoamide dehydrogenase | LTGGLAGMAK | SEQ ID NO: 524 |
| Q5F942 | Putative dihydrolipoamide dehydrogenase | NCIIAAGSR | SEQ ID NO: 525 |
| Q5F942 | Putative dihydro ipoamide dehydrogenase | IIDSSGALALKEVPGK | SEQ ID NO: 526 |
| Q5F942 | Putative dihydrolipoamide dehydrogenase | EPQRYDAVLVAAGR | SEQ ID NO: 527 |
| Q5F942 | Putative dihydrolipoamide dehydrogenase | APNGKLISAEK | SEQ ID NO: 528 |
| Q5F942 | Putative dihydrolipoamide dehydrogenase | TNVPHIYAIGDIVGQPMLAHK | SEQ ID NO: 529 |
| Q5F942 | Putative dihydrolipoamide dehydrogenase | AVHEGHVAAENCAGHK | SEQ ID NO: 530 |
| Q5F942 | Putative dihydrolipoamide dehydrogenase | VIPGVAYTSPEVAWVGETELSAK | SEQ ID NO: 531 |
| Q5F942 | Putative dihydrolipoamide dehydrogenase | AIANGCDNGFTK | SEQ ID NO: 532 |

TABLE 1-continued

| UniProtAC | Desc | Peptide | SEQ ID NO: |
|---|---|---|---|
| Q5F875 | Putative dihydrolipoamide succinyltransferase E2 component | IDTAATVAAEAPAAAPAEAAPAAVPAAAQNNAAMPAAAK | SEQ ID NO: 533 |
| Q5F875 | Putative dihydrolipoamide succinyltransferase E2 component | LAAETGVDVNVLQGSGR | SEQ ID NO: 534 |
| Q5F875 | Putative dihydrolipoamide succinyltransferase E2 component | VLKEDVQNAAAKPAAAVAPAVALPAGARPEER | SEQ ID NO: 535 |
| Q5F875 | Putative dihydrolipoamide succinyltransferase E2 component | VLKEDVQNAAAKPAAAVAPAVALPAGARPEERVPMSR | SEQ ID NO: 536 |
| Q5F875 | Putative dihydrolipoamide succinyltransferase E2 component | LLASQQENAILTTFNEVNMKPIMDLR | SEQ ID NO: 537 |
| Q5F875 | Putative dihydrolipoamide succinyltransferase E2 component | EAVLTLVAIKDALEDPVR | SEQ ID NO: 538 |
| Q5F898 | Putative D-lactate dehydrogenase | AALGEFESLPVSGEYIHR | SEQ ID NO: 539 |
| Q5F898 | Putative D-lactate dehydrogenase | FGTHQLPK | SEQ ID NO: 540 |
| Q5F898 | Putative D-lactate dehydrogenase | FLPDHLPK | SEQ ID NO: 541 |
| Q5F898 | Putative D-lactate dehydrogenase | FAVASAAIR | SEQ ID NO: 542 |
| Q5F898 | Putative D-lactate dehydrogenase | GAQYPAEHNVGHLYEAKPALK | SEQ ID NO: 543 |
| Q5F898 | Putative D-lactate dehydrogenase | KLDPTNSFNPGIGK | SEQ ID NO: 544 |
| Q5F533 | Putative DNA polymerase I | GGISTNEAVLEQLAPDYPLYK | SEQ ID NO: 545 |
| Q5F533 | Putative DNA polymerase I | LASNNPNLQNIPIR | SEQ ID NO: 546 |
| Q5F533 | Putative DNA polymerase I | AAINAPMQGTASDLIKR | SEQ ID NO: 547 |
| Q5F8J6 | Putative DNA-binding protein Hu | MNKSELIEAMEADISK | SEQ ID NO: 548 |
| Q5F8J6 | Putative DNA-binding protein Hu | MNKSELIEAIAQEADISKAAAQK | SEQ ID NO: 549 |
| Q5F8J6 | Putative DNA-binding protein Hu | ALDATTNAVTNALK | SEQ ID NO: 550 |
| Q5F8J6 | Putative DNA-binding protein Hu | TGEPLTIAAAK | SEQ ID NO: 551 |
| Q5F5I8 | Putative electron transfer flavoprotein alpha-subunit | QLSHSDRPELTQAK | SEQ ID NO: 552 |
| Q5F5I9 | Putative electron transfer flavoprotein beta-subunit | AVADKENPQIFFLGK | SEQ ID NO: 553 |
| Q5F5I9 | Putative electron transfer flavoprotein beta-subunit | KKPLEKLDSADLATDISPR | SEQ ID NO: 554 |
| Q5F5I9 | Putative electron transfer flavoprotein beta-subunit | LDSADLATDISPR | SEQ ID NO: 555 |

TABLE 1-continued

| UniProtA C | Desc | Peptide | SEQ ID NO: |
|---|---|---|---|
| Q5F5I9 | Putative electron transfer flavoprotein beta-subunit | VASVAELVEK | SEQ ID NO: 556 |
| Q5F8S3 | Putative ferredox in-NADP reductase | IILVHGVR | SEQ ID NO: 557 |
| Q5F8S3 | Putative ferredoxin-NADP reductase | TGVRGDYLIER | SEQ ID NO: 558 |
| Q5FAI4 | Putative fructose-bisphosphate aldolase | QLLDHAAENSYGLPAFNVNNLEQMR | SEQ ID NO: 559 |
| Q5FAI4 | Putative fructose-bisphosphate aldolase | AIMEAADQVNAPVIVQASAGAR | SEQ ID NO: 560 |
| Q5FAI4 | Putative fructose-bisphosphate aldolase | KYAGAPFLR | SEQ ID NO: 561 |
| Q5FAI4 | Putative fructose-bisphosphate aldolase | LSHDQMLTSVEDAVR | SEQ ID NO: 562 |
| Q5FAI4 | Putative fructose-bisphosphate aldolase | FTRPPTGDVLR | SEQ ID NO: 563 |
| Q5FAI4 | Putative fructose-bisphosphate aldolase | VINEYGGNIGETYGVPVEEIVEGIK | SEQ ID NO: 564 |
| Q5FA14 | Putative fructose-bisph osph ate aldolase | KVNIDTDIR | SEQ ID NO: 565 |
| Q5FAI4 | Putative fructose-bisphosphate aldolase | LASTGAVRR | SEQ ID NO: 566 |
| Q5F5J3 | Putative glyceraldehyde 3-phosphate dehydrogenase C | FQGTAELKDDAIVVNGR | SEQ ID NO: 567 |
| Q5F5J3 | Putative glyceraldehyde 3-phosphate dehydrogenase C | KVVISAPGGNDVK | SEQ ID NO: 568 |
| Q5F5J3 | Putative glyceraldehyde 3-phosphate dehydrogenase C | AAALNIVPNSTGAAK | SEQ ID NO: 569 |
| Q5F5J3 | Putative glyceraldehyde 3-phosphate dehydrogenase C | AIGLVIPELNGK | SEQ ID NO: 570 |
| Q5F5J3 | Putative glyceraldehyde 3-phosphate dehydrogenase C | AIGLVIPELNGKLDGSAQR | SEQ ID NO: 571 |
| Q5F5J3 | Putative glyceraldehyde 3-phosphate dehydrogenase C | VTVATGSLTELVSVLERPATK | SEQ ID NO: 572 |
| Q5F5J3 | Putative glyceraldehyde 3-phosphate dehydrogenase C | VPVATGSLTELVSVLERPATKEEINAAMK | SEQ ID NO: 573 |
| Q5F5J3 | Putative glyceraldehyde 3-phosphate dehydrogenase C | TLEYFAGKI | SEQ ID NO: 574 |
| Q5F8H0 | Putative GTP-binding protein | NIAIIAHVDHGK | SEQ ID NO: 575 |
| Q5F8H0 | Putative GTP-binding protein | VMDSNDLEKER | SEQ ID NO: 576 |
| Q5F8H0 | Putative GTP-binding protein | ALALGLKPIVVINK | SEQ ID NO: 577 |

TABLE 1-continued

| UniProtA | | | |
|---|---|---|---|
| C | Desc | Peptide | SEQ ID NO: |
| Q5F8H0 | Putative GTP-binding protein | LEETDESSDMRPLFDTILK | SEQ ID NO: 578 |
| Q5F8H0 | Putative GTP-binding protein | IKPGQTVAVMNHEQQIAQGR | SEQ ID NO: 579 |
| Q5F8H0 | Putative GTP-binding protein | INQLLGFK | SEQ ID NO: 580 |
| Q5F8H0 | Putative GTP--binding protein | EGYELAVGKPR | SEQ ID NO: 581 |
| Q5F8H0 | Putative GTP-binding protein | TRLEYHIPAR | SEQ ID NO: 582 |
| Q5F8H0 | Putative GTP-binding protein | LEYHIPAR | SEQ ID NO: 583 |
| Q5FAG0 | Putative GTP-binding protein | MQPAIVEFVDIAGLVAGASK | SEQ ID NO: 584 |
| Q5FAG0 | Putative GTP-binding protein | KLLPHLDEGKPVR | SEQ ID NO: 585 |
| Q5F7T8 | Putative isocitrate dehydrogenase | STIVYTHTDEAPALATQSLLPIVQAFAR | SEQ ID NO: 586 |
| Q5F7T8 | Putative isocitrate dehydrogenase | ILAAFPEYLTEAQR | SEQ ID NO: 587 |
| Q5F7T8 | Putative isocitrate dehydrogenase | LPNISASVPQLTAAIK | SEQ ID NO: 588 |
| Q5F7T8 | Putative isocitrate dehydrogenase | IKGSAVNPVLR | SEQ ID NO: 589 |
| Q5F7T8 | Putative isocitrate dehydrogenase | GSAVNPVLR | SEQ ID NO: 590 |
| Q5F7T8 | Putative isocitrate dehydrogenase | DAPVKDWVQLAVNR | SEQ ID NO: 591 |
| Q5F7T8 | Putative isocitrate dehydrogenase | LSNTPAVFWLDENRPHDK | SEQ ID NO: 592 |
| Q5F7T8 | Putative isocitrate dehydrogenase | LKNGEDTISVTGNVLR | SEQ ID NO: 593 |
| Q5F7T8 | Putative isocitrate dehydrogenase | DYLTDLFPILELGTSAK | SEQ ID NO: 594 |
| Q5F7T8 | Putative isocitrate dehydrogenase | HVQQFLEENHLR | SEQ ID NO: 595 |
| Q5F7T8 | Putative isocitrate dehydrogenase | AQVLADTLDAATEK | SEQ ID NO: 596 |
| Q5F7T8 | Putative isocitrate dehydrogenase | AAFAPLAAALTADEAK | SEQ ID NO: 597 |
| Q5F7T8 | Putative isocitrate dehydrogenase | AAFAPLAAALTADEAKIVEELSAVQGK | SEQ ID NO: 598 |
| Q5F7T8 | Putative isocitrate dehydrogenase | AAQAMRPSATFNQVLNAL | SEQ ID NO: 599 |
| Q5F8Q4 | Putative khg/kdpg 4-hydroxy-2-oxoglutarate aldolase | TPVGLEAIR | SEQ ID NO: 600 |
| Q5F8Q4 | Putative khg/kdpg 4-hydroxy-2-oxoglutarate aldolase | AVEDAGAVFAISPGLHESLAR | SEQ ID NO: 601 |

TABLE 1-continued

UniProtA

| C | Desc | Peptide | SEQ ID NO: |
|---|---|---|---|
| Q5F8X1 | Putative L-lactate dehydrogenase | NVGDLSSLSSWTAEQFDPR | SEQ ID NO: 602 |
| Q5F8X1 | Putative L-lactate dehydrogenase | SGADALVVSNHGGR | SEQ ID NO: 603 |
| Q5F9Z4 | Putative malic enzyme, malate dehydrogenase/oxaloacetate-decarboxylating | FHELPVPGK | SEQ ID NO: 604 |
| QF97Z4 | Putative malic enzyme, malate dehydrogenase/oxaloacetate-decarboxylating | ETRPDVVIGTGR | SEQ ID NO: 605 |
| Q5F9Z4 | Putative malic enzyme, malate dehydrogenase/oxaloacetate-decarboxylating | GALDVGATTINEEMKR | SEQ ID NO: 606 |
| Q5F9Z4 | Putative malic enzyme, malate dehydrogenase/oxaloacetate-decarboxylating | AAMESGVATRPIADLEAYAAK | SEQ ID NO: 607 |
| Q5F798 | Putative N utilisation substance protein A | EQNLNEFLAVKEDIVSGTVK | SEQ ID NO: 608 |
| Q5F798 | Putative N utilisation substance protein A | HGIIVEVVAGK | SEQ ID NO: 609 |
| Q5F798 | Putative N utilisation substance protein A | IDPQGTCIGVR | SEQ ID NO: 610 |
| Q5F798 | Putative N utilisation substance protein A | VNAVSNELSGER | SEQ ID NO: 611 |
| Q5F798 | Putative N utilisation substance protein A | LGEVSDDMR | SEQ ID NO: 612 |
| Q5F798 | Putative N utilisation substance protein A | NLEGVDADMLLSLAEAGITTR | SEQ ID NO: 613 |
| Q5F621 | Putative NADH dehydrogenase I chain G | SAPLQETSHAAVPAAR | SEQ ID NO: 614 |
| Q5F621 | Putative NADH dehydrogenase I chain G | LGLQDGQTAVAK | SEQ ID NO: 615 |
| Q5F7J5 | Putative nitrogen regulatory protein P-II | IGDGKIFVLPVEEAIR | SEQ ID NO: 616 |
| Q5F7J5 | Putative nitrogen regulatory protein P-II | IFVLPVEEAIR | SEQ ID NO: 617 |
| Q5F8K6 | Putative peptidyl-prolyl cis-trans isomerase | LPAHEAKPSFEQEK | SEQ ID NO: 618 |
| Q5F8K6 | Putative peptidyl-prolyl cis-trans isomerase | AKPANGKPAYVR | SEQ ID NO: 619 |
| Q5F8K6 | Putative peptidyl-prolyl cis-trans isomerase | QALAQQQSANTFDLLIR | SEQ ID NO: 620 |
| Q5F865 | Putative peroxiredoxin family protein/glutaredoxin | ALQDRTGQKVPSVVFR | SEQ ID NO: 621 |
| Q5F865 | Putative peroxiredoxin family protein/glutaredoxin | TGQKVPSVVFR | SEQ ID NO: 622 |

TABLE 1-continued

UniProtA

| C | Desc | Peptide | SEQ ID NO: |
|---|------|---------|------------|
| Q5F865 | Putative, peroxiredoxin family protein/glutaredoxin | VPSVVFR | SEQ ID NO: 623 |
| Q5F865 | Putative peroxiredoxin family protein/glutaredoxin | TRVGDTWKDVSTDDLFK | SEQ ID NO: 624 |
| Q5F865 | Putative peroxiredoxin family protein/glutaredoxin | VGDTWKDVSTDDLFK | SEQ ID NO: 625 |
| Q5F865 | Putative peroxiredoxin family protein/glutaredoxin | KVVVFSLPGAFTPTCSSSSHLPR | SEQ ID NO: 626 |
| Q5F865 | Putative peroxiredoxin family protein/glutaredoxin | VVVFSLPGAFTPTCSSSHLPR | SEQ ID NO: 627 |
| Q5F865 | Putative peroxiredoxin family protein/glutaredoxin | EDLGFGKR | SEQ ID NO: 628 |
| Q5F865 | Putative peroxiredoxin family protein/glutaredoxin | YSMLVNDGVVEK | SEQ ID NO: 629 |
| Q5F865 | Putative peroxiredoxin family protein/glutaredoxin | MFIEPEEPGDPFK | SEQ ID NO: 630 |
| Q5F865 | Putative peroxiredoxin family protein/glutaredoxin | MFIEPEEPGDPFKVSDADTMLK | SEQ ID NO: 631 |
| Q5F865 | Putative peroxiredoxin family protein/glutaredoxin | VSDADTMLK | SEQ ID NO: 632 |
| Q5F865 | Putative peroxiredoxin family protein/glutaredoxin | FVAPDWK | SEQ ID NO: 633 |
| Q5F865 | Putative, peroxiredoxin family protein/glutaredoxin | FVAPDWKAQESVAIFTKPGCQFCAK | SEQ ID NO: 634 |
| Q5F865 | Putative peroxiredoxin family protein/glutaredoxin | AQESVAIFTKPGCQFCAK | SEQ ID NO: 635 |
| Q5F865 | Putative peroxiredoxin family protein/glutaredoxin | VKQALQDK | SEQ ID NO: 636 |
| Q5F865 | Putative: peroxiredoxin family protein/glutaredoxin | VKQALQDKGSYEEIVLGK | SEQ ID NO: 637 |
| Q5F865 | Putative peroxiredoxin family protein/glutaredoxin | VKQALQDKGLSYEEIVLGKDATVTSVR | SEQ ID NO: 638 |
| Q5F865 | Putative peroxiredoxin family protein/glutaredoxin | QALQDKGLSYEEIVLGK | SEQ ID NO: 639 |
| Q5F865 | Putative peroxiredoxin family protein/glutaredoxin | QALQDKGLSYEEIVLGKDATVTSVR | SEQ ID NO: 640 |
| Q5F865 | Putative peroxiredoxin family proteiniglutaredoxin | GLSYEEIVLGKDATVTSVR | SEQ ID NO: 641 |

TABLE 1-continued

| UniProtA | | | |
|---|---|---|---|
| C | Desc | Peptide | SEQ ID NO: |
| Q5F865 | Putative peroxiredoxin family protein/glutaredoxin | AITGKMTAPQVFIGGK | SEQ ID NO: 642 |
| Q5F865 | Putative peroxiredoxin family protein/glutaredoxin | MTAPQVFIGGK | SEQ ID NO: 643 |
| Q5F865 | Putative peroxiredoxin family protein/glutaredoxin | YIGGSEDLEAYLAK | SEQ ID NO: 644 |
| Q5F865 | Putative peroxiredoxin family protein/glutaredoxin | YIGGSEDLEAYLAKN | SEQ ID NO: 645 |
| Q5F8Q3 | Putative phosphogluconate dehydratase | NQLGCSNLAHGYAAMPK | SEQ ID NO: 646 |
| Q5F8Q3 | Putative phosphogluconate dehydratase | YAAGHLAR | SEQ ID NO: 647 |
| Q5F8Q3 | Putative phosphogluconate dehydratase | ADVNHFTAAGGLPFVIR | SEQ ID NO: 648 |
| Q5F8Q3 | Putative phosphogluconate dehydratase | KADNPFSPDGGLR | SEQ ID NO: 649 |
| Q5F8Q3 | Putative phosphogluconate dehydratase | LTPPLGILQDR | SEQ ID NO: 650 |
| Q5F8Q3 | Putative phosphogluconate dehydratase | VPASIHMTPEALMGGNIAK | SEQ ID NO: 651 |
| Q5FA20 | Putative phosphotransacetylase | VLVVPVSAGLNTSAAAQAFAK | SEQ ID NO: 652 |
| Q5FA20 | Putative phosphotransacetylase | VAALDAANLVIEGIAPDADKIYLAGK | SEQ ID NO: 653 |
| Q5FA20 | Putative phosphotransacetylase | TGLTFFGSSDALKDVSVLAGR | SEQ ID NO: 654 |
| Q5FA20 | Putative phosphotransacetylase | DVSVLAGR | SEQ ID NO: 655 |
| Q5FA20 | Putative phosphotransacetylase | RLSPAQFR | SEQ ID NO: 656 |
| Q5FA20 | Putative phosphotransacetylase | IVLPEGAEPR | SEQ ID NO: 657 |
| Q5FA20 | Putative phosphotransacetylase | TVQAAAICHEK | SEQ ID NO: 658 |
| Q5FA20 | Putative phosphotransacetylase | TVQAAAICHEKGIAR | SEQ ID NO: 659 |
| Q5FA20 | Putative phosphotransacetylase | REEVEAVAKER | SEQ ID NO: 660 |
| Q5FA20 | Putative phosphotransacetylase | EKRPDLAIDGPLQYDAATVPGVGK | SEQ ID NO: 661 |
| Q5FA20 | Putative phosphotransacetylase | SKAPGSPVAGQATVLVFPDLNTGNCTYK | SEQ ID NO: 662 |
| Q5FA20 | Putative phosphotransacetylase | SANVLSVGPLLQGLR | SEQ ID NO: 663 |

TABLE 1-continued

| C | Desc | Peptide | SEQ ID NO: |
|---|---|---|---|
| Q5FAC8 | Putative pilus assembly protein | KTDAKLPK | SEQ ID NO: 664 |
| Q5FAC8 | Putative pilus assembly protein | YVIAKLPK | SEQ ID NO: 665 |
| Q5FAC8 | Putative pilus assembly protein | NIVASVPQNLATIEQLTYTAK | SEQ ID NO: 666 |
| Q5FAC8 | Putative pilus assembly protein | GIAQTVASQTNADVQCVHPAR | SEQ ID NO: 667 |
| Q5FAC8 | Putative pilus assembly protein | YFANDLKTDEQQFELDAPTLTK | SEQ ID NO: 668 |
| Q5FAC9 | Putative pilus assembly protein | ILDSLNEAVPGSTYLTSLDAVTADSYR | SEQ ID NO: 669 |
| Q5FAC9 | Putative pilus assembly protein | AAESKENPASGNAQEAN | SEQ ID NO: 670 |
| Q5F5Y3 | Putative ribonuclease E | FQIEHQIESAFSR | SEQ ID NO: 671 |
| Q5F5Y3 | Putative ribonuclease E | LKPALGESSHAACPR | SEQ ID NO: 672 |
| Q5F5Y3 | Putative ribonuclease E | GIESTALHVLR | SEQ ID NO: 673 |
| Q5F5Y3 | Putative ribonuclease E | AQVPVDVATFLLNEK | SEQ ID NO: 674 |
| Q5F5Y3 | Putative ribonuclease E | AQVPVDVATFLLNEKR | SEQ ID NO: 675 |
| Q5F5Y3 | Putative ribonuclease E | IRTDDVEEDGEPSYKR | SEQ ID NO: 676 |
| Q5F5Y3 | Putative ribonuclease E | VAEPEEDESAKPFGGEK | SEQ ID NO: 677 |
| Q5F5Y3 | Putative ribonuclease E | AARPEPAVK | SEQ ID NO: 678 |
| Q5F5Y3 | Putative ribonuclease E | HTSPAPTAAPEK | SEQ ID NO: 679 |
| Q5F5Y3 | Putative ribonuclease E | IFGGSETQAVPAAETSEKR | SEQ ID NO: 680 |
| Q5F5Y3 | Putative ribonuclease E | NVQPAAPVADAAPPETEGQTGKR | SEQ ID NO: 681 |
| Q5F5Y3 | Putative ribonuclease E | IEQYLNIHDTADKVR | SEQ ID NO: 682 |
| Q5F5Y3 | Putative ribonuclease E | AWAAQPEVQAGR | SEQ ID NO: 683 |
| Q5F870 | Putative succinate dehydrogenase flavoprotein subunit | IYQRPFGGHTAEHGK | SEQ ID NO: 684 |
| Q5F870 | Putative succinate dehydrogenase flavoprotein subunit | IDHIGAEK | SEQ ID NO: 685 |
| Q5F870 | Putative succinate dehydrogenase flavoprotein subunit | SVQLHAGVFR | SEQ ID NO: 686 |
| Q5F649 | Putative thiol: disulphide interchange protein | TEHVWQK | SEQ ID NO: 687 |

TABLE 1-continued

| UniProtAC | Desc | Peptide | SEQ ID NO: |
|---|---|---|---|
| Q5F649 | Putative thiol: disulphide interchange protein | LAAAVDMAAAESK | SEQ ID NO: 688 |
| Q5F649 | Putative thiadisulphide interchange protein | LAAAVDMAAAESKDVANSHIFDAMVNQK | SEQ ID NO: 689 |
| Q5F649 | Putative thiol: disulphide interchange protein | DVANSHIFDAMVNQK | SEQ ID NO: 690 |
| Q5F649 | Putative thiol: disulphide interchange protein | IKLQEPEVLKK | SEQ ID NO: 691 |
| Q5F649 | Putative thiol: disulphide interchange protein | VLAAYESPESQAR | SEQ ID NO: 692 |
| Q5F8S1 | Putative threonine synthase | AQMLYSLQDGNIHNIAVK | SEQ ID NO: 693 |
| Q5F8S1 | Putative threonine synthase | NSAHTYVTSSPSMDISK | SEQ ID NO: 694 |
| Q5F7Y3 | Putative transketolase | FLNHNPANPK | SEQ ID NO: 695 |
| Q5F7Y3 | Putative transketolase | AETGKPSIICCK | SEQ ID NO: 696 |
| Q5F7Y3 | Putative transketolase | THGAPLGADEIEATRK | SEQ ID NO: 697 |
| Q5F7I3 | Putative transketolase | LEAGWNELFAQYQAK | SEQ ID NO: 698 |
| Q5F7Y3 | Putative transketolase | YPAEAAFVR | SEQ ID NO: 699 |
| Q5F7Y3 | Putative transketolase | KLPENFDEYVQTALK | SEQ ID NO: 700 |
| Q5F7Y3 | Putative transketolase | KASQNSIEILAK | SEQ ID NO: 701 |
| Q5F7Y3 | Putative transketolase | DKGGNYIHYGVR | SEQ ID NO: 702 |
| Q5F7Y3 | Putative transketolase | VLAGQGIAVR | SEQ ID NO: 703 |
| Q5F7Y3 | Putative transketolase | YVGLNGAVVGINR | SEQ ID NO: 704 |
| Q5F7Y3 | Putative transketolase | AFGFTVDNVVDTVK | SEQ ID NO: 705 |
| Q5F5L4 | Putative twitching motility-like potein | INSALTPQPQK | SEQ ID NO: 706 |
| Q5F5L4 | Putative twitching motility-like protein | ELGLPEKLKDLAVAPR | SEQ ID NO: 707 |
| Q5F9P7 | Putative twitching motility-like protein | GSDLFVTTHFPPAMK | SEQ ID NO: 708 |
| Q5F9P7 | Putative twitching motility-like protein | LDGKITR | SEQ ID NO: 709 |
| Q5F9P7 | Putative twitching motility-like potein | ITDEPLTAEK | SEQ ID NO: 710 |
| Q5F5Q1 | Putative two-component system transcriptional response regulator | IGAIDFLEKPISLQK | SEQ ID NO: 711 |
| Q5FA55 | Putative two-component system transcriptional response regulator | STVPIIMILTAK | SEQ ID NO: 712 |

TABLE 1-continued

| UniProtAC | Desc | Peptide | SEQ ID NO: |
|---|---|---|---|
| Q5FA55 | Putative two-component system transcriptional response regulator | INAILRR | SEQ ID NO: 713 |
| Q5FA55 | Putative two-component system transcriptional response regulator | AQHSGEQNNAPNSISVSDVVLYPAKR | SEQ ID NO: 714 |
| Q5FA55 | Putative two-component system transcriptional response regulator | LGDASLIQTVR | SEQ ID NO: 715 |
| Q5F4X2 | Putative uncharacterized protein | VQWLDPVPEVLR | SEQ ID NO: 716 |
| Q5F537 | Putative uncharacterized protein | FGVIQTGLQLQGKPQSAPPTQK | SEQ ID NO: 717 |
| Q5F573 | Putative uncharacterized protein | AAAEHPLSVQNEER | SEQ ID NO: 718 |
| Q5F573 | Putative uncharacterized protein | KVNINIPFPQR | SEQ ID NO: 719 |
| Q5F5A6 | Putative uncharacterized protein | IVIMAALNVVHDLLK | SEQ ID NO: 720 |
| Q5F5E4 | Putative uncharacterized protein | SEQAAEGVYNYITVASLPR | SEQ ID NO: 721 |
| Q5F5P4 | Putative uncharacterized protein | QGDTLWGISGK | SEQ ID NO: 722 |
| Q5F5P4 | Putative uncharacterized protein | YLYSPWQWCR | SEQ ID NO: 723 |
| Q5F5P4 | Putative uncharacterized protein | LWGANRDQIHNPDLIYPGQVLVLR | SEQ ID NO: 724 |
| Q5F5P4 | Putative uncharacterized protein | DQIHNPDLIYPGQVLVLR | SEQ ID NO: 725 |
| Q5F5P4 | Putative uncharacterized protein | ISPDKEVSGYGIPAIDVNFYR | SEQ ID NO: 726 |
| Q5F5P4 | Putative uncharacterized protein | VFMQHPQIVSR | SEQ ID NO: 727 |
| Q5F5P4 | Putative uncharacterized protein | VFMQHPQIVSRK | SEQ ID NO: 728 |
| Q5F5P4 | Putative uncharacterized protein | VFMQHPQIVSRKETAAAPR | SEQ ID NO: 729 |
| Q5F5P4 | Putative uncharacterized protein | LLSGPEGR | SEQ ID NO: 730 |
| Q5F5P4 | Putative uncharacterized protein | INKNITDPDTGKFLGQEVARSGIVR | SEQ ID NO: 731 |
| Q5F5P4 | Putative uncharacterized protein | NITDPDTGKFLGQEVAFSGIVR | SEQ ID NO: 732 |
| Q5F5P4 | Putative uncharacterized protein | FLGQEVAFSGIVR | SEQ ID NO: 733 |
| Q5F5P4 | Putative uncharacterized protein | SLDYTDSALEQR | SEQ ID NO: 734 |
| Q5F5P4 | Putative uncharacterized protein | LKDNEYYTR | SEQ ID NO: 735 |
| Q5F5P4 | Putative uncharacterized protein | SIQPLVVETAISEIQQGDYLMK | SEQ ID NO: 736 |

TABLE 1-continued

UniProtA

| C | Desc | Peptide | SEQ ID NO: |
|---|---|---|---|
| Q5F5P4 | Putative uncharacterized protein | IVSVFEGVGVGGQFK | SEQ ID NO: 737 |
| Q5F5P4 | Putative uncharacterized protein | TTTIDKGGDDGLDKGAVLSLYKR | SEQ ID NO: 738 |
| Q5F5P4 | Putative uncharacterized protein | KKTMQVNLSNNLTEEPK | SEQ ID NO: 739 |
| Q5F5P4 | Putative uncharacterized protein | TMQVNLSNNLTEEPK | SEQ ID NO: 740 |
| Q5F5P4 | Putative uncharacterized protein | SRDTVELISTPAEEVGLAMVYHTAPK | SEQ ID NO: 741 |
| Q5F5P4 | Putative uncharacterized protein | DTVELISTPAEEVGLAMVYHTAPK | SEQ ID NO: 742 |
| Q5F5P4 | Putative uncharacterized protein | DLDNMPDQGR | SEQ ID NO: 743 |
| Q5F5W7 | Putative uncharacterized protein | IYLESKQARNIQK | SEQ ID NO: 744 |
| Q5F653 | Putative uncharacterized protein | TILHAPDKQSLTYK | SEQ ID NO: 745 |
| Q5F6A2 | Putative uncharacterized protein | LLTAGPNLLPDNPER | SEQ ID NO: 746 |
| Q5F6A4 | Putative uncharacterized protein | IDSSVIDAQVAAFR | SEQ ID NO: 747 |
| Q5F6A4 | Putative uncharacterized protein | AEDTPQLR | SEQ ID NO: 748 |
| Q5F6A4 | Putative uncharacterized protein | QSLLENEVVNTVVAQEVKR | SEQ ID NO: 749 |
| Q5F6A4 | Putative uncharacterized protein | SAEFKDALAK | SEQ ID NO: 750 |
| Q5F6A4 | Putative uncharacterized protein | KSGDDKKPSFK | SEQ ID NO: 751 |
| Q5F6K2 | Putative uncharacterized protein | VAPKPTPEQILNSGSIEK | SEQ ID NO: 752 |
| Q5F6M9 | Putative uncharacterized protein | AATPGVYTFILQATK | SEQ ID NO: 753 |
| Q5F6R9 | Putative uncharacterized protein | SAKNNGNVQR | SEQ ID NO: 754 |
| Q5F6V1 | Putative uncharacterized protein | RIMVGKNK | SEQ ID NO: 755 |
| Q5F755 | Putative uncharacterized protein | FKPLALGIDQDLIAALPQYDSALIAR | SEQ ID NO: 756 |
| Q5F7C9 | Putative uncharacterized protein | AGATDSEIAGALATAIALNAGAAYTYALR | SEQ ID NO: 757 |
| Q5F7C9 | Putative uncharacterized protein | ALEAVETQK | SEQ ID NO: 758 |
| Q5F7D9 | Putative uncharacterized protein | TEQETLQTIPSPK | SEQ ID NO: 759 |
| Q5F7E1 | Putative uncharacterized protein | VVFVSIDPERDTPEIIGK | SEQ ID NO: 760 |
| Q5F7E1 | Putative uncharacterized protein | QFNPDFIGLTATGGQNLPVIK | SEQ ID NO: 761 |

TABLE 1-continued

| UniProtA | | | |
|---|---|---|---|
| C | Desc | Peptide | SEQ ID NO: |
| Q5F7E4 | Putative uncharacterized protein | IVALVTVKPEYTETLAAQFKELVK | SEQ ID NO: 762 |
| Q5F7F5 | Putative uncharacterized protein | SVQINGQAAKP | SEQ ID NO: 763 |
| Q5F7W0 | Putative uncharacterized protein | VKPAGYAAPK | SEQ ID NO: 764 |
| Q5F7W0 | Putative uncharacterized protein | TAAVESRPAVPAAAQTPVKPAAQPPVQSAPQPAAPAAENK | SEQ ID NO: 765 |
| Q5F7W0 | Putative uncharacterized protein | AVPAPAPAPQSPAASPSGTR | SEQ ID NO: 766 |
| 5F7W0 | Putative uncharacterized protein | SVGGIVWQRPTQGK | SEQ ID NO: 767 |
| Q5F7X2 | Putative uncharacterized protein | ASAEEAVTEAK | SEQ ID NO: 768 |
| Q5F7X2 | Putative uncharacterized protein | ASAEEAVTEAKDAAAETK | SEQ ID NO: 769 |
| Q5F7X2 | Putative uncharacterized protein | ASAEEAVTEAKDAAAETKEAVSEAAKDTLNK | SEQ ID NO: 770 |
| Q5F7X2 | Putative uncharacterized protein | EAVSEAAKDTLNK | SEQ ID NO: 771 |
| Q5F7X2 | Putative uncharacterized protein | EAVSEAAKDTLNKAADAAQEAADKMKDAAK | SEQ ID NO: 772 |
| Q5F7X2 | Putative uncharacterized protein | AADAAQEAADKMK | SEQ ID NO: 773 |
| Q5F7X2 | Putative uncharacterized protein | AADAAQEAADKMKDAAK | SEQ ID NO: 774 |
| Q5F839 | Putative uncharacterized protein | HLVVAVDGSETSINALK | SEQ ID NO: 775 |
| Q5F839 | Putative uncharacterized protein | HAAELAGVNGAR | SEQ ID NO: 776 |
| Q5F839 | Putative uncharacterized protein | LTLVHVANPAEYMALAPEFLQHESYEAAAVAQGNEVLDAAER | SEQ ID NO: 777 |
| Q5F848 | Putative uncharacterized protein | TPAVQQPADAEVLK | SEQ ID NO: 778 |
| Q5F848 | Putative uncharacterized protein | KPTLPAANEMAR | SEQ ID NO: 779 |
| Q5F848 | Putative uncharacterized protein | APNESNAVTEQKPGLFKR | SEQ ID NO: 780 |
| Q5F883 | Putative uncharacterized protein | LRVEAQR | SEQ ID NO: 781 |
| Q5F884 | Putative uncharacterized protein | NILLPLATEHGQIAR | SEQ ID NO: 782 |
| Q5F884 | Putative uncharacterized protein | AALAGSNIDPIAFER | SEQ ID NO: 783 |
| Q5F885 | Putative uncharacterized protein | IAKDEPDMPRPK | SEQ ID NO: 784 |
| Q5F8C2 | Putative uncharacterized protein | LFDEHNELDDKITGLANNPVTSGAETIDELKK | SEQ ID NO: 785 |
| Q5F8C2 | Putative uncharacterized protein | LKLKDELYAILQK | SEQ ID NO: 786 |

TABLE 1-continued

| UniProtA | | | |
|---|---|---|---|
| C | Desc | Peptide | SEQ ID NO: |
| Q5F8C4 | Putative uncharacterized protein | ANENSPNIYFIR | SEQ ID NO: 787 |
| Q5F8D7 | Putative uncharacterized protein | IDDLGSTVQGR | SEQ ID NO: 788 |
| Q5F8D7 | Putative uncharacterized protein | LLDSQDPTAR | SEQ ID NO: 789 |
| Q5F8D7 | Putative uncharacterized protein | ATFYIVPNMNPDGSALGNLR | SEQ ID NO: 790 |
| Q5F8Q1 | Putative uncharacterized protein | SPIAFFNALSQK | SEQ ID NO: 791 |
| Q5F8Q1 | Putative uncharacterized protein | IVPTNHADSNTGLVR | SEQ ID NO: 792 |
| Q5F8T2 | Putative uncharacterized protein | NLDKTQAAAER | SEQ ID NO: 793 |
| Q5F8T2 | Putative uncharacterized protein | AAEQTGNAVEKGWDK | SEQ ID NO: 794 |
| Q5F8T2 | Putative uncharacterized protein | AAEQTGNAVEKGWDKTK | SEQ ID NO: 795 |
| Q5F8T2 | Putative uncharacterized protein | AAEQTGNAVEKGWDKTKEAVK | SEQ ID NO: 796 |
| Q5F8T2 | Putative uncharacterized protein | AAEQTGNAVEKGWDKTKEAVKK | SEQ ID NO: 797 |
| Q5F933 | Putative uncharacterized protein | AAVAAATNDVENKK | SEQ ID NO: 798 |
| Q5F933 | Putative uncharacterized protein | KQGVTDAAEQTESR | SEQ ID NO: 799 |
| Q5F933 | Putative uncharacterized protein | QGVTDAAEQTESR | SEQ ID NO: 800 |
| Q5F987 | Putative uncharacterized protein | LKQPRRR | SEQ ID NO: 801 |
| Q5F9G1 | Putative uncharacterized protein | GVAVINHPNPLQGGTNTNK | SEQ ID NO: 802 |
| Q5F9H4 | Putative uncharacterized protein | LNFGQIGSHIAGDGAVR | SEQ ID NO: 803 |
| Q5F9S3 | Putative uncharacterized protein | LGSLQEQRAPR | SEQ ID NO: 804 |
| Q5FAB8 | Putative uncharacterized protein | NAVDIGSKPNADVAWK | SEQ ID NO: 805 |
| Q5FAB8 | Putative uncharacterized protein | NKPAGIISHSVGK | SEQ ID NO: 806 |
| Q5FA46 | Putative zinc-binding alcohol dehydrogenas | VGQHVVVEPYIIRDDVPTGEGSNYHLSK | SEQ ID NO: 807 |
| Q5FA46 | Putative zinc-binding alcohol dehydrogenas | DMNFIGLGGCGGGLSEK | SEQ ID NO: 808 |
| Q5FA46 | Putative zinc-binding alcohol dehydrogenas | AGDVALVGGAGPIGLLLAAVLK | SEQ ID NO: 809 |
| Q5FA46 | Putative zinc-binding alcohol dehydrogenas | IKLDKLVSEGFER | SEQ ID NO: 810 |
| Q5FA46 | Putative zinc-binding alcohol dehydrogenas | LIHNNESAVK | SEQ ID NO: 811 |

TABLE 1-continued

| UniProtAC | Desc | Peptide | SEQ ID NO: |
|---|---|---|---|
| Q5F939 | Pyruvate dehydrogenase E1 component | AQYLLENLLK | SEQ ID NO: 812 |
| Q5F939 | Pyruvate dehydrogenase E1 component | MPHGTTTPYLNTVSVENEK | SEQ ID NO: 813 |
| Q5F939 | Pyruvate dehydrogenase E1 component | LTEDQLNNFR | SEQ ID NO: 814 |
| Q5F939 | Pyruvate dehydrogenase E1 component | EGLDNLIFVINCNLQR | SEQ ID NO: 815 |
| Q5F939 | Pyruvate dehydrogenase E1 component | IIQELEGNFAGAGWNVVK | SEQ ID NO: 816 |
| Q5F939 | Pyruvate dehydrogenase E1 component | LLAKDKDGILR | SEQ ID NO: 817 |
| Q5F939 | Pyruvate dehydrogenase E1 component | DGAYVREHFFNTPELK | SEQ ID NO: 818 |
| Q5F939 | Pyruvate dehydrogenase E1 component | ALVADMTDEQLWALNR | SEQ ID NO: 819 |
| Q5F939 | Pyruvate dehydrogenase E1 component | GGHDPQKVYNAYDR | SEQ ID NO: 820 |
| Q5F939 | Pyruvate dehydrogenase E1 component | AANHADGKPTVILAK | SEQ ID NO: 821 |
| Q5F939 | Pyruvate dehydrogenase E1 component | TIKGYGMGASGEGQNVAHQAK | SEQ ID NO: 822 |
| Q5F939 | Pyruvate dehydrogenase E1 component | GYGMGASGEGQNVAHQAK | SEQ ID NO: 823 |
| Q5F939 | Pyruvate dehydrogenase E1 component | ASLKQFR | SEQ ID NO: 824 |
| Q5F939 | Pyruvate dehydrogenase E1 component | RDALGGYLPQR | SEQ ID NO: 825 |
| Q5F939 | Pyruvate dehydrogenase E1 component | DALGGYLPQR | SEQ ID NO: 826 |
| Q5F939 | Pyruvate dehydrogenase E1 component | KPTQEVLEVPELSAFDAQLK | SEQ ID NO: 827 |
| Q5F939 | Pyruvate dehydrogenase E1 component | SSGEREFSTTMAFVR | SEQ ID NO: 828 |
| Q5F939 | Pyruvate dehydrogenase E1 component | ILSTLLKDKK | SEQ ID NO: 829 |
| Q5F939 | Pyruvate dehydrogenase E1 component | TFGMEGMFR | SEQ ID NO: 830 |
| Q5F939 | Pyruvate dehydrogenase E1 component | GQQYTPQDKDQLMFYK | SEQ ID NO: 831 |
| Q5F939 | Pyruvate dehydrogenase E1 component | IGDLAWAAGDMHAR | SEQ ID NO: 832 |
| Q5F939 | Pyruvate dehydrogenase E1 component | KVQLMGSGTILQEVIAGAELLK | SEQ ID NO: 833 |
| Q5F939 | Pyruvate dehydrogenase E1 component | VQLMGSGTILQEVIAGAELLK | SEQ ID NO: 834 |
| Q5F939 | Pyruvate dehydrogenase E1 component | ADFGVEADIWSCPSFNLLHR | SEQ ID NO: 835 |
| Q5F939 | Pyruvate dehydrogenase E1 component | LHPLEAEKVPFVTSQLQGHDGPVIAATDYIR | SEQ ID NO: 836 |

TABLE 1-continued

| C | Desc | Peptide | SEQ ID NO: |
|---|---|---|---|
| | UniProtA | | |
| Q5F939 | Pyruvate dehydrogenase E1 component | VPFVTSQLQGHDGPVIAATDYIR | SEQ ID NO: 837 |
| Q5F939 | Pyruvate dehydrogenase E1 component | AYIPNDYHVLGTDGFGR | SEQ ID NO: 838 |
| Q5F939 | Pyruvate dehydrogenase E1 component | FFEVDRYNVAVAALAALAEQGK | SEQ ID NO: 839 |
| Q5F939 | Pyruvate dehydrogenase E1 component | YNVAVAALAALAEQGK | SEQ ID NO: 840 |
| Q5F939 | Pyruvate dehydrogenase E1 component | YNVAVAALAALAEQGKVSK | SEQ ID NO: 841 |
| Q5F939 | Pyruvate dehydrogenase E1 component | VSKETVQQAIEK | SEQ ID NO: 842 |
| Q5F939 | Pyruvate dehydrogenase E1 component | YGIKADSAPSWK | SEQ ID NO: 843 |
| Q5F939 | Pyruvate dehydrogenase E1 component | YGIKADSAPSWKR | SEQ ID NO: 844 |
| Q5F939 | Pyruvate dehydrogenase E1 component | ADSAPSWKR | SEQ ID NO: 845 |
| Q5F5N5 | Pyruvate kinase | IVATLGPGSNNVELLEDMIR | SEQ ID NO: 846 |
| Q5F5N5 | Pyruvate kinase | VGGLNVVR | SEQ ID NO: 847 |
| Q5F5N5 | Pyruvate kinase | FNFSHGTPEFHQENAR | SEQ ID NO: 848 |
| Q5F5N5 | Pyruvate kinase | GGGLSAGALTEKDFR | SEQ ID NO: 849 |
| Q5F5N5 | Pyruvate kinase | GSTAVRPGLVSK | SEQ ID NO: 850 |
| Q5F5N5 | Pyruvate kinase | GDLAVEVGHAAVPALQK | SEQ ID NO: 851 |
| Q5F5N5 | Pyruvate kinase | HNITLPIFALTPSVSAQR | SEQ ID NO: 852 |
| Q5F9F5 | Ribose-phosphate pyrophosphokinase | FSDGEVAVELLENVR | SEQ ID NO: 853 |
| Q5F9F5 | Ribose-phosphate pyrophosphokinase | SVRVPISAK | SEQ ID NO: 854 |
| Q5F9F5 | Ribose-phosphate pyrophosphokinase | LVANMLYSAGIDR | SEQ ID NO: 855 |
| Q5F9F5 | Ribose-phosphate pyrophosphokinase | ANVAEVMNIIGDIQGK | SEQ ID NO: 856 |
| Q5F9F5 | Ribose-phosphate pyrophosphokinase | IASSEIDQVVVTDTIPLSEAAK | SEQ ID NO: 857 |
| Q5F9F5 | Ribose-phosphate pyrophosphokinase | QATIAGLLAETVR | SEQ ID NO: 858 |
| Q5F666 | Signal recognition particle protein | ILGMGDVLTLIEDVQK | SEQ ID NO: 859 |
| Q5F666 | Signal recognition particle protein | IAMGAGTTVQEVNK | SEQ ID NO: 860 |
| Q5F666 | Signal recognition particle protein | IAMGAGTTVQEVNKLLK | SEQ ID NO: 861 |

TABLE 1-continued

| UniProtA | | | |
|---|---|---|---|
| C | Desc | Peptide | SEQ ID NO: |
| Q5F7Y0 | Single-stranded DNA-binding protein | NENSGGAPYDEGYGQSQEAYQRPAQQSR | SEQ ID NO: 862 |
| Q5F7Y0 | Single-stranded DNA-binding protein | QPAPDAPSHPQEAPAAPR | SEQ ID NO: 863 |
| Q5F879 | Succinyl-CoA ligase [ADP-forming] subunit alpha | SVLINKDTK | SEQ ID NO: 864 |
| Q5F879 | Succinyl-CoA ligase [ADP-forming] subunit alpha | NGTFHSEQALAYGTK | SEQ ID NO: 865 |
| Q5F879 | Succinyl-CoA ligase [ADP-forming] subunit alpha | LVGPNCPGVITPGECK | SEQ ID NO: 866 |
| Q5F879 | Succinyi-CoA ligase [ADP-forming] subunit alpha | IGIMPGHIHTPGR | SEQ ID NO: 867 |
| Q5F879 | Succinyi-CoA ligase [ADP-forming] subunit alpha | MGHAGAIISGGK | SEQ ID NO: 868 |
| Q5F879 | Succinyi-CoA ligase [ADP-forming] subunit alpha | SPAELGTTMLEVLK | SEQ ID NO: 869 |
| Q5F5R0 | Transcription anti termination protein nusG | ANRPTPISQR | SEQ ID NO: 870 |
| Q5FA35 | Transcription termination factor Rho | DLKSEENLTGR | SEQ ID NO: 871 |
| Q5FA35 | Transcription termination factor Rho | AYNTVVPASGK | SEQ ID NO: 872 |
| Q5FA35 | Transcription termination factor Rho | ILTGGVDANALHRPK | SEQ ID NO: 873 |
| Q5F7X0 | Tryptophan-tRNA ligase | VLTGVTTTGTPHLGNYVGAIRPAVR | SEQ ID NO: 874 |
| Q5F7X0 | Tryptophan-tRNA ligase | YNALTSNPSQIEEILQAGAQK | SEQ ID NO: 875 |
| Q5F5L5 | Twitching motility/pilus retraction protein | MQITDLLAFGAK | SEQ ID NO: 876 |
| Q5F5L5 | Twitching motility/pilus retraction protein | NKASDLHLSSGISPMIR | SEQ ID NO: 877 |
| Q5F5L5 | Twitching motility/pilus retraction protein | ASDLHLSSGISPMIR | SEQ ID NO: 878 |
| Q5F5L5 | Twitching motility/pilus retraction protein | FRVNAFNTGR | SEQ ID NO: 879 |
| Q5F5L5 | Twitching motility/pilus retraction protein | TIPSTVLSLEELKAPSIFQK | SEQ ID NO: 880 |
| Q5F5L5 | Twitching motility/pilus retraction protein | KSLINQR | SEQ ID NO: 881 |
| Q5F5L5 | Twitching motility/pilus retraction protein | SMLSESLTAVISQNLLK | SEQ ID NO: 882 |
| Q5F5L5 | Twitching motility/pilus retraction protein | VASHEILIANPAVR | SEQ ID NO: 883 |

REFERENCES

This application refers to various issued patents, published patent applications, journal articles, and other publications, all of which are incorporated herein by reference in their entirety.

U.S. Patent Application Number 20080305157

Richard et. al., Clinical and Vaccine Immunology; 2014, 21(2):212

Alexander, J.; Del Guercio, M.-F.; Macwal, A.; Qiao, L.; Fikes, J.; Chesnut, R. W.; Paulson, J.; Bundle, D. R.; DeFrees, S.; Sette, A., Linear PADRE T helper epitope and carbohydrate B cell epitope conjugates induce specific high titer IgG antibody responses. J Immunol. 2000, 164 (3), 1625-1633.

Alnemri E S. 2010. Sensing cytoplasmic danger signals by the inflammasome. J. Clin. Immunol. 30:512-519. http://dx.doi.org/10.1007/s 10875-010-9419-0.

Alving, C. R., Lipopolysaccharide, lipid A, and liposomes containing lipid A as immunologic adjuvants. Immunobiology 1993, 187 (3-5), 430-46.

Alving, C. R.; Rao, M., Lipid A and liposomes containing lipid A as antigens and adjuvants. Vaccine 2008, 26 (24), 3036-3045.

Anderson, G. W.; Zimmerman, J. E.; Callahan, F. M., N-Hydroxysuccinimide esters in peptide synthesis. J Am. Chem. Soc. 1963, 85 (19), 3039.

Asare R, Kwaik Y A. 2010. Exploitation of host cell biology and evasion of immunity by *Francisella tularensis*. Front. Microbiol. 1:145. http://dx.doi.org/10.3389/fmicb.2010.00145.

Ashtekar A R, Katz J, Xu Q, Michalek S M. 2012. A mucosal subunit vaccine protects against lethal respiratory infection with *Francisella tularensis* LVS. PLoS One 7:e50460. http://dx.doi.org/10.1371/journal.pone.0050460.

Augustyniak, D.; Mleczko, J.; Gutowicz, J., The immunogenicity of the liposomeassociated outer membrane proteins (OMPs) of *Moraxella catarrhalis*. Cell Mol Biol Lett 2010, 15 (1), 70-89.

Baron S D. Singh R Metzger D W. 2007. Inactivated *Francisella tularensis* live vaccine strain protects against respiratory tularemia by intranasal vaccination in an immunoglobulin A-dependent fashion. Infect. Immun. 75: 2152-2162. http://dx.doi.org/10.1128/IAI.01606-06.

Barratt, G., Colloidal drug carriers: Achievements and perspectives. Cell. Mol. Life Sci. 2003, 60 (1), 21-37.

Barrigan L M, Tuladhar S, Brunton J C, Woolard M D, Chen C J, Saini D, Frothingham R, Sempowski G D, Kawula T H, Frelinger J A. 2013. Infection with *Francisella tularensis* live vaccine strain clpB leads to an altered yet protective immune response. Infect. Immun. 81:2028-2042. http://dx.doi.org/10.1128/IAI.00207-13.

Barry E M, Cole L E, Santiago A E. 2009. Vaccines against tularemia. Hum. Vaccin. 5:832-838.

Bergsbaken T, Fink S L, Cookson B T. 2009. Pyroptosis: host cell death and inflammation. Nat. Rev. Microbiol. 7:99-109. http://dx.doi.org/10.1038/nrmicro2070.

Bjune, G.; Hoiby, E. A.; Gronnesby, J. K.; Arnesen, 0.; Fredriksen, J. H.; Halstensen, A.; Holten, E.; Lindbak, A. K.; Nokleby, H.; Rosenqvist, E.; et al., Effect of outer membrane vesicle vaccine against group B meningococcal disease in Norway. Lancet 1991, 338 (8775), 1093-6.

Bouma, S. R.; Drislane, F. W.; Huestis, W. H., Selective extraction of membranebound proteins by phospholipid vesicles. J Biol Chem 1977, 252 (19), 6759-63.

Cartwright, K.; Morris, R.; Rumke, H.; Fox, A.; Borrow, R.: Begg, N.; Richmond, P.; Poolman, J., Immunogenicity and reactogenicity in UK infants of a novel meningococcal vesicle vaccine containing multiple class 1 (PorA) outer membrane proteins. Vaccine 1999, 17 (20-21), 2612-9.

Celli J, Zahrt T C. 2013. Mechanisms of *Francisella tularensis* intracellular pathogenesis. Cold Spring Harb. Perspect. Med. 3:a010314. http://dx.doi.org/10.1101/cshperspect.a010314.

Chen W, KuoLee R, Shen H, Bùsa M, Conlan J W. 2004. Toll-like receptor 4 (TLR4) does not confer a resistance advantage on mice against low-dose aerosol infection with virulent type A *Francisella tularensis*. Microb. Pathog. 37:185-191. http://dx.doi.org/10.1016/j.micpath.2004.06.010.

Chen W. Shen H, Webb A, KuoLee R, Conlan J W. 2003. Tularemia in BALB/c and C57B L/6 mice vaccinated with *Francisella tularensis* LVS and challenged intradermally, or by aerosol with virulent isolates of the pathogen: protection varies depending on pathogen virulence, route of exposure, and host genetic background. Vaccine 21:3690-3700. http://dx.doi.org/10.1016/S0264-410X (03)00386-4.

Cheng. Z.; Al Zaki, A.; Hui, J. Z.; Muzykantov. V. R.; Tsourkas, A., Multifunctional nanoparticles: Cost versus benefit of adding targeting and imaging capabilities. Science 2012, 338 (6109), 903-910.

Chevallet, M.; Luche, S.; Rabilloud, T., Silver staining of proteins in polyacrylamide gels. Nat. Protoc. 2006, 1 (4), 1852-1858.

Choksawangkam, W.; Kim, S.-K.; Cannon Joe, R.; Edwards Nathan, J.; Lee Sang, B.; Fenselau, C., Enrichment of plasma membrane proteins using nanoparticle pellicles: comparison between silica and higher density nanoparticles. J Proteome Res 2013.

Clay C D, Soni S, Gunn J S, Schlesinger L S. 2008. Evasion of complement-mediated lysis and complement C3 deposition are regulated by *Francisella tularensis* lipopolysaccharide O antigen. J. Immunol. 181: 5568-5578.

Clemens D L. Lee B Y, Horwitz M A. 2004. Virulent and avirulent strains of *Francisella tularensis* prevent acidification and maturation of their phagosomes and escape into the cytoplasm in human macrophages. Infect. Immun. 72:3204-3217. http://dx.doi.org/10.1128/AI.72.6.3204-3217.2004.

Cole L E, Elkins K L, Michalek S M, Qureshi N, Eaton L J, Rallabhandi P, Cuesta N, Vogel S N. 2006. Immunologic consequences of *Francisella tularensis* live vaccine strain infection: role of the innate immune response in infection and immunity. J. Immunol. 176:6888-6899.

Cole L E, Mann B J, Shirey K A, Richard K, Yang Y, Gearhart P J, Chesko K L, Viscardi R M, Vogel S N. 2011. Role of TLR signaling in *Francisella tularensis*-LPS-induced, antibody-mediated protection against *Francisella tularensis* challenge. J. Leukoc. Biol. 90:787-797. http://dx.doi.org/10.1189/jlb.0111014.

Cole L E, Santiago A, Barry E, Kang T J, Shirey K A, Roberts Z J, Elkins K L, Cross A S, Vogel S N. 2008. Macrophage proinflammatory response to *Francisella tularensis* live vaccine strain requires coordination of multiple signaling pathways. J. Immunol. 180:6885-6891.

Cole L E, Shirey K A, Barry E, Santiago A, Rallabhandi P, Elkins K L, Puche A C, Michalek S M, Vogel S N. 2007. Toll-like receptor 2-mediated signaling requirements for *Francisella tularensis* live vaccine strain infection of murine macrophages. Infect. Immun. 75:4127-4137. http://dx.doi.org/10.1128/IAI.01868-06.

Cole L E, Yang Y, Elkins K L, Fernandez E T, Qureshi N, Shlomchik M J, Herzenberg L A, Herzenberg L A. Vogel S N. 2009. Antigen-specific B-1a antibodies induced by *Francisella tularensis* LPS provide long-term protection against *F. tularensis* LVS challenge. Proc. Natl. Acad. Sci. U.S.A. 106:4343-4348. http://dx.doi.org/10.1073/pnas.0813411106.

Conlan J W, Chen W, Bosio C M, Cowley S C, Elkins K L. 2011. Infection of mice with *Francisella* as an immunological model. Curr. Protoc. Immunol. Chapter 19:Unit 19.14. http://dx.doi.org/10.1002/0471142735.im1914s93.

Conlan J W, Shen H, Golovliov I, Zingmark C, Oyston P C, Chen W, House R V, Sjöstedt A. 2010. Differential ability of novel attenuated targeted deletion mutants of *Francisella tularensis* subspecies *tularensis* strain SCHU S4 to protect mice against aerosol challenge with virulent bacteria: effects of host background and route of immunization. Vaccine 28:1824-1831. http://dx.doi.org/10.1016/j.vaccine.2009.12.001.

Corbel, M. J., Reasons for instability of bacterial vaccines. Dev. Biol. Stand. 1996, 87, 113-124.

Cowley S C, Elkins K L. 2011. Immunity to *Francisella*. Front. Microbiol. 2:26. http://dx.doi.org/10.3389/fmicb.2011.00026.

Crane D D, Warner S L, Bosio C M. 2009. A novel role for plasmid mediated degradation of opsonizing antibody in evasion of host immunity by virulent, but not attenuated, *Francisella tularensis*. J. Immunol. 183: 4593-4600. http://dx.doi.org/10.4049/jimmunol.0901655.

Cremer T J, Amer A, Tridandapani S, Butchar J P. 2009. *Francisella tularensis* regulates autophagy-related host cell signaling pathways. Autophagy 5:125-128. http://dx.doi.org/10.4161/auto.5.1.7305.

Daghastanli Katia, R. P.; Ferreira Rinaldo, B.; Thedei, G., Jr.; Maggio, B.; Ciancaglini, P., Lipid composition-dependent incorporation of multiple membrane proteins into liposomes. Colloids SuifB Biointeifaces 2004, 36 (3-4), 127-37.

Danoff E J, Wang X, Tung S H, Sinkov N A, Kemme A M, Raghavan S R. English D S. 2007. Surfactant vesicles for high-efficiency capture and separation of charged organic solutes. Langmuir 23:8965-8971. http://dx.doi.org/10.1021/la070215n.

de Moreno M R, Smith J F, Smith R V. 1985. Silver staining of proteins in polyacrylamide gels: increased sensitivity through a combined Coomassie blue-silver stain procedure. Anal. Biochem. 151:466-470. http://dx.doi.org/10.1016/0003-2697(85)90206-4.

De Pascalis R, Chou A Y. Bosio C M, Huang C Y, Follmann D A, Elkins K L. 2012. Development of functional and molecular correlates of vaccine-induced protection for a model intracellular pathogen, *F. tularensis* LVS. PLoS Pathog. 8:e1002494. http://dx.doi.org/10.1371/journal.ppat.1002494.

Denes A, Lopez-Castejon G, Brough D. 2012. Caspase-1: is IL-1 just the tip of the ICEberg? Cell Death Dis. 3:e338. http://dx.doi.org/10.1038/cddis.2012.86.

Dijkstra, J.; Mellors, J. W.; Ryan, J. L., Altered in vivo activity of liposome incorporated lipopolysaccharide and lipid A. Infect. Immun. 1989, 57 (11). 3357-63.

Dreisenbach V, Cowley S, Elkins K L. 2000. Purified lipopolysaccharide from *Francisella tularensis* live vaccine strain (LVS) induces protective immunity against LVS infection that requires B cells and gamma interferon. Infect. Immun. 68:1988-1996. http://dx.doi.org/10.1128/IA1.68.4.1988-1996.2000.

Dueñas A I, Aceves M, Orduña A, Díaz R, Sánchez Crespo M, García-Rodríguez C. 2006. *Francisella tularensis* LPS induces the production of cytokines in human monocytes and signals via Toll-like receptor 4 with much lower potency than *E. coli* LPS. Int. Immunol. 18:785-795. http://dx.doi.org/10.1093/intimm/dx1015.

Eigelsbach H T, Braun W, Herring R D. 1951. Studies on the variation of Bacterium tularense. J. Bacteriol. 61:557-569.

Elkins K L, Colombini S M, Meierovics A I, Chu M C, Chou A Y, Cowley S C. 2010. Survival of secondary lethal systemic *Francisella* LVS challenge depends largely on interferon gamma. Microbes Infect. 12:28-36. http://dx.doi.org/10.1016/j.micinf.2009.09.012.

Elkins K L, Cowley S, BosioCM.2003. Innate and adaptive immunoresponses to an intracellular bacterium, *Francisella tularensis* live vaccine strain. Microbes Infect. 5:135-142. http://dx.doi.org/10.1016/S1286-4579(02)00084-9.

Ellis, T. N.; Kuehn, M. J., Virulence and immunomodulatory roles of bacterial outer membrane vesicles. Microbial. Mol. Biol. Rev. 2010, 74 (1), 81-94.

Faraji, A. H.; Wipf, P., Nanoparticles in cellular drug delivery. Bioorg. Med. Chem. 2009, 17 (8), 2950-2962, 134

Foley J E, Nieto N C. 2010. Tularemia. Vet. Microbiol. 140:332-338. http://dx.doi.org/10.1016/j.vetmic.2009.07.017.

Forestal C A, Malik M, Catlett S V, Savitt A G, Benach J L, Sellati T J, Furie M B. 2007. *Francisella tularensis* has a significant extracellular phase in infected mice. J. Infect. Dis. 196:134-137. http://dx.doi.org/10.1086/518611.

Forssen, E. A.; Ross, M. E., Daunoxome treatment of solid tumors: Preclinical and clinical investigations. J Liposome Res. 1994, 481-512.

Foster, K. A.; Gorringe, A. R.; Hudson, M. J.; Reddin, K. M.: Robinson, A. Preparation of outer membrane vesicles from Gram negative bacteria and uses thereof as vaccines. 2002-GB57182003051379, 20021217, 2003.

Girard, P.; Pecreaux, J.; Lenoir, G.; Faison, P.; Rigaud, J.-L.: Bassereau, P., A new method for the reconstitution of membrane proteins into giant unilamellar vesicles. Biophys. J 2004, 87 (1), 419-429.

Golovliov I, Baranov V, Krocova Z, Kovarova H, Sjöstedt A. 2003. An attenuated strain of the facultative intracellular bacterium *Francisella tularensis* can escape the phagosome of monocytic cells. Infect. Immun. 71:5940-5950. http://dx.doi.org/10.1128/IA1.71.10.5940-5950.2003.

Gregoriadis, G.; Leathwood, P. D.; Ryman, B. E., Enzyme entrapment in liposomes. FEBS Letters 1971, 14 (2), 95-9.

Gregory A E, Titball R, Williamson D. 2013. Vaccine delivery using nanoparticles. Front. Microbiol. 3:13. http://dx.doi.org/10.3389/fcimb.2013.00013.

Gupta. R. K.; Siber, G. R., Adjuvants for human vaccines-current status, problems and future prospects. Vaccine 1995, 13 (14), 1263-76.

Hajjar A M, Harvey M D. Shaffer S A, Goodlett D R, Sjostedt A, Edebro H, Forsman M, Byström M, Pelletier M, Wilson C B, Miller S I, Skerrett S J, Ernst R K. 2006. Lack of in vitro and in vivo recognition of *Francisella tularensis* subspecies lipopolysaccharide by Toll-like receptors. Infect. Immun. 74:6730-6738. http://dx.doi.org/10.1128/IAI.00934-06.

Harris J, Sharp F A, Lavelle E C. 2010. The role of inflammasomes in the immunostimulatory effects of particulate vaccine adjuvants. Eur. J. Immunol. 40:634-638. http://dx.doi.org10.1002/eji.200940172.

Hartley G, Taylor R, Prior J, Newstead S, Hitchen P G, Morris H R, Dell A, Titball R W. 2006. Grey variants of the live vaccine strain of *Francisella tularensis* lack lipopolysaccharide O-antigen, show reduced ability to survive in macrophages and do not induce protective immunity in mice. Vaccine 24:989-996. http://dx.doi.org/10.1016/j.vaccine.2005.08.075.

Henry T, Brotcke A, Weiss D S, Thompson L J, Monack D M. 2007. Type I interferon signaling is required for activation of the inflammasome during *Francisella* infection. J. Exp. Med. 204:987-994. http://dx.doi.org/10.1084/jem.20062665.

Hickey A J, Hazlett K R, Kirimanjeswara G S, Metzger D W. 2011. Identification of *Francisella tularensis* outer membrane protein A (FopA) as a protective antigen for tularemia. Vaccine 29:6941-6947. http://dx.doi.org/10.1016/j.vaccine.2011.07.075.

Hoist, J.; Martin, D.; Arnold, R.; Huergo, C. C.; Oster, P.; O'Hallahan, J.; Rosenqvist, E., Properties and clinical performance of vaccines containing outer membrane vesicles from *Neisseria meningitidis*. Vaccine 2009, 27 (Suppl. 2), B3-B12.

Hornick R B, Eigelsbach H T. 1966. Aerogenic immunization of man with live Tularemia vaccine. Bacteriol. Rev. 30:532-538.

Humphries, H. E.; Williams, J. N.; Blackstone, R.; Jolley, K. A.; Yuen, H. M.; Christodoulides, M.; Heckels, J. E., Multivalent liposome-based vaccines containing different serosubtypes of PorA protein induce cross-protective bactericidal immune responses against *Neisseria meningitidis*. Vaccine 2006, 24 (1), 36-44.

Idanpaan-Heikkila, I.; Hoiby, E. A.; Chattopadhyay, P.; Airaksinen, U.; Michaelsen, T. M.; Wedege, E., Antibodies to meningococcal class 1 outer-membrane protein and its variable regions in patients with systemic meningococcal disease. J Med Microbiol 1995, 43 (5), 335-43.

Jia Q, Lee B Y, Bowen R, Dillon B J, Som S M, Horwitz M A. 2010. A *Francisella tularensis* live vaccine strain (LVS) mutant with a deletion in capB, encoding a putative capsular biosynthesis protein, is significantly more attenuated than LVS yet induces potent protective immunity in mice against *F. tularensis* challenge. Infect. Immun. 78:4341-4355, http://dx.doi.org/10.1128/IAI.00192-10.

Jones C L, Napier B A, Sampson T R, Llewellyn A C, Schroeder M R, Weiss D S. 2012. Subversion of host recognition and defense systems by *Francisella* spp. Microbiol. Mol. Biol. Rev. 76:383-404. http://dx.doi.org/10.1128/MMBR.05027-11.

Juruj C, Lelogeais V, Pierini R, Perret M, Py B F, Jamilloux Y, Broz P, Ader F, Faure M, Henry T. 2013. Caspase-1 activity affects AIM2 speck formation/stability through a negative feedback loop. Front. Cell. Infect. Microbiol. 3:14. http://dx.doi.org/10.3389/fcimb.2013.00014.

Kaler E W, Murthy A K, Rodriguez B E, Zasadzinski J A. 1989. Spontaneous vesicle formation in aqueous mixtures of single-tailed surfactants. Science 245:1371-1374. http://dx.doi.org/10.1126/science.2781283.

Katz J. Zhang P, Martin M, Vogel S N, Michalek S M. 2006. Toll-like receptor 2 is required for inflammatory responses to *Francisella tularensis* LVS. Infect. Immun. 74:2809-2816. http://dx.doi.org/10.1128/IAI.74.5.2809-2816.2006.

Kersten G F. Crommelin D J. 2003. Liposomes and ISCOMs. Vaccine 21:915-920. http://dx.doi.org/0.1016/S0264-410X(02)00540-6.

Kieffer T L, Cowley S, Nano F E, Elkins K L. 2003. *Francisella novicida* LPS has greater immunobiological activity in mice than *F. tularensis* LPS, and contributes to *F. novicida* murine pathogenesis. Microbes Infect. 5:397-403. http://dx.doi.org/10.1016/S1286-4579(03)00052-2.

Kingsley Jeffrey, D.; Dou, H.: Morehead, J.; Rabinow, B.; Gendelman Howard, E.; Destache Christopher, J., Nanotechnology: a focus on nanoparticles as a drug delivery system. J Neuroimmune Pharmacal. 2006, 1 (3), 340-50.

Koskela P, Herva E. 1982. Cell-mediated and humoral immunity induced by a live *Francisella tularensis* vaccine. Infect. Immun. 36:983-989.

KuoLee R, Harris G, Conlan J W, Chen W. 2011. Role of neutrophils and NADPH phagocyte oxidase in host defense against respiratory infection with virulent *Francisella tularensis* in mice. Microbes Infect. 13:447-456. http://dx.doi.org10.1016/j.micinf.2011.01.010.

Kurtz S L, Foreman O, Bosio C M, Anver M R, Elkins K L. 2013. Interleukin-6 is essential for primary resistance to *Francisella tularensis* live vaccine strain infection. Infect. Immun. 81:585-597. http://dx.doi.org/10.1128/IAI.01249-12.

Lasic, D. D., Novel applications of liposomes. Trends Biotechnol. 1998, 16 (7), 307-321.

Macdonald, A. G.; Martinac, B.; Bartlett, D. H., Patch-clamp experiments with porins extracted from a marine bacterium (Photo bacterium profundum strain SS9) and reconstituted in liposomes. Cell Biochem. Biophys. 2002, 37 (3), 157-167.

Mahawar M, Rabadi S M, Banik S, Catlett S V, Metzger D W, Malik M, Bakshi C S. 2013. Identification of a live attenuated vaccine candidate for tularemia prophylaxis. PLoS One 8:e61539. http://dx.doi.org/10.137/journal.pone.0061539.

Mann B J, Ark N M. 2009. Rationally designed tularemia vaccines. Expert Rev. Vaccines 8:877-885. http://dx.doi.org/10.1586/erv.09.51.

Mara-Koosham G, Hutt J A, Lyons C R, Wu T H. 2011. Antibodies contribute to effective vaccination against respiratory infection by type A *Francisella tularensis* strains. Infect. Immun. 79:1770-1778. http://dx.doi.org/10.1128/IAI.00605-10.

Mares C A, Ojeda S S, Morris E G, Li Q, Teale J M. 2008. Initial delay in the immune response to *Francisella tularensis* is followed by hypercytokinemia characteristic of severe sepsis and correlating with upregulation and release of damage-associated molecular patterns. Infect. Immun. 76: 3001-3010. http://dx.doi.org/10.1128/IAI.00215-08.

McCrumb F R, Jr. 1961. Aerosol infection of man with *Pasteurella tularensis*. Bacteriol. Rev. 25:262-267.

Morein B, Hu K F, Abusugra I. 2004. Current status and potential application of ISCOMs in veterinary medicine. Adv. Drug Deliv. Rev. 56:1367-1382. http://dx.doi.org/10.1016/j.addr.2004.02.004.

Nieves, W.; Asakrah, S.; Qazi, 0.; Brown, K. A.; Kurtz, J.; AuCoin, D. P.; McLachlan, J. B.; Roy, C. J.; Morici, L. A., A naturally derived outer-membrane vesicle vaccine protects against lethal pulmonary *Burkholderia pseudomallei* infection. Vaccine 2011, 29 (46), 8381-8389.

Ojogun V A, Lehmler H J, Knutson B L. 2009. Cationic-anionic vesicle templating from fluorocarbon/fluorocarbon and hydrocarbon/fluorocarbon surfactants. J. Colloid Interface Sci. 338:82-91. http://dx.doi.org/10.1016/j.jcis.2009.06.022.

Oyston P C, Sjostedt A, Titball R W. 2004. Tularaemia: bioterrorism defense renews interest in *Francisella tularensis*. Nat. Rev. Microbiol. 2:967-978. http://dx.doi.org/10.1038/nrmicro1045.

Pace, D.; Cuschieri, P.; Galea Debono, A.; Attard-Montalto, S., Epidemiology of pathogenic *Neisseria meningitidis* serogroup B serosubtypes in Malta: Implications for introducing PorA based vaccines. Vaccine 2008, 26 (47), 5952-5956.

Park. J.-H.; Rader, L. H.; Thomas, G. B.; Danoff, E. J.; English, D. S.; DeShong, P., Carbohydrate-Functionalized Surfactant Vesicles: Preparation and Lectin-Binding Studies. Soft Matter 2008, Submitted.

Parmar, M. M.; Edwards, K.; Madden, T. D., Incorporation of bacterial membrane proteins into liposomes: factors influencing protein reconstitution. Biochim. Biophys. Acta, Biomembr. 1999, 1421 (1). 77-90.

Petrosino J F, Xiang Q, Karpathy S E, Jiang H, Yerrapragada S, Liu Y, Gioia J, Hemphill L, Gonzalez A, Raghavan T M, Uzman A, Fox G E, Highlander S, Reichard M, Morton R J, Clinkenbeard K D, Weinstock G M. 2006. Chromosome rearrangement and diversification of *Francisella tularensis* revealed by the type B (OSU18) genome sequence. J. Bacteriol. 188:6977-6985. http://dx.doi.org/10.1128/JB.00506-06.

Prior J L, Prior R G, Hitchen P G, Diaper H, Griffin K F, Morris H R, Dell A, Titball R W. 2003. Characterization of the O antigen gene cluster and structural analysis of the O antigen of *Francisella tularensis* subsp. *tularensis*. J. Med. Microbiol. 52:845-851. http://dx.doi.org/10.1099/jmm.0.05184-0.

Racker, E., Reconstitution of membrane processes. Methods Enzymol. 1979, 55 (Biomembranes, Part F), 699-711.

Racker, E., Reconstitutions: past, present and future. Membr. Bioenerg., Int. Workshop 1979, 569-91.

Ramsey, R. B.; Hamner, M. B.; Alving, B. M.; Finlayson, J. S.; Alving. C. R.; Evatt, B. L., Effects of lipid A and liposomes containing lipid A on platelet and fibrinogen production in rabbits. Blood 1980, 56 (2), 307-10.

Richards. R. L.: Alving, C. R.; Wassef. N. M., Liposomal Subunit Vaccines: Effects of Lipid A and Aluminum Hydroxide on Immunogenicity. J Pharm. Sci. 1996, 85 (12), 1286-1289.

Richards, R. L.; Rao, M.; Wassef, N. M.; Glenn, G. M.; Rothwell, S. W.; Alving, C. R., Liposomes containing lipid A serve as an adjuvant for induction of antibody and cytotoxic T-cell responses against RTS,S malaria antigen. Infect. Immun. 1998, 66 (6), 2859-2865.

Richards. R. L.: Swartz, G. M., Jr.; Schultz, C.; Hayre, M. D.; Ward. G. S.; Ballou, W. R.; Chulay, J. D.; Hockmeyer, W. T.; Berman, S. L.; Alving, C. R., Immunogenicity of liposomal malaria sporozoite antigen in monkeys: adjuvant effects of aluminium hydroxide and non-pyrogenic liposomallipid A. Vaccine 1989, 7 (6), 506-12.

Rigaud, J. L., Membrane proteins: functional and structural studies using reconstituted proteoliposomes and 2-D crystals. Braz. J Med. Biol. Res. 2002, 35 (7), 753-766.

Rigaud, J. L.; Pitard, B., Liposomes as tools for the reconstitution of biological systems. Liposomes Tools Basic Res. Ind. 1995, 71-88.

Robbins, J. B.; Schneerson, R., Polysaccharide-protein conjugates: a new generation of vaccines. J Infect. Dis. 1990, 161 (5), 821-32.

Robinson D S, O'Garra A. 2002. Further checkpoints in Th1 development. Immunity 16:755-758. http://dx.doi.org/10.1016/S1074-7613(02) 00331-X.

Rockx-Brouwer D, Chong A, Wehrly T D, Child R, Crane D D, Celli J, Bosio C M. 2012. Low dose vaccination with attenuated *Francisella tularensis* strain SchuS4 mutants protects against tularemia independent of the route of vaccination. PLoS One 7:e37752. http://dx.doi.org/10.1371/journal.pone.0037752.

Rothman, E. S.: Serota. S.; Swem, D., Enol esters. II. N-Acylation of amides and imides. J Org. Chem. 1964, 29 (3), 646-50.

Rubálek M, Hernychová L, Havlasová J, Kasalová I, Neubauerová V, Stulík J, Macela A, Lundqvist M. Larsson P. 2003. Towards proteome database of *Francisella tularensis*. J. Chromatogr. B Analyt. Technol. Biomed. Life Sci. 787:149-177. http://dx.doi.org/10.1016/S1570-0232 (02)00730-4.

Ryden P, Twine S. Shen H, Harris G, Chen W, Sjostedt A, Conlan W. 2013. Correlates of protection following vaccination of mice with gene deletion mutants of *Francisella tularensis* subspecies *tularensis* strain, SCHU S4 that elicit varying degrees of immunity to systemic and respiratory challenge with wild-type bacteria. Mol. Immunol. 54:58-67. http://dx.doi.org/10.1016/j.molimm.2012.10.043.

Samad, A.; *Sultana*. Y.; Aqil, M., Liposomal drug delivery systems: an update review. Curr. Drug Deliv. 2007, 4 (4), 297-305.

Sanchez, S.; Abel, A.; Marzoa, J.; Gorringe, A.; Criado, T.; Ferreiros, C. M., Characterisation and immune responses to meningococcal recombinant porin complexes incorporated into liposomes. Vaccine 2009, 27 (39), 5338-5343.

Šegota S, Težak D. 2006. Spontaneous formation of vesicles. Adv. Colloid Interface Sci. 121:51-75. http://dx.doi.org/10.1016/j.cis.2006.01.002.

Shevchenko, A.; Tomas, H.; Havlis, J.; Olsen, J. V.; Mann, M., In-gel digestion for mass spectrometric characterization of proteins and proteomes. Nat. Pro toe. 2006, 1 (6), 2856-2860.

Shirey K A, Cole L E, Keegan A D, Vogel S N. 2008. *Francisella tularensis* live vaccine strain induces macrophage alternative activation as a survival mechanism. J. Immunol. 181:4159-4167.

Silvius. J. R., Solubilization and functional reconstitution of biomembrane components. Annu. Rev. Biophys. Biomol. Struct. 1992, 21, 323-48.

Singh A, Rahman T, Malik M, Hickey A J, Leifer C A, Hazlett K R, Sellati T J. 2013. Discordant results obtained with *Francisella tularensis* during in vitro and in vivo immunological studies are attributable to compromised bacterial structural integrity. PLoS One 8:e58513. http://dx.doi.org/10.1371/journal.pone.0058513.

Smith, P. K.; Krohn, R. I.; Hermanson, G. T.; Mallia. A. K.; Gartner, F. H.; Provenzano, M. D.; Fujimoto, E. K.; Goeke, N. M.; Olson, B. J.; Klenk, D. C., Measurement of protein using bicinchoninic acid. Anal. Biochem. 1985, 150 (1), 76-85.

Stallforth, P.; Lepenies, B.; Adibekian, A.; Seeberger Peter, H., Carbohydrates: A frontier in medicinal chemistry. J Med. Chem. 2009, 52 (18), 5561-77.

Stein, D. C.; Patrone, J. B.; Bish, S., Innate immune recognition of *Neisseria meningitidis* and *Neisseria gonorrhoeae*. Neisseria 2010, 95-122.

Tamauchi, H.; Tadakuma, T.; Yasuda, T.; Tsumita, T.; Saito, K., Enhancement of immunogenicity by incorporation of lipid A into liposomal model membranes and its application to membrane-associated antigens. Immunology 1983, 50 (4), 605-12.

Thomas G B, Rader L H, Park J, Abezgauz L, Danino D, DeShong P, English D S. 2009. Carbohydrate modified catanionic vesicles: probing multivalent binding at the bilayer interface. J. Am. Chem. Soc. 131:5471-5477. http://dx.doi.org/10.1021/ja8076439.

Titball R W, Petrosino J F. 2007. *Francisella tularensis* genomics and proteomics. Ann. N. Y. Acad. Sci. 1105: 98-121. http://dx.doi.org/10.1196/annals.1409.015.

Torchilin, V. P., Recent advances with liposomes as pharmaceutical carriers. Nat. Rev. Drug Disc. 2005, 4 (2), 145-160.

Twine S, Shen H, Harris G, Chen W, Sjöstedt A, Ryden P, Conlan W. 2012. BALB/c mice, but not C57BL/6 mice immunized with a _clpB mutant of *Francisella tularensis* subspecies *tularensis* are protected against respiratory challenge with wild-type bacteria: association of protection with post-vaccination and post-challenge immune responses. Vaccine 30: 3634-3645. http://dx.doi.org/10.1016/j.vaccine.2012.03.036.

Vamier, A.; Kermarrec, F.; Blesneac, I.; Moreau, C.; Liguori, L.; Lenormand, J. L.; Picollet-D'hahan, N., A Simple Method for the Reconstitution of Membrane Proteins into Giant Unilamellar Vesicles. J Membr. Biol. 2010, 233 (1-3), 85-92.

van de Waterbeemd, B.; Streefland, M.; van der Ley, P.; Zomer, B.; van Dijken, H.; Martens, D.; Wijffels, R.; van der Pol, L., Improved OMV vaccine against *Neisseria meningitidis* using genetically engineered strains and a detergent-free purification process. Vaccine 2010, 28 (30), 4810-4816.

Varki, A., Biological roles of oligosaccharides: All of the theories are correct. Glycobiology 1993, 3 (2), 97-130.

Vermont. C. L.; van Dijken, H. H.; Kuipers, A. J.; van Limpt. C. J.P.; Keijzers, W. C. M.; van der Ende, A.; de Groot, R.; van Alphen, L.; van den Dobbelsteen, G. P. J. M., Cross-reactivity of antibodies against PorA after vaccination with a meningococcal B outer membrane vesicle vaccine. Infect. Immun. 2003, 71 (4), 1650-1655.

Wang X, Danoff E J, Sinkov N A. Lee J H, Raghavan S R, English D S. 2006. Highly efficient capture and long-term encapsulation of dye by catanionic surfactant vesicles. Langmuir 22:6461-6464. http://dx.doi.org/10.1021/la0605135.

Wang, X.: Quinn, P. J., Endotoxins: lipopolysaccharides of gram-negative bacteria. Subcell. Biochem. 2010, 53 (Endotoxins), 3-25.

Wassef, N. M.; Alving, C. R.; Richards, R. L., Liposomes as carriers for vaccines. ImmunoMethods 1994, 4 (3), 217-22.

Wayne Conlan J, Oyston P C. 2007. Vaccines against *Francisella tularensis*. Ann. N. Y. Acad. Sci. 1105:325-350. http://dx.doi.org/10.1196/annals.1409.012.

Westphal, 0.; Jann, K.; Himmelspach, K., Chemistry and immunochemistry of bacteriallipopolysaccharides as cell wall antigens and endotoxins. Prog Allergy 1983, 33, 9-39.

Wetzler, L. M.; Blake, M. S.; Barry, K.; Gotschlich, E. C., Gonococcal porin vaccine evaluation: comparison of Por proteosomes, liposomes, and blebs isolated from rmp deletion mutants. J Infect Dis 1992, 166 (3), 551-5.

Wilton J M. 1978. Suppression by IgA of IgG-mediated phagocytosis by human polymorphonuclear leucocytes. Clin. Exp. Immunol. 34:423-428.

Working, P. K.; Newman, M. S.; Huang. S. K.; Mayhew, E.; Vaage, J.; Lasic, D. D., Pharmacokinetics, biodistribution and therapeutic efficacy of doxorubicin encapsulated in Stealth liposomes (Doxil). J Liposome Res. 1994, 667-87.

Wu T H, Hutt J A, Garrison K A, Berliba L S. Zhou Y, Lyons C R. 2005. Intranasal vaccination induces protective immunity against intranasal infection with virulent *Francisella tularensis* biovar A. Infect. Immun. 73: 2644-2654. http://dx.doi.org/10.1128/IAI.73.5.2644-2654.2005.

Yamasaki, R.; Bacon, B. E.; Nasholds, W.; Schneider, H.; Griffiss, J. M., Structural determination of oligosaccharides derived from lipooligosaccharide of *Neisseria gonorrhoeae* F62 by chemical, enzymatic, and two-dimensional NMR methods. Biochemistry 1991, 30 (43), 10566-75.

Zakirov, M. M.; Petrov. A. B.; Burkhanov, S. A.; Vartanian Iu, P.; Torchilin, V. P.; Trubetskoi, V. S.; Koshkina, N. V.; Dmitriev, B. A.; L'Vov V, L., The immunological activity of *Neisseria meningitidis* lipo-oligosaccharide incorporated into liposomes. Zh Mikrobiol Epidemiol Immunobiol 1995, (1), 49-53.

Zhu, J.; Xue, J.; Guo, Z.; Zhang, L.: Marchant, R. E., Biomimetic glycoliposomes as nanocarriers for targeting P-selectin on activated platelets. Bioconjugate Chem. 2007, 18 (5), 1366-1369.

Zhu, J.; Yan, F.: Guo, Z.; Marchant, R. E., Surface modification of liposomes by saccharides: Vesicle size and stability of lactosyl liposomes studied by photon correlation spectroscopy. J Colloid Interface Sci. 2005, 289 (2), 542-550.

Zollinger Wendell, D.; Babcock Janiine, G.; Moran Elizabeth, E.; Brandt Brenda, L.; Matyas Gary, R.; Wassef Nabila, M.; Alving Carl, R., Phase I study of a *Neisseria meningitidis* liposomal vaccine containing purified outer membrane proteins and detoxified lipooligosaccharide. Vaccine 2012, 30 (4), 712-21.

Example 1

Extraction of Components from *Neisseria gonorhoeae* Using Catanionic Surfactant Vesicles In this paper we describe how catanionic surfactant vesicles were used to extract membrane components from the Gram negative pathogen *Neisseria gonorrhoeae*. Catanionic vesicle extracts were prepared using the surfactants SDBS and CTAT in the presence of *N. gonorrhoeae* cell pellets. Colorimetric carbohydrate and protein assays of the resulting catanionic vesicles confirmed the presence of carbohydrate and protein in the resulting vesicles. Gel electrophoresis followed by silver staining further confirmed that vesicle extracts contained pathogen-derived LOS F62ΔlgtD and a subset of proteins. Western blotting confirmed that a select number of proteins were from the outer membrane of the *N. gonorrhoeae* bacterium, including porin and OPA. Mass spectrometric analysis of the catanionic vesicle extracts identified 138 total proteins, 29 of which were membrane proteins.

Methods

All chemicals and solvents were purchased from commercial suppliers and were used as received unless otherwise noted. All aqueous vesicle solutions were prepared from a Millipore (18MQ) water purification system and all assays used water purified using an Elix 5 (Millipore) water purification system unless otherwise stated. An Ocean Optics USB 2000 Spectrometer was used to measure UV-VIS absorbance of samples.

Cell Cultures.

Genetically modified *N. gonorrhoeae* F62-lgtD cells were grown to a maximum cell count for 48 h with an OD of 0.6-1.0 (650 nm) (106-109 CFU). A 20 mL aliquot of bacterial cell culture was spun down by centrifugation at 9,000 RPM for 30 min and the supernatant was decanted. Cell pellets were stored at −20° C. until needed.

Vesicle Preparation.

Sodium dodecylbenzenesulfonate (SDBS) was purchased from TCI America and was utilized without further purification. Cetyltrimethylammonium tosylate (CTAT) was purchased from Sigma and was recrystallized from ethanol-acetone to give a white powder. The purified solid was stored at room temperature in a desiccator containing Drierite.

Several vesicle preparation methods were tested to determine if the extraction varied between the order and type of addition of the surfactant components. The decided upon method, described below, was chosen based on Western blotting, which yielded the most protein bands. Procedures for the other preparation methods can be found in the Supporting Information.

Vesicle extracts were formed by adding a solution of SDBS directly to the bacterial cell pellet then adding solid CTAT to form I wt % total surfactant (26.9 mM total surfactant). This was done by adding 9.90 mL of an aqueous SDBS solution (0.0203 M) directly to the bacterial cell pellet and stirring for 1 h at room temperature. Then 30.0 mg of solid CTAT (0.0658 mmol) was added to the suspension and stirred for 1 h at room temperature.

Vesicles were centrifuged for 5 min at 5,000 RPM and the supernatant was decanted. The resulting colloidal supernatant, milky in appearance, was purified by gel filtration on Sephadex G-100 where a 1.0 mL aliquot of vesicle extract solution was added to a column (length 5.5 cm, diameter 1.5 cm) packed with G-100 Sephadex (Sigma). Vesicles were eluted with 1.0 mL aliquots of water to a total volume of 14.0 mL, yielding fourteen fractions.

Characterization of Vesicles.

All fractions from gel filtration were characterized for the presence of carbohydrate using a phenol-sulfuric colorimetric assay (FIG. 1). 41 Absorption studies by UV-VIS at 490 nm indicated the presence of carbohydrate in vesicle-containing fractions.

Vesicles were also analyzed for the presence of protein using a modified procedure of the Pierce bicinchoninic acid (BCA) assay (FIG. 1).42 The working reagent was prepared using a 50:1 v/v ratio of Reagent A (sodium carbonate, sodium bicarbonate, bicinchoninic acid, and sodium tartrate in 0.1 M sodium hydroxide) to Reagent B (4% copper (II) sulfate). The test-tube protocol was used in which 2.0 mL of working reagent was added to 0.1 mL of the sample. To prevent intact vesicles from scattering light and interfering with the absorbance of samples, 0.1 mL of 1-propanol was added to each sample to break up vesicles. After the addition of the working reagent, the samples were vortexed and incubated at 37° C. for 30 min. The absorbance was measured at 562 nm and compared to a bovine serum albumin standard curve to determine the total protein concentration in each sample.

Gel Electrophoresis.

Vesicle samples and a molecular weight standard were mixed with loading buffer (3×, details) and boiled for 10 min. Samples were loaded onto an SDS-polyacrylamide gel (Tris-tricine 16.5% v/v) using Tris-tricine IX as the running buffer and run for 4.5 h at 100 V on ice (Bio-Rad Model200/2.0 power supply).

Silver Staining.

After electrophoresis, the gels were incubated in a fixing solution (500 mL of 38% ethanol and 25 mL glacial acetic acid) overnight on a shaker at room temperature. Gels were silver stained according to a modified procedure. 43 The gel was transferred to 100 mL of an aqueous periodic acid (0.036 M) wash for 5 min and then rinsed four times with water for 30 min on a shaker. The silver staining solution was prepared by adding 4.0 mL of diluted silver nitrate (4.7 mmol) drop wise to Solution 1 (1 pellet sodium hydroxide, 25 mL water, 1.40 mL of 30% ammonium hydroxide). If a brown color was present, additional ammonium hydroxide was added drop wise until the solution became clear and colorless. The silver staining solution was brought to a final volume of 100 mL with water and the gel was incubated for 15 min with the solution on a shaker at room temperature.

After silver staining, the gel was washed with water six times for 15 min each. The gel was then incubated in a developing solution (95 µL formaldehyde 37% solution, 1 mL citric acid 25 mg/mL, 500 mL water) until bands became visible. The gel was washed in water and then imaged.

Protection Experiments.

Vesicle-containing fractions were digested using 10 µL proteinase K (25 mg/mL) for a 500 µL sample incubated at 37° C. Aliquots were taken after 18 h, 23 h, and 46 h. A control of the cell pellet was prepared by suspending the pellet in 1.0 mL of water. Proteinase K was added to the cell pellet suspension and a sample of whole cell lysate and incubated at 37° C. Aliquots were taken after 18 h, 23 h, and 46 h and all samples were analyzed by electrophoresis and silver staining.

The original samples from the proteinase K digestion were also digested with trypsin (0.25%, Corning cellgro), where 10 µL was added to 500 µL of sample and incubated at 37° C. Aliquots were taken after 18 h, 23 h, and 46 h and all samples were analyzed by electrophoresis and silver staining.

Western Blotting.

After electrophoresis, Western blotting was performed in which the gel was sandwiched with nitrocellulose and transferred for 30 min at 2 Amps in a Tris-tricine IX/MeOH solution on ice. The nitrocellulose was then air dried for 10 min and incubated in casein filler solution on a shaker overnight at room temperature.

The nitrocellulose was rinsed with a PBS/Tween-20 solution 5 times for 15 min and then incubated with heat goat serum (1:500) primary antibody solution prepared in casein filler on a shaker for 2 h. The nitrocellulose was rinsed with a PBS 1×/Tween-20 solution five times for 15 min each and then incubated with donkey anti-goat HRP (Jackson ImmunoResearch laboratories Inc.) (1:100,000) secondary antibody solution prepared in casein filler on a shaker for 2 h. The nitrocellulose was rinsed with a PBS 1×/Tween-20 solution five times for 15 min each and then incubated with a standard Western blotting chemiluminescence solution (PerkinElmer, Waltham, Mass.) and analyzed using autoradiograph film.

Proteomics Analysis.

Vesicle extracts were prepared from cell pellets formed from 20 mL, 40 mL, or 60 mL of cells. Known amounts of protein were spotted from these preparations in each lane of a one-dimensional gel (Tris-HCl, 8-16% gradient). Whole cell lysate was spotted in a fourth lane. The gel was developed and stained with Coomassie blue stain (Sigma). Fifteen slices were cut from each lane and subjected to overnight in-gel tryptic digestion (13 ng/µL) using a standard procedure. 44 The resulting peptides were extracted and injected into a capLC-MS/MS LTQ-orbitrap (Thermo-Fisher, San Jose, Calif.) as described elsewhere. 45 Peptide and protein candidates were analyzed using the search program MASCOT 2.3 (Matrix Science, London, UK), and protein identifications were based on the number of associated tryptic peptides and the reliability of the peptide identifications. Two protein databases were searched, one compiled of all *Neisseria* sequences from NCBinr (www.ncbi.nlm.nih.gov.com) and one comprised from only the proteins in NCBinr from the species *N. gonorrhoeae*. Subcellular locations of the proteins were assigned using the Protein Information Resource.

Results

Vesicle extractions of *N. gonorrhoeae* were characterized using a colorimetric carbohydrate assay, a BCA protein assay, silver staining after gel electrophoresis, Western blotting, and mass spectrometry-based proteomics. The results indicate that membrane components from bacteria were extracted successfully into surfactant vesicles. (see Table 1). The best method for extraction was using an SDBS solution to disrupt the cell pellet followed by addition of solid CTAT to the lysate solution. We propose that this method worked most effectively because the solution of SDBS first lysed the bacteria, freeing surface antigens, and then solubilized all membrane components. After the addition of CTAT, membrane components were efficiently captured during the formation of vesicles and were able to readily associate with the vesicle bilayer.

All vesicle preparation methods were purified by gel filtration and all resulting fractions were tested for the presence of carbohydrate and protein using a carbohydrate colorimetric assay and the BCA protein assay (FIG. 1). Vesicles extracted by all five methods had comparable amounts of carbohydrate and protein. Both assays serve to quantitatively determine the amount of carbohydrate and protein, respectively.

Figure 3:
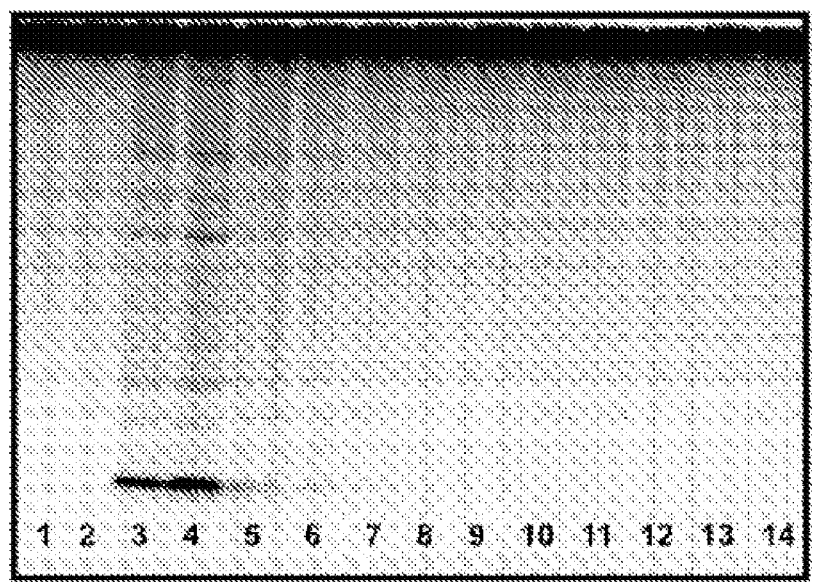
FIG. 3: Vesicle extract fractions from gel filtration analyzed by silver staining. Lanes were loaded with 1 μL of sample and analyzed by SDS-polyacrylamide Tris-tricine 16.5% v/v gels followed by silver staining. Lanes 1 and 2 represent the void volume and are free of protein and carbohydrate. Lanes 3 and 4 correspond to vesicle containing fractions and indicate the presence of a range of proteins and a high concentration of the carbohydrate LOS F62ΔlgtD with the darkest band at the bottom of the gel. Lanes 5-14 show the diminishing presence of proteins and LOS.

Samples from loaded vesicles were compared to the whole cell lysate and original cell pellet (FIG. 2). The presence of LOS in vesicles was confirmed by electrophoresis of a standard of LOS F62ΔlgtD. Silver staining confirmed the presence of carbohydrate, specifically LOS F62ΔlgtD, seen at the bottom of the gel (FIG. 2). LOS is presumed to incorporate easily into vesicles because the lipid tail associates with the lipophilic bilayer. Different proteins were shown to be extracted using vesicles, compared to the lysate. Furthermore, samples extracted by vesicles had different protein profiles when compared to that of the original cell pellet. (FIG. 2). Gel electrophoresis followed by silver staining was performed on all fractions of the described method in order to characterize the carbohydrates and proteins that were incorporated into the vesicles (FIG. 3). These images indicate that numerous proteins were incorporated into the vesicles and few components come out in later fractions.

Figure 5:
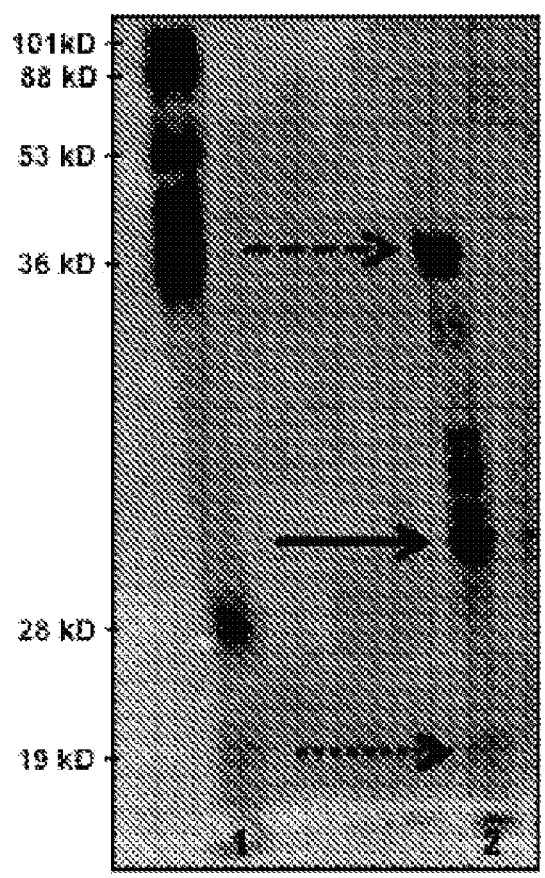
FIG. 5: Western blotting of vesicle-containing fractions, lysate, and supernatant. The purified vesicle extract (2) shows antibody binding to several proteins and LOS, specifically porin (36 kD) and OPA (25-30 kD). The lysate fraction (1) does not show any antibody binding, indication that vesicles contain surface antigens.

Western blotting of the loaded materials from these surfactant vesicles showed the presence of LOS and the membrane proteins porin (36 kD) and OPA (25-30 kD) (FIG. 5). Further analysis by mass spectrometry confirmed the presence of these proteins (FIG. 4). Analysis of tryptic digests of the lanes from vesicle-containing fractions by mass spectrometry also identified 293 unique proteins in the vesicle extract, including ribosomal proteins as well as outer membrane bound proteins.

Figure 6:
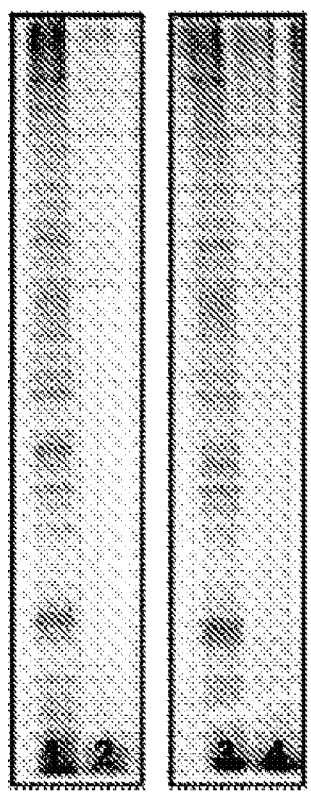
FIG. 6: Proteinase K digestion. Lanes 1 and 3 show the protein pattern of the GC lysate and vesicle extract, respectively, after silver staining. Lanes 2 and 4 contain GC lysate and vesicle extract purified by gel filtration and show digestion of all protein bands and retention of LOS at the bottom of the gel.

Protection experiments were carried out to test if bacterial proteins are translocated to the interior of the vesicles. Loaded vesicles were digested with proteinase K to determine if being associated with vesicles protected proteins. A whole cell lysate was incubated as a control. Both vesicle samples and the whole cell lysate showed complete digestion using this enzyme (FIG. 6). Since proteinase K is a nonspecific digestion enzyme, these results demonstrate that any protein at the surface of vesicles was digested completely by the enzyme. This proteolytic enzyme does not digest the carbohydrate LOS.

Figure 7:
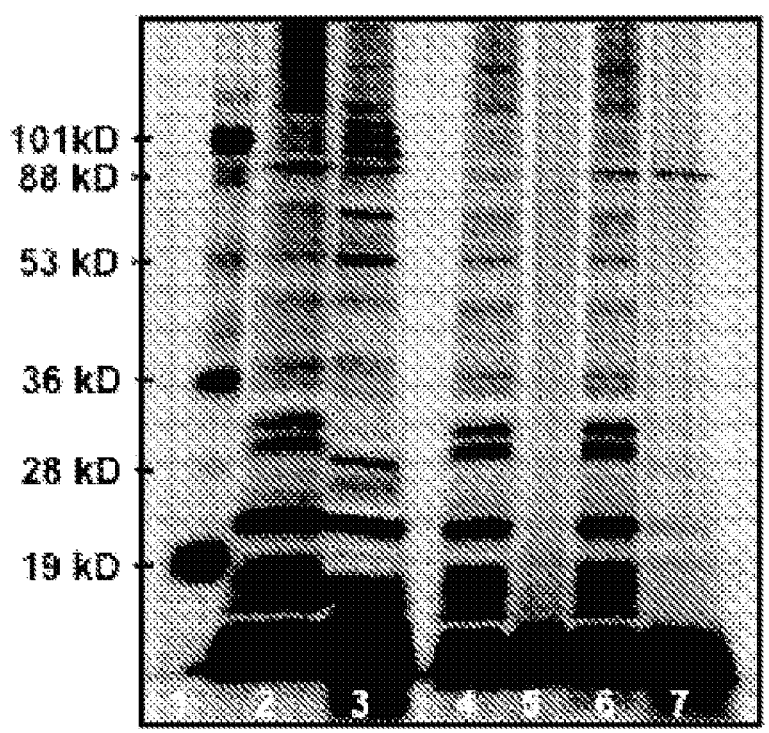
FIG. 7: Protection from trypsin digestion. GC lysate and surfactant GC vesicle extract samples.
Figure 8:
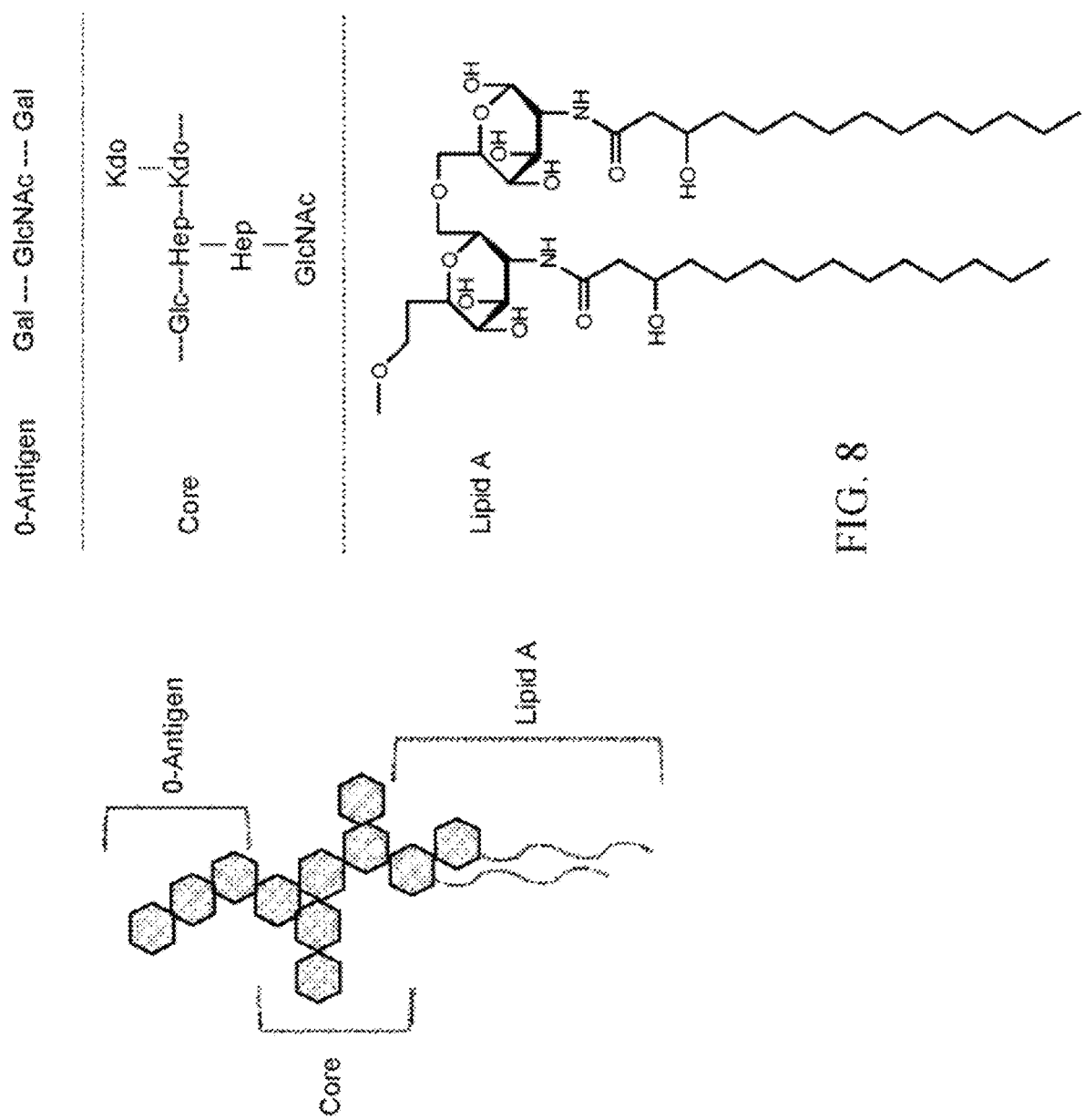
FIG. 8: Chemical structure of lipooligosaccharide components from the Gramnegative bacteria N. gonorrhoeae. The various regions include the 0-antigen, core, and lipid A.

Digestion of the loaded vesicles using trypsin gave a different pattern. Digested proteins in the form of peptide units were seen in great concentrations at the bottom of the gel (FIG. 7). The vesicle samples showed protection for a few proteins, while the whole cell lysate fraction was completely cleaved by trypsin. This indicates that vesicles contain proteins embedded in the bilayer, where they are protected from cleavage from trypsin, but not proteinase K.

In another proteomic experiment, material was extracted from three different starting amounts of cells. Four lanes were developed in the gel, containing 20 µg of whole cell lysate, 39 µg of sample from a 20 mL pellet, 52 µg of sample from a 40 mL pellet, and 67 µg of sample from a 60 mL pellet. After trypsin digestion, the peptides were analyzed by HPLC-MS/MS. A search against all proteins from the genus *Neisseria* identified 229 proteins with high reliability (FIG. 4). Of these, 45 were classified as membrane proteins. When the limited protein database was searched, which contained proteins associated only with the species *N. gonorrhoeae*, 29 membrane proteins were identified out of 138 total identifications (FIG. 4). Major protein bands based on silver staining were found to contain outer membrane proteins. Western Blotting confirmed the presence of pilin, porin, and OPA.

Catanionic surfactant vesicles are soft, cell-like models that can incorporate antigens, making them ideal vaccine agents. This work offers a way to extract membrane components from pathogenic bacteria for potential vaccine formulation. Membrane components of a cell would be useful if they could be easily separated. The vesicle extraction procedure introduced here offers potential enrichment of LOS and other membrane components from *N. gonorrhoeae*. These vesicles are stable at room temperature for prolonged periods of time and offer an improvement over conventional liposomes. The described vesicle extraction is currently being studied for use with other pathogens. Future research will be devoted to challenging animals and testing to determine if protection occurred from vesicle extracts containing neisserial proteins. Because the structure of LOS involved in the meningococcal disease is identical to that expressed by the *N. gonorrhoeae* F62ΔlgtD used in vesicle extractions, additional work will be devoted to generating a universal vaccine able to protect against all serotypes of *N. meningitidis*.

Example 2

Figure 9:
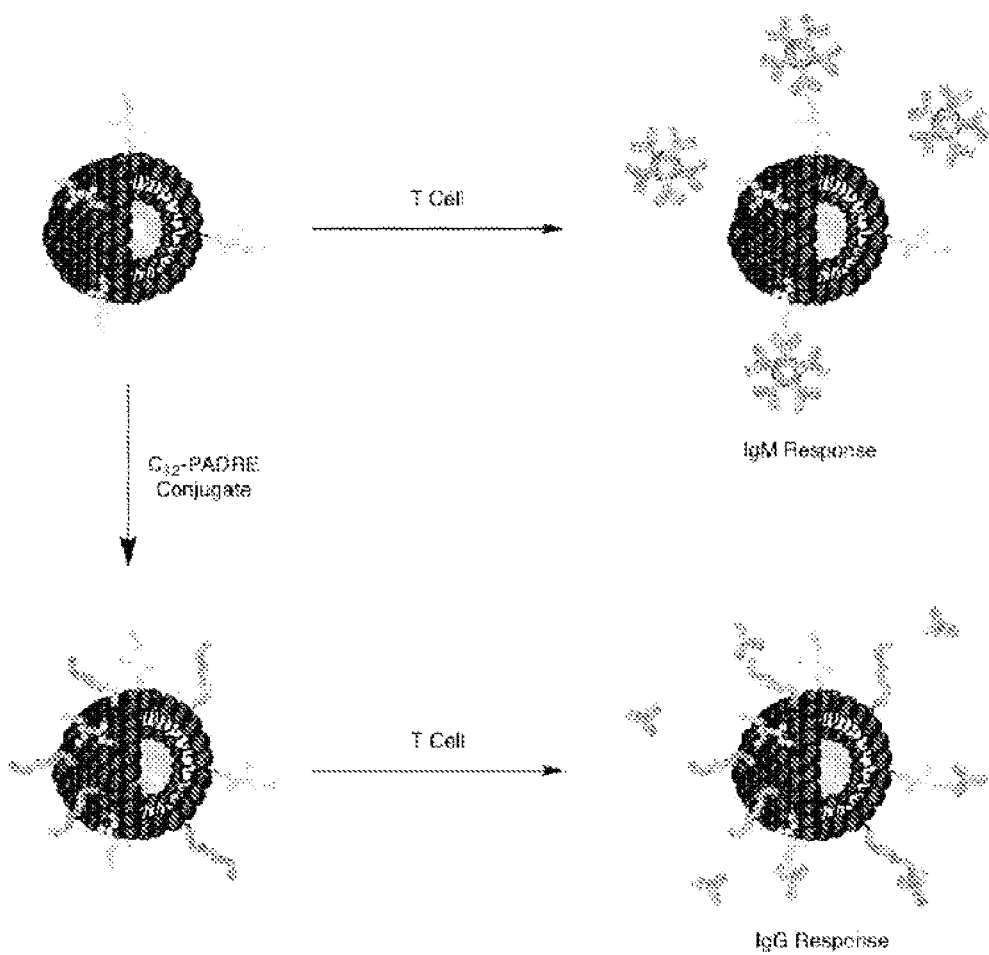
FIG. 9: Immune response of LOS vs. C12-PADRE/LOS conjugated catanionic vesicles. Vesicles loaded with only carbohydrate would generate IgM antibodies. Addition of the epitope C12-PADRE to LOS functionalized vesicles would generate IgG antibodies.

Loading Complex Carbohydrates and Peptides into Catanionic Surfactant Vesicles for Use in Vaccine Applications We were interested in developing carbohydrate-based vaccines against Gramnegative bacteria, specifically *N. gonorrhoeae* and *F. tularensis* by utilizing catanionic surfactant vesicles for incorporation of surface antigens onto the outer leaflet. The resulting functionalized vesicles would display the antigens on the surface of the vesicle in a manner analogous to their presence in bacterial pathogens. Vaccine studies by our lab were performed using catanionic surfactant vesicles that LOS and LPS) and Pan DR helper T cell epitope (PADRE) peptide conjugate. The peptide PADRE was chosen for co-incorporation into vesicles because the peptide is a synthetic epitope that has been shown to stimulate the production of IgG antibodies. Specifically, PADRE has been shown to augment the potency of vaccines designed to stimulate T-cells in developing a potent immune response against the carbohydrate antigens that could be presented. We undertook this study to determine if liposaccharides and PADRE inserted into a catanionic vesicles would be capable of eliciting an immune response against the carbohydrate component (FIG. 9).

Results

Catanionic Vaccines for *Neisseria gonorrhoeae.*

Surface antigens from Gram-negative bacteria trigger the immune response and therefore offer the potential to be used in vaccine development. Components on the *N. gonorrhoeae* cell membrane that trigger immune stimulation are LOS, porins (PorA and PorB), pili, and OP A. To date, no one has been able to exploit the immunological potential of neisserial LOS as a vaccine candidate.

Figure 10:
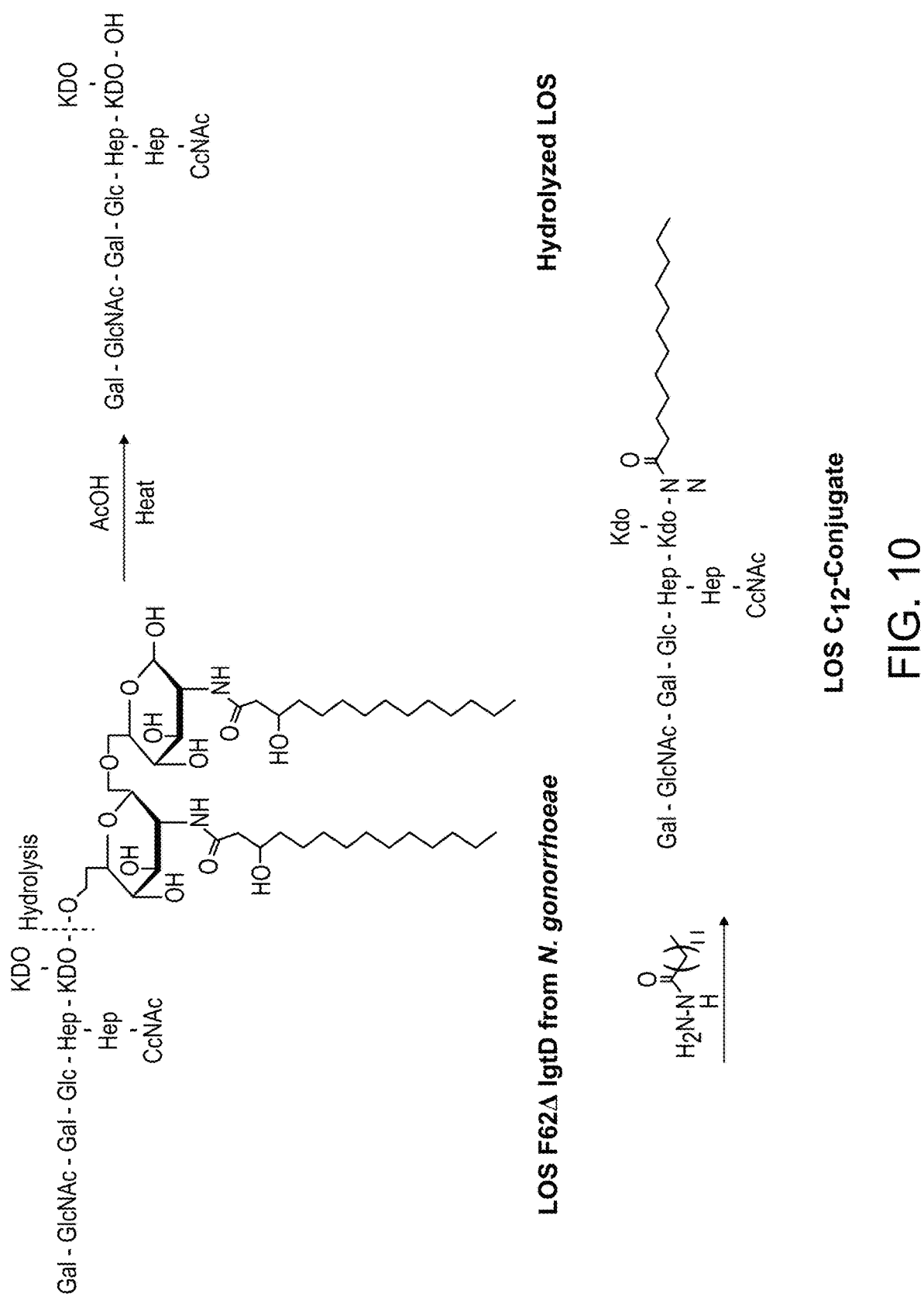
FIG. 10: Preparation of LOS conjugate from N. gonorrhoeae. The toxic lipid A portion was cleaved from the oligosaccharide using hot acetic acid and a hydrophobic C12-linker was added.

Previous research in the DeShong group utilized LOS from *N. gonorrhoeae* for its incorporation into catanionic vesicles. In order to avoid toxicity associated with lipid A, the lipid A region was cleaved (FIG. 10). A C12-conjugate was added to the oligosaccharide to provide an anchor for insertion into vesicles. While this method was effective when preparing functionalized vesicles, incorporation of the lipid A region into liposomes is known to lower its toxicity. Consequently, we studied vesicles loaded with the entire liposaccharide unit to determine if lipid A toxicity is removed after incorporation into catanionic systems.

Figure 11:
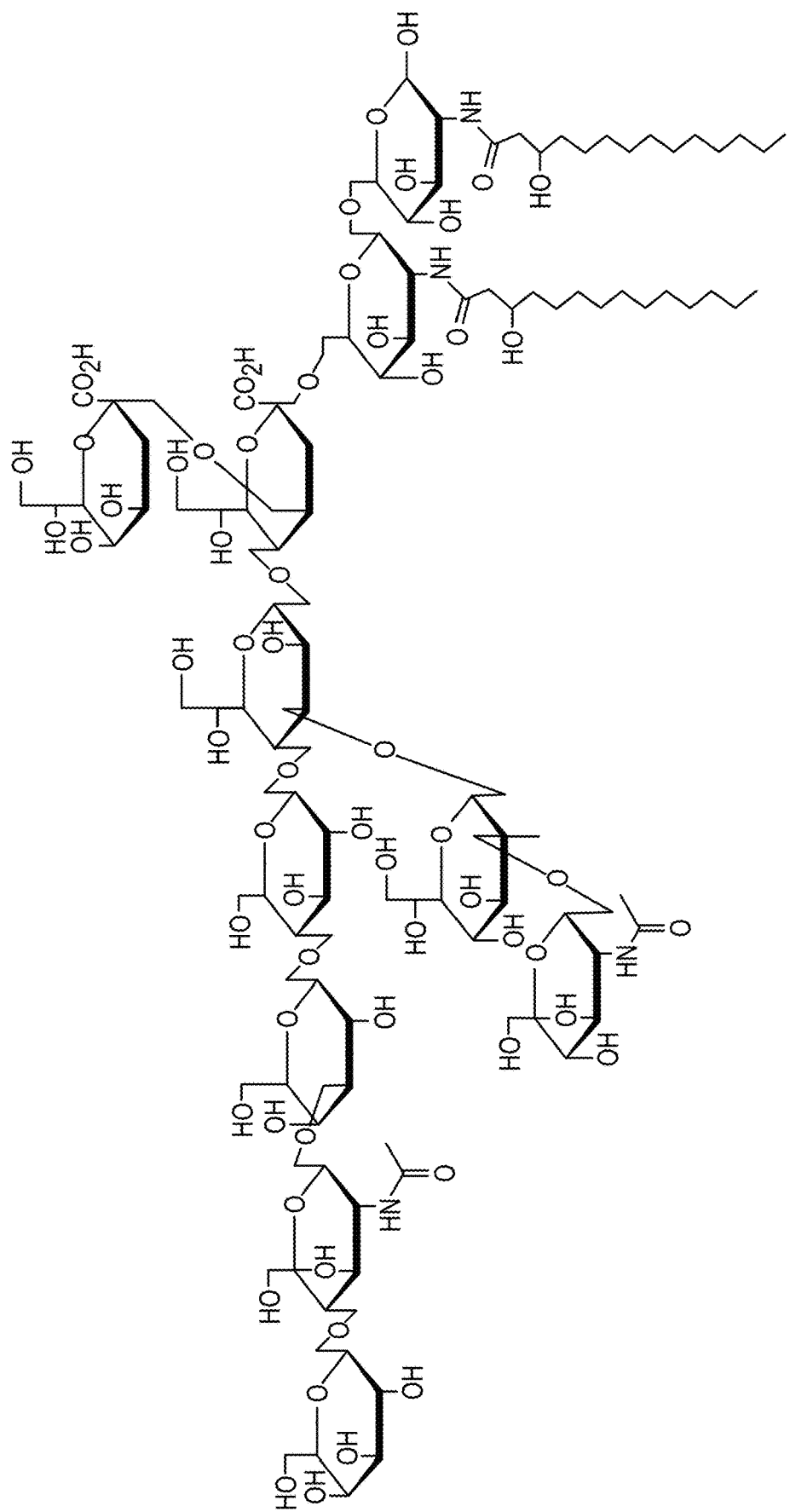
FIG. 11: Chemical structure of lipooligosaccharide (LOS) F62~lgtD purified from N. gonorrhoeae. 0-Antigen: Gal~1-4GlcNAc~1-3Gal-1-; Core: -4Glc~1-4Hepal-(-3Hepal-GlcNAcal)5Kdo4-(-2aKdo); lipid A.
Figure 12:
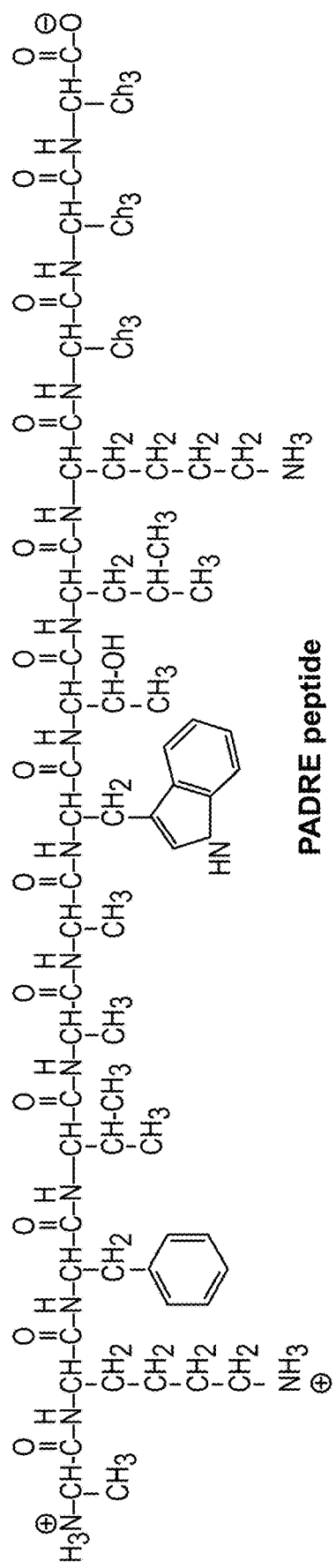
FIG. 12: Chemical (AKFVAAWTLKAAASEQ—ID NO:1), structure of unconjugated PADRE peptide.
Figure 13:
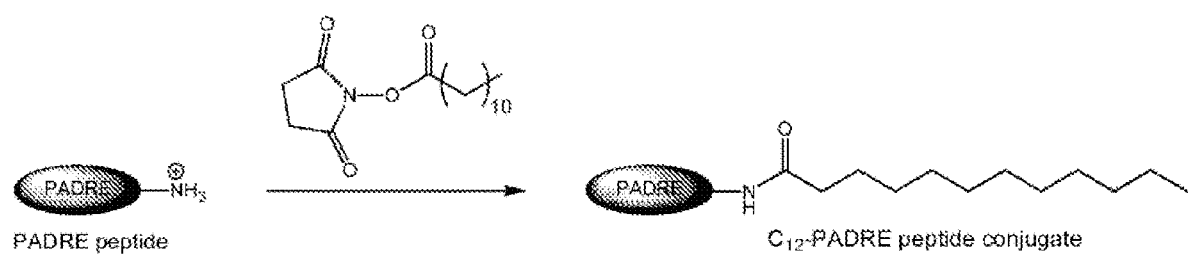
FIG. 13: Synthesis of C12-PADRE peptide conjugate. Conjugated PADRE peptide contains a hydrophobic moiety, which allows for incorporation into the membrane of vesicle bilayers.
Figure 15:
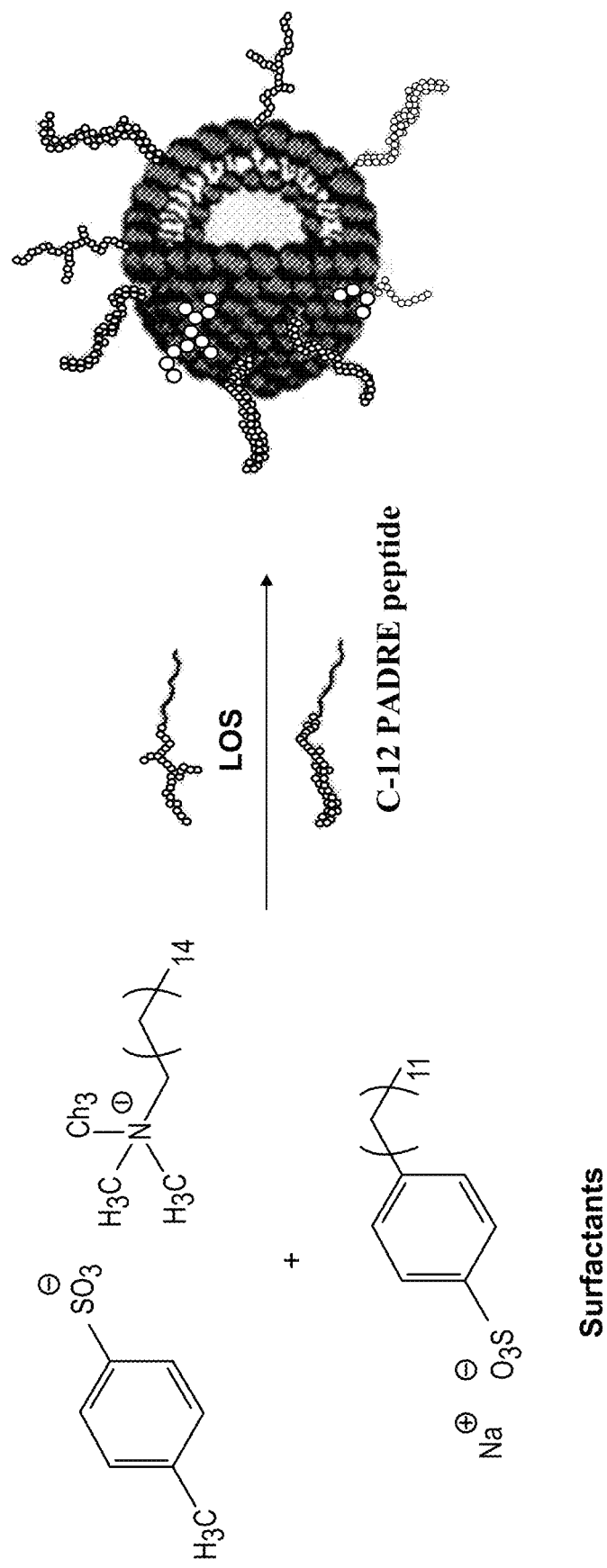
FIG. 15: Preparation of TRIAD vaccine formulated with catanionic surfactant vesicles containing the C12-PADRE peptide conjugate and LOS from N. gonorrhoeae. Ratio of conjugate components can be adjusted during vesicle formation to control the surface decoration of antigens.
Figure 18:
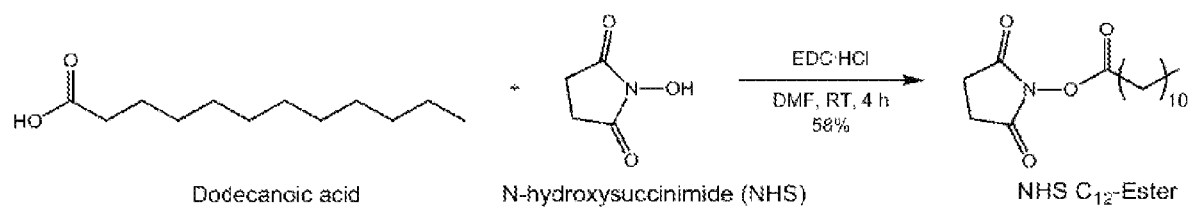
FIG. 18: Synthesis of N-dodecanoylsuccinimide.
Figure 19:
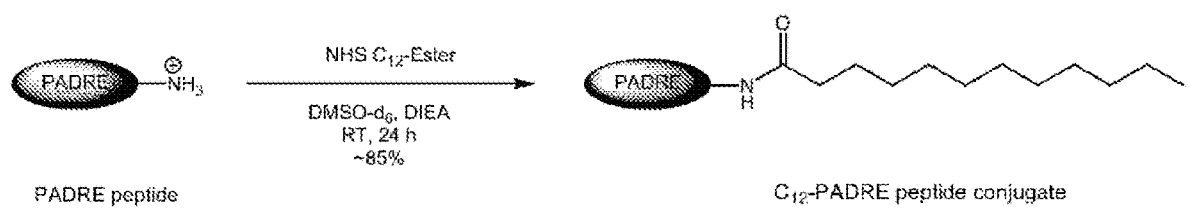
FIG. 19: Synthesis of dodecanoic acid tethered to PADRE peptide.

Catanionic vesicles were prepared by adding native LOS derived from *N. gonorrhoeae* F62~lgtD (a strain that produces lacto-N-neotetraose LOS) (FIG. 11). Addition of this isolated pathogenic component should decorate the exterior membrane of vesicles (FIG. 9). Vesicles were purified by SEC and the presence of saccharide in the vesicle-containing fractions was confirmed using the phenol/sulfuric acid assay (described previously) (FIG. 14). Next, we developed a glycoconjugate-based vaccine (TRIAD) that contained the liposaccharide component and an epitope unit that would trigger the immune system. We utilized LOS and Pan DR helper T cell epitope (PADRE) peptide conjugate that possesses the ability to bind to a large number of HLA class II molecules. PADRE (FIG. 12) was coupled with N-dodecanoylsuccinimide to form dodecanoic acid tethered PADRE conjugate that inserted into the vesicle bilayer (FIG. 13). Both components were inserted into surfactant vesicles using a 10:1 w/w of LOS and C12-PADRE, respectively, and were purified by SEC (FIG. 15). Vesicle-containing fractions were analyzed by the phenol/sulfuric acid carbohydrate assay and by fluorescence. Results confirmed the presence of carbohydrate and phenylalanine and tryptophan residues in vesicle-containing fractions from SEC. These catanionic surfactant vesicle formulations were stable at room temperature for years, unlike typical liposomal vaccine formulations. Furthermore, TRIAD is so robust that it can be autoclaved without any appreciable loss of structural integrity.

Animal Studies with Vesicle Antigens.

Mice were treated with TRIAD vaccine that contained LOS and C12-PADRE at a ratio of 10:1. Antibody levels were determined by ELISA immunoassay by immunizing with 2 mg of LOS equivalent. Antibody titers for both LOS and LOS/C12-PADRE vesicles showed the generation of antibodies after mice were inoculated. Treatment with LOS vesicles showed that only primary antibodies were present (IgM). These results indicated that only a primary immune response was achieved. Inoculation with LOS/C12-PADRE showed that our vaccine induced a high titer anti-LOS antibody response, with the majority of the elicited antibody being IgG (FIG. 16). Intraperitoneal immunization of mice with our vaccine construct produced no observable adverse effects in mice, while intraperitoneal immunization with equivalent amounts of purified LOS induced significant adverse effects. Therefore, catanionic vesicles loaded with LOS/C12-PADRE may have generated IgG antibodies that recognize LOS (FIG. 9). Immunogenic recognition of LOS in our TRIAD carbohydrate-based vaccine and may offer protection against *N. gonorrhoeae* in challenged mice. Furthermore, the LOS from the strain F62~lgtD contains the same LOS found in *N. meningitidis*. Therefore, a vaccine derived from F62~lgtD LOS could offer protection against both gonorrhea and meningitis. This would allow a method to make vaccines against both pathogens without having to work directly with *N. meningitidis*.

Catanionic Vaccines for *Francisella tularensis.*

Figure 17:
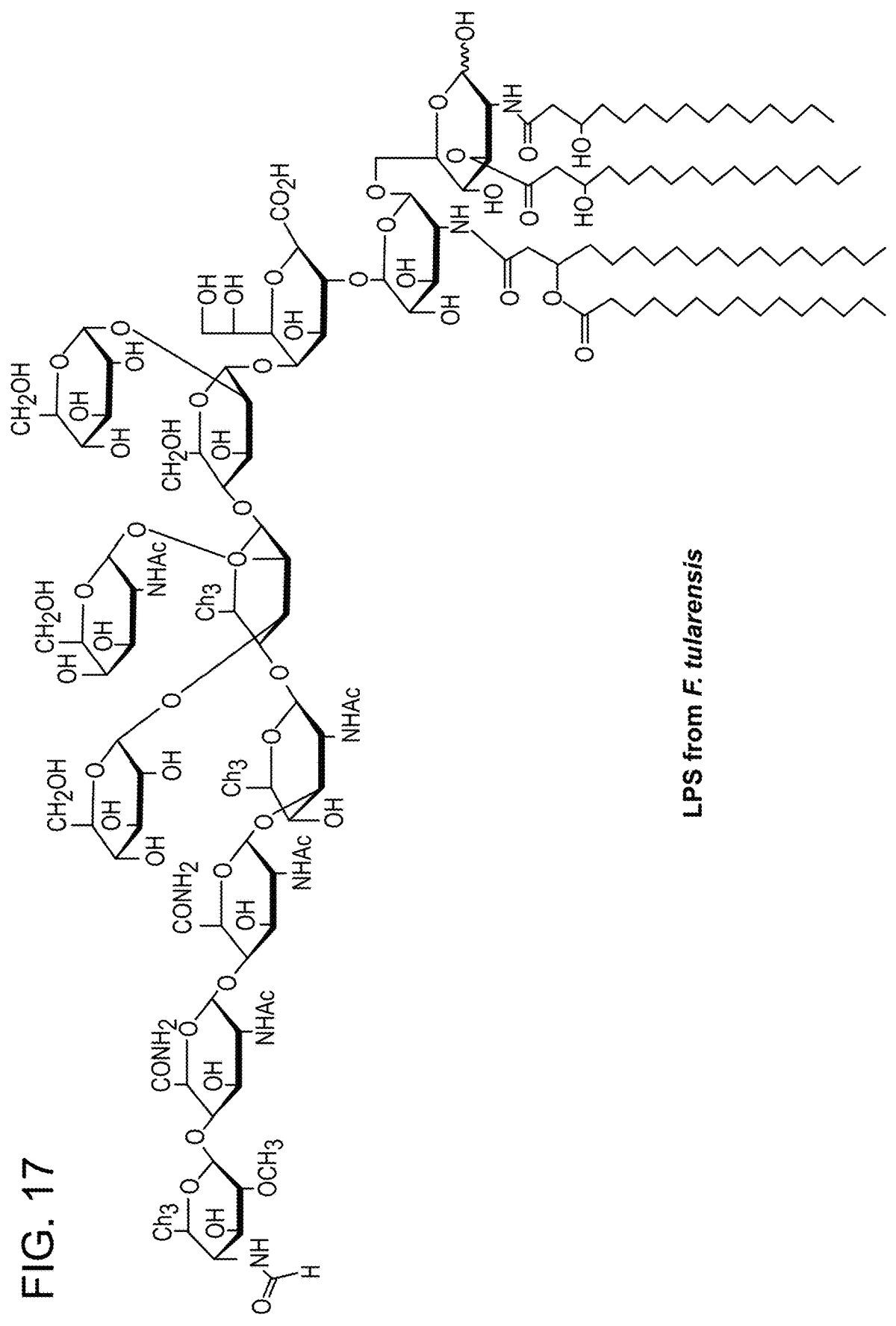

Similar catanionic vaccines were performed in *F. tularensia*. Catanionic vesicles were prepared in the same manner as before, but native LPS from *F. tularensis* was substituted for LOS (FIG. 17). After inoculation of LPS control vesicles, mice challenged with the virulent strain of *F. tularensis* died within four hours. Conversely, four out of five mice inoculated with LPS/C12-PADRE vesicles survived for four days after being challenged. One mouse even survived for two weeks. These results showed that mice vaccinated using LPS/C12-PADRE vesicles survived longer than the control group. These vaccines offer promise toward the development of vesicle-based vaccines to combat tularemia infections. Further vaccine studies are currently underway to determine the antibody titers using the ELISA immunoassay. Furthermore, the ratio of peptide conjugate to saccharide can be controlled in vesicle-based vaccines in order to control the immune system's response to the peptide.

We have devised a safe and effective way of generating a large IgG titer against carbohydrate with a small dose of vaccine. A single dose of TRIAD injected intraperitoneally induced a robust antibody response against carbohydrate without adverse effects. The generated response was mostly IgG and reached a maximum titer with one dose of the vaccine. We believe that this will allow us to generate a universal vaccine capable of protecting against all serotypes of *N. meningitidis*. This vaccine platform also readily lends itself to further modifications in that it is possible to include additional neisserial proteins.

Methods

All chemicals and solvents were purchased from commercial suppliers unless otherwise noted. CTAT was purified by recrystallization in ethanol/acetone prior to use.

Synthesis of N-Dodecanoylsuccinimide.

A solution of dodecanoic acid (0.539 mmol, 0.108 g), N-hydroxysuccinimide (NHS) (0.573 mmol, 0.0660 g), 1-ethyl-3-(3-dimethylaminopropyl)-carbodiimide hydrochloride (EDC.HCl) (0.574 mmol, 0.110 g) in DMF was stirred at room temperature for 4 h (FIG. 18). The solution was diluted with ethyl acetate (20 mL) and washed with H20 (20 mL), saturated aqueous NaHC03 (20 mL), and H20 (20 mL×2). The organic layer was dried over MgS04, filtered, and concentrated in vacuo. Purification after recrystallization (diethyl ether/hexane) afforded 0.0977 g (58%) of N-dodecanoylsuccinimide as white shiny crystals: Rr=0.85 (diethyl ether/hexane); mp 78-79° C. (lit. 15 78-81° C.); IR (thin film, NaCl) 2929 (m), 2852 (m), 1744 (s); 1H NMR (CDCl, 400 MHz) δ 2.84 (s, 4H), δ 2.61 (t, J=8 Hz, 2H), δ 1.75 (m, J=8 Hz, 2H), δ 1.41 (m, 16H), 8 0.89 (t, J=8 Hz, 3H).

Synthesis of Dodecanoic Acid Tethered PADRE Peptide Conjugate.

To a solution of PADRE peptide (FIG. 17) (GenScript) (1.445 μmol, 1.950 mg, 2.890 μM) in 0.5 mL of DMSO-d6 was added a solution of N-dodecanoylsuccinimide (1.445 μmol, 0.430 mg, 2.89 μM) in 0.5 mL of DMSO-d6 followed by a solution of diisopropylethylamine (50 μL, 1.44 μmol, 28.7 mM) in DMSO-d6. The resulting solution was mixed well by vortexing and stirred at room temperature for 24 h. 1H NMR analysis of the reaction mixture indicated that approximately 85% of NHS C12-ester was reacted with PADRE by comparing the integration of starting material to product. The reaction mixture was concentrated in vacuo and stored at −20° C.

Isolation and Characterization of LOS.

The LOS was purified from *N. gonorrhoeae* F62~lgtD, a strain genetically modified to produce only the lacto-N-neotetraose LOS (L 7 immunotype), using a hot phenol/water extraction.

Synthesis and Characterization of Surfactant Vesicles.

Vesicles prepared with a molar excess of SDBS will be referred to as SDBS-rich (anionic). To prepare vesicles with the liposaccharides shown in FIG. 12 and FIG. 17, the liposaccharide was weighed directly into a vial containing 70.0 mg of SDBS (0.200 mmol) and 30.0 mg of CTAT (0.0658 mmol). Specifically, 1 mg of LOS or LPS and 0.2 mg of C12-PADRE conjugate were used to give a 10:1 w/w ratio of antigens in vesicles. Then 9.90 mL of water was added and samples were stirred for 60 min. Vesicles were purified from free conjugate by SEC, described previously. The incorporation of carbohydrate and C12-PADRE-conjugate were determined by colorimetric assays to determine the quantity retained in vesicle-containing fractions. The phenol/sulfuric acid colorimetric assay is described previously. The absorbance was measured at the Amax (~490 nm) and compared to a standard curve, prepared for LOS and LPS to determine the total carbohydrate concentration in each sample.

Animal Trials.

Mice were immunized by the Stein lab intraperitonealy with either 10 μg of purified LOS alone, or 8.5 μg of conjugated vaccine (Vs-OS-PADRE). On day 21 and 42, mice were boosted with an equivalent amount of vaccine or oligosaccharide and blood samples were taken. Serum was recovered from all mice on day 51 in a terminal bleed.

Example 3

Catanionic Surfactant Vesicle Vaccine Fully Protects Mice Against *Francisella tularensis* LVS Challenge and Partially Protects Against *Francisella tularensis* Schu 54 Challenge

*Francisella tularensis* is a Gram-negative immune-evasive coccobacillus that causes tularemia in humans and animals. A safe and efficacious vaccine that is protective against multiple *F. tularensis* strains has yet to be developed. In this study, we tested a novel vaccine approach using artificial pathogens, synthetic nanoparticles made from catanionic surfactant vesicles that are functionalized by the incorporation of either *F. tularensis* type B live vaccine strain (*F. tularensis* LVS [LVS-V]) or *F. tularensis* type A Schu S4 strain (*F. tularensis* Schu S4 [Schu S4-V]) components. The immunization of C57BL/6 mice with "bare" vesicles, which did not express *F. tularensis* components, partially protected against *F. tularensis* LVS, presumably through activation of the innate immune response, and yet it failed to protect against the *F. tularensis* Schu S4 strain. In contrast, immunization with LVS-V fully protected mice against intraperitoneal (i.p.) *F. tularensis* LVS challenge, while immunization of mice with either LVS-V or Schu S4-V partially protected C57BL/6 mice against an intranasal (i.n.) *F. tularensis* Schu S4 challenge and significantly increased the mean time to death for nonsurvivors, particularly following the i.n. and heterologous (i.e., i.p./i.n.) routes of immunization. LVS-V immunization, but not immunization with empty vesicles, elicited high levels of IgG against nonlipopolysaccharide (non-LPS) epitopes that were increased after *F. tularensis* LVS challenge and significantly increased early cytokine production. Antisera from LVS-V-immunized mice conferred passive protection against challenge with *F. tularensis* LVS.

Methods

Vesicle Preparation and Purification.

The vesicle preparation method was adapted from a protocol developed by Kaler et al. and refined by Thomas et al. To prepare cultures for vaccine preparation, the stocks were grown to mid-log phase in Mueller-Hinton broth (MHB) (Becton, Dickinson Microbiology Systems), supplemented with 1% IsoVitaleX (Becton, Dickinson), 0.1% glucose (Sigma), and 0.025% ferric pyrophosphate (Sigma) at 37° C., while shaking. *F. tularensis* Schu S4 (FSC237; BEI Resources) was grown in Trypticase soy broth (TSB) (Becton, Dickinson Microbiology Systems) supplemented with 0.1% L-cysteine hydrochloride (Sigma), 0.1% glucose (Sigma), and 0.1% ferric pyrophosphate (Sigma) at 37° C., while shaking. To prepare 10 ml of vesicles, 25 ml (or 3 to 100 ml for experiments measuring the effects of protein loading on vesicle size and stability) of overnight *F. tularensis* cultures (optical density at 600 nm [OD600], 0.4 to 0.6) was pelleted by centrifugation and lysed in a 7.07-g/liter solution of the anionic surfactant sodium dodecylbenzenesulfonate (SDBS) (Tokyo Chemical Company. Ltd., Tokyo, Japan) in ultrapure endotoxin-free water (Sigma. St. Louis, Mo.). After 1 h. 30 mg of the ethanol-acetone recrystallized form of the cationic surfactant cetyltrimethylammonium tosylate (CTAT) (Sigma) per 10 ml of lysed bacteria was added, for a 3:1 molar ratio of SDBS to CTAT, and the vesicles were allowed to self-assemble overnight at room temperature with stirring. At this point, Schu S4-V preparations were plated on Mueller-Hinton blood plates and kept at 37° C. to ensure the sterility of the vaccine preparations for safe removal from the biosafety level 3 (BSL-3) laboratory. No colonies were detected on any of the plates (data not shown). The vesicle preparations were stored at 4° C. during this time. To separate the vesicles from free surfactants and cellular debris, the vesicle preparations were centrifuged to pellet large detritus, and the resulting supernatant was purified by size exclusion chromatography over a column composed of 10 ml of washed and packed Sephadex G-100 (Sigma). The vesicles remained stable at 4 to 25° C. for ≥5 months (data not shown). The protein content in the vesicles was determined by a modified version of the detergent-compatible (DC) protein assay with Reagent S (Bio-Rad, Hercules, Calif.), using bovine serum albumin (BSA) as a standard (Pierce, Rockford, Ill.). The vesicles varied in size, with radii ranging from 70 to 105 nm in bare vesicles and 80 to 120 nm in vesicles containing *F. tularensis* components, as determined by dynamic light scattering (DLS) with an LS-DYNA (Livermore Software Technology Corporation) set to a 90° angle, utilizing PhotoCore 5.3.8 analysis software for cumulants algorithm. Zeta potential was measured with a Malvern Zetasizer Nano ZS90, using phosphate-buffered saline (PBS) as an electrolyte source. Zeta potential measures surface charge on the vesicles and has been found to correlate with the stability of vesicles.

Immunization Protocol and *F. tularensis* Challenge.

Wild-type 6- to 8-week-old female C57BL/6 mice were purchased from Jackson Laboratories (Bar Harbor, Me.) and housed in a specific-pathogen-free facility at the University of Maryland Baltimore, Md., and in the animal BSL-3 (ABSL-3) suite at the University of Virginia. The mice were immunized with either the *F. tularensis* LVS (LVS-V) or the *F. tularensis* Schu S4 (S4-V) vesicles (35 µg protein) by either intraperitoneal (i.p.), intranasal (i.n.), or subcutaneous (s.c.) routes, as indicated, up to three times in 2-week intervals, with the last dose administered 14 days prior to live bacterial challenge. Where indicated, the resting period between the immunization and challenge was extended from 14 to 28 days. As a negative control, the mice received bare vesicles made in endotoxin-free water in the absence of bacterial pellets but purified identically to LVS-V and S4-V. For passive immunization experiments, the mice received 60 µl pooled serum samples from naive mice or from vesicle- or LVS-V-immunized animals by the intravenous (i.v.) route 1 day prior to challenge. The mice were challenged by the i.p. route with up to 100,000 CFU *F. tularensis* LVS or by the i.n. route with up to 50 CFU *F. tularensis* Schu S4. The challenge doses of *F. tularensis* LVS used in these studies were determined prior to each experiment to kill ≥80% of unimmunized mice.

The mice were checked twice daily for clinical symptoms of *F. tularensis* infection for 21 days following challenge. Clinical scores were assigned as follows: for mice infected with *F. tularensis* LVS, a score of 0 was assigned for healthy mice with normal behavior (exploring cage, feeding, alert), 1 for mild illness (usually marked by lower activity and weight loss), 2 for mild-moderate illness (mice showing symptoms of score 1 plus piloerection), 3 for moderate-severe illness (mice showing symptoms of score 2 plus assuming a hunched posture), 4 for severe illness (mice showing symptoms of score 3 and minimal activity or blepharitis [crustiness around the eye] involving one or both eyes), 4+ for moribund illness (mice showing symptoms of score 3 and were nonresponsive to stimulation [these mice were euthanized]), and 5 for mice found dead in their cage. Mice with scores of 4+ and 5 were reported on the day of death only and were excluded from analysis on subsequent days. The arithmetic means±the standard errors of the means (SEM) of the clinical scores were reported. For mice infected with the *F. tularensis* Schu S4 strain, a score of 0 was assigned for healthy mice with normal mouse behavior (exploring cage, feeding, alert), 1 for mild illness (decreased movement), 2 for moderate illness (decreased motion, eye closure), 3 for severe illness (motionless, eye closure, increased respirations, ruffled fur), and 4 for mice that were moribund (no motion in response to external stimuli plus meeting the criteria in reference 3) or dead. The moribund mice were euthanized.

To measure the blood serum antibody titers in *F. tularensis* LVS-infected mice, ~200 µl blood was collected at the indicated intervals. Each mouse was euthanized and bled at the termination of the experiments. All animal experiments were conducted with Institutional Animal Care and Use Committee approval.

ELISA, Silver Stain, and Western Blots.

Enzyme-linked immunosorbent assays (ELISAs) were performed as previously described. Briefly, ELISA plates were coated with 2 µg/ml purified lipopolysaccharide from *F. tularensis* LVS (*F. tularensis* LVS LPS) or with $5\pm107$ CFU/ml *F. tularensis* LVS. After washing, the plates were blocked with 10% fetal bovine serum (FBS). The serum samples were serially diluted in 10% FBS and 0.05% Tween 20 and were added to the coated plates for 90 min at 37° C. After extensive washing, horseradish peroxidase (HRP)-conjugated secondary antibodies (SouthernBiotech) were added to the wells at a 1:20.000 dilution. Detection was achieved using the 2,2'=−azinobis(3 ethylbenzthiazolinesulfonic acid) (ABTS) system (Sigma) and the plates were read on a universal microplate reader, ELx800 (Bio-Tek Instruments, Inc.). The data were analyzed in MS Excel; the antibody titers were defined as the serum dilution corresponding to an average OD value of 3 standard deviations above the background OD values. The data for each mouse were graphed on a logarithmic scale, and the geometric mean was calculated for each group of mice at each time point. The geometric means were graphed separately in FIG. 22D for easier comparison.

Silver staining of membranes was performed as previously described. Briefly, vesicles and bacterial pellets were boiled in Laemmli sample buffer (with β-mercaptoethanol but without protease inhibitor cocktail) and separated by PAGE on Tris-glycine gels (12%, 10 to 20% gradient, or 4 to 20% gradient, as indicated) (Bio-Rad). The gels were fixed overnight in 40% ethanol, 0.5% glacial acetic acid, and washed for 5 min in 0.83% periodic acid (Sigma). After washing with water, the gels were stained with a basic solution of 0.8% silver nitrate (Sigma) for 15 min, washed extensively, and developed with 0.007% formaldehyde and 50 µg/ml citric acid for 10 min. The gels were washed with water, at which time they continued to develop and were scanned after 10 min.

For Western blots, vesicle and bacterial samples were boiled in Laemmli sample buffer and separated by PAGE as described above. The gels were transferred to an Immobilon-P membrane (Millipore) by wet transfer. The membranes were blocked in 5% milk in Tris-buffered saline-Tween 20 (TBST) (Bio-Rad). Pooled serum samples from LVS-V- or Schu S4-V immunized mice were diluted 1:106 or 1:105, respectively, in 5% milk-TBST and incubated with the membranes overnight at 4° C. or 2 h at room temperature (RT). The dilutions of anti-LVS-V or anti-Schu S4-V were based on preliminary experiments that optimized the detection of bands in the *F. tularensis* lysates. After washing, HRP-conjugated human adsorbed goat-anti-mouse IgG1, IgG2b, IgG2c, and IgG3 secondary antibodies (Southern Biotech) were diluted 1:20,000 in 5% milk-TBST and incubated with the membranes for 60 min at RT. After extensive washing, the ECL Plus detection kit (GE Healthcare) was used to visualize the bands, which were recorded on BioMax MR film (Kodak). *F. tularensis* LPS-specific rabbit antibodies were kindly provided by Karen Elkins (FDA). Purified *F. tularensis* LVS DnaK and Tul4 were prepared as described previously.

Comparison of Different *F. tularensis* Strains by Western Blot Analysis.

*F. tularensis* strains Schu S4, MA00-2987, WY96-3418, KY99-3387, OR96-0246 (BEI Resources, Inc.) and *F. tularensis* LVS were grown in enriched TSB medium as described above. To estimate equal loading, each bacterial culture was grown overnight and was diluted to an OD600 of 0.300 prior to pelleting the bacteria and lysis in Laemmli sample buffer. PAGE, silver staining, and Western blot analysis were carried out as detailed above.

Real-Time PCR.

To assess the initial inflammatory responses, each mouse was euthanized 4 h after the first i.p. immunization with saline, vesicles, or LVS-V. Total RNA was extracted from the liver samples, and real-time PCR analysis was performed as previously described. In this study, we report the relative gene expression normalized to the expression of mouse hypoxanthine phosphoribosyltransferase (HPRT). All primer pairs used in this study have been published. The cytokine protein levels were measured by the Cytokine Core Laboratory (University of Maryland Baltimore [UMB]). Statistics. The data were analyzed with GraphPad Prism 4 for Windows (GraphPad Software, Inc., San Diego, Calif.). Specific tests include Fisher's exact test for comparisons of survival at day 14 post challenge, the log rank test for analysis of survival curves, the one-way analysis of variance (ANOVA), followed by a Tukey's post hoc test for analyses of multiple groups of data, and the Mann-Whitney test (nonparametric t test) for analyses of two groups of data.

Fuctionalization of Vesicles Used for Immunization in FIG. 20.

The T cell epitope PADRE was conjugated to dodecanoic acid employing the N-hydroxysuccinimide methodology described below. The lipid A portion of LPS is sufficiently hydrophobic to be incorporated into the vesicle leaflet, and therefore, no modification of LPS was required. Whole LPS isolated from Ft LVS (1) and/or the C12-modified PADRE peptide were incorporated during the assembly of catanionic vesicles as both surfactants were mixed concurrently at the same ratios as described in the text. These vesicles were administered to mice by i.p. injections twice, two weeks apart. Two weeks following the second immunization, mice were challenged with Ft LVS (FIG. 20) and survival of each individual mouse was followed for two weeks. Mice were bled prior to each injection and 11 days post-challenge. Antibody detection in sera were carried out by a FACS-based bead assay as previously described.

Conjugation of PADRE to a C12 Hydrophobic Tail.

A hydrophobic tail for the PADRE peptide was attached to the amino terminus as follows: A solution of dodecanoic acid (0.539 mmol, 0.108 g), N-hydroxysuccinimide (0.573 mmol, 0.0660 g), 1-ethyl-3-(3-dimethylaminopropyl)-carbodiimide hydrochloride (EDC.HCl) (0.574 mmol, 0.110 g) in dimethylformamide (DMF) was stirred at room temperature for 4 h. The solution was diluted with ethyl acetate (20 mL) and washed with H20 (20 mL), saturated aqueous $NaHCO_3$ (20 mL), and H20 (20 mL×2). The organic layer was dried over MgSO4, filtered, and concentrated in vacuo. Purification after recrystallization (diethyl ether/hexane) resulted in 0.0977 g (58%) of N-dodecanoylsuccinimide ester as white, shiny crystals: Rf=0.85 (diethyl ether/hexane); mp 78-79° C. (lit.(3) 78-81° C.); IR (thin film, NaCl) 2929 (m), 2852 (m), 1744 (s); 1H NMR (CDCl3, 400 MHz) δ 2.84 (s, 4H), δ 2.61 (t, J=8 Hz, 2H), δ 1.75 (m, J=8 Hz, 2H), δ 1.41 (m, 16H), δ 0.89 (t, J=8 Hz, 3H). To a solution of PADRE peptide (GenScript) (1.445 μmol, 1.950 mg, 2.890 μM) in 0.5 mL of DMSO-d6 (deuterated) was added a solution of Ndodecanoylsuccinimide (1.445 μmol, 0.430 mg, 2.89 μM) in 0.5 mL of DMSO-d6 followed by a solution of diisopropylethylamine (50 μL, 1.44 μmol, 28.7 mM) in DMSO-d6. The resulting solution was mixed well by vortexing and stirred at room temperature for 24 h. 1H NMR analysis of the reaction mixture indicated that approximately 85% of the N-hydroxysuccinimide C12-ester was reacted with PADRE by comparing the integration of starting material to product. The reaction mixture was concentrated in vacuo and stored at −20° C.

Results

Immunization with F. tularensis LVS LPS-V Protects Against F. tularensis LVS but not F. tularensis Schu S4 Challenge.

Figure 20C:
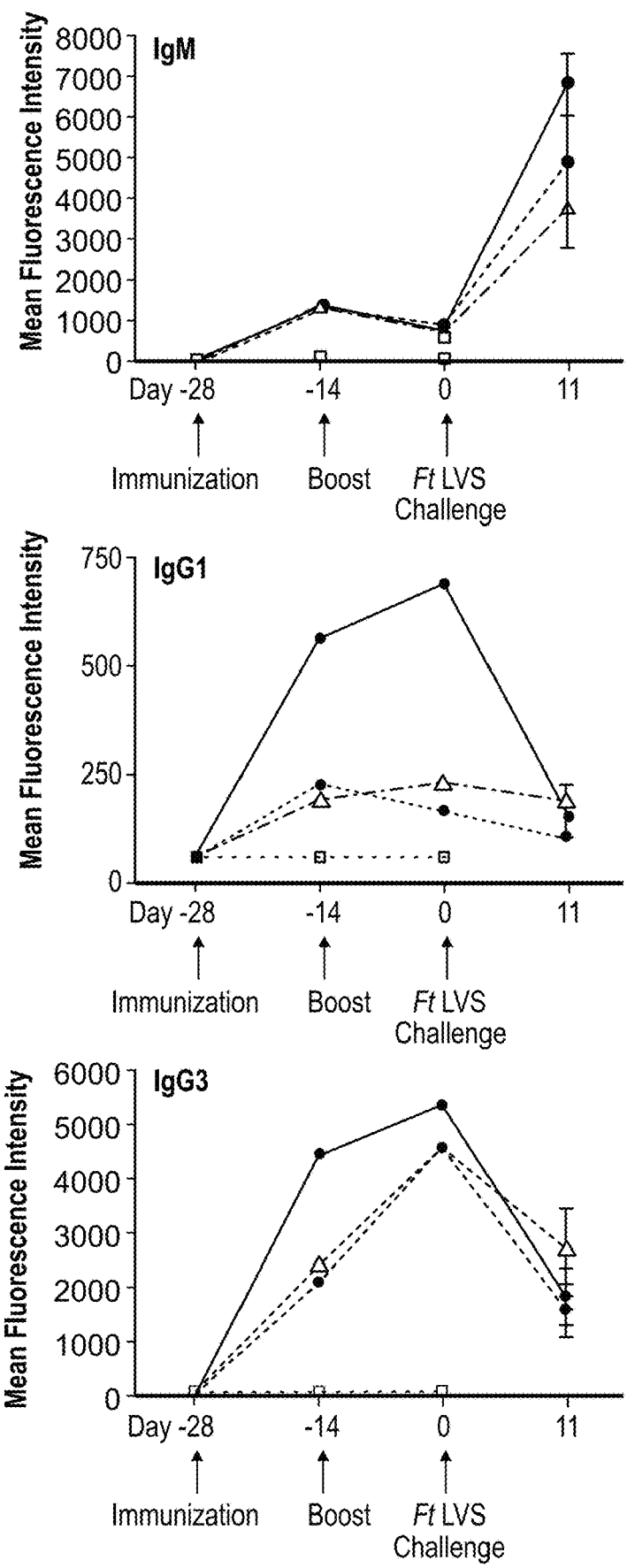
FIG. 20: Functionalized catanionic vesicles displaying F. tularensis LVS LPS as the only F. tularensis component are protective against F. tularensis LVS challenge, but fail to induce robust IgG antibody responses. (A.) Schematic of experimental protocol. Mice were injected twice, two weeks apart (D −28, D −14), by intraperitoneal injection (i.p.), with either purified F. tularensis LVS LPS in its soluble form (LPS), purified F. tularensis LVS LPS included in surfactant vesicles (LPSvesicles), the T cell epitope, C12-PADRE, covalently coupled to surfactant vesicles (PADRE-vesicles), or purified F. tularensis LVS LPS and C12-PADRE covalently coupled to vesicles (LPS-PADRE-vesicles). Two weeks after the second immunization, all mice were challenged i.p. with about 6000 colony forming units (CFU) F. tularensis LVS per mouse. (B.) Survival of individual mice after the F. tularensis LVS challenge. (C.) Sera were collected prior to each immunization, prior to challenge, and on the 11th day following challenge. Sera from each time point were pooled, except for serum from the last time point in which each survivor was bled individually. Antibody titers to whole F. tularensis LVS were measured by FACS-based bead assay utilizing isotype-specific secondary antibodies for detection as previously described (Cole et al., PNAS 106. 2009.). Error bars represent standard error of the mean for 5 mice. The results are representative of one of two separate experiments with similar outcomes.
Figure 21A:
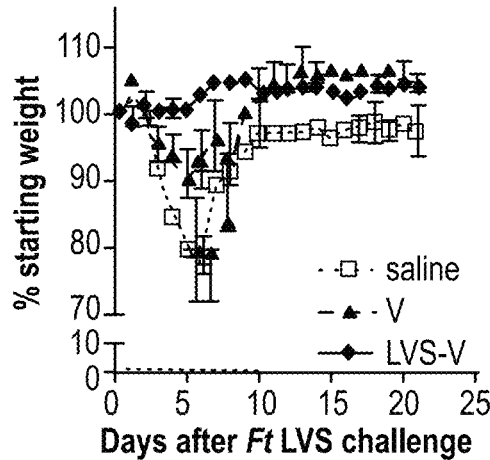
FIG. 21: LVS-V nanoparticles fully protect mice against F. tularensis (Ft) LVS challenge. (A to C) In experiment 1, mice were injected twice, 2 weeks apart (days −28 and −14), i.p. with sterile saline (white square, dotted line), catanionic vesicles formed in the presence of F. tularensis LVS (LVS-V, 35 pig protein) (black diamond, solid line), or the equivalent amount of bare catanionic vesicles (V) (black triangle, dashed line). Two weeks after the second immunization, all mice were challenged i.p. with 30,000 CFU F. tularensis LVS per mouse. (D to F) In experiment 2, the challenge dose was increased to 70,000 CFU F. tularensis LVS per mouse. (G to I) In experiment 3, the time after final immunization was increased to 4 weeks. Everything else was kept the same as for experiment 1. In each experiment, the percent starting weight (A, D, and G), and the severity of tularemia symptoms (B, E, and H), from 0 for healthy to 5 for dead, and survival of the individual mice following challenge (C, F, and I) are shown. Clinical scores were assigned as follows: for mice infected with F. tularensis LVS, a score of 0 was assigned for healthy mice with normal behavior (exploring cage, feeding, alert), 1 for mild illness (usually marked by lower activity and weight loss), 2 for mild-moderate illness (mice showing symptoms of score 1 plus piloerection), 3 for moderate-severe illness (mice showing symptoms of score 2 plus assuming a hunched posture), 4 for severe illness (mice showing symptoms of score 3 and minimal activity or blepharitis [crustiness around the eye] involving one or both eyes), 4+ for moribund illness (mice showing symptoms of score 3 and were nonresponsive to stimulation [these mice were euthanized]), and 5 for mice found dead in their cage. Mice with scores of 4+ and 5 were reported on the day of death only and were excluded from analysis on subsequent days. The arithmetic means+/−the standard errors of the means (SEM) of the clinical scores were reported.
Figure 21D:
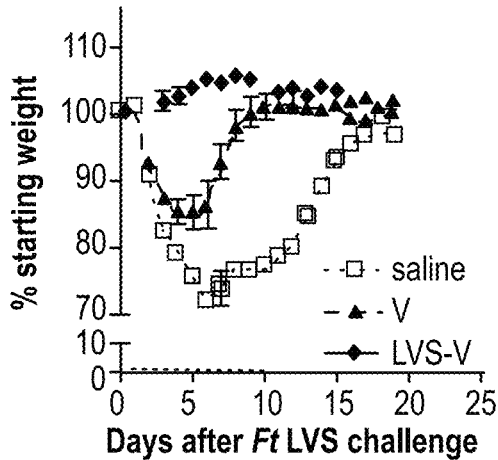
Figure 21B:
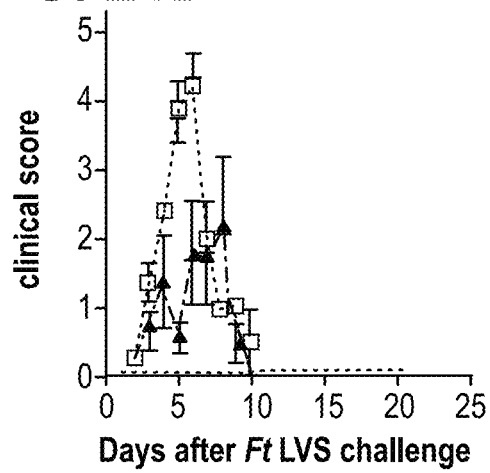
Figure 21E:
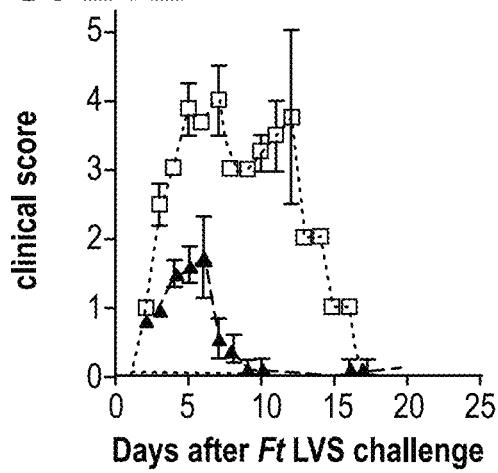
Figure 21C:
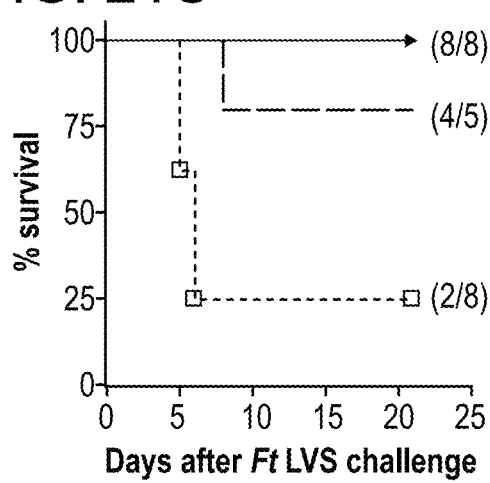
Figure 21F:
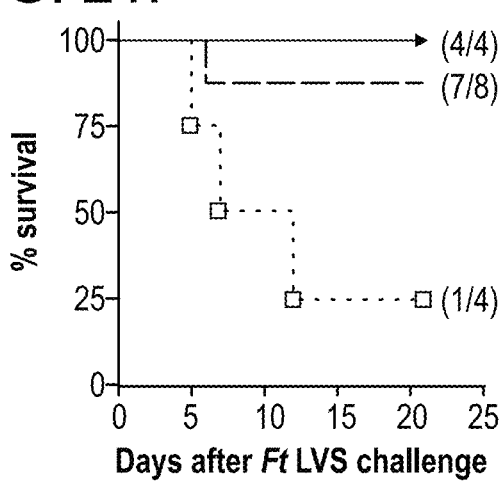
Figure 21G:
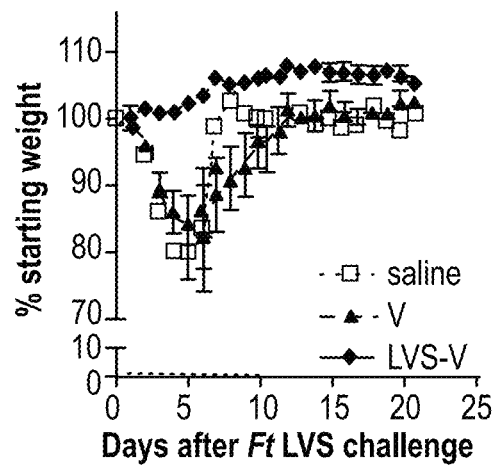
Figure 21H:
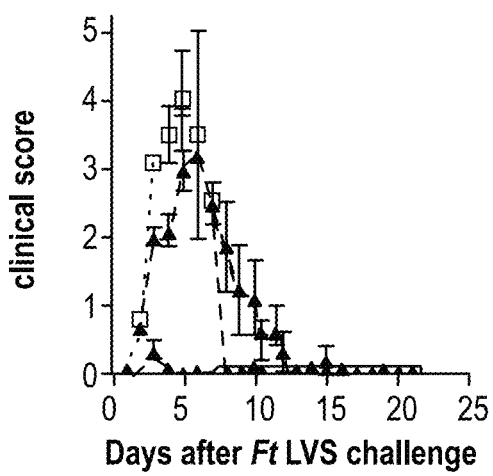
Figure 21I:
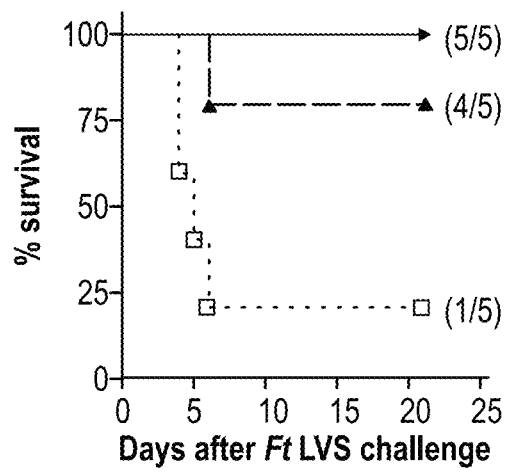

We previously demonstrated that immunization with LPS from F. tularensis LVS (F. tularensis LVS LPS) only 2 days prior to live bacterial challenge fully protected mice against a lethal challenge with F. tularensis LVS. This protection was attributable to B1a cell- and antibody-mediated responses. The same regimen did not protect against F. tularensis Schu S4 challenge, despite the fact that both F. tularensis LVS and F. tularensis Schu S4 share the same O antigen, and therefore, antibodies should be cross-protective. In an attempt to improve the effectiveness of F. tularensis LVS LPS as a vaccine, we initially incorporated the purified F. tularensis LVS LPS, with or without a promiscuous The cell epitope called PADRE, into catanionic vesicles that were used as a delivery system. PADRE was covalently modified at the N terminus with a C12 hydrophobic tail via amide linkage (C12-PADRE) to enable its coupling to the vesicles. Catanionic vesicles form when two surfactants with oppositely charged head groups and sufficiently long hydrophobic tails (≥C10) are combined in the appropriate ratio (i.e., a molar ratio of 3:1 is ideal for SDBS and CTAT). Indeed, surfactant-based catanionic vesicles have been shown to be more stable than phospholipid-based vesicles. Mice immunized with two doses of purified F. tularensis LVS LPS (as a positive control) or with catanionic vesicles functionalized with F. tularensis LVS LPS (≥C12-PADRE), administered 2 weeks apart (FIG. 20A), survived i.p. challenge with F. tularensis LVS 2 weeks after final immunization (FIG. 20B). However, no protection was seen when similarly immunized mice were i.n. challenged with F. tularensis Schu S4. A serum IgM anti-LPS antibody response was induced in immunized mice, which significantly increased following challenge, regardless of the immunogen used (FIG. 20C). The purified F. tularensis LVS LPS also induced a detectable serum IgG anti-LPS response (FIG. 20C). The levels of IgG1 antibodies were significantly reduced in the vesicle-immunized mice, and to a lesser extent, IgG3 levels were also reduced compared to the controls (FIG. 20C). Therefore, we sought a new approach that would lead to a subunit vaccine that would both increase the IgG response and protect against infection with F. tularensis Schu S4.

Immunization with F. tularensis LVS-Vesicles Elicits Full Protection Against F. tularensis LVS Challenge.

Since F. tularensis LVS LPS-V failed to protect against F. tularensis Schu S4 challenge, we next modified our catanionic vesicle system in an effort to develop an improved F. tularensis subunit vaccine. We hypothesized that immunization with a subunit vaccine that contained a diverse assortment of the F. tularensis ligands, including hydrophobic and amphiphilic bacterial molecules, as well as bacterial DNA, would enable concurrent engagement of multiple innate and adaptive signaling pathways. We theorized that a strong pathogen-specific inflammatory response, coupled with a specific high-titer IgG anti-F. tularensis antibody response, would protect not only against F. tularensis LVS challenge but also against F. tularensis Schu S4 challenge. To this end, we prepared control vesicles by combining anionic and cationic surfactants in endotoxin-free water. To prepare vesicles containing F. tularensis components, the anionic surfactant was first added to pelleted cultures of F. tularensis LVS or F. tularensis Schu S4 to lyse the bacteria, and then the cationic surfactant was added to produce vesicles that incorporated bacterial components from the bacterial lysates. The resulting *F. tularensis* nanoparticles are referred to as LVS-V and Schu S4-V, respectively. No living organisms grew on Mueller-Hinton blood plates after contact with anionic surfactant (data not shown). The vesicles were subsequently purified over a Sephadex G-100 column to separate free bacterial components and unincorporated surfactants from the vesicles prior to immunizing the mice.

Initially, the mice were immunized twice by the i.p. route, 2 weeks apart, with sterile saline (as a control), LVS-V (35 µg protein), or an equivalent volume of bare vesicles as an additional control. Two weeks after the second immunization, all mice were challenged by the i.p. route with the indicated dose of *F. tularensis* LVS. Weight loss, clinical symptoms, and the survival of each mouse were monitored for 3 weeks. FIG. 21 shows the results of two separate experiments at this immunization schedule, with challenge doses of 30,000 CFU *F. tularensis* LVS/mouse (FIG. 1A to C) or 70,000 CFU *F. tularensis* LVS/mouse (FIG. 21 D to F). One experiment in which the resting period after immunization was extended to 4 weeks prior to challenge with 30,000 CFU *F. tularensis* LVS/mouse is also shown (FIG. 21 G to I). In the saline-immunized groups, mice suffered rapid weight loss (FIGS. 21 A, D, and G) and exhibited infection-associated clinical symptoms (FIGS. 21 B, E, and H) starting on the second day after infection and either expired or started to recover 5 to 6 days after infection. Seventy-five to 80% of the mice immunized twice with saline and challenged with *F. tularensis* LVS died when challenged with 30,000 (FIGS. 21 C and I) or 70,000 CFU *F. tularensis* LVS (FIG. 21 F). Immunization with LVS-V fully protected mice, as evidenced by the 100% survival rate at both challenge doses and the complete absence of weight loss and other clinical signs of disease, whether the resting time allowed between the final immunization and challenge was 2 weeks or 4 weeks (FIG. 21). Surprisingly, in both challenges carried out 2 weeks postimmunization, ≥80% of mice that were immunized with plain vesicles suffered only moderate weight loss during the peak infection period and survived *F. tularensis* LVS challenge (FIG. 1). Empty vesicle-immunized animals that were challenged 4 weeks after the second immunization exhibited more severe weight loss, similar to the saline controls (FIG. 21 G), suggesting that the effect of bare vesicle immunization might wane by 4 weeks postimmunization, but in contrast to the saline controls, the majority of these animals recovered (FIG. 21 I).

LVS-Vinduced Robust Antibody Responses, Including Isotype Class Switching.

Figure 22C:
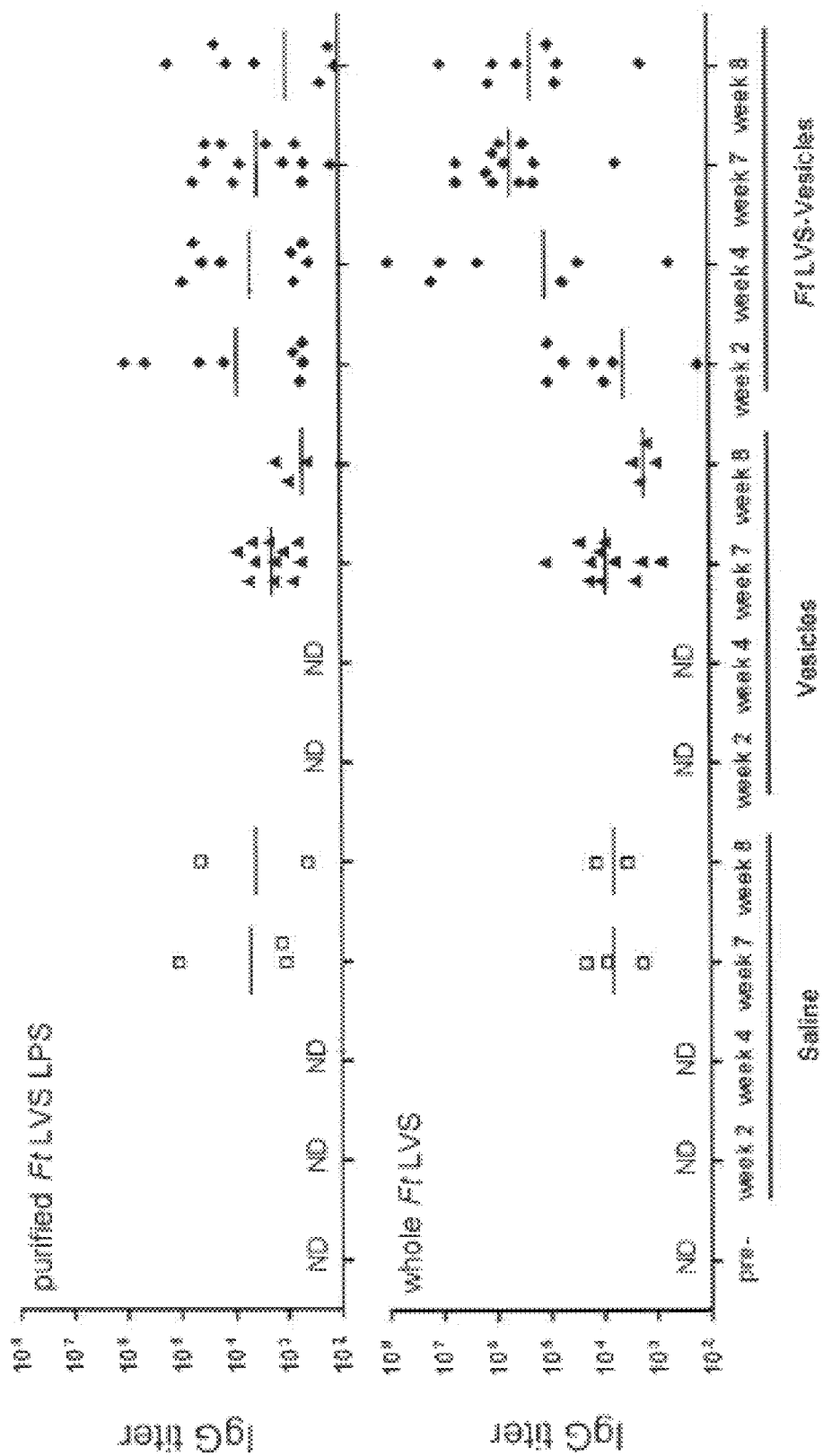
FIG. 22: LVS-V induce robust antibody responses where IgM is essentially all anti-LPS antibody and IgG is predominantly directed against non-LPS epitopes. (A) Schematic of immunization and bleeding schedule. The mice were immunized and challenged as described in FIG. 21. The mice were challenged again 22 days following the primary challenge to determine the effect on antibody responses. (B) ELISA data measuring F. tularensis-specific IgM. (C) ELISA data measuring F. tularensis specific IgG (all subclasses). Microwell plates were coated with purified F. tularensis LVS LPS (top panels) or whole F. tularensis LVS bacteria (bottom panels) to distinguish between LPS-specific and overall anti-F. tularensis antibody levels. The titers are shown on a log scale. Each symbol represents one mouse. ND, none detected. (D) The geometric means of the ELISA titers detected in B and C were replotted for easier visual comparison between the antibody levels directed against whole F. tularensis LVS (filled symbols, solid lines) and those against purified F. tularensis LVS LPS (open symbols, dashed lines) in both IgG (black square, black) and IgM (black triangle, gray) assays. , p<0.01; *, p<0.001.

To test whether immunization with LVS-V resulted in augmented humoral antibody responses, mice were immunized twice with saline, empty control vesicles, or LVS-V and challenged with 30,000 CFU *F. tularensis* LVS (challenge 1) by i.p. injection as described above, and then survivors, as well as a new group of saline-treated mice, were challenged i.p. with 50,000 CFU *F. tularensis* LVS (challenge 2) to determine if re-exposure would boost antibody responses in mice previously exposed to *F. tularensis* antigens by immunization and/or by the first challenge. Blood serum samples were collected prior to each immunization and challenge, as well as 1 week following the second challenge (FIG. 22A), and the antibody titers were measured by ELISA. To assess the levels of serum antibody directed against LPS and non-LPS epitopes, ELISA plates were coated with either purified *F. tularensis* LVS LPS or whole *F. tularensis* LVS (FIGS. 22 B and C). Isotype-specific antibodies were detected with secondary antibodies against mouse IgM (FIG. 22B) or a cocktail of secondary antibodies against all four mouse IgG subclasses (FIG. 22C).

Figure 22D:
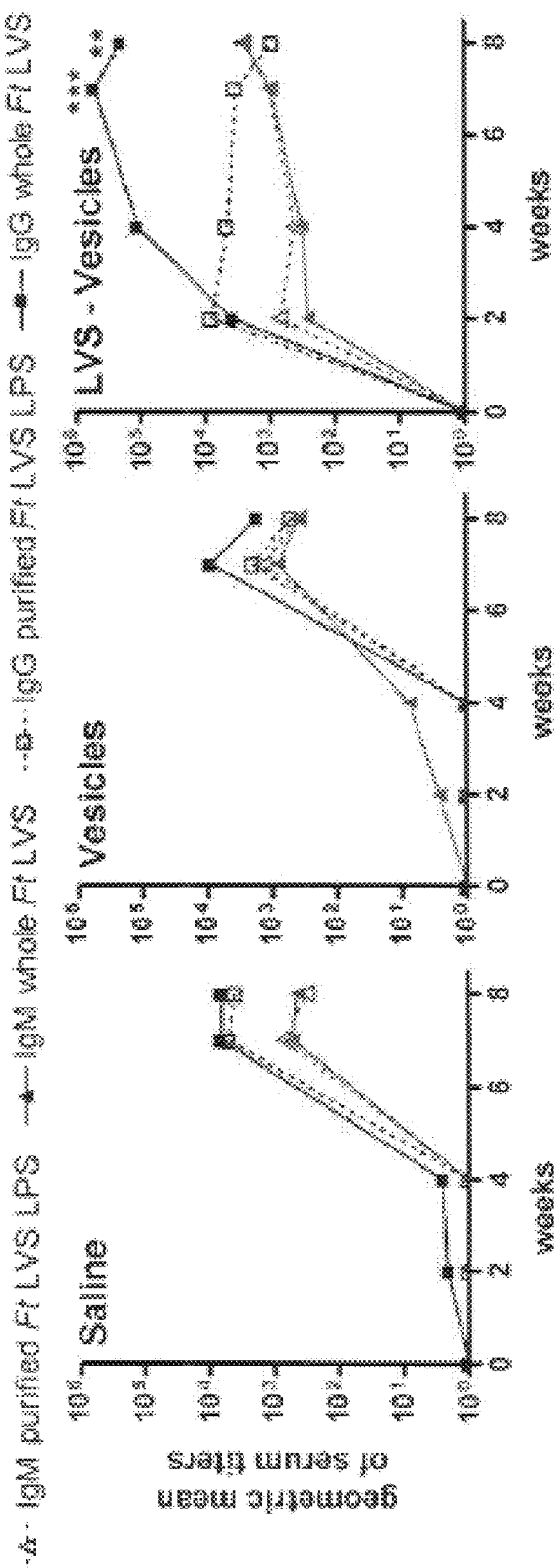

While no *F. tularensis*-specific IgM response was observed in mice immunized with saline or vesicles (weeks 2 and 4), a low but significant IgM titer followed live bacterial challenge (weeks 7 and 8). Only mice immunized with LVS-V produced detectable levels of *F. tularensis*-specific antibodies prior to live bacterial challenge: IgM titers were detected as early as 2 weeks after the first immunization and increased after challenge with live *F. tularensis* LVS (weeks 7 and 8). The IgM antibody titers were similar when assayed on plates coated with either purified *F. tularensis* LVS LPS or whole *F. tularensis* LVS (FIG. 22B), indicating that essentially all of the IgM produced was directed against the LPS. Immunization with LVS-V, but not saline or bare vesicles, also induced antibody isotype switching to IgG. IgG titers were detectable 14 days after the first immunization, and were increased 2 weeks after the second immunization (FIG. 22C) when assayed by ELISA on plates coated with whole *F. tularensis* LVS. Notably, the prechallenge (week 4) antibody titers directed against whole bacteria exceeded anti-LPS IgG titers by >10-fold, indicating that the IgG responses were predominantly directed against non-LPS epitopes (FIG. 22D). Non-LPS-specific IgG antibodies remained strong and further increased to a titer of ~106 following live bacterial challenge. Consistent with the responses to natural infections (12, 39), the antibody responses produced by immunization with saline or vesicles were detected only after live infection (week 7 and later) and were directed predominantly against the *F. tularensis* LPS. Thus, immunization of mice with LVS-V induces a strong IgG response to *F. tularensis*.

Passive Immunization Using Serum Samples from LVS-V-Immunized Mice Protects Against *F. tularensis* LVS Challenge.

Figure 23A:
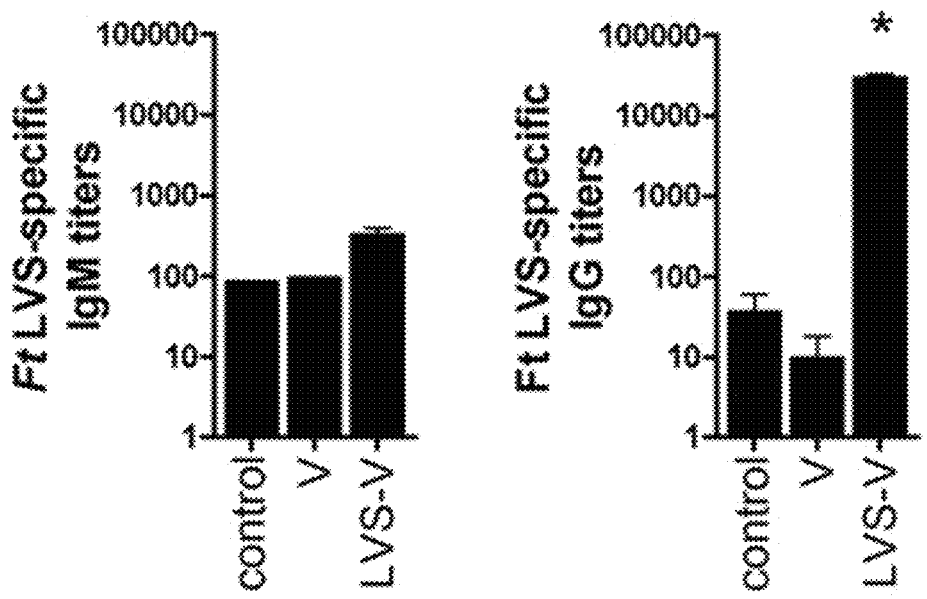
FIG. 23: Passive immunization protects against F. tularensis LVS challenge. (A) IgM and IgG titers against whole F. tularensis LVS were measured by ELISA in pooled donor serum of saline-immunized mice (control serum) or of mice previously immunized twice i.p. with empty vesicles or LVS-V (x axis). *, p<0.05 by Student t test. (B to D) Sixty microliters of serum was transferred to naive 6- to 8-week-old mice by tail vein injection 1 day prior to challenge with 100,000 CFU F. tularensis LVS. The percent starting weight (B), severity of clinical symptoms (C), and survival (D) were measured following challenge. The combined data from two independent experiments are shown (n=7). The error bars represent the standard errors of the means (SEM). *, p<0.05; ***, p<0.001 by log rank test.
Figure 23B:
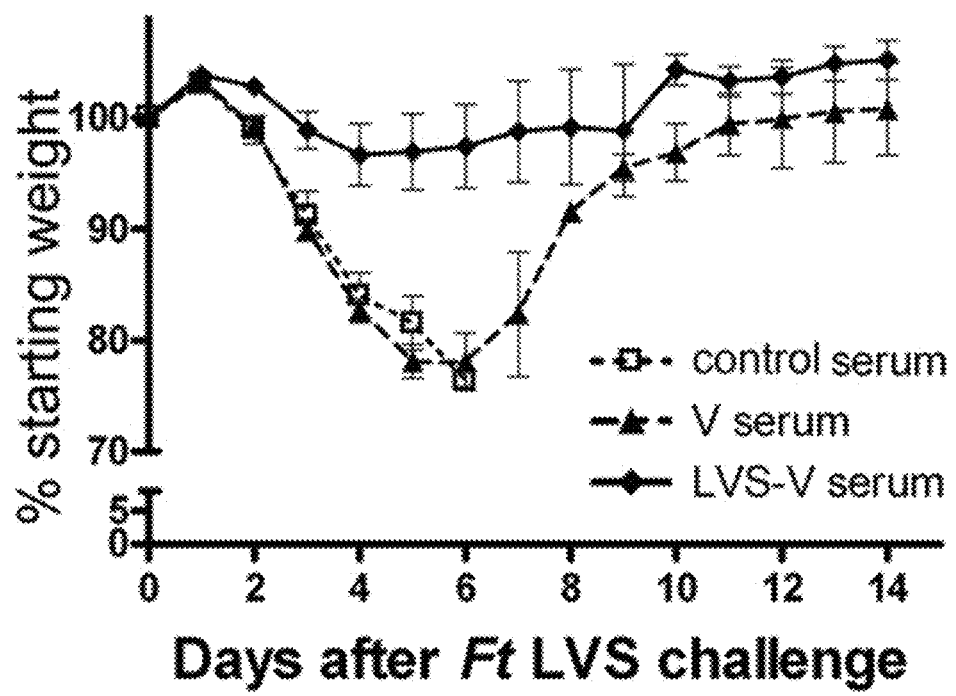
Figures 23C, 23D:
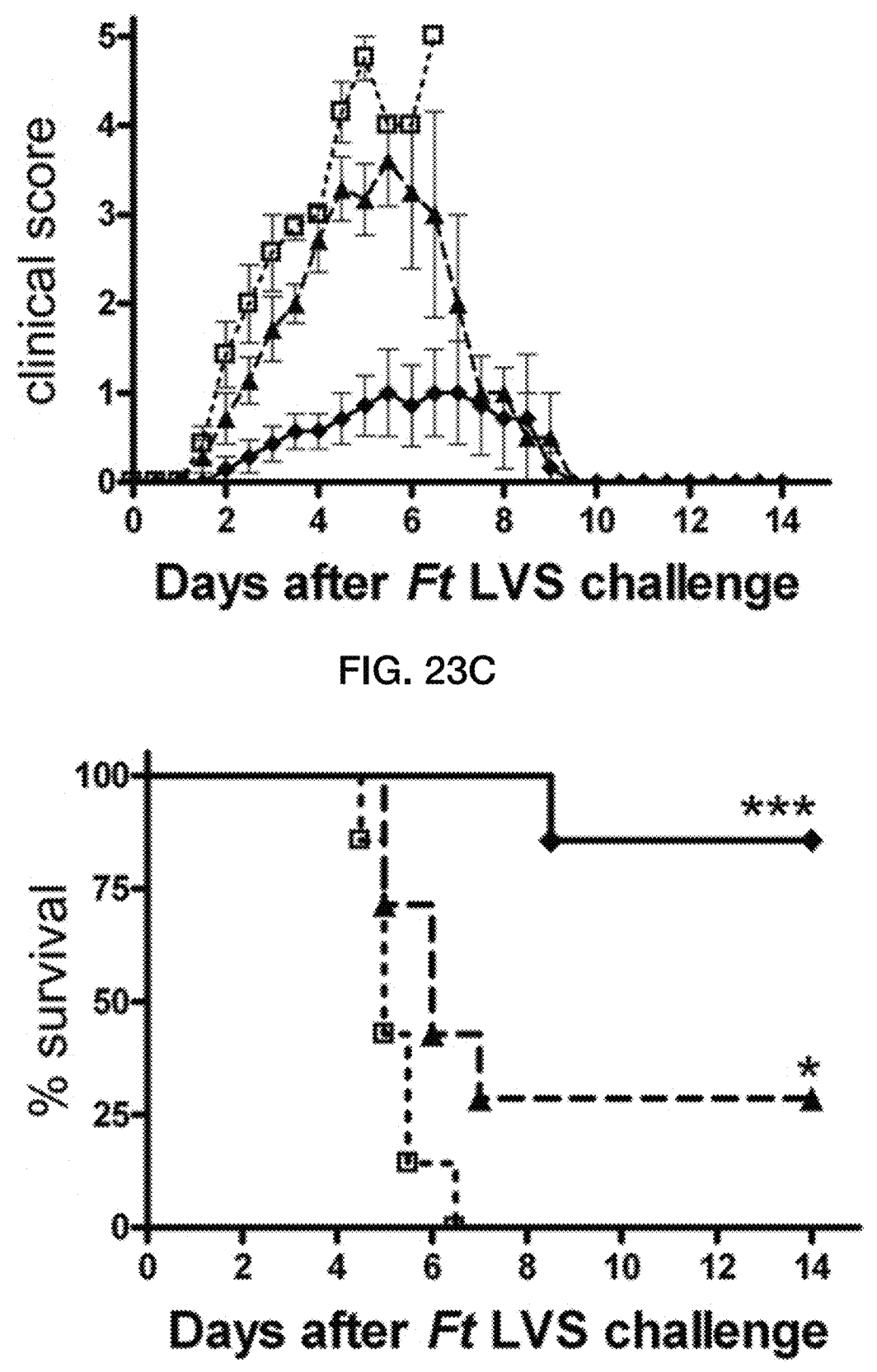

Since we observed high antibody titers following LVS-V immunization directed predominantly against non-LPS epitopes, we sought to test whether these antibodies would be protective in *F. tularensis* LVS challenge. Donor mice were immunized as described above with either saline, LVS-V, or vesicles. Two weeks following the second immunization, serum samples were harvested and pooled according to the immunogen the donor mice received. It is noteworthy that these mice were not challenged with *F. tularensis* LVS. *F. tularensis*-specific IgM and IgG titers were measured by ELISA. Similar to the data in FIG. 2, serum samples from LVS-V-immunized mice contained significantly elevated levels of *F. tularensis*-specific IgG when assayed by ELISA against whole organisms (FIG. 23A). Sixty microliters of each serum pool was administered to naive mice by i.v. injection. The recipient mice were challenged 24 h later with 100,000 CFU *F. tularensis* LVS per mouse by the i.p. route, and weight loss, clinical symptoms, and survival were recorded for each mouse over the course of 2 weeks. Mice that received serum from saline-immunized mice (control serum) expired in 4 to 6 days (FIG. 23D). Mice that received serum from LVS-V-immunized mice experienced essentially no weight loss and much less severe clinical symptoms than controls (FIGS. 23 B and C). Six of seven of these animals (86%) recovered in the second week following infection (FIG. 3C) (P=0.0002 compared to control serum recipients). Mice that received serum from bare vesicle-immunized mice showed a slight delay in the onset of clinical symptoms (FIG. 23C) but mirrored the control serum recipients with respect to weight loss (FIG. 23B). Five of seven recipients of sera from empty vesicle-immunized donors died with the same kinetics as the control serum recipients (FIG. 23D). These data suggest that the survival in *F. tularensis* LVS challenge correlates with IgG anti-*F. tularensis* antibody titer. Despite protection against *F. tularensis* LVS challenge, serum from an LVS-V-immunized donor, transferred i.v., did not protect against an i.n. challenge with 50 CFU *F. tularensis* Schu S4 (data not shown).

LVS-V Induces Cytokine Gene and Protein Expression In Vivo.

Figure 24A:
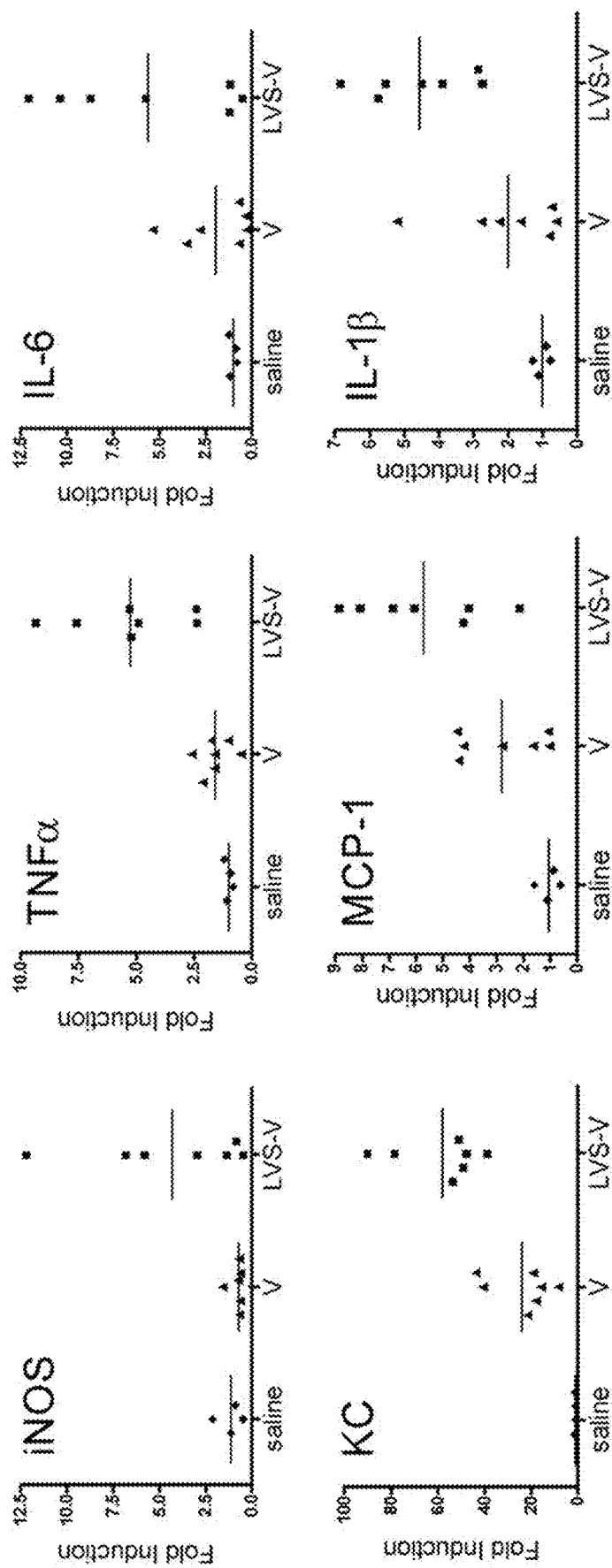
FIG. 24: Comparison of cytokine gene and protein expression induced early after empty vesicle versus LVS-V administration. The mice were injected i.p. with saline, LVS-V (35 µg protein), or the equivalent amount of empty vesicles. (A) Four hours after vaccination, each mouse was euthanized and the liver harvested. Gene induction of iNOS and cytokine and chemokine genes representative of inflammatory responses was measured by qRT-PCR. Each symbol represents an individual mouse. (B) After immunization, mice were bled at the indicated time points and cytokine protein levels were measured in the serum samples of individual mice by the Luminex assay. The average serum concentrations±the SEM of 5 mice are shown for KC and IL-6.

Because partial protection of mice that were immunized with empty vesicles was observed in response to lethal *F. tularensis* LVS challenge (FIG. 21), despite antibody responses that were no different than those of naive animals (FIG. 22), we sought to test the inflammatory potentials of the surfactant vesicles, as this is often a property of adjuvants. Mice were injected i.p. with either saline, bare vesicles, or LVS-V at the same dose as used for immunization. Four hours later, each mouse was bled and euthanized and the livers harvested for reverse transcription-quantitative PCR (qRT-PCR) analysis of proinflammatory gene expression. Compared to the saline controls, LVS-V induced significantly higher levels of the following genes: keratinocyte chemoattractant (KC), 58-fold (P=0.0061); monocyte chemoattractant protein 1 (MCP-1), 5.7-fold (P=0.0061); tumor necrosis factor alpha (TNF-$\alpha$), 5.3-fold (P±0.0061); and IL-1$\beta$, 4.6-fold (P_0.0061) (FIG. 4A). IFN-$\beta$, IFN-$\gamma$, gamma interferon inducible protein 10 (IP-10), RANTES (data not shown), IL-6, and inducible nitric oxide synthase (iNOS) (FIG. 24A) were induced in only some of the LVS-V-treated mice by 4 h, and consequently, the mean induction values for these genes were not statistically significantly different compared to those of the saline controls. Only a few of these inflammatory genes were induced in the livers of mice treated with plain vesicles and to a much lower level than those induced by LVS-V (FIG. 24A). KC and IL-6 proteins were also detected in the serum samples of mice 4 h after immunization with LVS-V but decreased rapidly thereafter (FIG. 24B). No difference was observed in the Th2-inducing cytokines IL-4 and IL-13 (data not shown). Spleens were also harvested 4 h after injection and showed similar expression patterns but lower levels of induction of proinflammatory genes (data not shown).

Reproducibility of Size and Stability of *F. tularensis* Nanoparticles.

Figure 25A:
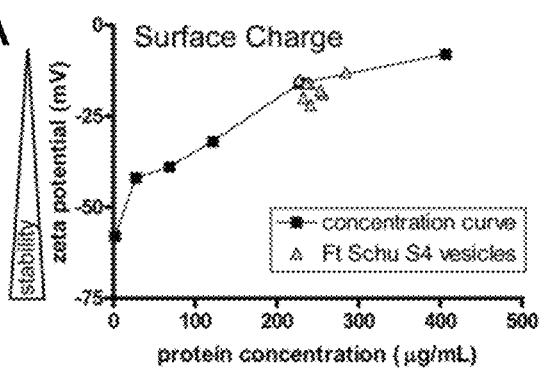
FIG. 25: Surface charge, but not size, of vesicles is affected by the *F. tularensis* protein content of the nanoparticles. The vesicles prepared from different sized bacterial pellets (as described in the Methods) were analyzed for (A.) zeta potential and (B.) average radius (solid squares). In addition, the same analysis was carried out for multiple individually prepared preparations of catanionic vesicles produced in the presence of *F. tularensis* Schu S4 strain (Schu S4-V) (gray triangles). Each data point represents a distinct batch of vesicle vaccine. (C.) Silver stain and (D.) Western analysis of four independent batches of Schu S4-V.
Figure 25B:
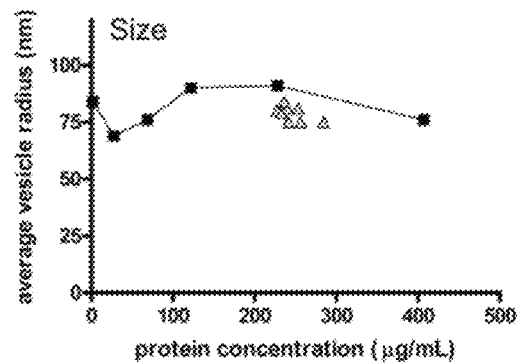
Figures 25C, 25D:
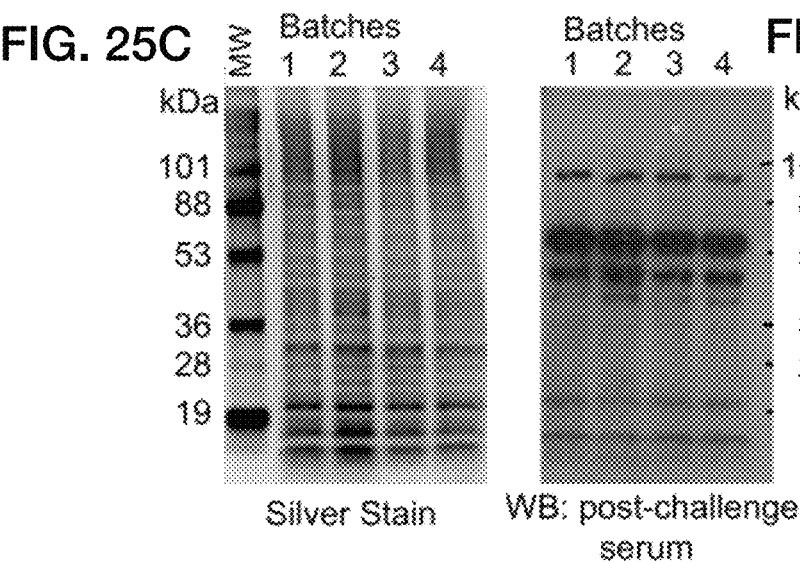

To optimize our immunization protocol, we tested whether the size or stability of the *F. tularensis* nanoparticles was affected by the protein content of the vesicles. *F. tularensis* LVS pellets containing increasing numbers of bacteria (from ⅛-fold below up to 4-fold above the standard input concentration of 25 ml of overnight culture) were processed into vesicles using the identical amounts of surfactants and water for each preparation, as described in Methods. Purified nanoparticles were analyzed for protein content and physical characteristics. Measurement of the zeta potential, a measure of vesicle stability, revealed that vesicles that incorporated more bacterial components (as evidenced by increased protein concentration of the purified vesicle preparations) exhibited lower surface charges (FIG. 25A). Lower surface charge is typically associated with the destabilization of vesicles, yet no differences in toxicity were observed between mice immunized with vesicles of low versus high surface charge (data not shown). The average vesicle size (~80-nm radius) was also not significantly affected by the amount of bacterial starting material incorporated in the vesicles (FIG. 25B). Importantly, different batches of *F. tularensis* nanoparticles prepared from either *F. tularensis* LVS or *F. tularensis* Schu S4 using the standard protocol of 25 ml of overnight bacterial culture exhibited a high consistency of physical parameters, such as average radius and surface charge (FIGS. 25 A and B).

*F. tularensis* LVS LPS and Proteins, Including Epitopes Recognized by Immune Mouse Serum, are Extracted into Vesicles with a High Degree of Consistency.

Figure 26A:
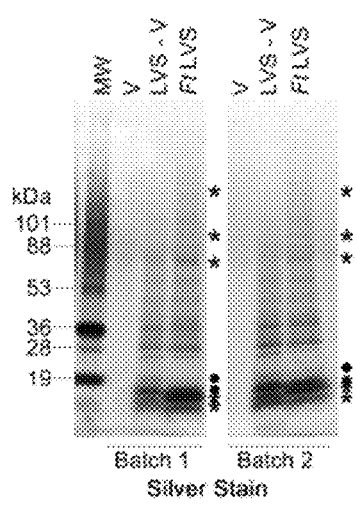
FIG. 26: LVS-V are made with a high degree of consistency and are immunogenic. *F. tularensis* LVS molecules were incorporated into surfactant vesicles to form LVS vesicles. Lysates derived from a sampling of the *F. tularensis* bacterial pellets prior to the addition of surfactants (Ft LVS) and empty control vesicles (V) were also included for comparison. (A) Samples were separated by SDS PAGE on a 10 to 20% gradient gel and silver stained for total protein. Asterisks and filled circles mark bands that were extracted with low and high efficiency into vesicles, respectively. (B) The same samples were subjected to Western analysis (WB) with sera from mice that had been immunized twice with LVS-V (prechallenge) and challenged twice with *F. tularensis* LVS (postchallenge) as described in FIG. 22. The silver stain and serum blots are representative of 8 separate experiments.
Figure 26B:
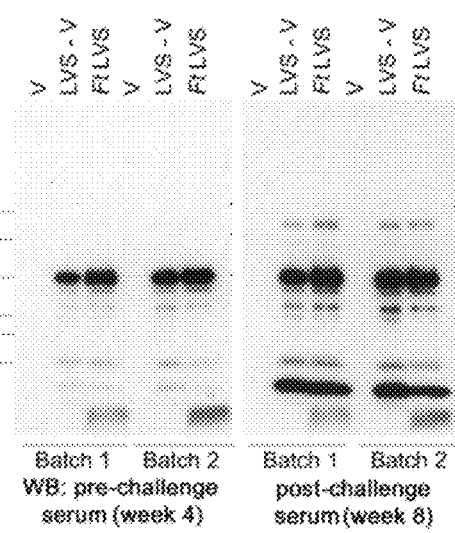
Figure 27A:
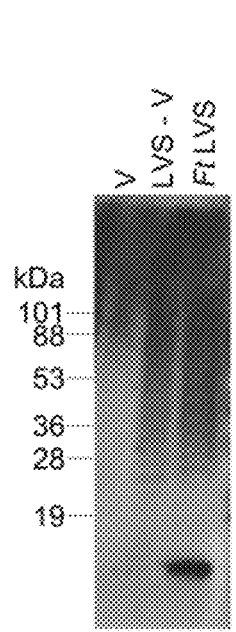
FIG. 27: Catanionic vesicles associate with bacterial LPS in addition to the proteins, and addition of protease inhibitors does not significantly affect the components incorporated into the vesicles. *F. tularensis* LVS molecules were incorporated into surfactant vesicles (V) to form LVS-vesicles (LVS-V). Lysates derived from a sampling of the bacterial colonies prior to the addition of surfactants was also included for comparison (Ft LVS). (A.) Samples were separated by SDS-PAGE on a 10-20% gradient gel and were subjected to Western analysis with rabbit antibodies directed against *F. tularensis* LVS LPS. (B.-C.) V, LVS-V, and *F. tularensis* LVS lysates were produced in the absence or presence of Roche Complete protease inhibitor cocktail. Samples were separated by SDS-PAGE on a 4-20% gradient gel and compared by (B.) Western analysis with mouse sera of LVS-V-immunized mice harvested two weeks after the second immunization, prior to *F. tularensis* LVS challenge. (C.) Samples were also compared by silver staining.
Figure 27B:
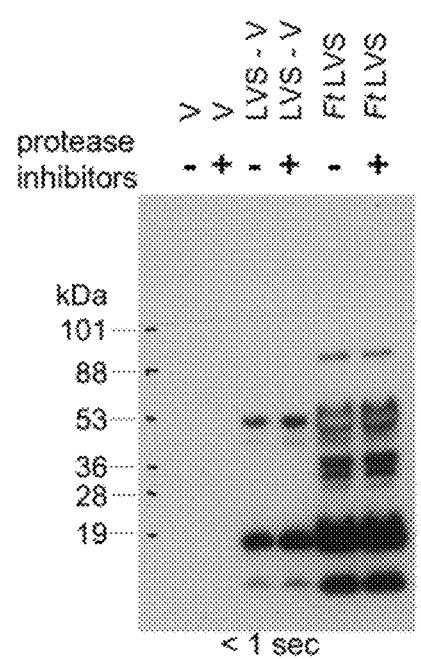
Figure 27C:
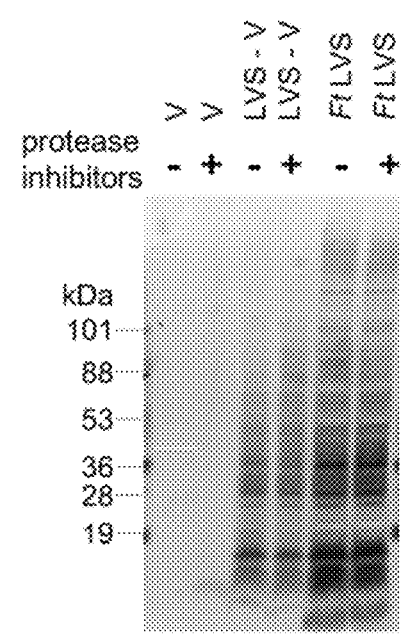

FIG. 26A shows a silverstained gel in which two independently prepared batches of empty vesicles and LVS-V (designated batch 1 and batch 2), as well as lysed samples of the *F. tularensis* LVS pellets from which the respective LVS-V batches were produced, were electrophoresed side by side. Silver staining revealed that there were no detectable bands in the bare vesicles, whereas most *F. tularensis* LVS proteins were consistently extracted into LVS-V preparations (FIG. 26A). Some bands, such as the one with an apparent molecular mass of ~20 kDa, were enriched in the vesicles, while other proteins were less efficiently incorporated. Western analysis using a polyclonal anti-*F. tularensis* LPS antibody shows that *F. tularensis* LPS is also incorporated into LVS-V, as evidenced by the typical LPS ladder (FIG. 27). Bands detected by Western analysis using serum samples from immunized mice before and after *F. tularensis* LVS challenge are also consistently incorporated into LVS-V (FIG. 26B). The vesicles that were made in the absence of *F. tularensis* LVS and served as control immunogens were also free from contamination, as evidenced by the absence of bands in the silver stain and Western analyses (FIG. 26). Similar batch-to-batch uniformity was observed in vesicles extracted from *F. tularensis* Schu S4 by silver stain and Western analysis (FIG. 27).

Antibody Epitope Specificity Matures Following Infection with Live *F. tularensis* LVS.

FIG. 26C also illustrates maturation of the IgG antibody response in mice that were immunized with *F. tularensis* nanoparticles, as evidenced by a comparison of the diversity of antigens detected by Western analysis in serum samples collected before and after challenge with *F. tularensis* LVS. Using serum samples collected immediately prior to challenge (two weeks after the second immunization with LVS-V) and a secondary anti-mouse IgG antibody, 5 prominent bands were detected in the LVS-V samples, one of which exhibited an apparent molecular mass of ~55 kDa and was the predominant species detected by Western analysis. Minor bands with molecular masses of ~50 kDa, ~40 kDa, ~20 kDa, and ~12 kDa were also consistently detected at the same exposure. Immunoreactive bands of ~95 kDa, ~45 kDa, ~37 kDa, ~33 kDa, and ~10 kDa were also present in LVS-V but were detected only after a long exposure (data not shown). A very low-molecular-weight species was detected exclusively in the *F. tularensis* LVS whole-cell lysates by Western analysis with both the anti-LPS antibody (FIG. 27) and the LVS-V immune serum (FIG. 26B).

Among the low-molecular-weight bands detected in silver staining, none were found that corresponded to the *F. tularensis* LVS lysate-specific band. In serum samples collected 1 week following a second *F. tularensis* LVS challenge, IgG responses to the minor band at ~12 kDa were greatly enhanced to reveal a second immunodominant band. The responses to all other bands were also enhanced to various degrees, with the greatest increase seen at bands with apparent molecular masses of ~95 kDa, ~37 kDa, and ~12 kDa. After the exposure to live bacteria, new minor bands with apparent molecular masses of ~86 kDa, ~67 kDa, and ~22 kDa were detected. This same pattern was seen in both batches of LVS-V and *F. tularensis* LVS lysates. The same bands were detected regardless of whether LVS-V was produced in the absence or presence of protease inhibitors (FIGS. 27 B and C).

Figures 28A, 28B:
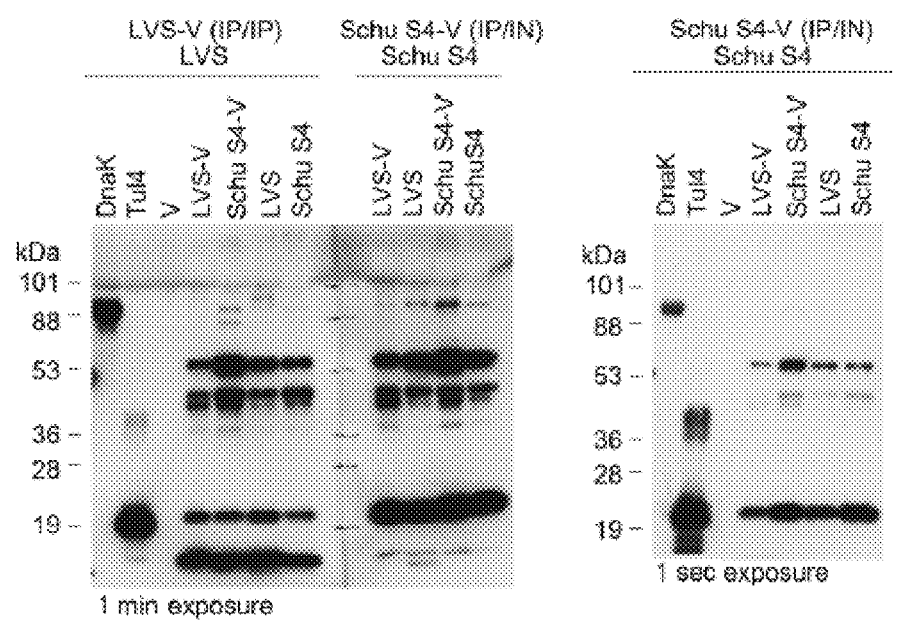

In the next series of experiments, blood serum samples were pooled from mice vaccinated with LVS-V (i.p./i.p.) and challenged with *F. tularensis* LVS (i.p.) and from mice vaccinated with Schu S4-V (i.p./i.n.) and challenged with *F. tularensis* Schu S4 (i.n.). In preliminary studies, we found that a 1:1,000,000 dilution of anti-LVS-V serum and a 1:100,000 dilution of the anti-Schu S4-V serum gave equivalent results in ELISA (data not shown). These dilutions were chosen for Western analysis, where they also detected several bands with the same intensity. A recent *F. tularensis* LVS subunit vaccine composed of Tul4 and DnaK successfully protected mice against intranasal challenge with *F. tularensis* LVS. Indeed, both purified Tul4 and DnaK preparations were detected with antisera from mice immunized and challenged homologously with either LVS-V and *F. tularensis* LVS or Schu S4-V and *F. tularensis* Schu S4 (FIGS. 28 A and B). The anti-Schu S4 serum reacted more strongly with Tul4 than the anti-LVS serum (note in FIG. 28B that these were exposed for only 1 s, because a longer exposure of the Tul4 protein detected by the anti-Schu S4-V antiserum was grossly overexposed). No bands were detected in bare vesicles with either antiserum preparation (FIGS. 28 A and B). Five predominant bands (including one that appears to be a doublet) were detected by the two antisera: the anti-LVS-V serum detected bands at molecular masses of ~55 kDa, ~40 kDa (doublet), ~20 kDa, ~12 kDa, and a faint band at ~90 kDa (FIG. 28A). Interestingly, the anti-Schu S4-V antiserum detected the same bands but differed in the intensity of the bands. Specifically, the ~12-kDa band was poorly detected, the ~20-kDa species was more strongly detected, and the ~90-kDa band, while still faint, was more apparent than in blots developed using the anti-LVS-V antiserum (FIGS. 28 A and B). Taken together, these data confirm our finding that the antibody response matures following exposure to live bacterial challenge (FIG. 26) and they extend it by showing that several immunodominant species are differentially detected by serum produced in response to LVS-V immunization/*F. tularensis* LVS challenge versus Schu S4-V immunization/*F. tularensis* Schu S4 challenge.

*F. tularensis* Epitopes Recognized by Either LVS or Schu S4 Antiserum are Found in Other *F. tularensis* Strains as Well.

We sought to test whether the epitopes recognized by the immune sera from LVS-V-immunized LVS-challenged mice and Schu S4-Vimmunized Schu S4-challenged mice would be present in other strains, including some that are clinically relevant. *F. tularensis* strains MA00-2987 (A1 strain), WY96-3418 (A2 strain), and KY99-3387 and OR96-0246 (B strains) were grown in enriched TSB. The samples were subjected to Western analysis with the antisera described above. Approximately equal loading was confirmed by silver staining (data not shown). Prebleed serum failed to detect any bands by Western analysis (data not shown). Serum samples collected 2 weeks after the second immunization with LVS-V (i.p./i.p.) but prior to *F. tularensis* LVS challenge (week 4) (FIG. 29A), after i.p. challenge with *F. tularensis* LVS (week 8) (FIG. 7B), or after immunization (i.p./i.n.) with Schu S4-V and i.n. challenge with Schu S4 (FIG. 29C) each showed remarkable consistency in their binding patterns across different *F. tularensis* strains. Interestingly, antiserum from the LVS-V-immunized *F. tularensis* LVS challenge survivors recognized an additional high-molecular-weight band in the type A1 (Schu S4, MA00) and A2 (WY96) strains (molecular mass, ~105 kDa) not detected in the type B strains (*F. tularensis* KY99, OR96, and LVS).

LVS-V and Schu S4-V Immunization Partially Protect Against i.n. Schu S4 Challenge.

The most pressing need for a *Francisella* vaccine is for the protection of populations in case of aerosol releases of virulent type A strains of *F. tularensis*. Since LVS-V appears to be proinflammatory early after immunization and induces robust anti-*F. tularensis* antibody titers, we sought to test whether the *F. tularensis* nanoparticles might also protect against *F. tularensis* Schu S4, the most extensively studied model strain of the type A clade. Initially, the mice were immunized as before (i.p./i.p., 2 weeks apart) with either sterile PBS, LVS-V, or the same volume of empty vesicles. Two weeks following the second immunization, all mice were challenged i.n. with ~10 CFU *F. tularensis* Schu S4. The mice immunized with PBS rapidly developed tularemia, and all either died or had to be euthanized by the end of day 5 post challenge. In contrast to LVS challenge, mice that had been immunized with empty vesicles were not protected against Schu S4 challenge and developed clinical symptoms with similar kinetics as the saline-immunized mice and exhibited a nonsignificant delay in time to death. However, in mice vaccinated with LVS-V, we observed a delay in the onset of clinical symptoms, and one of five mice survived (data not shown).

To improve on the partial protection gained by LVS-V immunization against Schu S4 challenge, the mice were next immunized with Schu S4-V rather than LVS-V. Utilizing the same immunization regimen as for LVS-V with Schu S4-V (i.p./i.p., 2 weeks apart), only one of 10 mice survived i.n. challenge with ~20 CFU *F. tularensis* Schu S4. However, the onset of symptoms and time to death from tularemia were delayed by almost 2 days, which was significant by the Mann-Whitney test (nonparametric t test) compared to animals that had been immunized with vesicles only (FIG. 30).

Heterologous Routes of Immunization with Schu S4-V Result in Improved Protection Against Schu S4 Challenge.

Figure 31A:
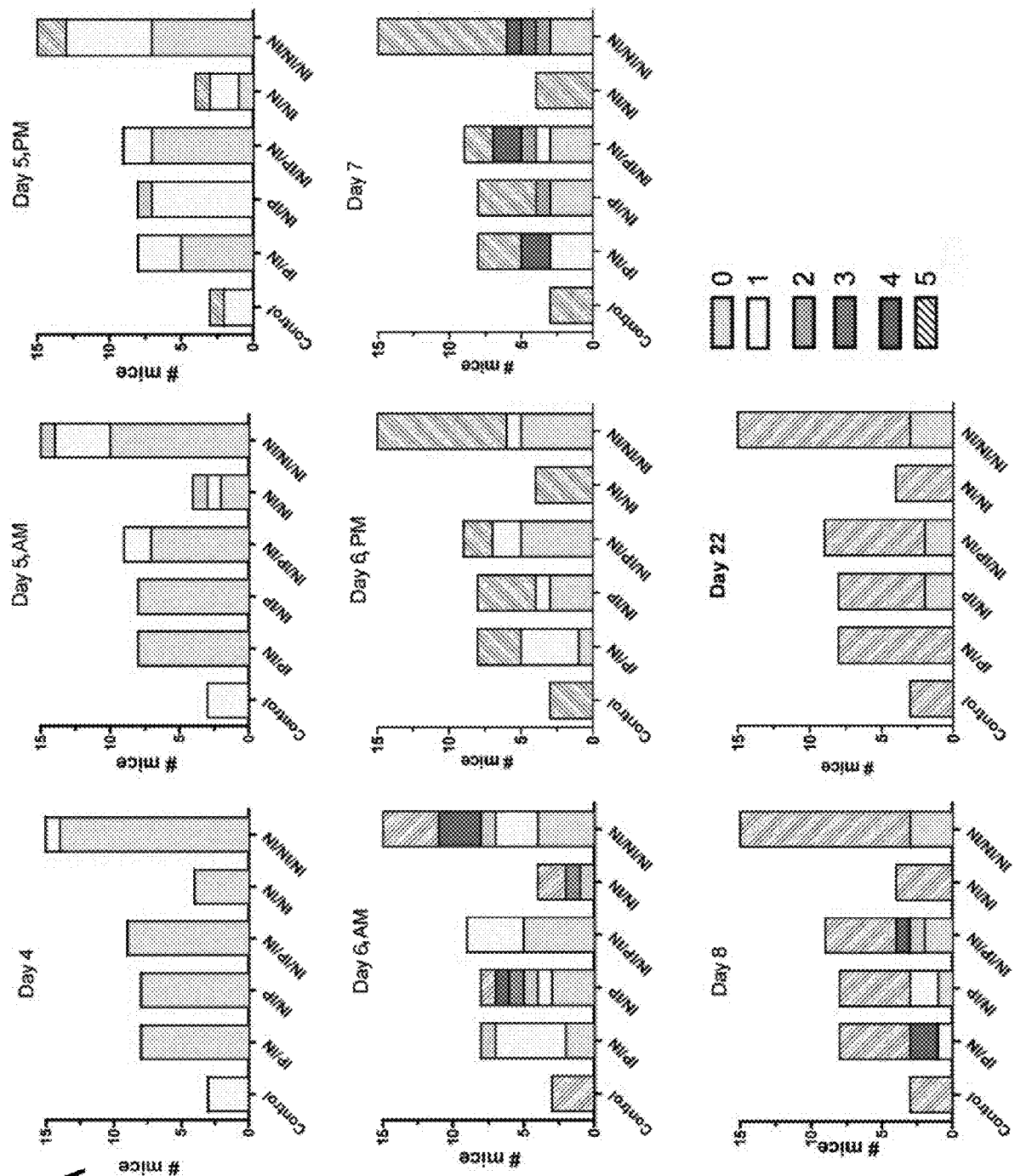
FIG. 31: Mice immunized with Schu S4-V show a delay in clinical symptoms after i.n. challenge with Ft Schu S4 and the route of immunization affects IgG titer. (A.) Clinical scoring of individual mice on indicated days: Green (0)—healthy, Yellow (1)—mild illness, Light Orange (2)—moderate illness, Dark orange (3)—severe illness, Red (4)—moribund or dead, Black Hatch (5)—cumulative total of dead mice in each group. These results represent a single representative experiment in which all mice were assessed twice daily. (B.) Ft specific IgG titers from pooled sera obtained one week after the second and third immunizations (mean and SEM).
Figure 31B:
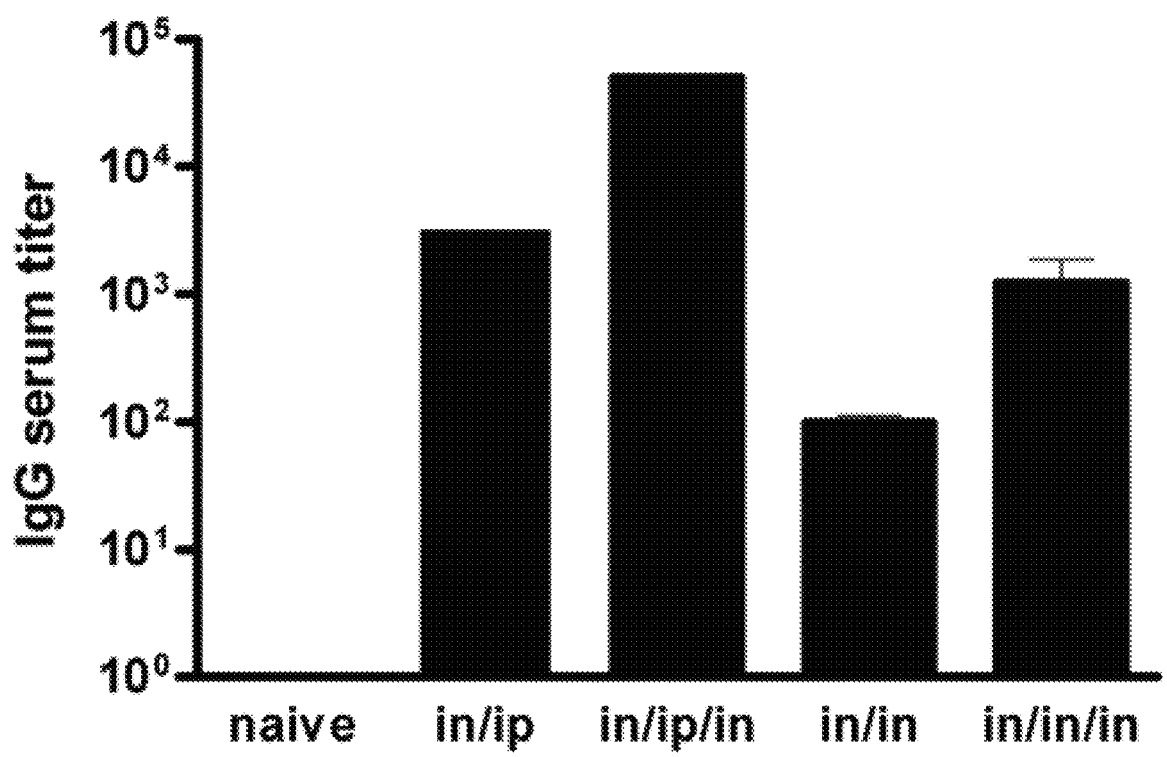
Figure 32:
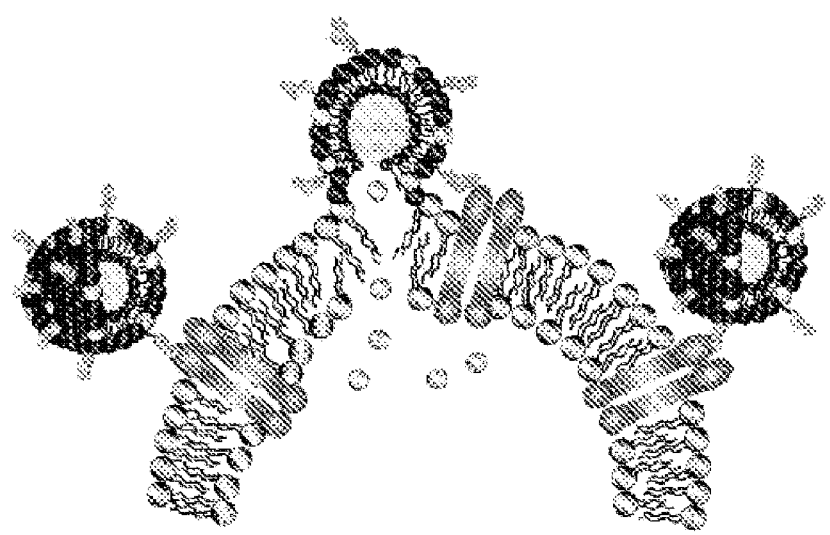
FIG. 32: Targeting of catanionic surfactant vesicles to cells.
Figure 33:
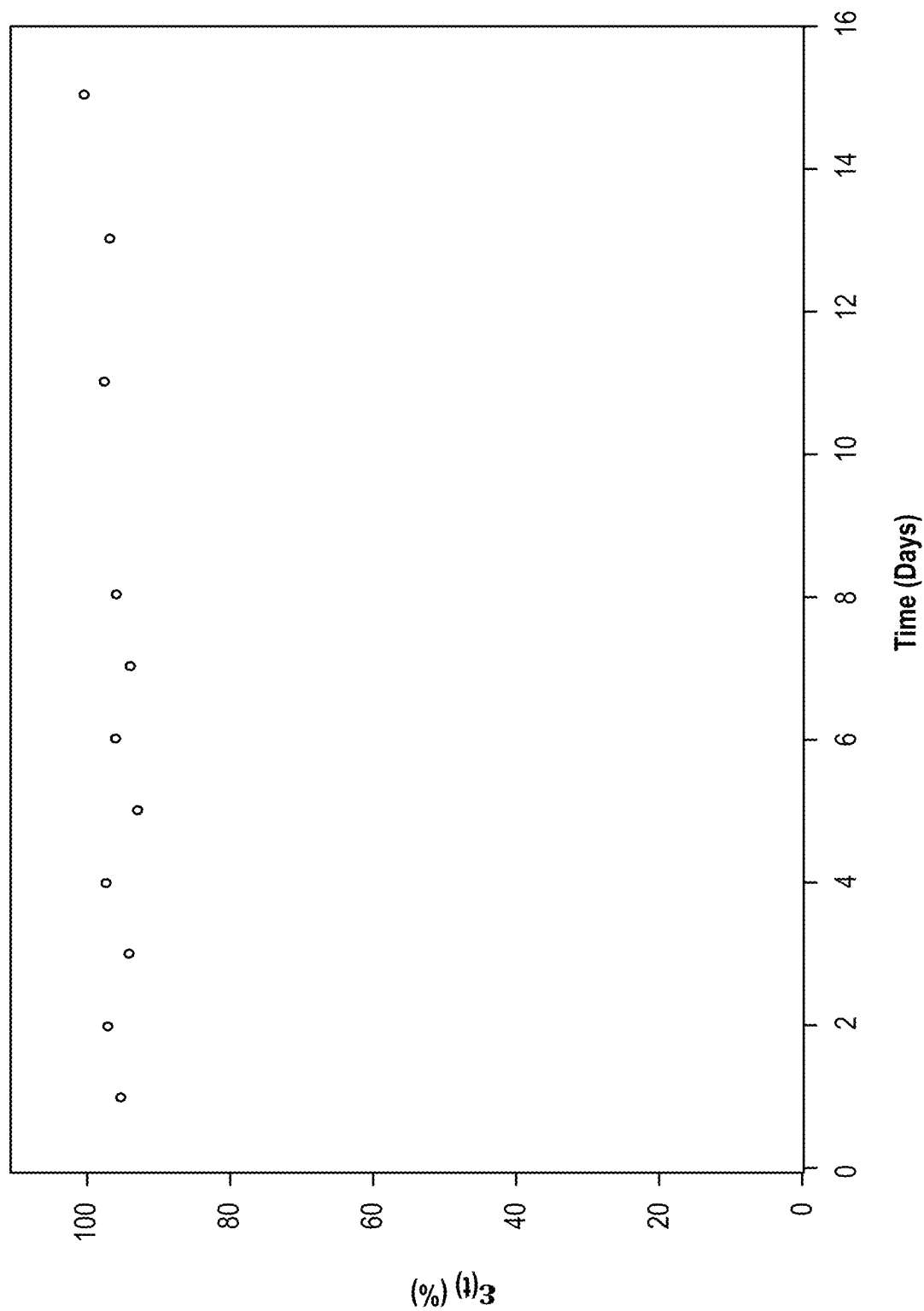
FIG. 33: Retention of doxorubicin over fifteen days in catanionic surfactant vesicles. Concentration of doxorubicin vesicle stock solution was 33 µM. After purification by SEC, vesicle-containing fractions contained ~23 µM of the drug.

Since the number of immunizations and the route of administration affect the strength and type of the subsequent immune response, we compared outcomes from Schu S4 challenge following immunization with either 2 or 3 doses, as well as by diverse administration routes. The results from 5 independent experiments are summarized in Table 1. In each experiment, the control group of mice was immunized with bare vesicles, and all of these mice died within 5 days (on average), even with a challenge dose as low as 3 CFU *F. tularensis* Schu S4 per mouse. All mice that received Schu S4-V by i.p. and/or by i.n. route displayed a delayed onset of symptoms and delayed time to death by 1 day. In mice immunized via the subcutaneous (s.c.) route, the time to death was delayed less but was still statistically significant. No mice survived challenge after two immunizations with Schu S4-V by combinations involving the s.c. route or i.n. route only. Improved partial protection was gained through heterologous prime-boost using i.p./i.n. and i.n./i.p. routes. In the single most effective experiment, four of six mice (66%) that were immunized with Schu S4-V i.p./i.n. survived challenge with ~22 CFU live *F. tularensis* Schu S4 (data not shown). The clinical scores of a representative experiment are shown in FIG. S3 in the supplemental material and illustrate the effects of the various immunization regimens. The addition of a third i.n. immunization also improved the outcome of challenge, assessed by a slight improvement in the fraction of survivors and further delay in time to death in nonsurvivors (FIG. 30; FIG. 31A). Systemic *F. tularensis* specific IgG titers were also increased following a third i.n. immunization (FIG. 31B). Heterologous immunization routes (i.e., i.n. and i.p. administration, with two immunizations) showed similar titers compared to three doses administered solely through the i.n. route, and the administration of a third i.n. dose further increased IgG titers. Regardless of the route of immunization, the blood serum IgG levels of mice that survived Schu S4 i.n. challenge (bled 21 days postchallenge) were approximately 10-fold higher than those of nonsurvivors (bled 5 to 8 days postchallenge at the time of euthanasia) (i.e., average titers of ~125,000 and ~12,000, respectively). Together, these data show that significant partial protection against virulent type A challenge can be achieved with two doses as a heterologous (i.p./i.n.) prime-boost immunization or by three i.n. immunizations with Schu S4-V.

Antigen Identification.

In this experiment, cell lysates from *Francisella tularensis* LVS mutant strains were subjected to SDS-PAGE followed by Western analysis using sera from mice immunized twice with either LVS-V or Schu S4-V by intraperitoneal injections. The sera from our immunized mice failed to detect discrete bands (circles) corresponding to FopA and Tul4 proteins (FIG. 47).

Example 4

Drug Delivery Application for Catanionic Surfactant Vesicles

There is interest in extending the role of catanionic vesicle systems for drug delivery application in order to provide an alternative to their liposomal counterparts. Catanionic vesicles can be easily prepared, are stable for yeats, and can be sterilized by autoclaving. Furthermore, catanionic vesicles can be functionalized, allowing the ability for targeted drug delivery of a payload to specific tissues. Toward this goal, we studied catanionic vesicles loaded with the drug candidates doxorubicin, maytansine, and paclitaxel. A for targeted delivery applications, we studied the cytotoxicity of doxorubicin-loaded catanionic vesicles fuctionalized with a targeting agent.

Methods

Doxorubicin.

To prepare doxorubicin-loaded vesicles, an aqueous solution of doxorubicin was prepared. To increase solubility of doxorubicin, the solution was sonicated in a water bath until full dissolution. Then, 70.0 mg of SDBS (0.200 mmol) and 30.0 mg of CTAT (0.0658 mmol) was weighed into the vial followed by the addition of 9.90 mL of the doxorubicin solution and stirring for 60 min. Vesicles were purified from free drug by SEC and analyzed by UVNIS. A 0.5 mL portion of each vesicle fraction was transferred to an empty vial where 0.5 mL absolute ethanol was added to the sample to prevent light scattering during absorption measurements. The samples were vortexed and the absorbance was measured at 480 nm.

Maytansine.

To prepare maytansine vesicles, maytansine was dissolved in THF (5.1 mg/mL). A 196 μL (1.00 mg) aliquot of the solution was added to a vial containing 70.0 mg of SDBS (0.200 mmol) and 30.0 mg of CTAT (0.0658 mmol). Then, X mL of water was added and stirred for 60 min. Vesicles were purified from free drug by SEC and analyzed by UVNIS. A 0.5 mL portion of each vesicle fraction was transferred to an empty vial where 0.5 mL absolute ethanol was added to the sample to prevent light scattering during absorption measurements. The samples were vortexed and the absorbance was measured at 290 nm.

Paclitaxel.

To prepare paclitaxel vesicles, 0.5 mg of paclitaxel was dissolved in 9.90 mL (0.200 mmol) of an SDBS solution (7.07 mg/mL). The solution was stirred for 60 min. Then 30.0 mg of CTAT (0.0658 mmol) was added and stirred for 60 min. Vesicles were purified from free drug by SEC and analyzed by UVNIS. A 0.5 mL portion of each vesicle fraction was transferred to an empty vial where 0.5 mL absolute ethanol was added to the sample to prevent light scattering during absorption measurements. The samples were vortexed and the absorbance was measured at 445 nm.

Results

In order for catanionic vesicles to be used in drug delivery, their loading efficiency and toxicity were studied. In addition, drug loaded catanionic vesicles were functionalized with targeting agents toward cell lines that over express the receptor specific to the targeting agent. Cell toxicity was compared between targeted and untargeted catanionic vesicles in order to determine if targeting increased drug uptake into cells (FIG. 32).

Doxorubicin Loaded Catanionic Surfactant Vesicles.

Catanionic surfactant vesicles were loaded with the drug doxorubicin in order to determine the retention of the drug over time. Vesicles were loaded with 19 μg/mL doxorubicin (33 μM) and an aliquot of the vesicle stock suspension was purified by SEC each day over 15 days. Vesicles were 140±10 nm in diameter and their size did not change over the 15 day timeframe, as determined by DLS. These results indicated that catanionic vesicles loaded with doxorubicin are larger in size when compared to unloaded vesicles (~120 nm) and remained stable over time.

Vesicle-containing fractions from each day were disrupted with ethanol and analyzed by UVNIS. Catanionic vesicle fractions purified on different days all showed complete retention of doxorubicin (FIG. 33). These results indicated that doxorubicin was loaded into catanionic vesicles and that these systems did not leak drug over time.

Since vesicles were proven to incorporate and retain doxorubicin at low concentrations, we wanted to determine the maximum loading of drug in vesicles. Catanionic vesicle stock solutions were prepared containing 100 μg/mL (172 μM), 150 μg/mL (259 μM), 200 μg/mL (345 μM), and 300 μg/mL (517 μM) of doxorubicin. When using high concentration stock solutions of doxorubicin (200 μg/mL and 300 μg/mL), vesicles formed but a red precipitate was observed. Catanionic vesicles containing these concentrations were centrifuged and the precipitate was removed. Suspensions were purified by SEC and vesicle containing fractions eventually formed a red precipitate. These result indicated that doxorubicin gradually leaked out of vesicles. If full retention of the drug is require, catanionic vesicles cannot be loaded with >200 μg/mL (345 μM) of doxorubicin.

Vesicles prepared with 100 μg/mL and 150 μg/mL doxorubicin stock solutions were stable over an extended period and did not precipitate drug, even after purification by SEC (FIG. 34). These results showed that vesicles could be initially loaded with a maximum of 150 μg/mL of doxorubicin and after SEC contained 88 μg/mL of doxorubicin.

After determining the maximum loading of doxorubicin into catanionic vesicles, we were interested in studying the toxicity of these drug formulations. As a benchmark for toxicity in humans, a typical dose of doxorubicin is 40-60 mg/m2. For a typical person, this amount equates to a total dose of from about 150 to about 200 mg of doxorubicin. The dose limiting toxicity (DLT) for doxorubicin is myelosuppression where nausea, vomiting, cardiotoxicity, and alopecia are other side effects. In order to determine toxicity of doxorubicin loaded catanionic vesicles compared to the free drug, catanionic vesicles were loaded with doxorubicin and incubated in several different cell lines. The WST-1 cell proliferation assay was used to measure the cytotoxic effects of catanionic vesicles.

The cytotoxicity of catanionic vesicles was initially studied in the human hepatocellular carcinoma cell line HepG2. These cells exhibit many of the characteristics of normal liver cells. Since many drugs are toxic to the liver, these cell lines are used for screening the cytotoxicity of new drugs. HepG2 cells were used to study doxorubicin loaded catanionic vesicles to determine if the toxicity of the drug in vesicles was less than free drug. The WST-1 cell proliferation assay was used to determine whether formazan dye was taken up by live cells. In this assay, mitochondrial enzymes of living cells break down the dye so that the product absorbs at a specific wavelength. In other words, when cells are proliferating, formazan dye accumulates and when cells are not proliferating, dye levels drop.

Figure 35:
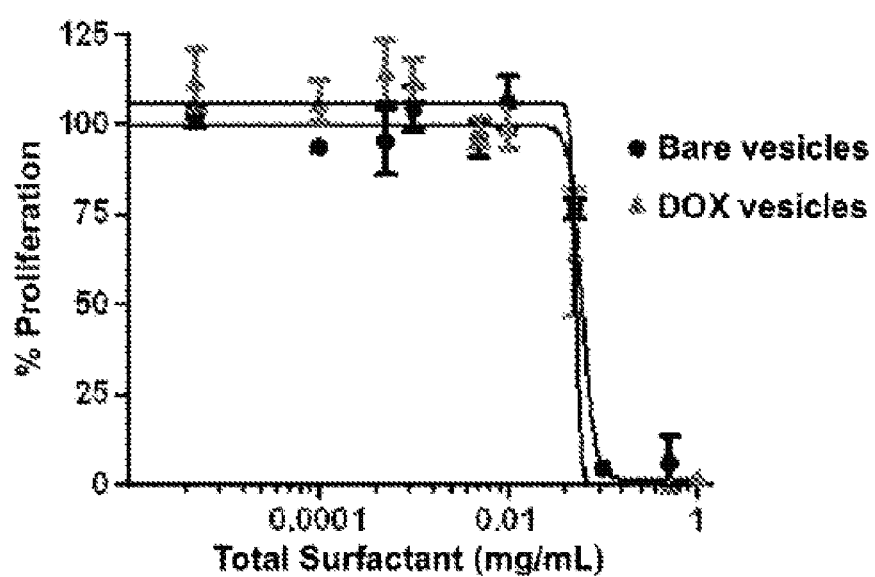
FIG. 35: WST-1 cell proliferation assay on HepG2 cells treated with bare vesicles and doxorubicin loaded vesicles. Cells were treated for 72 h. Bare vesicles IC50=58 µg/mL and doxorubicin vesicles IC50=51 µg/mL.
Figure 36:
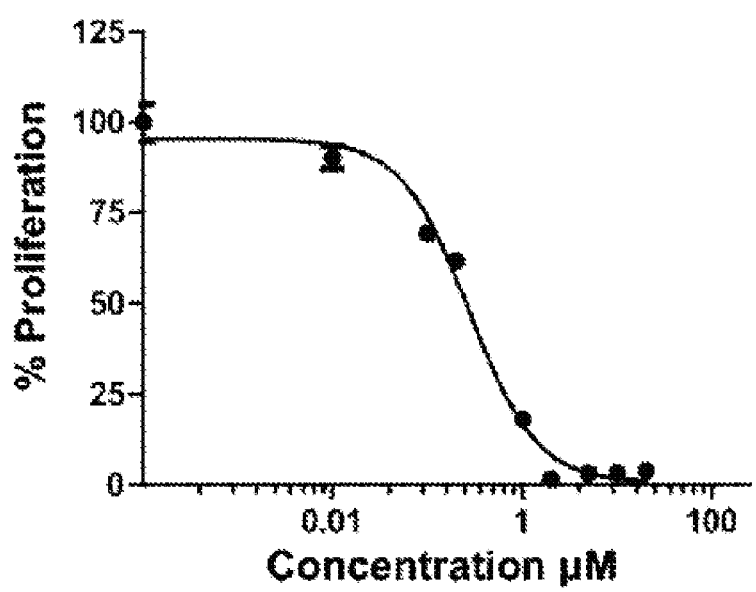
FIG. 36: WST-1 cell proliferation assay on HepG2 cells treated with doxorubicin. Free drug was incubated with cells for 72 h. IC50=0.16 µg/mL.

Results of toxicity studies in HepG2 cells yielded an IC50 of 51 µg/mL for DOX-loaded vesicles and an IC50 of 0.16 µg/mL for free DOX (FIGS. 35 and 36). These results indicated a 300-fold reduction in doxorubicin's IC50 values compared to free drug. Therefore, the toxicity of doxorubicin is greatly reduced when loaded into catanionic vesicles.

Figure 37:
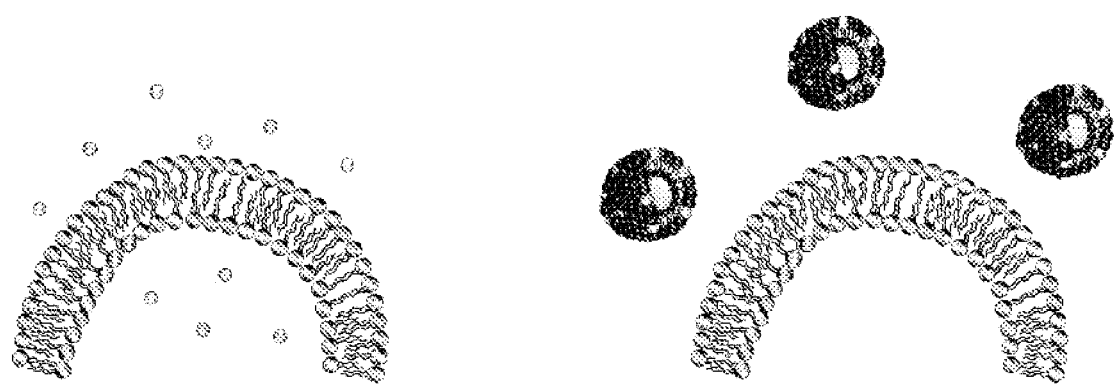
FIG. 37: Free doxorubicin compared to doxorubicin loaded catanionic vesicles incubated with normal cells.

Next, we wanted to determine the toxicity of bare vesicles (unloaded vesicles) in HepG2 cells. The IC50 of bare catanionic vesicles was 58 µg/mL (FIG. 35). This IC50 value indicated that bare and DOX-loaded catanionic vesicles have the same cytotoxicity. Therefore, the toxicity of DOX-loaded vesicles resulted from the catanionic vesicles themselves and not from DOX. Therefore, DOX-loaded and bare vesicles showed that the toxicity of doxorubicin is completely removed when loaded within catanionic systems (FIG. 37).

Targeted Doxorubicin Loaded Catanionic Surfactant Vesicles.

Figure 38:
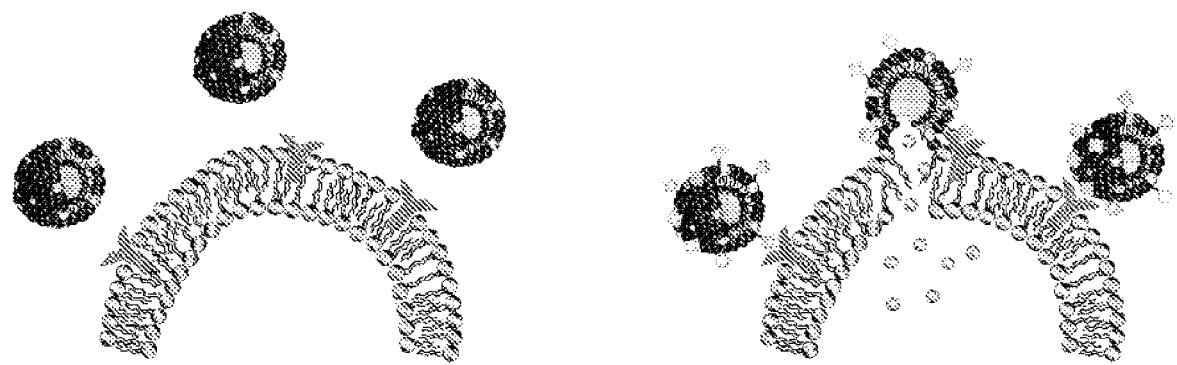
FIG. 38: Doxorubicin loaded untargeted and targeted catanionic vesicles incubated with normal cells vs. cells that over express a receptor.

Since DOX-loaded and unloaded catanionic vesicles have low toxicity in normal liver cells, we wanted to study these systems with the addition of a targeting moiety. We studied targeted DOX-loaded catanionic vesicles to determine if toxicity increased as a result of uptake into cells via targeting agent-receptor binding (FIG. 38).

Figure 39:
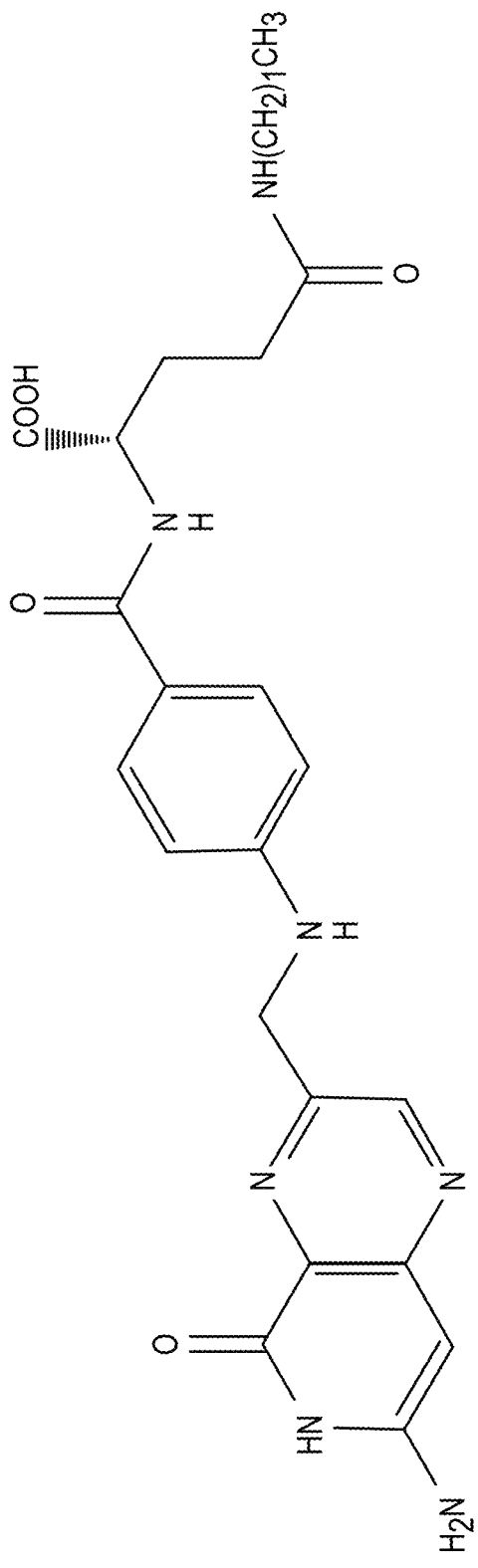
FIG. 39: Chemical structure of C12-folate conjugate.
Figure 40:
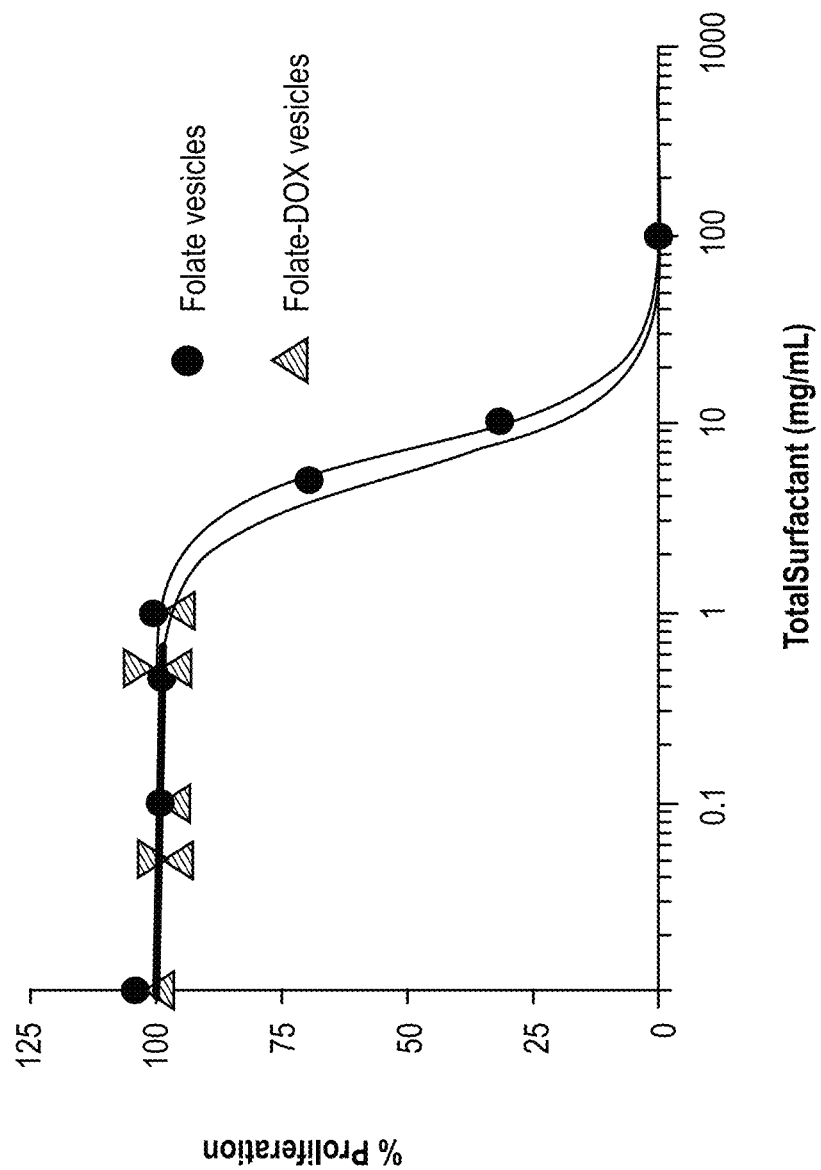
FIG. 40: WST-1 cell proliferation assay on A549 cells treated with folate targeted catanionic vesicles. Cells were treated for 72 h. Folate vesicles IC50=7.2 µg/mL, Folate-DOX vesicles IC50=5.6 µg/mL.

DOX-loaded catanionic vesicles were functionalized with C12-folate conjugate (FIG. 39). Cytotoxicity of targeted DOX-loaded vesicles was determined in two different cell lines. Cells were grown in folate-depleted media so that the folate in media did not compete with the folate-targeting moiety on vesicles. A549 cells were chosen for initial studies because they minimally express the folate receptor. Cytotoxicity IC50 values of targeted bare vesicles and targeted-DOX vesicles in HepG2 cells were 7.2 µg/mL and 5.6 µg/mL, respectively (FIG. 40). Therefore, both targeted-unloaded and targeted DOX-loaded vesicles had similar toxicities.

Figure 41:
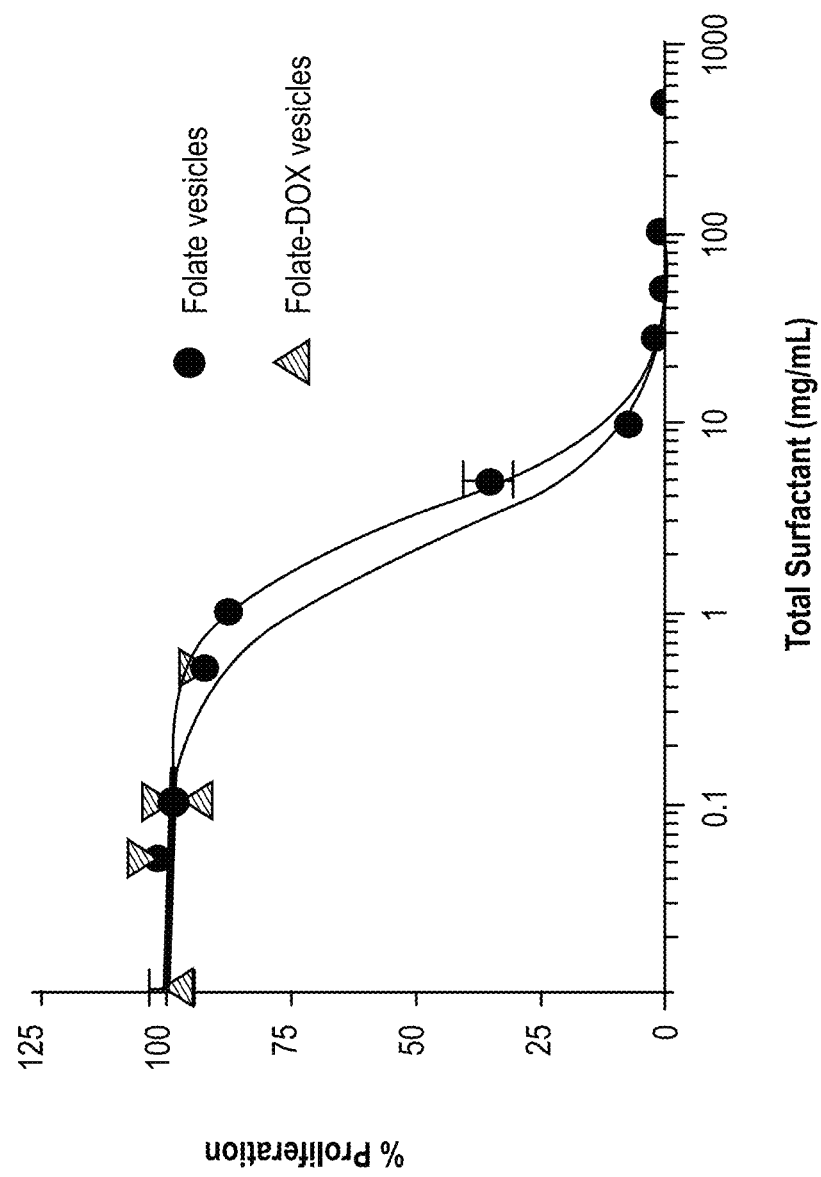
FIG. 41: WST-1 cell proliferation assay on ovarian IGROV-1 cells, which over express folate, treated with folate targeted catanionic vesicles. Cells were treated for 72 h. Folate vesicles IC50=3.4 µg/mL, Folate-DOX vesicles IC50=2.2 µg/mL.

Next, we wanted to determine the cytotoxicity of these systems when incubated in IGROV-1 cells. These cells were chosen because they highly express the folate receptor. Cytotoxicity IC50 values of targeted bare vesicles and targeted-DOX vesicles were 3.4 µg/mL and 2.2 µg/mL, respectively (FIG. 41). These results indicated that targeted vesicles were not more toxic when incubated with cells that over express the specific receptor.

Figure 42:
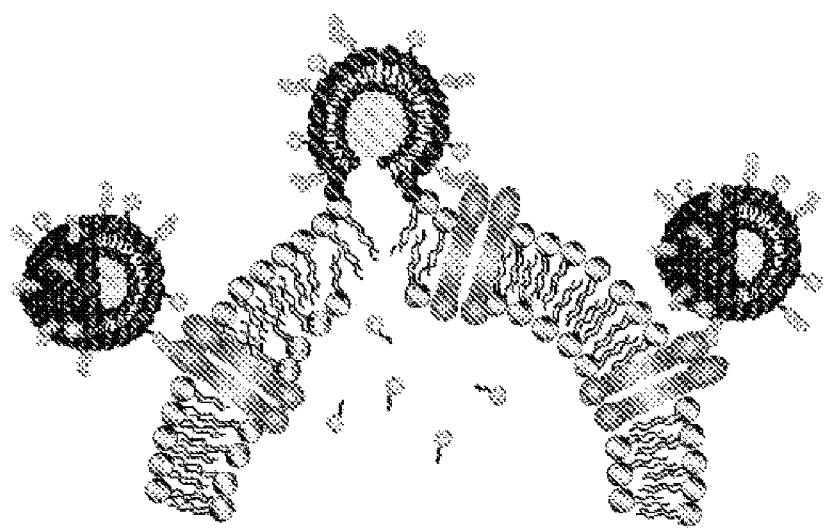
FIG. 42.

Results from toxicity studies with catanionic vesicles did not show increased toxicity of targeted catanionic vesicles. However, there could be several explanations as to why toxicity did not increase: 1) catanionic vesicles were not loaded with enough targeting agent or 2) catanionic vesicles were not taken up by cells. In order to study the latter possibility, future work will be devoted to determine whether catanionic vesicles enter cells. Catanionic vesicles will be loaded with a dye and functionalized with a targeting agent. Fluorescently labeled catanionic vesicles will be incubated with cells and studied by microscopy to observe the rate at which catanionic vesicles with and without a targeting agent are endocytosed by cells (FIG. 42).

Maytansine Loaded Catanionic Surfactant Vesicles.

Figure 43:
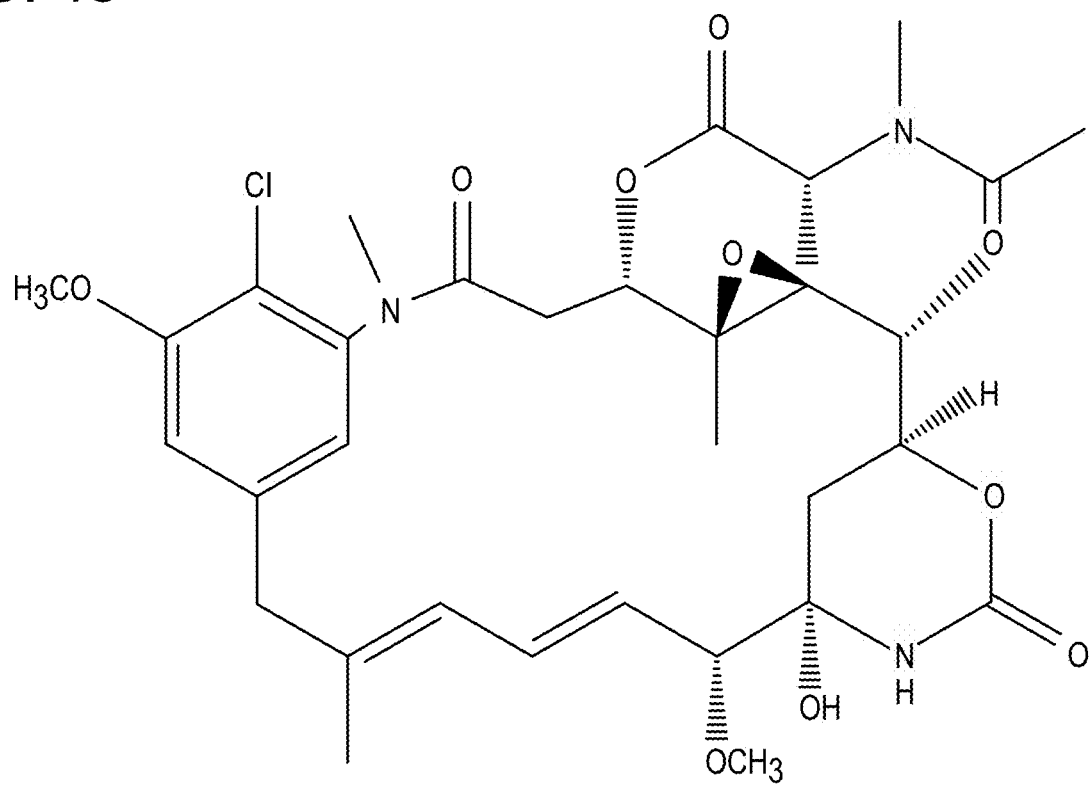
FIG. 43: Chemical structure of maytansine.
Figure 44:
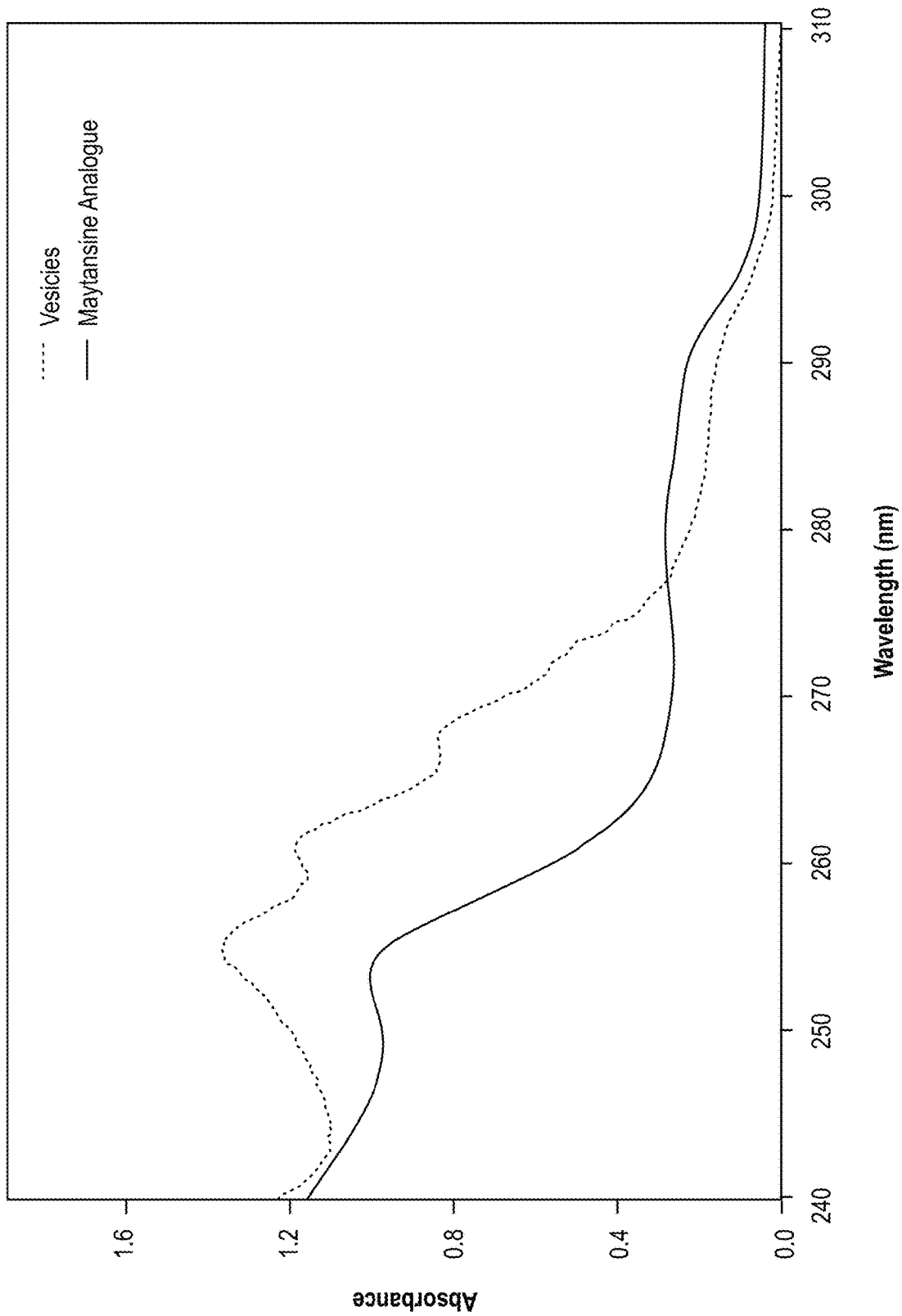
FIG. 44: Absorbance of a maytansine analogue and maytansine loaded vesicle fraction from SEC. The maytansine analogue absorbs light at 290 nm.

Maytansine is an extremely toxic drug that is insoluble in water and most solvents (FIG. 43). Catanionic vesicles were loaded with the neutral hydrophobic drug maytansine in the hope that the drug could be solubilized and incorporated for drug delivery. Maytansine was solubilized in THF and then added during vesicle formation. This solubilization was required in order for maytansine to dissolve so that the drug could be incorporated into catanionic vesicles. Vesicles had a hydrodynamic radius of 126±3 nm and were purified by SEC. All fractions were disrupted with ethanol and measured by UV NIS. Unfortunately, maytansine does not contain a good chromophore (FIG. 43). Maytansine has an absorbance at 290 nm, which is close to the absorbance of the surfactants used in our catanionic vesicles. UV NIS of the vesicle-containing fraction showed a peak at 290 nm and was compared to bare vesicle containing fractions (FIG. 44). It was difficult to officially determine whether the drug was successfully incorporated since the absorbance of maytansine and the surfactants absorb light in the same region. For this reason, a drug should be modified with a fluorescent tag so that incorporation into vesicles can be determined.

Paclitaxel Loaded Catanionic Surfactant Vesicles.

Figure 45:
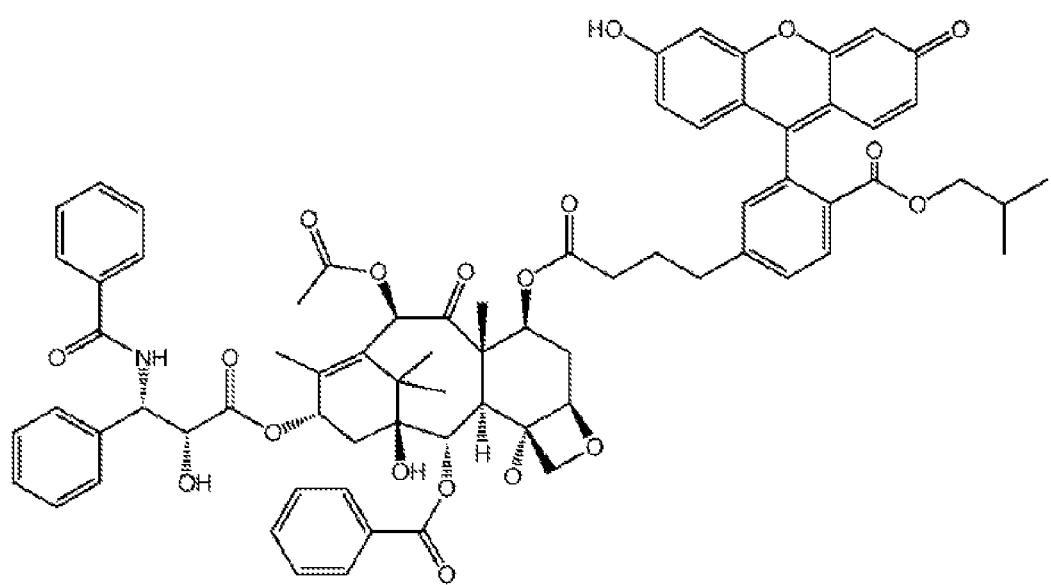
FIG. 45: Chemical structure of paclitaxel fluorescein derivative.
Figure 46:
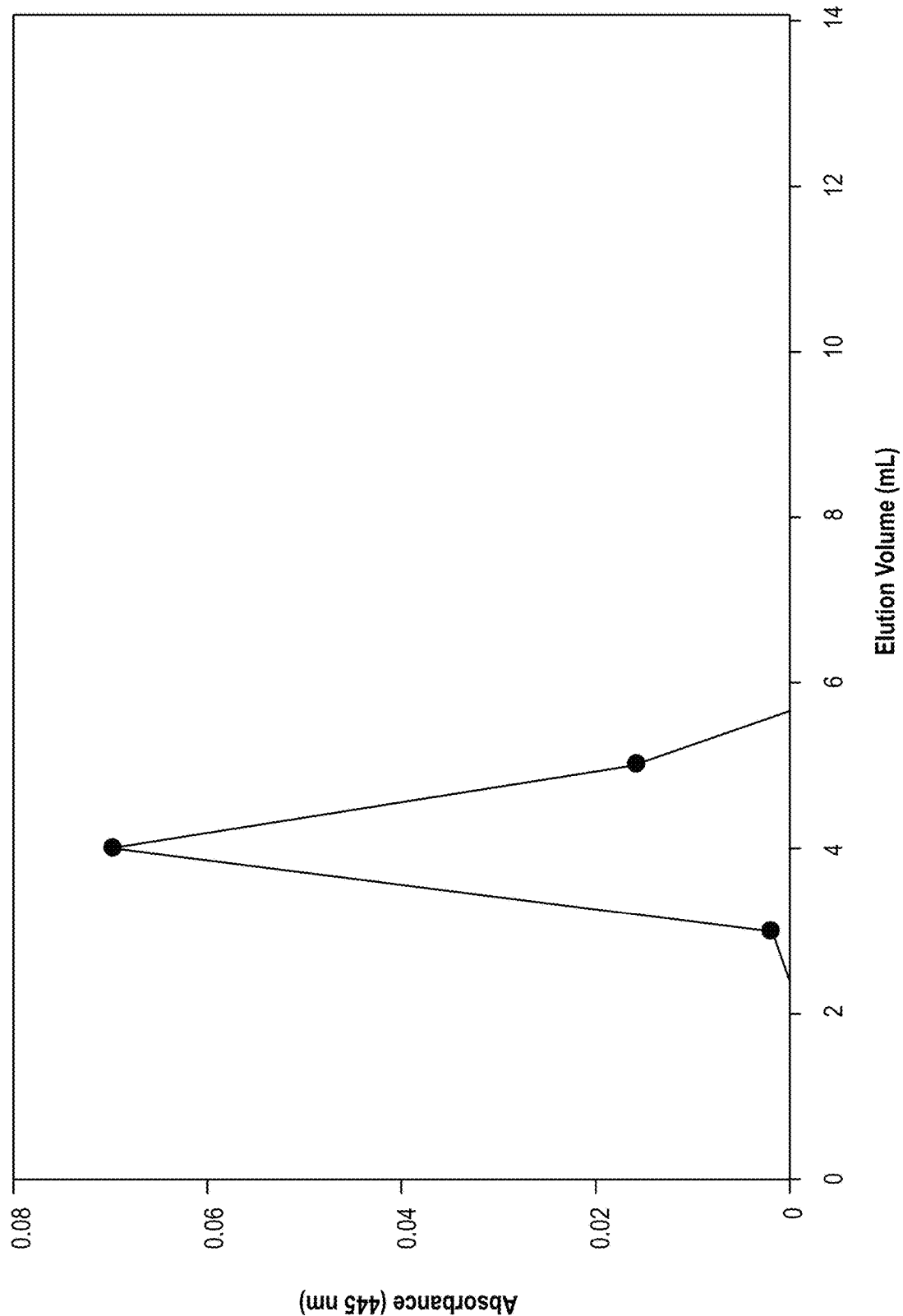
FIG. 46: Absorbance of paclitaxel loaded vesicles at 445 nm. After purification by SEC, vesicle-containing fractions contained 0.9 µM of drug.

Since the lack of a chromophore made it difficult to characterize it loading in catanionic vesicles, vesicles were loaded with a drug containing a fluorescent label. Paclitaxel fluorescein derivative (FIG. 45) was added to vesicles prepared with dry surfactants and water. These vesicles formed but did not yield yellow suspensions. Due to the insolubility of paclitaxel, the drug was not incorporated during vesicle formation. Therefore, a solution of SDBS was used to solubilize paclitaxel by incorporating the drug into the hydrophobic region of micelles. Then, solid CTAT was added, and yellow catanionic vesicles formed. After purification by SEC, vesicle-containing fractions remained yellow in color. These results indicated the presence of paclitaxel within catanionic vesicles, likely by the initial incorporation of the drug into micelles followed by incorporated into the bilayer leaflet after the addition of the second surfactant. Fractions were disrupted with ethanol and their absorbance was measured at 445 nm. Results of UV NIS show that paclitaxel conjugate was successfully incorporated in vesicles (FIG. 46).

Catanionic vesicles can be loaded with drug molecules and functionalized with targeting agents. Catanionic vesicles loaded with doxorubicin showed low toxicity in the presence of normal liver cells. Catanionic vesicles could be used for drug delivery of doxorubicin similar to the liposomal formulation Doxil. Targeted catanionic vesicles did not increase toxicity of drug-loaded vesicles, but further studies will be performed in order to increase the targeting agent and to determine whether catanionic vesicles are incorporated into cells. We have also shown incorporation of other drugs into catanionic vesicles. Fluorescently labeled drugs allow for better characterization in catanionic vesicles.

Example 5

Methods for Whole Cell Extraction with Catanionic Vesicles

Here we describe how catanionic surfactant vesicles can extract membrane components from the Gram negative pathogen *Neisseria gonorrhoeae* using alternate methodologies. It is advantages to have methods that have a preference for the incorporation of higher or lower molecular weight molecules.

Methods

In the case of *Neisseria gonorrhoeae*, further modifications were performed by modifying the fourth extraction methodology into two methods (see FIG. 1 for reference), methods 4-I and 4-II. These methods do not result in complete cell lysis. The cells were spun down in media and the supernatant was removed, leaving the pellet in the bottom.

In Method 4-I, 30 mg of CTAT, 71 mg SDBS, 6.9 mL of Millipore water, and 3 mL of cell suspension were mixed and then stirred for 15 minutes. The mixture was centrifuged for 1 hour and the supernatant was decanted. 1 mL of the sample of supernatant was purified on the column.

In Method 4-II, 9.9 mL of preformed vesicles (1% SDBS rich), 3 mL cell suspension, and 5.91 mL of Millipore water were mixed and then stirred for 1 hour. The mixture was centrifuged for 1 hour and the supernatant was decanted. 1 mL of the sample of supernatant was purified on the column.

Results

Figure 48:
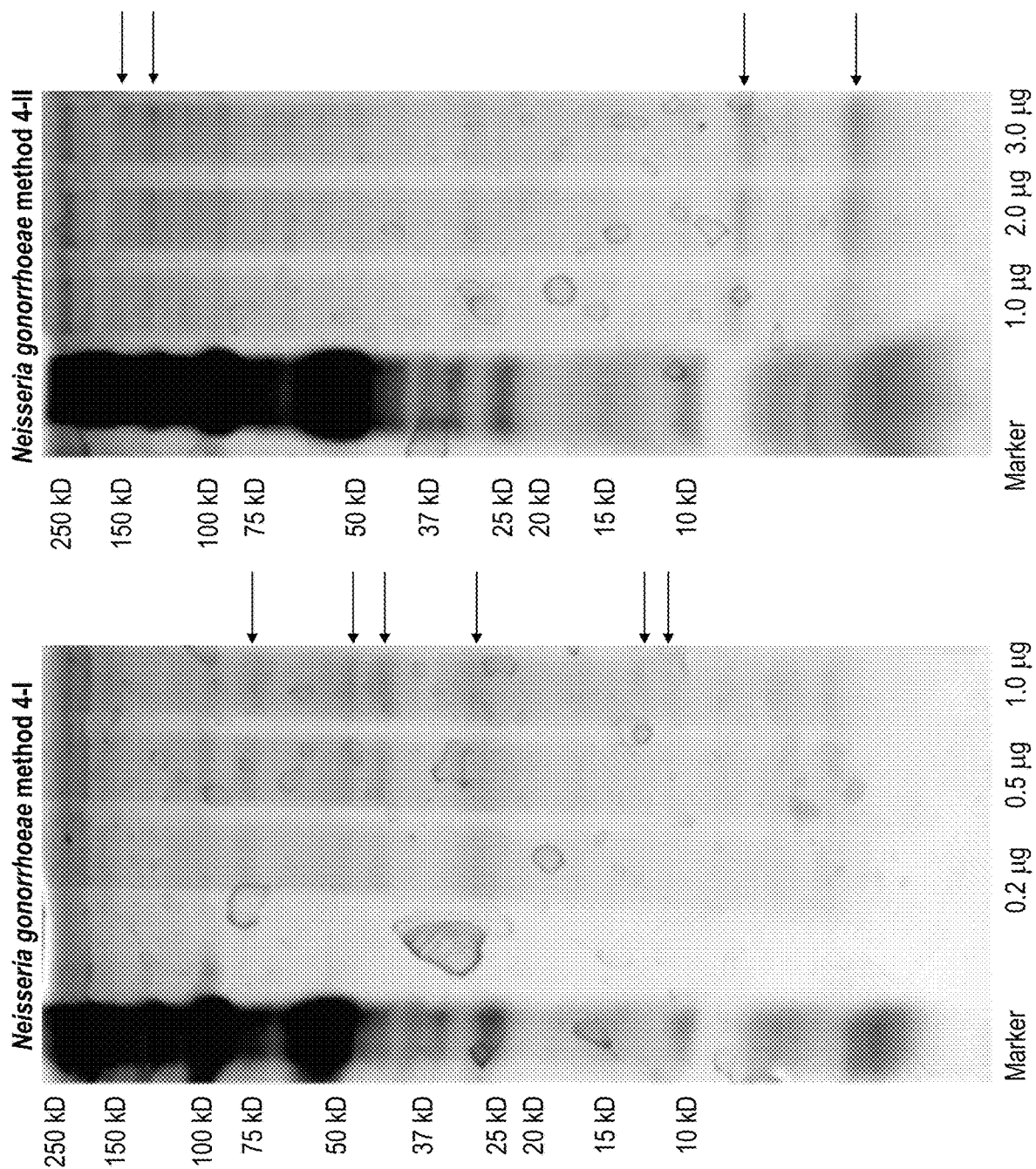
FIG. 48: The proteins preferentially extracted using the various methods were further analyzed by gel electrophoresis. Silver staining of vesicles derived from extraction of *Neisseria gonorrhoeae* by Methods 4-I and 4-11 are provided.
Figure 49:
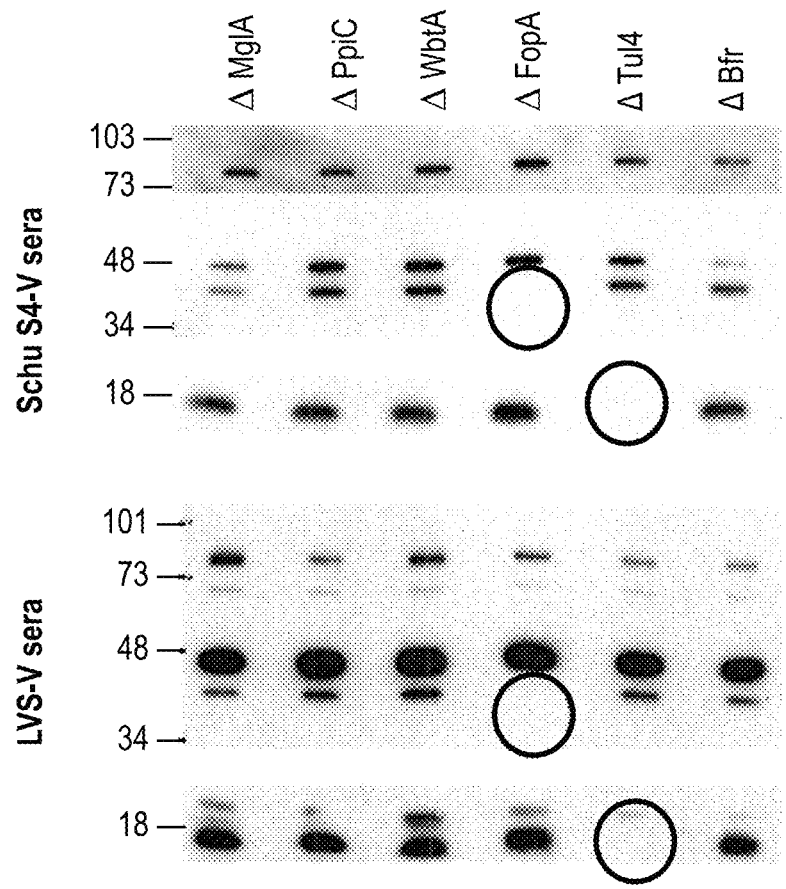
FIG. 49. Mice were immunized twice, i.p./i.p., with either Schu S4-V or LVS-V. Western blots (4-20% gradient gel) of bacterial lysates from well-characterized Ft LVS deletion mutants and WT Ft strains were probed with sera harvested 2 weeks after immunization. Mice were not challenged with live bacteria.

The amounts of protein and carbohydrate collected for each method are shown in FIG. 47. The proteins preferentially extracted using the various methods were further analyzed by gel electrophoresis. Silver staining of vesicles derived from extraction of *Neisseria gonorrhoeae* by Methods 4-I and 4-II are shown in FIG. 48.

The images of *Neisseria gonorrhoeae* gels show that the extraction methodologies are extracting different proteins. The main differences in the gel are marked in FIG. 48. Method 4-II seems to have extracted higher concentrations of low molecular weight proteins while Method 4-I seems to have extracted higher concentrations of higher molecular weight proteins. This seems to be consistent with the results from colorimetric and BCA assays because, as can be seen from FIG. 47, Method 4-II extracts more carbohydrates, rather than proteins, than does Method 4-I. Some of the bands that seem to show up in F62ΔlgtD strain from *Neisseria gonorrhoeae* Methods 4-I and 4-II seem to be from porin, multiple lipoproteins, and LPS, all known cell surface components. Method 4-II seems to be extracting more carbohydrate content than protein content from *Neisseria gonorrhoeae*.

What is claimed is:

1. A method of generating an antibody response against *Neisseria gonorrhoeae* in a subject in need thereof, comprising administering to the subject a therapeutically effective amount of a composition comprising a catanionic surfactant vesicle;

wherein the catanionic surfactant vesicle comprises a unilamellar bilayer comprising a mixture of oppositely charged single-tailed surfactants and one or a plurality of *Neisseria gonorrhoeae* immunogens from whole *Neisseria gonorrhoeae* cell extract;

wherein the one or plurality of *Neisseria gonorrhoeae* immunogens comprise at least one membrane-bound sugar, or at least one membrane-bound polypeptide or at least one combination of a membrane-bound sugar and membrane-bound polypeptide; and wherein the membrane-bound sugar, the membrane-bound polypeptide, or the combination of the membrane-bound sugar and membrane-bound polypeptide is positioned at least partially in the unilamellar bilayer;

wherein the catanionic surfactant vesicle comprises bacterial lipooligosaccharide (LOS) or lipopolysaccharide (LPS) and one or a plurality of *Neisseria gonorrhoeae* lipoproteins or *Neisseria gonorrhoeae* membrane-bound protein; and wherein the catanionic surfactant vesicle comprises a percentage of carbohydrate from about 0% to about 25% by weight.

2. The method of claim 1, wherein the catanionic surfactant vesicle comprises a percentage of carbohydrate from about 0.1% to about 16% by weight.

3. The method of claim 1, wherein the one or plurality of *Neisseria gonorrhoeae* immunogens comprise one or a combination of pilin, porA, porB, OPA, DnaK, Tul4, and FopA.

4. The method of claim 1, wherein the one or plurality of *Neisseria gonorrhoeae* immunogens comprises Pan HLA- DR reactive epitope (PADRE) individually or conjugated to one or a plurality of membrane-bound sugar molecules.

5. The method of claim 1, wherein the catanionic surfactant vesicle is lyophilized.

\* \* \* \* \*

```
SEQUENCE LISTING

<160> NUMBER OF SEQ ID NOS: 883

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Lys Phe Val Ala Ala Trp Thr Leu Lys Ala Ala Ala
1               5                   10

<210> SEQ ID NO 2
<211> LENGTH: 9
<212> TYPE: PRT
<213> ORGANISM: Neisseria gonorrhoeae

<400> SEQUENCE: 2

Asn Ala Gln Gly Glu Ile Glu Val Lys
1               5

<210> SEQ ID NO 3
<211> LENGTH: 20
<212> TYPE: PRT
<213> ORGANISM: Neisseria gonorrhoeae

<400> SEQUENCE: 3

Val Gly Asp Phe Val Thr Val Thr Ile Glu Ser Val Glu Asn Gly Phe
1               5                   10                  15

Gly Glu Thr Lys
            20

<210> SEQ ID NO 4
<211> LENGTH: 11
<212> TYPE: PRT
<213> ORGANISM: Neisseria gonorrhoeae
```

<400> SEQUENCE: 4

Gly Gly Leu Thr Val Met Ile Ser Ser Ile Arg
1               5                   10

<210> SEQ ID NO 5
<211> LENGTH: 14
<212> TYPE: PRT
<213> ORGANISM: Neisseria gonorrhoeae

<400> SEQUENCE: 5

Ala Phe Leu Pro Gly Ser Leu Val Asp Val Arg Pro Val Lys
1               5                   10

<210> SEQ ID NO 6
<211> LENGTH: 22
<212> TYPE: PRT
<213> ORGANISM: Neisseria gonorrhoeae

<400> SEQUENCE: 6

Ala Phe Leu Pro Gly Ser Leu Val Asp Val Arg Pro Val Lys Asp Thr
1               5                   10                  15

Ser His Phe Glu Gly Lys
            20

<210> SEQ ID NO 7
<211> LENGTH: 12
<212> TYPE: PRT
<213> ORGANISM: Neisseria gonorrhoeae

<400> SEQUENCE: 7

Arg Ala Val Leu Glu Ala Thr Leu Gly Glu Glu Arg
1               5                   10

<210> SEQ ID NO 8
<211> LENGTH: 12
<212> TYPE: PRT
<213> ORGANISM: Neisseria gonorrhoeae

<400> SEQUENCE: 8

Ala Val Leu Glu Ala Thr Leu Gly Glu Glu Arg Lys
1               5                   10

<210> SEQ ID NO 9
<211> LENGTH: 14
<212> TYPE: PRT
<213> ORGANISM: Neisseria gonorrhoeae

<400> SEQUENCE: 9

Lys Ala Leu Leu Glu Asn Leu Gln Glu Gly Ser Val Ile Lys
1               5                   10

<210> SEQ ID NO 10
<211> LENGTH: 13
<212> TYPE: PRT
<213> ORGANISM: Neisseria gonorrhoeae

<400> SEQUENCE: 10

Ala Leu Leu Glu Asn Leu Gln Glu Gly Ser Val Ile Lys
1               5                   10

<210> SEQ ID NO 11
<211> LENGTH: 18
<212> TYPE: PRT

<213> ORGANISM: Neisseria gonorrhoeae

<400> SEQUENCE: 11

Arg Val Lys His Pro Ser Glu Val Leu Glu Val Gly Gln Glu Val Glu
1               5                   10                  15

Ala Lys

<210> SEQ ID NO 12
<211> LENGTH: 17
<212> TYPE: PRT
<213> ORGANISM: Neisseria gonorrhoeae

<400> SEQUENCE: 12

Val Lys His Pro Ser Glu Val Leu Glu Val Gly Gln Glu Val Glu Ala
1               5                   10                  15

Lys

<210> SEQ ID NO 13
<211> LENGTH: 12
<212> TYPE: PRT
<213> ORGANISM: Neisseria gonorrhoeae

<400> SEQUENCE: 13

Gln Leu Gly Glu Asp Pro Trp Ser Gly Leu Thr Arg
1               5                   10

<210> SEQ ID NO 14
<211> LENGTH: 7
<212> TYPE: PRT
<213> ORGANISM: Neisseria gonorrhoeae

<400> SEQUENCE: 14

Arg Tyr Pro Gln Ala Thr Arg
1               5

<210> SEQ ID NO 15
<211> LENGTH: 21
<212> TYPE: PRT
<213> ORGANISM: Neisseria gonorrhoeae

<400> SEQUENCE: 15

Gln Leu Glu Gly Asp Pro Phe Gly Asn Phe Ile Ser Val Asn Asp Lys
1               5                   10                  15

Gly Ser Leu Val Lys
            20

<210> SEQ ID NO 16
<211> LENGTH: 17
<212> TYPE: PRT
<213> ORGANISM: Neisseria gonorrhoeae

<400> SEQUENCE: 16

Leu Lys Glu Gly Asp Glu Val Glu Ala Val Ile Val Thr Val Asp Arg
1               5                   10                  15

Lys

<210> SEQ ID NO 17
<211> LENGTH: 24
<212> TYPE: PRT
<213> ORGANISM: Neisseria gonorrhoeae

<400> SEQUENCE: 17

```
Glu Ala Leu Asn Ser Val Asn Ala Ala Ala Asn Ala Asn Ala Gly Thr
1               5                   10                  15

Thr Ser Leu Gly Asp Leu Leu Lys
            20

<210> SEQ ID NO 18
<211> LENGTH: 9
<212> TYPE: PRT
<213> ORGANISM: Neisseria gonorrhoeae

<400> SEQUENCE: 18

Gly Gln Val Pro Gln Leu Pro Ala Arg
1               5

<210> SEQ ID NO 19
<211> LENGTH: 13
<212> TYPE: PRT
<213> ORGANISM: Neisseria gonorrhoeae

<400> SEQUENCE: 19

Phe Ala Ser Asp Gly Ile Leu Ile Glu Thr Ala Lys Arg
1               5                   10

<210> SEQ ID NO 20
<211> LENGTH: 14
<212> TYPE: PRT
<213> ORGANISM: Neisseria gonorrhoeae

<400> SEQUENCE: 20

Gly Asp Gln Leu Ala Gly Gln Ile Lys Glu Glu Gly Ser Arg
1               5                   10

<210> SEQ ID NO 21
<211> LENGTH: 19
<212> TYPE: PRT
<213> ORGANISM: Neisseria gonorrhoeae

<400> SEQUENCE: 21

Leu Glu Ala Pro Gln Val Ser Ala Thr Thr Val Ser Glu Lys Glu His
1               5                   10                  15

Ala Thr Arg

<210> SEQ ID NO 22
<211> LENGTH: 16
<212> TYPE: PRT
<213> ORGANISM: Neisseria gonorrhoeae

<400> SEQUENCE: 22

Val Ala Ser Asn Ala Glu Phe Ala Pro Phe Glu Ser Leu Asp Ser Lys
1               5                   10                  15

<210> SEQ ID NO 23
<211> LENGTH: 16
<212> TYPE: PRT
<213> ORGANISM: Neisseria gonorrhoeae

<400> SEQUENCE: 23

Gly Asn Val Glu Gly Phe Asp Val Asp Leu Met Asn Ala Met Ala Lys
1               5                   10                  15

<210> SEQ ID NO 24
<211> LENGTH: 9
<212> TYPE: PRT
<213> ORGANISM: Neisseria gonorrhoeae
```

```
<400> SEQUENCE: 24

Ala Gly Asn Phe Lys Ile Glu Phe Lys
1               5

<210> SEQ ID NO 25
<211> LENGTH: 20
<212> TYPE: PRT
<213> ORGANISM: Neisseria gonorrhoeae

<400> SEQUENCE: 25

Gln Ser Met Asp Phe Ser Asp Pro Tyr Phe Glu Ile Thr Gln Val Val
1               5                   10                  15

Leu Val Pro Lys
            20

<210> SEQ ID NO 26
<211> LENGTH: 15
<212> TYPE: PRT
<213> ORGANISM: Neisseria gonorrhoeae

<400> SEQUENCE: 26

Val Gly Val Val Thr Gly His Thr Gly Asp Phe Ser Val Ser Lys
1               5                   10                  15

<210> SEQ ID NO 27
<211> LENGTH: 8
<212> TYPE: PRT
<213> ORGANISM: Neisseria gonorrhoeae

<400> SEQUENCE: 27

Leu Leu Gly Asn Asp Asn Pro Lys
1               5

<210> SEQ ID NO 28
<211> LENGTH: 9
<212> TYPE: PRT
<213> ORGANISM: Neisseria gonorrhoeae

<400> SEQUENCE: 28

Phe Glu Asn Val Pro Leu Ile Ile Lys
1               5

<210> SEQ ID NO 29
<211> LENGTH: 22
<212> TYPE: PRT
<213> ORGANISM: Neisseria gonorrhoeae

<400> SEQUENCE: 29

Glu Leu Glu Asn Gly Gly Leu Asp Ser Val Val Ser Asp Ser Ala Val
1               5                   10                  15

Ile Ala Asn Tyr Val Lys
            20

<210> SEQ ID NO 30
<211> LENGTH: 20
<212> TYPE: PRT
<213> ORGANISM: Neisseria gonorrhoeae

<400> SEQUENCE: 30

Gly Met Asp Phe Val Thr Leu Pro Asp Phe Thr Thr Glu His Tyr Gly
1               5                   10                  15

Ile Ala Val Arg
```

20

<210> SEQ ID NO 31
<211> LENGTH: 13
<212> TYPE: PRT
<213> ORGANISM: Neisseria gonorrhoeae

<400> SEQUENCE: 31

Leu Ile Leu Val Leu Asn Cys Gly Ser Ser Ser Leu Lys
1               5                   10

<210> SEQ ID NO 32
<211> LENGTH: 24
<212> TYPE: PRT
<213> ORGANISM: Neisseria gonorrhoeae

<400> SEQUENCE: 32

Val Val Ser Gly Gly Glu Leu Tyr Asn Glu Ser Ile Leu Val Asp Asp
1               5                   10                  15

Glu Val Ile Ala Gly Ile Glu Lys
            20

<210> SEQ ID NO 33
<211> LENGTH: 17
<212> TYPE: PRT
<213> ORGANISM: Neisseria gonorrhoeae

<400> SEQUENCE: 33

Cys Ile Pro Leu Ala Pro Leu His Asn Pro Ala His Leu Leu Gly Leu
1               5                   10                  15

Arg

<210> SEQ ID NO 34
<211> LENGTH: 22
<212> TYPE: PRT
<213> ORGANISM: Neisseria gonorrhoeae

<400> SEQUENCE: 34

Gly Leu Pro Asn Val Val Phe Asp Thr Ser Phe His Gln Thr Met
1               5                   10                  15

Pro Glu Val Ala Tyr Lys
            20

<210> SEQ ID NO 35
<211> LENGTH: 9
<212> TYPE: PRT
<213> ORGANISM: Neisseria gonorrhoeae

<400> SEQUENCE: 35

Tyr Gly Ala His Gly Thr Ser Tyr Arg
1               5

<210> SEQ ID NO 36
<211> LENGTH: 12
<212> TYPE: PRT
<213> ORGANISM: Neisseria gonorrhoeae

<400> SEQUENCE: 36

Phe Val Ala Asp Glu Thr Ala His Phe Leu Gly Lys
1               5                   10

<210> SEQ ID NO 37
<211> LENGTH: 15

```
<212> TYPE: PRT
<213> ORGANISM: Neisseria gonorrhoeae

<400> SEQUENCE: 37

Phe Val Ala Asp Glu Thr Ala His Phe Leu Gly Lys Asp Lys Lys
1               5                   10                  15

<210> SEQ ID NO 38
<211> LENGTH: 17
<212> TYPE: PRT
<213> ORGANISM: Neisseria gonorrhoeae

<400> SEQUENCE: 38

Asp Thr Ser Met Gly Leu Thr Pro Leu Glu Gly Leu Val Met Gly Thr
1               5                   10                  15

Arg

<210> SEQ ID NO 39
<211> LENGTH: 14
<212> TYPE: PRT
<213> ORGANISM: Neisseria gonorrhoeae

<400> SEQUENCE: 39

Thr Ile Glu Glu Glu Ala Ala Lys Gly His Lys Gly Ala Lys
1               5                   10

<210> SEQ ID NO 40
<211> LENGTH: 13
<212> TYPE: PRT
<213> ORGANISM: Neisseria gonorrhoeae

<400> SEQUENCE: 40

Phe Gly Asn Ala Gly Val Ile Thr Thr Ala Asp Ser Lys
1               5                   10

<210> SEQ ID NO 41
<211> LENGTH: 20
<212> TYPE: PRT
<213> ORGANISM: Neisseria gonorrhoeae

<400> SEQUENCE: 41

Ala Val Ala Val Val Ile Pro Thr Asn Glu Glu Leu Met Ile Ala His
1               5                   10                  15

Asp Thr Ala Arg
            20

<210> SEQ ID NO 42
<211> LENGTH: 10
<212> TYPE: PRT
<213> ORGANISM: Neisseria gonorrhoeae

<400> SEQUENCE: 42

Cys Asn His His Asn Pro Leu Ser Ala Arg
1               5                   10

<210> SEQ ID NO 43
<211> LENGTH: 13
<212> TYPE: PRT
<213> ORGANISM: Neisseria gonorrhoeae

<400> SEQUENCE: 43

Phe Ile Gly Gly Ser Met Gly Ser Val Val Gly Glu Arg
1               5                   10
```

```
<210> SEQ ID NO 44
<211> LENGTH: 11
<212> TYPE: PRT
<213> ORGANISM: Neisseria gonorrhoeae

<400> SEQUENCE: 44

Thr Ser Ala Ala Leu His Leu Leu Thr Glu Lys
1               5                   10

<210> SEQ ID NO 45
<211> LENGTH: 23
<212> TYPE: PRT
<213> ORGANISM: Neisseria gonorrhoeae

<400> SEQUENCE: 45

Ala Ala Leu Gly Ile Pro Ala Leu Pro Leu Asn Ala Gln Gln Thr Ala
1               5                   10                  15

Asp Leu Val Glu Leu Leu Lys
            20

<210> SEQ ID NO 46
<211> LENGTH: 17
<212> TYPE: PRT
<213> ORGANISM: Neisseria gonorrhoeae

<400> SEQUENCE: 46

Asn Pro Pro Ala Gly Glu Gly Glu Phe Leu Val Glu Leu Leu Ala His
1               5                   10                  15

Arg

<210> SEQ ID NO 47
<211> LENGTH: 22
<212> TYPE: PRT
<213> ORGANISM: Neisseria gonorrhoeae

<400> SEQUENCE: 47

Val Lys Ala Ser Phe Leu Ala Ala Val Ala Glu Gly Ser Ala Ser Ser
1               5                   10                  15

Pro Leu Val Ser Pro Lys
            20

<210> SEQ ID NO 48
<211> LENGTH: 20
<212> TYPE: PRT
<213> ORGANISM: Neisseria gonorrhoeae

<400> SEQUENCE: 48

Ala Ser Phe Leu Ala Ala Val Ala Glu Gly Ser Ala Ser Ser Pro Leu
1               5                   10                  15

Val Ser Pro Lys
            20

<210> SEQ ID NO 49
<211> LENGTH: 13
<212> TYPE: PRT
<213> ORGANISM: Neisseria gonorrhoeae

<400> SEQUENCE: 49

Ala Lys Val Pro Glu Lys Ile Thr Val Thr Val Phe Lys
1               5                   10

<210> SEQ ID NO 50
```

-continued

```
<211> LENGTH: 15
<212> TYPE: PRT
<213> ORGANISM: Neisseria gonorrhoeae

<400> SEQUENCE: 50

Asp Gly Ile Thr Pro Asp Lys Pro Gly Glu Val Gly Pro Ile Lys
1               5                   10                  15

<210> SEQ ID NO 51
<211> LENGTH: 21
<212> TYPE: PRT
<213> ORGANISM: Neisseria gonorrhoeae

<400> SEQUENCE: 51

Asp Gly Ile Thr Pro Asp Lys Pro Gly Glu Val Gly Pro Ile Lys Leu
1               5                   10                  15

Leu Glu Glu Leu Lys
            20

<210> SEQ ID NO 52
<211> LENGTH: 19
<212> TYPE: PRT
<213> ORGANISM: Neisseria gonorrhoeae

<400> SEQUENCE: 52

Ala Lys Gly His Pro Val Ala Tyr Val Gly Asp Val Val Gly Thr Gly
1               5                   10                  15

Ser Ser Arg

<210> SEQ ID NO 53
<211> LENGTH: 17
<212> TYPE: PRT
<213> ORGANISM: Neisseria gonorrhoeae

<400> SEQUENCE: 53

Gly His Pro Val Ala Tyr Val Gly Asp Val Val Gly Thr Gly Ser Ser
1               5                   10                  15

Arg

<210> SEQ ID NO 54
<211> LENGTH: 18
<212> TYPE: PRT
<213> ORGANISM: Neisseria gonorrhoeae

<400> SEQUENCE: 54

Gly His Pro Val Ala Tyr Val Gly Asp Val Val Gly Thr Gly Ser Ser
1               5                   10                  15

Arg Lys

<210> SEQ ID NO 55
<211> LENGTH: 22
<212> TYPE: PRT
<213> ORGANISM: Neisseria gonorrhoeae

<400> SEQUENCE: 55

Lys Ser Ala Thr Asn Ser Val Ile Trp His Thr Gly Glu Asp Ile Pro
1               5                   10                  15

Phe Val Pro Asn Lys Arg
            20

<210> SEQ ID NO 56
<211> LENGTH: 21
```

```
<212> TYPE: PRT
<213> ORGANISM: Neisseria gonorrhoeae

<400> SEQUENCE: 56

Ser Ala Thr Asn Ser Val Ile Trp His Thr Gly Glu Asp Ile Pro Phe
1               5                   10                  15

Val Pro Asn Lys Arg
            20

<210> SEQ ID NO 57
<211> LENGTH: 25
<212> TYPE: PRT
<213> ORGANISM: Neisseria gonorrhoeae

<400> SEQUENCE: 57

Ile Ala Pro Ile Phe Phe Asn Thr Gln Glu Asp Ser Gly Ala Leu Pro
1               5                   10                  15

Ile Glu Val Asp Val Ser Ala Leu Lys
            20                  25

<210> SEQ ID NO 58
<211> LENGTH: 13
<212> TYPE: PRT
<213> ORGANISM: Neisseria gonorrhoeae

<400> SEQUENCE: 58

Ser Gln Val Leu Leu Asp Glu Val Gln Ala Gly Gly Arg
1               5                   10

<210> SEQ ID NO 59
<211> LENGTH: 19
<212> TYPE: PRT
<213> ORGANISM: Neisseria gonorrhoeae

<400> SEQUENCE: 59

Ala Cys Gly Leu Pro Glu Gly Gln Gly Val Arg Pro Gly Thr Tyr Cys
1               5                   10                  15

Glu Pro Arg

<210> SEQ ID NO 60
<211> LENGTH: 15
<212> TYPE: PRT
<213> ORGANISM: Neisseria gonorrhoeae

<400> SEQUENCE: 60

Met Thr Thr Val Gly Ser Gln Asp Thr Thr Gly Pro Met Thr Arg
1               5                   10                  15

<210> SEQ ID NO 61
<211> LENGTH: 12
<212> TYPE: PRT
<213> ORGANISM: Neisseria gonorrhoeae

<400> SEQUENCE: 61

Thr His Lys Glu Leu Pro Ala Phe Ile Ser Thr Arg
1               5                   10

<210> SEQ ID NO 62
<211> LENGTH: 18
<212> TYPE: PRT
<213> ORGANISM: Neisseria gonorrhoeae

<400> SEQUENCE: 62
```

```
Gly Gly Val Ser Leu Arg Pro Gly Asp Gly Val Ile His Ser Trp Leu
1               5                   10                  15

Asn Arg

<210> SEQ ID NO 63
<211> LENGTH: 12
<212> TYPE: PRT
<213> ORGANISM: Neisseria gonorrhoeae

<400> SEQUENCE: 63

Asp Leu Val Asn Ala Ile Pro Leu Tyr Ala Ile Lys
1               5                   10

<210> SEQ ID NO 64
<211> LENGTH: 11
<212> TYPE: PRT
<213> ORGANISM: Neisseria gonorrhoeae

<400> SEQUENCE: 64

Leu Asn Lys Glu Pro Ile Ile Glu Tyr Met Lys
1               5                   10

<210> SEQ ID NO 65
<211> LENGTH: 11
<212> TYPE: PRT
<213> ORGANISM: Neisseria gonorrhoeae

<400> SEQUENCE: 65

Leu Leu Glu Gly Lys Ser Asp Ile Pro Val Arg
1               5                   10

<210> SEQ ID NO 66
<211> LENGTH: 13
<212> TYPE: PRT
<213> ORGANISM: Neisseria gonorrhoeae

<400> SEQUENCE: 66

Glu Leu Ser Asp Glu Gly His Tyr Gly Val Leu Gly Arg
1               5                   10

<210> SEQ ID NO 67
<211> LENGTH: 11
<212> TYPE: PRT
<213> ORGANISM: Neisseria gonorrhoeae

<400> SEQUENCE: 67

Glu Gly Ala Thr Val Met Ser Thr Ser Thr Arg
1               5                   10

<210> SEQ ID NO 68
<211> LENGTH: 17
<212> TYPE: PRT
<213> ORGANISM: Neisseria gonorrhoeae

<400> SEQUENCE: 68

Asn Thr Phe Val Tyr Leu Gly Ser Ala Glu Leu Ala Ala Ile Cys Ser
1               5                   10                  15

Lys

<210> SEQ ID NO 69
<211> LENGTH: 26
<212> TYPE: PRT
<213> ORGANISM: Neisseria gonorrhoeae
```

```
<400> SEQUENCE: 69

Leu Gly Lys Ile Pro Thr Val Glu Glu Tyr Gln Ala Asn Ile Gly Ile
1               5                   10                  15

Ile Asn Glu Gln Gly Asp Lys Ile Tyr Arg
            20                  25

<210> SEQ ID NO 70
<211> LENGTH: 23
<212> TYPE: PRT
<213> ORGANISM: Neisseria gonorrhoeae

<400> SEQUENCE: 70

Ile Pro Thr Val Glu Glu Tyr Gln Ala Asn Ile Gly Ile Ile Asn Glu
1               5                   10                  15

Gln Gly Asp Lys Ile Tyr Arg
            20

<210> SEQ ID NO 71
<211> LENGTH: 11
<212> TYPE: PRT
<213> ORGANISM: Neisseria gonorrhoeae

<400> SEQUENCE: 71

Asn Ala Ser Asp Glu His Tyr Thr Ile Phe Lys
1               5                   10

<210> SEQ ID NO 72
<211> LENGTH: 24
<212> TYPE: PRT
<213> ORGANISM: Neisseria gonorrhoeae

<400> SEQUENCE: 72

Lys Met Thr Tyr Leu Pro Leu Phe Asp Ala Ser Glu Leu Lys Ala Gly
1               5                   10                  15

Asp Glu Thr Gly Gly Thr Val Arg
            20

<210> SEQ ID NO 73
<211> LENGTH: 16
<212> TYPE: PRT
<213> ORGANISM: Neisseria gonorrhoeae

<400> SEQUENCE: 73

Ile Leu Leu Gly Ser Pro Asp Lys Glu Met Lys Glu Ile Ser Glu Lys
1               5                   10                  15

<210> SEQ ID NO 74
<211> LENGTH: 12
<212> TYPE: PRT
<213> ORGANISM: Neisseria gonorrhoeae

<400> SEQUENCE: 74

Asn Phe Asn Ile Gln Tyr Val Ala Pro His Pro Arg
1               5                   10

<210> SEQ ID NO 75
<211> LENGTH: 13
<212> TYPE: PRT
<213> ORGANISM: Neisseria gonorrhoeae

<400> SEQUENCE: 75

Ala Phe Phe Arg Lys Leu Ile Ala Asn Asp Val Ala Lys
1               5                   10
```

<210> SEQ ID NO 76
<211> LENGTH: 15
<212> TYPE: PRT
<213> ORGANISM: Neisseria gonorrhoeae

<400> SEQUENCE: 76

Ala Leu Gln Thr Ala Gly Val Gln Pro Cys Gly Leu Gly Ala Arg
1               5                   10                  15

<210> SEQ ID NO 77
<211> LENGTH: 9
<212> TYPE: PRT
<213> ORGANISM: Neisseria gonorrhoeae

<400> SEQUENCE: 77

Ala Gln Val Gly Gly Ile Ile Gln Lys
1               5

<210> SEQ ID NO 78
<211> LENGTH: 10
<212> TYPE: PRT
<213> ORGANISM: Neisseria gonorrhoeae

<400> SEQUENCE: 78

Ala Gln Val Gly Gly Ile Ile Gln Lys Arg
1               5                   10

<210> SEQ ID NO 79
<211> LENGTH: 21
<212> TYPE: PRT
<213> ORGANISM: Neisseria gonorrhoeae

<400> SEQUENCE: 79

Ala Gly Gln Pro Leu Tyr Gln Ile Asp Ser Ser Thr Tyr Glu Ala Gly
1               5                   10                  15

Leu Glu Ser Ala Arg
            20

<210> SEQ ID NO 80
<211> LENGTH: 12
<212> TYPE: PRT
<213> ORGANISM: Neisseria gonorrhoeae

<400> SEQUENCE: 80

Ala Gln Leu Ala Thr Ala Gln Ala Thr Leu Ala Lys
1               5                   10

<210> SEQ ID NO 81
<211> LENGTH: 14
<212> TYPE: PRT
<213> ORGANISM: Neisseria gonorrhoeae

<400> SEQUENCE: 81

Ser Ala Glu Ala Gly Val Lys Ala Ala Gln Ala Ala Ile Lys
1               5                   10

<210> SEQ ID NO 82
<211> LENGTH: 8
<212> TYPE: PRT
<213> ORGANISM: Neisseria gonorrhoeae

<400> SEQUENCE: 82

Ser Ala Gly Ile Asn Leu Asn Arg

```
<210> SEQ ID NO 83
<211> LENGTH: 15
<212> TYPE: PRT
<213> ORGANISM: Neisseria gonorrhoeae

<400> SEQUENCE: 83

Ser Arg Ile Thr Ala Pro Ile Ser Gly Phe Ile Gly Gln Ser Lys
1               5                   10                  15

<210> SEQ ID NO 84
<211> LENGTH: 13
<212> TYPE: PRT
<213> ORGANISM: Neisseria gonorrhoeae

<400> SEQUENCE: 84

Ile Thr Ala Pro Ile Ser Gly Phe Ile Gly Gln Ser Lys
1               5                   10

<210> SEQ ID NO 85
<211> LENGTH: 19
<212> TYPE: PRT
<213> ORGANISM: Neisseria gonorrhoeae

<400> SEQUENCE: 85

Val Ser Glu Gly Thr Leu Leu Asn Ala Gly Asp Thr Thr Val Leu Ala
1               5                   10                  15

Thr Ile Arg

<210> SEQ ID NO 86
<211> LENGTH: 18
<212> TYPE: PRT
<213> ORGANISM: Neisseria gonorrhoeae

<400> SEQUENCE: 86

Gln Thr Asn Pro Met Tyr Val Asn Val Thr Gln Ser Ala Ser Glu Val
1               5                   10                  15

Met Lys

<210> SEQ ID NO 87
<211> LENGTH: 17
<212> TYPE: PRT
<213> ORGANISM: Neisseria gonorrhoeae

<400> SEQUENCE: 87

Ala Ala Val Ser Asn Asp Gln Asn Ile Leu Met Pro Gly Leu Tyr Val
1               5                   10                  15

Arg

<210> SEQ ID NO 88
<211> LENGTH: 21
<212> TYPE: PRT
<213> ORGANISM: Neisseria gonorrhoeae

<400> SEQUENCE: 88

Val Leu Met Asp Gln Val Ala Ala Asp Asn Ala Phe Ile Val Pro Gln
1               5                   10                  15

Gln Ala Val Thr Arg
            20

<210> SEQ ID NO 89
```

```
<211> LENGTH: 18
<212> TYPE: PRT
<213> ORGANISM: Neisseria gonorrhoeae

<400> SEQUENCE: 89

Gly Ala Lys Asp Thr Val Met Ile Val Asn Ala Gln Gly Gly Met Glu
1               5                   10                  15

Pro Arg

<210> SEQ ID NO 90
<211> LENGTH: 29
<212> TYPE: PRT
<213> ORGANISM: Neisseria gonorrhoeae

<400> SEQUENCE: 90

Glu Trp Ala Pro Ser Glu Asn Gln Ala Ala Pro Gln Ala Gly Val
1               5                   10                  15

Gln Thr Ala Ser Glu Ala Lys Pro Ala Ser Glu Ala Lys
            20                  25

<210> SEQ ID NO 91
<211> LENGTH: 21
<212> TYPE: PRT
<213> ORGANISM: Neisseria gonorrhoeae

<400> SEQUENCE: 91

Leu Ser Glu Val Leu Ser Thr Leu Pro Ala Thr Val Gln Gln Tyr Gly
1               5                   10                  15

Val Thr Val Ser Lys
            20

<210> SEQ ID NO 92
<211> LENGTH: 15
<212> TYPE: PRT
<213> ORGANISM: Neisseria gonorrhoeae

<400> SEQUENCE: 92

Ala Asn Thr Asp Gly Ser Asn Ile Tyr Leu Lys Asp Val Ala Lys
1               5                   10                  15

<210> SEQ ID NO 93
<211> LENGTH: 13
<212> TYPE: PRT
<213> ORGANISM: Neisseria gonorrhoeae

<400> SEQUENCE: 93

Thr Asp Ala Thr Leu Ala Gln Val Thr Gln Leu Ala Lys
1               5                   10

<210> SEQ ID NO 94
<211> LENGTH: 13
<212> TYPE: PRT
<213> ORGANISM: Neisseria gonorrhoeae

<400> SEQUENCE: 94

Thr Ala Ser Gly Ser Asp Ala Val Ala Val Ala Gly Lys
1               5                   10

<210> SEQ ID NO 95
<211> LENGTH: 11
<212> TYPE: PRT
<213> ORGANISM: Neisseria gonorrhoeae

<400> SEQUENCE: 95
```

Ala Ser Gly Leu Phe Asp Pro Ser Thr Val Arg
1               5                   10

<210> SEQ ID NO 96
<211> LENGTH: 11
<212> TYPE: PRT
<213> ORGANISM: Neisseria gonorrhoeae

<400> SEQUENCE: 96

Ala Gly Gly Leu Glu Asp Ser Pro Gln Leu Lys
1               5                   10

<210> SEQ ID NO 97
<211> LENGTH: 14
<212> TYPE: PRT
<213> ORGANISM: Neisseria gonorrhoeae

<400> SEQUENCE: 97

Ala Ala Ala Ala Ala Gln Gly Ile Ser Phe Ala Asp Ile Arg
1               5                   10

<210> SEQ ID NO 98
<211> LENGTH: 20
<212> TYPE: PRT
<213> ORGANISM: Neisseria gonorrhoeae

<400> SEQUENCE: 98

Thr Ala Leu Ala Ser Ala Leu Ser Ser Ser Tyr Val Ser Asp Phe Pro
1               5                   10                  15

Asn Gln Gly Arg
            20

<210> SEQ ID NO 99
<211> LENGTH: 14
<212> TYPE: PRT
<213> ORGANISM: Neisseria gonorrhoeae

<400> SEQUENCE: 99

Met Gln Pro Ala Asp Ile Leu Asn Leu Thr Val Pro Asn Lys
1               5                   10

<210> SEQ ID NO 100
<211> LENGTH: 24
<212> TYPE: PRT
<213> ORGANISM: Neisseria gonorrhoeae

<400> SEQUENCE: 100

Ser Gly Val Ala Val Pro Leu Ser Thr Ile Ala Thr Val Ser Trp Glu
1               5                   10                  15

Asn Gly Thr Glu Gln Ser Val Arg
            20

<210> SEQ ID NO 101
<211> LENGTH: 20
<212> TYPE: PRT
<213> ORGANISM: Neisseria gonorrhoeae

<400> SEQUENCE: 101

Leu Ser Ala Ser Pro Ala Thr Gly Val Ser Thr Gly Gln Ala Met Ala
1               5                   10                  15

Ala Val Gln Lys
            20

<210> SEQ ID NO 102
<211> LENGTH: 11
<212> TYPE: PRT
<213> ORGANISM: Neisseria gonorrhoeae

<400> SEQUENCE: 102

Ala Gly Ile Thr Gly Ser Asp Asp Lys Gln Tyr
1               5                   10

<210> SEQ ID NO 103
<211> LENGTH: 11
<212> TYPE: PRT
<213> ORGANISM: Neisseria gonorrhoeae

<400> SEQUENCE: 103

Tyr Gly Gly Thr Ser Val Gly Ser Pro Glu Arg
1               5                   10

<210> SEQ ID NO 104
<211> LENGTH: 14
<212> TYPE: PRT
<213> ORGANISM: Neisseria gonorrhoeae

<400> SEQUENCE: 104

Ala Ala Val Thr Gly Ile Ala Phe Asp Lys Asn Gln Ala Arg
1               5                   10

<210> SEQ ID NO 105
<211> LENGTH: 15
<212> TYPE: PRT
<213> ORGANISM: Neisseria gonorrhoeae

<400> SEQUENCE: 105

Thr Pro Ala Ser Phe Glu Pro Ser Ile Asp Tyr Val Val Thr Lys
1               5                   10                  15

<210> SEQ ID NO 106
<211> LENGTH: 9
<212> TYPE: PRT
<213> ORGANISM: Neisseria gonorrhoeae

<400> SEQUENCE: 106

Glu Leu Ala Asn Pro Gly Pro Glu Arg
1               5

<210> SEQ ID NO 107
<211> LENGTH: 13
<212> TYPE: PRT
<213> ORGANISM: Neisseria gonorrhoeae

<400> SEQUENCE: 107

Val Leu Asn Asp Leu Gly Leu Arg Gln Pro Pro Asn Arg
1               5                   10

<210> SEQ ID NO 108
<211> LENGTH: 11
<212> TYPE: PRT
<213> ORGANISM: Neisseria gonorrhoeae

<400> SEQUENCE: 108

Ile Ala His Asn Glu Glu Glu Ala Leu Val Lys
1               5                   10

<210> SEQ ID NO 109

```
<211> LENGTH: 19
<212> TYPE: PRT
<213> ORGANISM: Neisseria gonorrhoeae

<400> SEQUENCE: 109

Ala Glu Glu Ile Gly Tyr Pro Leu Val Val Arg Pro Ser Tyr Val Leu
1               5                   10                  15

Gly Gly Arg

<210> SEQ ID NO 110
<211> LENGTH: 18
<212> TYPE: PRT
<213> ORGANISM: Neisseria gonorrhoeae

<400> SEQUENCE: 110

Val Pro Gln Tyr Thr Thr Thr Ala Gly Gly Glu Ala Met Ser Glu Gly
1               5                   10                  15

Ala Lys

<210> SEQ ID NO 111
<211> LENGTH: 30
<212> TYPE: PRT
<213> ORGANISM: Neisseria gonorrhoeae

<400> SEQUENCE: 111

Thr Thr Ser Lys Cys Pro Val Thr His Leu Thr Met Asn Asn Gly Ala
1               5                   10                  15

Pro Val Ala Asp Asn Gln Asn Ser Leu Thr Ala Gly Pro Arg
            20                  25                  30

<210> SEQ ID NO 112
<211> LENGTH: 26
<212> TYPE: PRT
<213> ORGANISM: Neisseria gonorrhoeae

<400> SEQUENCE: 112

Cys Pro Val Thr His Leu Thr Met Asn Asn Gly Ala Pro Val Ala Asp
1               5                   10                  15

Asn Gln Asn Ser Leu Thr Ala Gly Pro Arg
            20                  25

<210> SEQ ID NO 113
<211> LENGTH: 13
<212> TYPE: PRT
<213> ORGANISM: Neisseria gonorrhoeae

<400> SEQUENCE: 113

Gly Pro Leu Leu Thr Gln Asp Leu Trp Leu Asn Glu Lys
1               5                   10

<210> SEQ ID NO 114
<211> LENGTH: 7
<212> TYPE: PRT
<213> ORGANISM: Neisseria gonorrhoeae

<400> SEQUENCE: 114

Glu Val Ile Pro Glu Arg Arg
1               5

<210> SEQ ID NO 115
<211> LENGTH: 8
<212> TYPE: PRT
<213> ORGANISM: Neisseria gonorrhoeae
```

<400> SEQUENCE: 115

Phe Thr Thr Val Ala Gly Glu Arg
1               5

<210> SEQ ID NO 116
<211> LENGTH: 9
<212> TYPE: PRT
<213> ORGANISM: Neisseria gonorrhoeae

<400> SEQUENCE: 116

Leu Phe Asn Tyr Ala Asp Ala Gln Arg
1               5

<210> SEQ ID NO 117
<211> LENGTH: 8
<212> TYPE: PRT
<213> ORGANISM: Neisseria gonorrhoeae

<400> SEQUENCE: 117

Gln Ile Pro Val Asn Arg Pro Arg
1               5

<210> SEQ ID NO 118
<211> LENGTH: 11
<212> TYPE: PRT
<213> ORGANISM: Neisseria gonorrhoeae

<400> SEQUENCE: 118

Ala Leu Phe Asn Leu Met Asn Asp Ala Gln Lys
1               5                   10

<210> SEQ ID NO 119
<211> LENGTH: 19
<212> TYPE: PRT
<213> ORGANISM: Neisseria gonorrhoeae

<400> SEQUENCE: 119

Gln Ala Leu Phe Asp Asn Thr Ala Ala Ala Met Gly Asp Ala Pro Asp
1               5                   10                  15

Phe Ile Lys

<210> SEQ ID NO 120
<211> LENGTH: 21
<212> TYPE: PRT
<213> ORGANISM: Neisseria gonorrhoeae

<400> SEQUENCE: 120

Gln Ala Leu Phe Asp Asn Thr Ala Ala Ala Met Gly Asp Ala Pro Asp
1               5                   10                  15

Phe Ile Lys Tyr Arg
            20

<210> SEQ ID NO 121
<211> LENGTH: 11
<212> TYPE: PRT
<213> ORGANISM: Neisseria gonorrhoeae

<400> SEQUENCE: 121

Cys Asp Pro Ala Tyr Gly Glu Gly Val Ala Lys
1               5                   10

<210> SEQ ID NO 122

```
<211> LENGTH: 14
<212> TYPE: PRT
<213> ORGANISM: Neisseria gonorrhoeae

<400> SEQUENCE: 122

Ile Thr His Val Thr Thr Gly Ile Ala Gly Asn His Ile Arg
1               5                   10

<210> SEQ ID NO 123
<211> LENGTH: 16
<212> TYPE: PRT
<213> ORGANISM: Neisseria gonorrhoeae

<400> SEQUENCE: 123

Val His Ile Ile Thr Gly Ala Ser Thr Ala Val Gln Asn Val Gln Lys
1               5                   10                  15

<210> SEQ ID NO 124
<211> LENGTH: 18
<212> TYPE: PRT
<213> ORGANISM: Neisseria gonorrhoeae

<400> SEQUENCE: 124

Met Glu Phe Val Tyr Asp Val Ala Glu Ser Ala Val Ser Pro Ala Val
1               5                   10                  15

Ile Lys

<210> SEQ ID NO 125
<211> LENGTH: 21
<212> TYPE: PRT
<213> ORGANISM: Neisseria gonorrhoeae

<400> SEQUENCE: 125

Val Ile Gly Leu Gly Gly Gly Gly Cys Asn Ala Ile Asn Asn Met Val
1               5                   10                  15

Ala Asn Asn Val Arg
            20

<210> SEQ ID NO 126
<211> LENGTH: 16
<212> TYPE: PRT
<213> ORGANISM: Neisseria gonorrhoeae

<400> SEQUENCE: 126

Ser Val Glu Phe Ile Ser Ala Asn Thr Asp Ala Gln Ser Leu Ala Lys
1               5                   10                  15

<210> SEQ ID NO 127
<211> LENGTH: 10
<212> TYPE: PRT
<213> ORGANISM: Neisseria gonorrhoeae

<400> SEQUENCE: 127

Arg Ile Gln Leu Gly Thr Asn Leu Thr Arg
1               5                   10

<210> SEQ ID NO 128
<211> LENGTH: 9
<212> TYPE: PRT
<213> ORGANISM: Neisseria gonorrhoeae

<400> SEQUENCE: 128

Ile Gln Leu Gly Thr Asn Leu Thr Arg
1               5
```

<210> SEQ ID NO 129
<211> LENGTH: 12
<212> TYPE: PRT
<213> ORGANISM: Neisseria gonorrhoeae

<400> SEQUENCE: 129

Gly Leu Gly Ala Gly Ala Asn Pro Asp Ile Gly Arg
1               5                   10

<210> SEQ ID NO 130
<211> LENGTH: 15
<212> TYPE: PRT
<213> ORGANISM: Neisseria gonorrhoeae

<400> SEQUENCE: 130

Gly Ile Ala Met Met Gly Ser Gly Tyr Ala Gln Gly Ile Asp Arg
1               5                   10                  15

<210> SEQ ID NO 131
<211> LENGTH: 21
<212> TYPE: PRT
<213> ORGANISM: Neisseria gonorrhoeae

<400> SEQUENCE: 131

Met Ala Thr Asp Gln Ala Ile Ser Ser Pro Leu Leu Asp Asp Val Thr
1               5                   10                  15

Leu Asp Gly Ala Arg
            20

<210> SEQ ID NO 132
<211> LENGTH: 14
<212> TYPE: PRT
<213> ORGANISM: Neisseria gonorrhoeae

<400> SEQUENCE: 132

Gly Val Leu Val Asn Ile Thr Thr Ala Pro Gly Cys Leu Lys
1               5                   10

<210> SEQ ID NO 133
<211> LENGTH: 13
<212> TYPE: PRT
<213> ORGANISM: Neisseria gonorrhoeae

<400> SEQUENCE: 133

Ile Val Asn Gln Ser Ala His Pro Asp Leu Glu Cys Lys
1               5                   10

<210> SEQ ID NO 134
<211> LENGTH: 11
<212> TYPE: PRT
<213> ORGANISM: Neisseria gonorrhoeae

<400> SEQUENCE: 134

Ile Thr Ile Ile Ala Thr Gly Leu Lys Glu Lys
1               5                   10

<210> SEQ ID NO 135
<211> LENGTH: 9
<212> TYPE: PRT
<213> ORGANISM: Neisseria gonorrhoeae

<400> SEQUENCE: 135

Gly Ala Val Asp Pro Thr Pro Ala Arg

```
<210> SEQ ID NO 136
<211> LENGTH: 30
<212> TYPE: PRT
<213> ORGANISM: Neisseria gonorrhoeae

<400> SEQUENCE: 136

Gly Ala Val Asp Pro Thr Pro Ala Arg Glu Val Glu Ala Val Ala Pro
1               5                   10                  15
Ser Lys Gln Glu Gln Ser His Asn Val Glu Gly Met Ile Arg
            20                  25                  30

<210> SEQ ID NO 137
<211> LENGTH: 21
<212> TYPE: PRT
<213> ORGANISM: Neisseria gonorrhoeae

<400> SEQUENCE: 137

Glu Val Glu Ala Val Ala Pro Ser Lys Gln Glu Gln Ser His Asn Val
1               5                   10                  15
Glu Gly Met Ile Arg
            20

<210> SEQ ID NO 138
<211> LENGTH: 17
<212> TYPE: PRT
<213> ORGANISM: Neisseria gonorrhoeae

<400> SEQUENCE: 138

Val Arg Asp Gln Phe Gly His Ser Asp Lys Asp Ala Leu Leu Asn Ser
1               5                   10                  15
Lys

<210> SEQ ID NO 139
<211> LENGTH: 24
<212> TYPE: PRT
<213> ORGANISM: Neisseria gonorrhoeae

<400> SEQUENCE: 139

Thr Ser His Val Arg Asp Gly Lys Pro Ser Gly Gly Pro Val Met Met
1               5                   10                  15
Pro Lys Pro Gln Pro Ala Val Lys
            20

<210> SEQ ID NO 140
<211> LENGTH: 11
<212> TYPE: PRT
<213> ORGANISM: Neisseria gonorrhoeae

<400> SEQUENCE: 140

Lys Pro Ala Lys Pro Gln Asp Ser Ala Met Arg
1               5                   10

<210> SEQ ID NO 141
<211> LENGTH: 12
<212> TYPE: PRT
<213> ORGANISM: Neisseria gonorrhoeae

<400> SEQUENCE: 141

Asn Leu Gln Glu Gln Asp Ala Val Tyr Ile Ala Lys
1               5                   10
```

<210> SEQ ID NO 142
<211> LENGTH: 11
<212> TYPE: PRT
<213> ORGANISM: Neisseria gonorrhoeae

<400> SEQUENCE: 142

Ser Lys Ser Ile Lys Leu Asn Val Pro Gly Arg
1               5                   10

<210> SEQ ID NO 143
<211> LENGTH: 9
<212> TYPE: PRT
<213> ORGANISM: Neisseria gonorrhoeae

<400> SEQUENCE: 143

Ser Ile Lys Leu Asn Val Pro Gly Arg
1               5

<210> SEQ ID NO 144
<211> LENGTH: 20
<212> TYPE: PRT
<213> ORGANISM: Neisseria gonorrhoeae

<400> SEQUENCE: 144

Ala Gly Leu Glu Leu Pro Val Leu Glu Ala Ser Ile Gly His Asp Val
1               5                   10                  15

Val Asp Ile Arg
            20

<210> SEQ ID NO 145
<211> LENGTH: 18
<212> TYPE: PRT
<213> ORGANISM: Neisseria gonorrhoeae

<400> SEQUENCE: 145

Ile Phe Ile Leu His Ala Asp His Glu Gln Asn Ala Ser Thr Ser Thr
1               5                   10                  15

Val Arg

<210> SEQ ID NO 146
<211> LENGTH: 9
<212> TYPE: PRT
<213> ORGANISM: Neisseria gonorrhoeae

<400> SEQUENCE: 146

Arg Asp Tyr Val Pro Ala Gly Glu Arg
1               5

<210> SEQ ID NO 147
<211> LENGTH: 18
<212> TYPE: PRT
<213> ORGANISM: Neisseria gonorrhoeae

<400> SEQUENCE: 147

Met Lys Ile Ala Asn Ser Ile Thr Glu Leu Ile Gly Asn Thr Pro Leu
1               5                   10                  15

Val Lys

<210> SEQ ID NO 148
<211> LENGTH: 16
<212> TYPE: PRT
<213> ORGANISM: Neisseria gonorrhoeae

```
<400> SEQUENCE: 148

Ile Ala Asn Ser Ile Thr Glu Leu Ile Gly Asn Thr Pro Leu Val Lys
1               5                   10                  15

<210> SEQ ID NO 149
<211> LENGTH: 9
<212> TYPE: PRT
<213> ORGANISM: Neisseria gonorrhoeae

<400> SEQUENCE: 149

Gly Leu Lys Ala Glu Val Ala Val Lys
1               5

<210> SEQ ID NO 150
<211> LENGTH: 21
<212> TYPE: PRT
<213> ORGANISM: Neisseria gonorrhoeae

<400> SEQUENCE: 150

Thr Phe Gly Ala Glu Leu Ile Leu Thr Pro Ala Ala Glu Gly Met Ala
1               5                   10                  15

Gly Ala Ile Ala Lys
            20

<210> SEQ ID NO 151
<211> LENGTH: 16
<212> TYPE: PRT
<213> ORGANISM: Neisseria gonorrhoeae

<400> SEQUENCE: 151

Ala Gln Ser Leu Val Asp Ala His Pro Asp Thr Tyr Phe Met Pro Arg
1               5                   10                  15

<210> SEQ ID NO 152
<211> LENGTH: 12
<212> TYPE: PRT
<213> ORGANISM: Neisseria gonorrhoeae

<400> SEQUENCE: 152

Gln Phe Asp Asn Glu Ala Asn Pro Glu Val His Arg
1               5                   10

<210> SEQ ID NO 153
<211> LENGTH: 13
<212> TYPE: PRT
<213> ORGANISM: Neisseria gonorrhoeae

<400> SEQUENCE: 153

Gln Phe Asp Asn Glu Ala Asn Pro Glu Val His Arg Lys
1               5                   10

<210> SEQ ID NO 154
<211> LENGTH: 20
<212> TYPE: PRT
<213> ORGANISM: Neisseria gonorrhoeae

<400> SEQUENCE: 154

Gly Pro His Pro Ile Gln Gly Ile Gly Ala Gly Phe Ile Pro Thr Val
1               5                   10                  15

Leu Asn Thr Lys
            20

<210> SEQ ID NO 155
```

<210> SEQ ID NO 155
<211> LENGTH: 18
<212> TYPE: PRT
<213> ORGANISM: Neisseria gonorrhoeae

<400> SEQUENCE: 155

Ile Tyr Asp Ser Ile Ala Lys Val Pro Asn Glu Ala Ala Phe Glu Thr
1               5                   10                  15

Ala Arg

<210> SEQ ID NO 156
<211> LENGTH: 11
<212> TYPE: PRT
<213> ORGANISM: Neisseria gonorrhoeae

<400> SEQUENCE: 156

Val Pro Asn Glu Ala Ala Phe Glu Thr Ala Arg
1               5                   10

<210> SEQ ID NO 157
<211> LENGTH: 21
<212> TYPE: PRT
<213> ORGANISM: Neisseria gonorrhoeae

<400> SEQUENCE: 157

Glu Gly Ile Leu Ala Gly Ile Ser Ser Gly Ala Ala Val Trp Ser Ala
1               5                   10                  15

Leu Gln Leu Ala Lys
            20

<210> SEQ ID NO 158
<211> LENGTH: 19
<212> TYPE: PRT
<213> ORGANISM: Neisseria gonorrhoeae

<400> SEQUENCE: 158

Gln Pro Glu Asn Glu Gly Lys Leu Ile Val Val Leu Leu Pro Ser Tyr
1               5                   10                  15

Gly Glu Arg

<210> SEQ ID NO 159
<211> LENGTH: 12
<212> TYPE: PRT
<213> ORGANISM: Neisseria gonorrhoeae

<400> SEQUENCE: 159

Leu Ile Val Val Leu Leu Pro Ser Tyr Gly Glu Arg
1               5                   10

<210> SEQ ID NO 160
<211> LENGTH: 16
<212> TYPE: PRT
<213> ORGANISM: Neisseria gonorrhoeae

<400> SEQUENCE: 160

Leu Gly Ile Pro Met Leu Ala Leu Phe Pro Val Val Thr Ala Asn Lys
1               5                   10                  15

<210> SEQ ID NO 161
<211> LENGTH: 16
<212> TYPE: PRT
<213> ORGANISM: Neisseria gonorrhoeae

<400> SEQUENCE: 161

Ala Gln Glu Ala Tyr Asn Pro Glu Gly Leu Val Pro Ser Thr Val Arg
1               5                   10                  15

<210> SEQ ID NO 162
<211> LENGTH: 20
<212> TYPE: PRT
<213> ORGANISM: Neisseria gonorrhoeae

<400> SEQUENCE: 162

Ser Gln Tyr Asp Val Val Ile Gly Ala Gly Pro Gly Gly Tyr Val
1               5                   10                  15

Ala Ala Ile Arg
            20

<210> SEQ ID NO 163
<211> LENGTH: 14
<212> TYPE: PRT
<213> ORGANISM: Neisseria gonorrhoeae

<400> SEQUENCE: 163

Thr Asn Leu Pro Asn Val Trp Ala Ile Gly Asp Val Val Arg
1               5                   10

<210> SEQ ID NO 164
<211> LENGTH: 11
<212> TYPE: PRT
<213> ORGANISM: Neisseria gonorrhoeae

<400> SEQUENCE: 164

Ala Ser Asp Glu Gly Val Ala Val Ala Glu Arg
1               5                   10

<210> SEQ ID NO 165
<211> LENGTH: 8
<212> TYPE: PRT
<213> ORGANISM: Neisseria gonorrhoeae

<400> SEQUENCE: 165

Ile Val Gly Asp Val Ile Gly Lys
1               5

<210> SEQ ID NO 166
<211> LENGTH: 13
<212> TYPE: PRT
<213> ORGANISM: Neisseria gonorrhoeae

<400> SEQUENCE: 166

Ile Ile Asp Phe Val Asp Ile Leu Ser Lys Pro Glu Arg
1               5                   10

<210> SEQ ID NO 167
<211> LENGTH: 16
<212> TYPE: PRT
<213> ORGANISM: Neisseria gonorrhoeae

<400> SEQUENCE: 167

Lys Asn Lys Gly Gly Gln Gly Ser Ile Ala Ile Asn Thr Gly Glu Arg
1               5                   10                  15

<210> SEQ ID NO 168
<211> LENGTH: 15
<212> TYPE: PRT
<213> ORGANISM: Neisseria gonorrhoeae

<400> SEQUENCE: 168

```
Leu Ile Asn Leu Asp Glu Gly Glu Thr Leu Val Ser Leu Glu Arg
1               5                   10                  15

<210> SEQ ID NO 169
<211> LENGTH: 11
<212> TYPE: PRT
<213> ORGANISM: Neisseria gonorrhoeae

<400> SEQUENCE: 169

Val Lys Gly Ile Gly Pro Ala Val Leu Ala Lys
1               5                   10

<210> SEQ ID NO 170
<211> LENGTH: 13
<212> TYPE: PRT
<213> ORGANISM: Neisseria gonorrhoeae

<400> SEQUENCE: 170

Leu Lys Asp Gln Ala Ser Val Gly Ala Pro Ala Pro Lys
1               5                   10

<210> SEQ ID NO 171
<211> LENGTH: 19
<212> TYPE: PRT
<213> ORGANISM: Neisseria gonorrhoeae

<400> SEQUENCE: 171

Glu Ala Phe Asn Thr Ala His Glu Ile Ser Ala Tyr Ser Leu Pro Ala
1               5                   10                  15

Leu Ala Lys

<210> SEQ ID NO 172
<211> LENGTH: 12
<212> TYPE: PRT
<213> ORGANISM: Neisseria gonorrhoeae

<400> SEQUENCE: 172

Thr Leu Ala Ala Ser Gly Ile Ala Asp Phe Gly Lys
1               5                   10

<210> SEQ ID NO 173
<211> LENGTH: 10
<212> TYPE: PRT
<213> ORGANISM: Neisseria gonorrhoeae

<400> SEQUENCE: 173

Ala Met Gln Ala Gln Ile Thr Ala Glu Arg
1               5                   10

<210> SEQ ID NO 174
<211> LENGTH: 12
<212> TYPE: PRT
<213> ORGANISM: Neisseria gonorrhoeae

<400> SEQUENCE: 174

Ala Met Gln Ala Gln Ile Thr Ala Glu Arg Glu Lys
1               5                   10

<210> SEQ ID NO 175
<211> LENGTH: 19
<212> TYPE: PRT
<213> ORGANISM: Neisseria gonorrhoeae

<400> SEQUENCE: 175
```

```
Ile Ala Glu Ser Glu Gly Arg Lys Ile Glu Gln Ile Asn Leu Ala Ser
1               5                   10                  15

Gly Gln Arg
```

<210> SEQ ID NO 176
<211> LENGTH: 12
<212> TYPE: PRT
<213> ORGANISM: Neisseria gonorrhoeae

<400> SEQUENCE: 176

```
Lys Ile Glu Gln Ile Asn Leu Ala Ser Gly Gln Arg
1               5                   10
```

<210> SEQ ID NO 177
<211> LENGTH: 11
<212> TYPE: PRT
<213> ORGANISM: Neisseria gonorrhoeae

<400> SEQUENCE: 177

```
Ile Glu Gln Ile Asn Leu Ala Ser Gly Gln Arg
1               5                   10
```

<210> SEQ ID NO 178
<211> LENGTH: 22
<212> TYPE: PRT
<213> ORGANISM: Neisseria gonorrhoeae

<400> SEQUENCE: 178

```
Glu Ala Glu Ile Gln Gln Ser Glu Gly Glu Ala Gln Ala Ala Val Asn
1               5                   10                  15

Ala Ser Asn Ala Glu Lys
            20
```

<210> SEQ ID NO 179
<211> LENGTH: 18
<212> TYPE: PRT
<213> ORGANISM: Neisseria gonorrhoeae

<400> SEQUENCE: 179

```
Gln Ile Ala Ala Ala Leu Gln Thr Gln Gly Gly Ala Asp Ala Val Asn
1               5                   10                  15

Leu Lys
```

<210> SEQ ID NO 180
<211> LENGTH: 14
<212> TYPE: PRT
<213> ORGANISM: Neisseria gonorrhoeae

<400> SEQUENCE: 180

```
Ile Ala Glu Gln Tyr Val Ala Ala Phe Asn Asn Leu Ala Lys
1               5                   10
```

<210> SEQ ID NO 181
<211> LENGTH: 11
<212> TYPE: PRT
<213> ORGANISM: Neisseria gonorrhoeae

<400> SEQUENCE: 181

```
Thr Asp Leu Asn Thr Leu Phe Ala Asn Leu Lys
1               5                   10
```

<210> SEQ ID NO 182

```
<211> LENGTH: 13
<212> TYPE: PRT
<213> ORGANISM: Neisseria gonorrhoeae

<400> SEQUENCE: 182

Thr Asp Leu Asn Thr Leu Phe Ala Asn Leu Lys Gln Arg
1               5                   10

<210> SEQ ID NO 183
<211> LENGTH: 12
<212> TYPE: PRT
<213> ORGANISM: Neisseria gonorrhoeae

<400> SEQUENCE: 183

Asn Pro Lys Tyr Thr Gln Gln Ser Leu Leu Glu Arg
1               5                   10

<210> SEQ ID NO 184
<211> LENGTH: 9
<212> TYPE: PRT
<213> ORGANISM: Neisseria gonorrhoeae

<400> SEQUENCE: 184

Tyr Thr Gln Gln Ser Leu Leu Glu Arg
1               5

<210> SEQ ID NO 185
<211> LENGTH: 9
<212> TYPE: PRT
<213> ORGANISM: Neisseria gonorrhoeae

<400> SEQUENCE: 185

Phe Leu Ala Phe Glu Gln Val Phe Lys
1               5

<210> SEQ ID NO 186
<211> LENGTH: 16
<212> TYPE: PRT
<213> ORGANISM: Neisseria gonorrhoeae

<400> SEQUENCE: 186

Val Leu Ile Ser Gly Ser Gly Asn Val Ala Gln Tyr Ala Ala Glu Lys
1               5                   10                  15

<210> SEQ ID NO 187
<211> LENGTH: 20
<212> TYPE: PRT
<213> ORGANISM: Neisseria gonorrhoeae

<400> SEQUENCE: 187

Ala Ser Asn Ala Gly Gly Val Ala Thr Ser Gly Leu Glu Met Ser Gln
1               5                   10                  15

Asn Ala Ile Arg
            20

<210> SEQ ID NO 188
<211> LENGTH: 18
<212> TYPE: PRT
<213> ORGANISM: Neisseria gonorrhoeae

<400> SEQUENCE: 188

Val Gly Asp Lys Val Asn Tyr Val Asn Gly Ala Asn Ile Ala Gly Phe
1               5                   10                  15

Val Lys
```

<210> SEQ ID NO 189
<211> LENGTH: 16
<212> TYPE: PRT
<213> ORGANISM: Neisseria gonorrhoeae

<400> SEQUENCE: 189

Gly Gly Tyr Ala Pro Val Ala Pro Ile Asp Cys Gly Gln Asp Leu Arg
1               5                   10                  15

<210> SEQ ID NO 190
<211> LENGTH: 7
<212> TYPE: PRT
<213> ORGANISM: Neisseria gonorrhoeae

<400> SEQUENCE: 190

Phe Ala Thr Leu Val Lys Arg
1               5

<210> SEQ ID NO 191
<211> LENGTH: 14
<212> TYPE: PRT
<213> ORGANISM: Neisseria gonorrhoeae

<400> SEQUENCE: 191

Ala Leu Asn Ala Ile Thr Asn Pro Ser Thr Asn Ser Tyr Lys
1               5                   10

<210> SEQ ID NO 192
<211> LENGTH: 15
<212> TYPE: PRT
<213> ORGANISM: Neisseria gonorrhoeae

<400> SEQUENCE: 192

Ala Leu Asn Ala Ile Thr Asn Pro Ser Thr Asn Ser Tyr Lys Arg
1               5                   10                  15

<210> SEQ ID NO 193
<211> LENGTH: 10
<212> TYPE: PRT
<213> ORGANISM: Neisseria gonorrhoeae

<400> SEQUENCE: 193

Leu Val Pro His Phe Glu Ala Pro Thr Lys
1               5                   10

<210> SEQ ID NO 194
<211> LENGTH: 16
<212> TYPE: PRT
<213> ORGANISM: Neisseria gonorrhoeae

<400> SEQUENCE: 194

Leu Val Pro His Phe Glu Ala Pro Thr Lys Leu Ala Tyr Ser Ala Lys
1               5                   10                  15

<210> SEQ ID NO 195
<211> LENGTH: 13
<212> TYPE: PRT
<213> ORGANISM: Neisseria gonorrhoeae

<400> SEQUENCE: 195

Ser Ala Ser Ile Arg Ile Pro Ser Val Asn Ser Ser Lys
1               5                   10

```
<210> SEQ ID NO 196
<211> LENGTH: 10
<212> TYPE: PRT
<213> ORGANISM: Neisseria gonorrhoeae

<400> SEQUENCE: 196

Ala Ala Asp Lys Val Gln Thr Ala Leu Lys
1               5                   10

<210> SEQ ID NO 197
<211> LENGTH: 10
<212> TYPE: PRT
<213> ORGANISM: Neisseria gonorrhoeae

<400> SEQUENCE: 197

Phe Thr Ala Pro Thr Leu Val Thr Thr Arg
1               5                   10

<210> SEQ ID NO 198
<211> LENGTH: 11
<212> TYPE: PRT
<213> ORGANISM: Neisseria gonorrhoeae

<400> SEQUENCE: 198

Tyr Ile Pro Glu Ile Val His Gly Asp Lys Arg
1               5                   10

<210> SEQ ID NO 199
<211> LENGTH: 15
<212> TYPE: PRT
<213> ORGANISM: Neisseria gonorrhoeae

<400> SEQUENCE: 199

Ile Leu Ile Ile Gly Gly Glu Val Val Pro Tyr Ala Leu Ala Arg
1               5                   10                  15

<210> SEQ ID NO 200
<211> LENGTH: 19
<212> TYPE: PRT
<213> ORGANISM: Neisseria gonorrhoeae

<400> SEQUENCE: 200

Ala Tyr Thr Phe Asp Asp Val Leu Leu Val Pro Ala His Ser Thr Val
1               5                   10                  15

Leu Pro Arg

<210> SEQ ID NO 201
<211> LENGTH: 20
<212> TYPE: PRT
<213> ORGANISM: Neisseria gonorrhoeae

<400> SEQUENCE: 201

Glu Ile Thr Leu Asn Leu Pro Leu Leu Ser Ala Ala Met Asp Thr Val
1               5                   10                  15

Thr Glu Ala Arg
            20

<210> SEQ ID NO 202
<211> LENGTH: 20
<212> TYPE: PRT
<213> ORGANISM: Neisseria gonorrhoeae

<400> SEQUENCE: 202

Arg His Glu Ser Gly Val Val Lys Asp Pro Val Thr Val Ala Pro Thr
```

-continued

```
                1               5                  10                  15

Thr Leu Ile Arg
            20

<210> SEQ ID NO 203
<211> LENGTH: 19
<212> TYPE: PRT
<213> ORGANISM: Neisseria gonorrhoeae

<400> SEQUENCE: 203

His Glu Ser Gly Val Val Lys Asp Pro Val Thr Val Ala Pro Thr Thr
1               5                  10                  15

Leu Ile Arg

<210> SEQ ID NO 204
<211> LENGTH: 14
<212> TYPE: PRT
<213> ORGANISM: Neisseria gonorrhoeae

<400> SEQUENCE: 204

Thr Thr Glu Phe Pro Asn Ala Asn Lys Asp Ser Glu Gly Arg
1               5                  10

<210> SEQ ID NO 205
<211> LENGTH: 16
<212> TYPE: PRT
<213> ORGANISM: Neisseria gonorrhoeae

<400> SEQUENCE: 205

Val Gly Ala Ala Val Gly Thr Gly Gly Asp Thr Asp Glu Arg Val Lys
1               5                  10                  15

<210> SEQ ID NO 206
<211> LENGTH: 21
<212> TYPE: PRT
<213> ORGANISM: Neisseria gonorrhoeae

<400> SEQUENCE: 206

Ile Val Ala Gly Val Gly Val Pro Gln Leu Thr Ala Ile His Asn Val
1               5                  10                  15

Ala Glu Ala Leu Lys
            20

<210> SEQ ID NO 207
<211> LENGTH: 10
<212> TYPE: PRT
<213> ORGANISM: Neisseria gonorrhoeae

<400> SEQUENCE: 207

Ala Cys Lys Glu Phe Thr Ile Thr Leu Lys
1               5                  10

<210> SEQ ID NO 208
<211> LENGTH: 11
<212> TYPE: PRT
<213> ORGANISM: Neisseria gonorrhoeae

<400> SEQUENCE: 208

Ala Ser Met Gly His Asn Leu Val Ile Ala Lys
1               5                  10

<210> SEQ ID NO 209
<211> LENGTH: 16
```

-continued

```
<212> TYPE: PRT
<213> ORGANISM: Neisseria gonorrhoeae

<400> SEQUENCE: 209

Leu Ile Gly Gly Gly Glu Glu Ser Ser Leu Thr Leu Asp Pro Ala Lys
1               5                   10                  15

<210> SEQ ID NO 210
<211> LENGTH: 15
<212> TYPE: PRT
<213> ORGANISM: Neisseria gonorrhoeae

<400> SEQUENCE: 210

Phe Ala Cys Thr Phe Pro Gly His Gly Ala Leu Met Asn Gly Lys
1               5                   10                  15

<210> SEQ ID NO 211
<211> LENGTH: 20
<212> TYPE: PRT
<213> ORGANISM: Neisseria gonorrhoeae

<400> SEQUENCE: 211

Phe Ala Cys Thr Phe Pro Gly His Gly Ala Leu Met Asn Gly Lys Val
1               5                   10                  15

Thr Leu Val Asp
            20

<210> SEQ ID NO 212
<211> LENGTH: 19
<212> TYPE: PRT
<213> ORGANISM: Neisseria gonorrhoeae

<400> SEQUENCE: 212

Asp Ser Ala Pro Ala Ala Ser Ala Ala Ala Pro Ser Ala Asp Asn Gly
1               5                   10                  15

Ala Ala Lys

<210> SEQ ID NO 213
<211> LENGTH: 20
<212> TYPE: PRT
<213> ORGANISM: Neisseria gonorrhoeae

<400> SEQUENCE: 213

Asp Ser Ala Pro Ala Ala Ser Ala Ala Pro Ser Ala Asp Asn Gly
1               5                   10                  15

Ala Ala Lys Lys
            20

<210> SEQ ID NO 214
<211> LENGTH: 16
<212> TYPE: PRT
<213> ORGANISM: Neisseria gonorrhoeae

<400> SEQUENCE: 214

Glu Ile Val Phe Gly Thr Thr Val Gly Asp Phe Gly Asp Met Val Lys
1               5                   10                  15

<210> SEQ ID NO 215
<211> LENGTH: 10
<212> TYPE: PRT
<213> ORGANISM: Neisseria gonorrhoeae

<400> SEQUENCE: 215
```

Glu Gln Ile Gln Ala Glu Leu Glu Lys Lys
1               5                   10

<210> SEQ ID NO 216
<211> LENGTH: 23
<212> TYPE: PRT
<213> ORGANISM: Neisseria gonorrhoeae

<400> SEQUENCE: 216

Glu His Asn Leu Asp Ile Thr Glu Ala Phe Gln Val Pro Thr Ala Pro
1               5                   10                  15

Leu Gly Leu Tyr Pro Gly Lys
            20

<210> SEQ ID NO 217
<211> LENGTH: 24
<212> TYPE: PRT
<213> ORGANISM: Neisseria gonorrhoeae

<400> SEQUENCE: 217

Leu Lys Ser Leu Glu Glu Val Lys Asp Gly Ser Thr Val Ser Ala Pro
1               5                   10                  15

Asn Asp Pro Ser Asn Phe Ala Arg
            20

<210> SEQ ID NO 218
<211> LENGTH: 22
<212> TYPE: PRT
<213> ORGANISM: Neisseria gonorrhoeae

<400> SEQUENCE: 218

Ser Leu Glu Glu Val Lys Asp Gly Ser Thr Val Ser Ala Pro Asn Asp
1               5                   10                  15

Pro Ser Asn Phe Ala Arg
            20

<210> SEQ ID NO 219
<211> LENGTH: 16
<212> TYPE: PRT
<213> ORGANISM: Neisseria gonorrhoeae

<400> SEQUENCE: 219

Asp Gly Ser Thr Val Ser Ala Pro Asn Asp Pro Ser Asn Phe Ala Arg
1               5                   10                  15

<210> SEQ ID NO 220
<211> LENGTH: 12
<212> TYPE: PRT
<213> ORGANISM: Neisseria gonorrhoeae

<400> SEQUENCE: 220

Ala Leu Val Met Leu Asn Glu Leu Gly Trp Ile Lys
1               5                   10

<210> SEQ ID NO 221
<211> LENGTH: 12
<212> TYPE: PRT
<213> ORGANISM: Neisseria gonorrhoeae

<400> SEQUENCE: 221

Leu Lys Asp Gly Ile Asn Pro Leu Thr Ala Ser Lys
1               5                   10

```
<210> SEQ ID NO 222
<211> LENGTH: 11
<212> TYPE: PRT
<213> ORGANISM: Neisseria gonorrhoeae

<400> SEQUENCE: 222

Ile Val Glu Leu Glu Ala Ala Gln Leu Pro Arg
1               5                   10

<210> SEQ ID NO 223
<211> LENGTH: 20
<212> TYPE: PRT
<213> ORGANISM: Neisseria gonorrhoeae

<400> SEQUENCE: 223

Leu Thr Glu Ala Leu Phe Gln Glu Pro Ser Phe Ala Tyr Val Asn Trp
1               5                   10                  15

Ser Ala Val Lys
            20

<210> SEQ ID NO 224
<211> LENGTH: 22
<212> TYPE: PRT
<213> ORGANISM: Neisseria gonorrhoeae

<400> SEQUENCE: 224

Thr Ala Asp Lys Asp Ser Gln Trp Leu Lys Asp Val Thr Glu Ala Tyr
1               5                   10                  15

Asn Ser Asp Ala Phe Lys
            20

<210> SEQ ID NO 225
<211> LENGTH: 17
<212> TYPE: PRT
<213> ORGANISM: Neisseria gonorrhoeae

<400> SEQUENCE: 225

Arg Phe Glu Gly Tyr Lys Tyr Pro Ala Ala Trp Asn Glu Gly Ala Ala
1               5                   10                  15

Lys

<210> SEQ ID NO 226
<211> LENGTH: 16
<212> TYPE: PRT
<213> ORGANISM: Neisseria gonorrhoeae

<400> SEQUENCE: 226

Phe Glu Gly Tyr Lys Tyr Pro Ala Ala Trp Asn Glu Gly Ala Ala Lys
1               5                   10                  15

<210> SEQ ID NO 227
<211> LENGTH: 15
<212> TYPE: PRT
<213> ORGANISM: Neisseria gonorrhoeae

<400> SEQUENCE: 227

Ala Gly Val Gln Thr Tyr Arg Ser Val Glu His Thr Asp Gly Lys
1               5                   10                  15

<210> SEQ ID NO 228
<211> LENGTH: 18
<212> TYPE: PRT
<213> ORGANISM: Neisseria gonorrhoeae
```

```
<400> SEQUENCE: 228

Ala Gly Val Gln Thr Tyr Arg Ser Val Glu His Thr Asp Gly Lys Val
1               5                   10                  15

Ser Lys

<210> SEQ ID NO 229
<211> LENGTH: 31
<212> TYPE: PRT
<213> ORGANISM: Neisseria gonorrhoeae

<400> SEQUENCE: 229

Ala Gly Val Gln Thr Tyr Arg Ser Val Glu His Thr Asp Gly Lys Val
1               5                   10                  15

Ser Lys Val Glu Thr Gly Ser Glu Ile Ala Asp Phe Gly Ser Lys
            20                  25                  30

<210> SEQ ID NO 230
<211> LENGTH: 11
<212> TYPE: PRT
<213> ORGANISM: Neisseria gonorrhoeae

<400> SEQUENCE: 230

Ser Val Glu His Thr Asp Gly Lys Val Ser Lys
1               5                   10

<210> SEQ ID NO 231
<211> LENGTH: 24
<212> TYPE: PRT
<213> ORGANISM: Neisseria gonorrhoeae

<400> SEQUENCE: 231

Ser Val Glu His Thr Asp Gly Lys Val Ser Lys Val Glu Thr Gly Ser
1               5                   10                  15

Glu Ile Ala Asp Phe Gly Ser Lys
            20

<210> SEQ ID NO 232
<211> LENGTH: 16
<212> TYPE: PRT
<213> ORGANISM: Neisseria gonorrhoeae

<400> SEQUENCE: 232

Val Ser Lys Val Glu Thr Gly Ser Glu Ile Ala Asp Phe Gly Ser Lys
1               5                   10                  15

<210> SEQ ID NO 233
<211> LENGTH: 13
<212> TYPE: PRT
<213> ORGANISM: Neisseria gonorrhoeae

<400> SEQUENCE: 233

Val Glu Thr Gly Ser Glu Ile Ala Asp Phe Gly Ser Lys
1               5                   10

<210> SEQ ID NO 234
<211> LENGTH: 14
<212> TYPE: PRT
<213> ORGANISM: Neisseria gonorrhoeae

<400> SEQUENCE: 234

Ile Gly Phe Lys Gly Gln Glu Asp Leu Gly Asn Gly Leu Lys
1               5                   10
```

<210> SEQ ID NO 235
<211> LENGTH: 10
<212> TYPE: PRT
<213> ORGANISM: Neisseria gonorrhoeae

<400> SEQUENCE: 235

Gly Gln Glu Asp Leu Gly Asn Gly Leu Lys
1               5                   10

<210> SEQ ID NO 236
<211> LENGTH: 21
<212> TYPE: PRT
<213> ORGANISM: Neisseria gonorrhoeae

<400> SEQUENCE: 236

Ala Val Trp Gln Leu Glu Gln Gly Ala Ser Val Ala Gly Thr Asn Thr
1               5                   10                  15

Gly Trp Gly Asn Lys
            20

<210> SEQ ID NO 237
<211> LENGTH: 28
<212> TYPE: PRT
<213> ORGANISM: Neisseria gonorrhoeae

<400> SEQUENCE: 237

Ala Val Trp Gln Leu Glu Gln Gly Ala Ser Val Ala Gly Thr Asn Thr
1               5                   10                  15

Gly Trp Gly Asn Lys Gln Ser Phe Val Gly Leu Lys
            20                  25

<210> SEQ ID NO 238
<211> LENGTH: 14
<212> TYPE: PRT
<213> ORGANISM: Neisseria gonorrhoeae

<400> SEQUENCE: 238

Gln Ser Phe Val Gly Leu Lys Gly Gly Phe Gly Thr Ile Arg
1               5                   10

<210> SEQ ID NO 239
<211> LENGTH: 9
<212> TYPE: PRT
<213> ORGANISM: Neisseria gonorrhoeae

<400> SEQUENCE: 239

Ala Gly Ser Leu Asn Ser Pro Leu Lys
1               5

<210> SEQ ID NO 240
<211> LENGTH: 14
<212> TYPE: PRT
<213> ORGANISM: Neisseria gonorrhoeae

<400> SEQUENCE: 240

Phe Thr Gly Asn Val Leu Glu Ile Ser Gly Met Ala Gln Arg
1               5                   10

<210> SEQ ID NO 241
<211> LENGTH: 18
<212> TYPE: PRT
<213> ORGANISM: Neisseria gonorrhoeae

<400> SEQUENCE: 241

```
Tyr Asp Ser Pro Glu Phe Ala Gly Phe Ser Gly Ser Val Gln Tyr Ala
1               5                   10                  15

Pro Lys

<210> SEQ ID NO 242
<211> LENGTH: 22
<212> TYPE: PRT
<213> ORGANISM: Neisseria gonorrhoeae

<400> SEQUENCE: 242

Leu Val Gly Gly Tyr Asp Asn Asn Ala Leu Tyr Val Ser Val Ala Ala
1               5                   10                  15

Gln Gln Gln Asp Ala Lys
            20

<210> SEQ ID NO 243
<211> LENGTH: 8
<212> TYPE: PRT
<213> ORGANISM: Neisseria gonorrhoeae

<400> SEQUENCE: 243

Val Ser Tyr Ala His Gly Phe Lys
1               5

<210> SEQ ID NO 244
<211> LENGTH: 26
<212> TYPE: PRT
<213> ORGANISM: Neisseria gonorrhoeae

<400> SEQUENCE: 244

Gly Thr Val Asp Ser Ala Asn His Asp Asn Thr Tyr Asp Gln Val Val
1               5                   10                  15

Val Gly Ala Glu Tyr Asp Phe Ser Lys Arg
            20                  25

<210> SEQ ID NO 245
<211> LENGTH: 15
<212> TYPE: PRT
<213> ORGANISM: Neisseria gonorrhoeae

<400> SEQUENCE: 245

Arg Thr Ser Ala Leu Val Ser Ala Gly Trp Leu Gln Glu Gly Lys
1               5                   10                  15

<210> SEQ ID NO 246
<211> LENGTH: 14
<212> TYPE: PRT
<213> ORGANISM: Neisseria gonorrhoeae

<400> SEQUENCE: 246

Thr Ser Ala Leu Val Ser Ala Gly Trp Leu Gln Glu Gly Lys
1               5                   10

<210> SEQ ID NO 247
<211> LENGTH: 18
<212> TYPE: PRT
<213> ORGANISM: Neisseria gonorrhoeae

<400> SEQUENCE: 247

Thr Ser Ala Leu Val Ser Ala Gly Trp Leu Gln Glu Gly Lys Gly Ala
1               5                   10                  15

Asp Lys
```

<210> SEQ ID NO 248
<211> LENGTH: 29
<212> TYPE: PRT
<213> ORGANISM: Neisseria gonorrhoeae

<400> SEQUENCE: 248

Thr Ser Ala Leu Val Ser Ala Gly Trp Leu Gln Glu Gly Lys Gly Ala
1               5                   10                  15

Asp Lys Ile Val Ser Thr Ala Ser Ala Val Val Leu Arg
            20                  25

<210> SEQ ID NO 249
<211> LENGTH: 15
<212> TYPE: PRT
<213> ORGANISM: Neisseria gonorrhoeae

<400> SEQUENCE: 249

Gly Ala Asp Lys Ile Val Ser Thr Ala Ser Ala Val Val Leu Arg
1               5                   10                  15

<210> SEQ ID NO 250
<211> LENGTH: 11
<212> TYPE: PRT
<213> ORGANISM: Neisseria gonorrhoeae

<400> SEQUENCE: 250

Ile Val Ser Thr Ala Ser Ala Val Val Leu Arg
1               5                   10

<210> SEQ ID NO 251
<211> LENGTH: 10
<212> TYPE: PRT
<213> ORGANISM: Neisseria gonorrhoeae

<400> SEQUENCE: 251

Thr Val Glu Ile Lys Gln Pro Gln Ile Arg
1               5                   10

<210> SEQ ID NO 252
<211> LENGTH: 15
<212> TYPE: PRT
<213> ORGANISM: Neisseria gonorrhoeae

<400> SEQUENCE: 252

Val Ile His Asn Ala Asp Val Ala Ala Tyr Asp Asp Ala Gly Lys
1               5                   10                  15

<210> SEQ ID NO 253
<211> LENGTH: 7
<212> TYPE: PRT
<213> ORGANISM: Neisseria gonorrhoeae

<400> SEQUENCE: 253

Ile Lys Asp Ala Leu Val Arg
1               5

<210> SEQ ID NO 254
<211> LENGTH: 15
<212> TYPE: PRT
<213> ORGANISM: Neisseria gonorrhoeae

<400> SEQUENCE: 254

Asn Asn Leu Leu Pro Thr Leu Ala Ala Asn Ala Asn Gly Ser Arg

<210> SEQ ID NO 255
<211> LENGTH: 20
<212> TYPE: PRT
<213> ORGANISM: Neisseria gonorrhoeae

<400> SEQUENCE: 255

Ala Gly Val Ile Ser Ala Val Ala Leu Arg Gln Gln Glu Ala Leu Ile
1               5                   10                  15

Glu Ser Ala Lys
            20

<210> SEQ ID NO 256
<211> LENGTH: 23
<212> TYPE: PRT
<213> ORGANISM: Neisseria gonorrhoeae

<400> SEQUENCE: 256

Asn Ala Leu Ala Thr Leu Ile Asn Arg Pro Ile Pro Glu Asp Leu Pro
1               5                   10                  15

Ala Gly Leu Pro Leu Asp Lys
            20

<210> SEQ ID NO 257
<211> LENGTH: 17
<212> TYPE: PRT
<213> ORGANISM: Neisseria gonorrhoeae

<400> SEQUENCE: 257

Leu Pro Ala Gly Leu Ser Ser Glu Val Leu Leu Asp Arg Pro Asp Ile
1               5                   10                  15

Arg

<210> SEQ ID NO 258
<211> LENGTH: 17
<212> TYPE: PRT
<213> ORGANISM: Neisseria gonorrhoeae

<400> SEQUENCE: 258

Ala Ala Glu His Ala Leu Lys Gln Ala Asn Ala Asn Ile Gly Ala Ala
1               5                   10                  15

Arg

<210> SEQ ID NO 259
<211> LENGTH: 10
<212> TYPE: PRT
<213> ORGANISM: Neisseria gonorrhoeae

<400> SEQUENCE: 259

Gln Ala Asn Ala Asn Ile Gly Ala Ala Arg
1               5                   10

<210> SEQ ID NO 260
<211> LENGTH: 17
<212> TYPE: PRT
<213> ORGANISM: Neisseria gonorrhoeae

<400> SEQUENCE: 260

Leu Thr Gly Ser Val Gly Thr Gly Ser Val Glu Leu Gly Gly Leu Phe
1               5                   10                  15

Lys

<210> SEQ ID NO 261
<211> LENGTH: 16
<212> TYPE: PRT
<213> ORGANISM: Neisseria gonorrhoeae

<400> SEQUENCE: 261

Tyr Lys His Gly Val Ser Gly Ala Leu Asp Leu Leu Asp Ala Glu Arg
1               5                   10                  15

<210> SEQ ID NO 262
<211> LENGTH: 11
<212> TYPE: PRT
<213> ORGANISM: Neisseria gonorrhoeae

<400> SEQUENCE: 262

Asn Lys Ile Ser Thr Val Ser Asp Tyr Phe Arg
1               5                   10

<210> SEQ ID NO 263
<211> LENGTH: 9
<212> TYPE: PRT
<213> ORGANISM: Neisseria gonorrhoeae

<400> SEQUENCE: 263

Ile Ser Thr Val Ser Asp Tyr Phe Arg
1               5

<210> SEQ ID NO 264
<211> LENGTH: 11
<212> TYPE: PRT
<213> ORGANISM: Neisseria gonorrhoeae

<400> SEQUENCE: 264

Val Ser Val Gly Tyr Asp Phe Gly Gly Trp Arg
1               5                   10

<210> SEQ ID NO 265
<211> LENGTH: 7
<212> TYPE: PRT
<213> ORGANISM: Neisseria gonorrhoeae

<400> SEQUENCE: 265

Val Ala Tyr Gly His Val Arg
1               5

<210> SEQ ID NO 266
<211> LENGTH: 13
<212> TYPE: PRT
<213> ORGANISM: Neisseria gonorrhoeae

<400> SEQUENCE: 266

Thr Glu Pro Ser Thr Val Phe Asn Tyr Leu Pro Val Lys
1               5                   10

<210> SEQ ID NO 267
<211> LENGTH: 15
<212> TYPE: PRT
<213> ORGANISM: Neisseria gonorrhoeae

<400> SEQUENCE: 267

Val Gly Asp Thr Tyr Asn Asp Thr His Gly Ser Ala Ile Ile Lys
1               5                   10                  15

```
<210> SEQ ID NO 268
<211> LENGTH: 10
<212> TYPE: PRT
<213> ORGANISM: Neisseria gonorrhoeae

<400> SEQUENCE: 268

Gly Lys Leu Asn Ile Gln Ile Thr Pro Lys
1               5                   10

<210> SEQ ID NO 269
<211> LENGTH: 14
<212> TYPE: PRT
<213> ORGANISM: Neisseria gonorrhoeae

<400> SEQUENCE: 269

Ile Leu Asp Thr Asp Ile Gln Thr Asn Glu Asp Lys Thr Arg
1               5                   10

<210> SEQ ID NO 270
<211> LENGTH: 13
<212> TYPE: PRT
<213> ORGANISM: Neisseria gonorrhoeae

<400> SEQUENCE: 270

Gln Gln Met Thr Ala Val Leu Gly Glu Ile Gln Asn Arg
1               5                   10

<210> SEQ ID NO 271
<211> LENGTH: 13
<212> TYPE: PRT
<213> ORGANISM: Neisseria gonorrhoeae

<400> SEQUENCE: 271

Ile Tyr Val Asn Glu Ile His Ile Thr Gly Asn Asn Lys
1               5                   10

<210> SEQ ID NO 272
<211> LENGTH: 19
<212> TYPE: PRT
<213> ORGANISM: Neisseria gonorrhoeae

<400> SEQUENCE: 272

Thr Lys Glu Ile Pro Phe Phe Glu Asn Phe Tyr Gly Gly Gly Leu Gly
1               5                   10                  15

Ser Val Arg

<210> SEQ ID NO 273
<211> LENGTH: 14
<212> TYPE: PRT
<213> ORGANISM: Neisseria gonorrhoeae

<400> SEQUENCE: 273

Gly Leu Val Leu Phe Asn Glu Asp Gln Ser Phe Leu Asn Lys
1               5                   10

<210> SEQ ID NO 274
<211> LENGTH: 9
<212> TYPE: PRT
<213> ORGANISM: Neisseria gonorrhoeae

<400> SEQUENCE: 274

Gly Ala Tyr Ile Ala Ala Ala Asn Arg
1               5
```

```
<210> SEQ ID NO 275
<211> LENGTH: 24
<212> TYPE: PRT
<213> ORGANISM: Neisseria gonorrhoeae

<400> SEQUENCE: 275

Ala Val Ala Ala Leu Arg Pro Gly Met Thr Lys Asp Gln Val Leu Leu
1               5                   10                  15

Leu Leu Gly Ser Pro Ile Leu Arg
            20

<210> SEQ ID NO 276
<211> LENGTH: 11
<212> TYPE: PRT
<213> ORGANISM: Neisseria gonorrhoeae

<400> SEQUENCE: 276

Asn Ala Tyr Phe Asp Lys Ala Ser Gln Gly Arg
1               5                   10

<210> SEQ ID NO 277
<211> LENGTH: 41
<212> TYPE: PRT
<213> ORGANISM: Neisseria gonorrhoeae

<400> SEQUENCE: 277

Ala Ser Gln Gly Arg Val Glu Cys Gly Asp Ala Val Ala Val Pro Glu
1               5                   10                  15

Pro Glu Pro Ala Pro Val Ala Val Val Glu Gln Ala Pro Gln Tyr Val
            20                  25                  30

Asp Glu Thr Ile Ser Leu Ser Ala Lys
        35                  40

<210> SEQ ID NO 278
<211> LENGTH: 11
<212> TYPE: PRT
<213> ORGANISM: Neisseria gonorrhoeae

<400> SEQUENCE: 278

Thr Leu Phe Gly Phe Asp Lys Asp Ser Leu Arg
1               5                   10

<210> SEQ ID NO 279
<211> LENGTH: 19
<212> TYPE: PRT
<213> ORGANISM: Neisseria gonorrhoeae

<400> SEQUENCE: 279

Thr Leu Phe Gly Phe Asp Lys Asp Ser Leu Arg Ala Glu Ala Gln Asp
1               5                   10                  15

Asn Leu Lys

<210> SEQ ID NO 280
<211> LENGTH: 12
<212> TYPE: PRT
<213> ORGANISM: Neisseria gonorrhoeae

<400> SEQUENCE: 280

Asp Ser Leu Arg Ala Glu Ala Gln Asp Asn Leu Lys
1               5                   10

<210> SEQ ID NO 281
<211> LENGTH: 7
```

```
<212> TYPE: PRT
<213> ORGANISM: Neisseria gonorrhoeae

<400> SEQUENCE: 281

Thr Asn Val Gln Ser Val Arg
1               5

<210> SEQ ID NO 282
<211> LENGTH: 12
<212> TYPE: PRT
<213> ORGANISM: Neisseria gonorrhoeae

<400> SEQUENCE: 282

Val Glu Gly His Thr Asp Phe Met Gly Ser Glu Lys
1               5                   10

<210> SEQ ID NO 283
<211> LENGTH: 20
<212> TYPE: PRT
<213> ORGANISM: Neisseria gonorrhoeae

<400> SEQUENCE: 283

Val Glu Gly His Thr Asp Phe Met Gly Ser Glu Lys Tyr Asn Gln Ala
1               5                   10                  15

Leu Ser Glu Arg
            20

<210> SEQ ID NO 284
<211> LENGTH: 8
<212> TYPE: PRT
<213> ORGANISM: Neisseria gonorrhoeae

<400> SEQUENCE: 284

Tyr Asn Gln Ala Leu Ser Glu Arg
1               5

<210> SEQ ID NO 285
<211> LENGTH: 18
<212> TYPE: PRT
<213> ORGANISM: Neisseria gonorrhoeae

<400> SEQUENCE: 285

Arg Ala Tyr Val Val Ala Asn Asn Leu Val Ser Asn Gly Val Pro Ala
1               5                   10                  15

Ser Arg

<210> SEQ ID NO 286
<211> LENGTH: 17
<212> TYPE: PRT
<213> ORGANISM: Neisseria gonorrhoeae

<400> SEQUENCE: 286

Ala Tyr Val Val Ala Asn Asn Leu Val Ser Asn Gly Val Pro Ala Ser
1               5                   10                  15

Arg

<210> SEQ ID NO 287
<211> LENGTH: 23
<212> TYPE: PRT
<213> ORGANISM: Neisseria gonorrhoeae

<400> SEQUENCE: 287

Ile Ser Ala Val Gly Leu Gly Glu Ser Gln Ala Gln Met Thr Gln Val
```

```
                1               5                  10                  15

Cys Gln Ala Glu Val Ala Lys
            20

<210> SEQ ID NO 288
<211> LENGTH: 11
<212> TYPE: PRT
<213> ORGANISM: Neisseria gonorrhoeae

<400> SEQUENCE: 288

Glu Ala Leu Ile Ala Cys Ile Glu Pro Asp Arg
1               5                  10

<210> SEQ ID NO 289
<211> LENGTH: 16
<212> TYPE: PRT
<213> ORGANISM: Neisseria gonorrhoeae

<400> SEQUENCE: 289

Glu Ala Leu Ile Ala Cys Ile Glu Pro Asp Arg Arg Val Asp Val Lys
1               5                  10                  15

<210> SEQ ID NO 290
<211> LENGTH: 7
<212> TYPE: PRT
<213> ORGANISM: Neisseria gonorrhoeae

<400> SEQUENCE: 290

Ile Arg Ser Ile Val Thr Arg
1               5

<210> SEQ ID NO 291
<211> LENGTH: 15
<212> TYPE: PRT
<213> ORGANISM: Neisseria gonorrhoeae

<400> SEQUENCE: 291

Ser Leu Lys Gln Met Lys Glu Gln Gly Ala Glu Ile Asp Leu Lys
1               5                  10                  15

<210> SEQ ID NO 292
<211> LENGTH: 8
<212> TYPE: PRT
<213> ORGANISM: Neisseria gonorrhoeae

<400> SEQUENCE: 292

Phe Leu Gln Glu Gln Gln Ala Lys
1               5

<210> SEQ ID NO 293
<211> LENGTH: 16
<212> TYPE: PRT
<213> ORGANISM: Neisseria gonorrhoeae

<400> SEQUENCE: 293

Ala Asn Lys Glu Lys Gly Glu Ala Phe Leu Lys Glu Asn Ala Ala Lys
1               5                  10                  15

<210> SEQ ID NO 294
<211> LENGTH: 20
<212> TYPE: PRT
<213> ORGANISM: Neisseria gonorrhoeae

<400> SEQUENCE: 294
```

```
Ala Asn Lys Glu Lys Gly Glu Ala Phe Leu Lys Glu Asn Ala Ala Lys
1               5                   10                  15

Asp Gly Val Lys
            20

<210> SEQ ID NO 295
<211> LENGTH: 13
<212> TYPE: PRT
<213> ORGANISM: Neisseria gonorrhoeae

<400> SEQUENCE: 295

Asp Gly Val Lys Thr Thr Ala Ser Gly Leu Gln Tyr Lys
1               5                   10

<210> SEQ ID NO 296
<211> LENGTH: 16
<212> TYPE: PRT
<213> ORGANISM: Neisseria gonorrhoeae

<400> SEQUENCE: 296

Asp Gly Val Lys Thr Thr Ala Ser Gly Leu Gln Tyr Lys Ile Thr Lys
1               5                   10                  15

<210> SEQ ID NO 297
<211> LENGTH: 9
<212> TYPE: PRT
<213> ORGANISM: Neisseria gonorrhoeae

<400> SEQUENCE: 297

Thr Thr Ala Ser Gly Leu Gln Tyr Lys
1               5

<210> SEQ ID NO 298
<211> LENGTH: 12
<212> TYPE: PRT
<213> ORGANISM: Neisseria gonorrhoeae

<400> SEQUENCE: 298

Thr Thr Ala Ser Gly Leu Gln Tyr Lys Ile Thr Lys
1               5                   10

<210> SEQ ID NO 299
<211> LENGTH: 20
<212> TYPE: PRT
<213> ORGANISM: Neisseria gonorrhoeae

<400> SEQUENCE: 299

Gln Gly Glu Gly Lys Gln Pro Thr Lys Asp Asp Ile Val Thr Val Glu
1               5                   10                  15

Tyr Glu Gly Arg
            20

<210> SEQ ID NO 300
<211> LENGTH: 11
<212> TYPE: PRT
<213> ORGANISM: Neisseria gonorrhoeae

<400> SEQUENCE: 300

Leu Ile Asp Gly Thr Val Phe Asp Ser Ser Lys
1               5                   10

<210> SEQ ID NO 301
<211> LENGTH: 22
<212> TYPE: PRT
```

```
<213> ORGANISM: Neisseria gonorrhoeae

<400> SEQUENCE: 301

Ala Asn Gly Gly Pro Ala Thr Phe Pro Leu Ser Gln Val Ile Pro Gly
1               5                   10                  15

Trp Thr Glu Gly Val Arg
            20

<210> SEQ ID NO 302
<211> LENGTH: 26
<212> TYPE: PRT
<213> ORGANISM: Neisseria gonorrhoeae

<400> SEQUENCE: 302

Leu Leu Lys Glu Gly Gly Glu Ala Thr Phe Tyr Ile Pro Ser Asn Leu
1               5                   10                  15

Ala Tyr Arg Glu Gln Gly Ala Gly Glu Lys
            20                  25

<210> SEQ ID NO 303
<211> LENGTH: 16
<212> TYPE: PRT
<213> ORGANISM: Neisseria gonorrhoeae

<400> SEQUENCE: 303

Glu Gly Gly Glu Ala Thr Phe Tyr Ile Pro Ser Asn Leu Ala Tyr Arg
1               5                   10                  15

<210> SEQ ID NO 304
<211> LENGTH: 12
<212> TYPE: PRT
<213> ORGANISM: Neisseria gonorrhoeae

<400> SEQUENCE: 304

Ile Gly Pro Asn Ala Thr Leu Val Phe Asp Val Lys
1               5                   10

<210> SEQ ID NO 305
<211> LENGTH: 18
<212> TYPE: PRT
<213> ORGANISM: Neisseria gonorrhoeae

<400> SEQUENCE: 305

Ile Gly Ala Pro Glu Asn Ala Pro Ala Lys Gln Pro Asp Gln Val Asp
1               5                   10                  15

Ile Lys

<210> SEQ ID NO 306
<211> LENGTH: 19
<212> TYPE: PRT
<213> ORGANISM: Neisseria gonorrhoeae

<400> SEQUENCE: 306

Ile Gly Ala Pro Glu Asn Ala Pro Ala Lys Gln Pro Asp Gln Val Asp
1               5                   10                  15

Ile Lys Lys

<210> SEQ ID NO 307
<211> LENGTH: 21
<212> TYPE: PRT
<213> ORGANISM: Neisseria gonorrhoeae

<400> SEQUENCE: 307
```

-continued

```
Ile Gly Ala Pro Glu Asn Ala Pro Ala Lys Gln Pro Asp Gln Val Asp
1               5                   10                  15

Ile Lys Lys Val Asn
            20

<210> SEQ ID NO 308
<211> LENGTH: 9
<212> TYPE: PRT
<213> ORGANISM: Neisseria gonorrhoeae

<400> SEQUENCE: 308

Phe Lys Ala Thr Val Glu Ser Val Arg
1               5

<210> SEQ ID NO 309
<211> LENGTH: 13
<212> TYPE: PRT
<213> ORGANISM: Neisseria gonorrhoeae

<400> SEQUENCE: 309

Thr Val Val Gln Asp Trp Gly Tyr Ala Val Phe Gly Lys
1               5                   10

<210> SEQ ID NO 310
<211> LENGTH: 18
<212> TYPE: PRT
<213> ORGANISM: Neisseria gonorrhoeae

<400> SEQUENCE: 310

Val Val Asp Gly Phe Asp Val Asp Ala Ile Glu Ser Val Ser Thr
1               5                   10                  15

Lys Arg

<210> SEQ ID NO 311
<211> LENGTH: 16
<212> TYPE: PRT
<213> ORGANISM: Neisseria gonorrhoeae

<400> SEQUENCE: 311

Glu Leu Leu Pro Pro Ile Ala His Leu Tyr Glu Leu Pro Ile Ser Lys
1               5                   10                  15

<210> SEQ ID NO 312
<211> LENGTH: 8
<212> TYPE: PRT
<213> ORGANISM: Neisseria gonorrhoeae

<400> SEQUENCE: 312

Glu Ala Ser Gly Leu Val His Arg
1               5

<210> SEQ ID NO 313
<211> LENGTH: 12
<212> TYPE: PRT
<213> ORGANISM: Neisseria gonorrhoeae

<400> SEQUENCE: 313

Ala Asp Asn Tyr Val Ile Trp Phe Glu Asn Leu Arg
1               5                   10

<210> SEQ ID NO 314
<211> LENGTH: 14
<212> TYPE: PRT
```

<213> ORGANISM: Neisseria gonorrhoeae

<400> SEQUENCE: 314

Asn Ala Ser Leu Gly Glu Met Ile Ser Gln Leu Thr Glu Lys
1               5                   10

<210> SEQ ID NO 315
<211> LENGTH: 13
<212> TYPE: PRT
<213> ORGANISM: Neisseria gonorrhoeae

<400> SEQUENCE: 315

Val Pro Gly Gly Phe Ala Thr Thr Ala Asp Ala Tyr Arg
1               5                   10

<210> SEQ ID NO 316
<211> LENGTH: 11
<212> TYPE: PRT
<213> ORGANISM: Neisseria gonorrhoeae

<400> SEQUENCE: 316

Ala Phe Leu Ala His Asn Gly Leu Asn Glu Arg
1               5                   10

<210> SEQ ID NO 317
<211> LENGTH: 18
<212> TYPE: PRT
<213> ORGANISM: Neisseria gonorrhoeae

<400> SEQUENCE: 317

Val His Lys Gly Phe Glu His Asp Ile Val Ala Leu Ser Ala Gly Val
1               5                   10                  15

Gln Arg

<210> SEQ ID NO 318
<211> LENGTH: 15
<212> TYPE: PRT
<213> ORGANISM: Neisseria gonorrhoeae

<400> SEQUENCE: 318

Gly Phe Glu His Asp Ile Val Ala Leu Ser Ala Gly Val Gln Arg
1               5                   10                  15

<210> SEQ ID NO 319
<211> LENGTH: 11
<212> TYPE: PRT
<213> ORGANISM: Neisseria gonorrhoeae

<400> SEQUENCE: 319

Met Ile Phe Thr Asp Lys Ala Glu Ala Gly Lys
1               5                   10

<210> SEQ ID NO 320
<211> LENGTH: 18
<212> TYPE: PRT
<213> ORGANISM: Neisseria gonorrhoeae

<400> SEQUENCE: 320

Asp Gly Leu Asp Gly Lys Leu Tyr Ile Leu Gln Ala Arg Pro Glu Thr
1               5                   10                  15

Val Lys

<210> SEQ ID NO 321

```
<211> LENGTH: 12
<212> TYPE: PRT
<213> ORGANISM: Neisseria gonorrhoeae

<400> SEQUENCE: 321

Leu Tyr Ile Leu Gln Ala Arg Pro Glu Thr Val Lys
1               5                   10

<210> SEQ ID NO 322
<211> LENGTH: 18
<212> TYPE: PRT
<213> ORGANISM: Neisseria gonorrhoeae

<400> SEQUENCE: 322

Val Arg Asp Glu Met Gly Leu Thr Asn Val Glu Ile Met Ile Pro Phe
1               5                   10                  15

Val Arg

<210> SEQ ID NO 323
<211> LENGTH: 9
<212> TYPE: PRT
<213> ORGANISM: Neisseria gonorrhoeae

<400> SEQUENCE: 323

Ala Leu Lys Glu Asn Gly Leu Glu Arg
1               5

<210> SEQ ID NO 324
<211> LENGTH: 24
<212> TYPE: PRT
<213> ORGANISM: Neisseria gonorrhoeae

<400> SEQUENCE: 324

Lys Ala Glu Leu Leu Leu Asn Ser Ser Asp Lys Asn Thr Glu Gln Ala
1               5                   10                  15

Ala Ala Pro Ala Ala Glu Gln Asn
            20

<210> SEQ ID NO 325
<211> LENGTH: 12
<212> TYPE: PRT
<213> ORGANISM: Neisseria gonorrhoeae

<400> SEQUENCE: 325

Lys Ile Thr Gln Glu Asp Ile Thr Val Phe Thr Arg
1               5                   10

<210> SEQ ID NO 326
<211> LENGTH: 14
<212> TYPE: PRT
<213> ORGANISM: Neisseria gonorrhoeae

<400> SEQUENCE: 326

Ala Gly Leu Pro Leu Met Gln Ala Phe Glu Ile Val Ala Arg
1               5                   10

<210> SEQ ID NO 327
<211> LENGTH: 11
<212> TYPE: PRT
<213> ORGANISM: Neisseria gonorrhoeae

<400> SEQUENCE: 327

Gly Gln Val Glu Gln Gly Ser Ser Leu Ser Arg
1               5                   10
```

<210> SEQ ID NO 328
<211> LENGTH: 18
<212> TYPE: PRT
<213> ORGANISM: Neisseria gonorrhoeae

<400> SEQUENCE: 328

Ser Ile Asp Ala Ala Ser Leu Asn Asn Leu Arg Asp Glu Leu Ala Ser
1               5                   10                  15

Ile Arg

<210> SEQ ID NO 329
<211> LENGTH: 14
<212> TYPE: PRT
<213> ORGANISM: Neisseria gonorrhoeae

<400> SEQUENCE: 329

Ile Ala Gln Ser Pro Glu Asn Gly Gly Asn Pro Asp Gly Lys
1               5                   10

<210> SEQ ID NO 330
<211> LENGTH: 16
<212> TYPE: PRT
<213> ORGANISM: Neisseria gonorrhoeae

<400> SEQUENCE: 330

Ser Ser Ile Leu Asn Leu Ser Ala Ile Ala Thr Thr Tyr Gln Ala Lys
1               5                   10                  15

<210> SEQ ID NO 331
<211> LENGTH: 18
<212> TYPE: PRT
<213> ORGANISM: Neisseria gonorrhoeae

<400> SEQUENCE: 331

Val Gln Met Tyr Ser Ala Ser Val Ser Thr Tyr Pro Gly Ser Ser Ser
1               5                   10                  15

Ser Arg

<210> SEQ ID NO 332
<211> LENGTH: 12
<212> TYPE: PRT
<213> ORGANISM: Neisseria gonorrhoeae

<400> SEQUENCE: 332

Lys Asp Ile Glu Gly Asn Asp Ser Asp Leu Ala Lys
1               5                   10

<210> SEQ ID NO 333
<211> LENGTH: 17
<212> TYPE: PRT
<213> ORGANISM: Neisseria gonorrhoeae

<400> SEQUENCE: 333

Thr Gln Asn Gly Lys Tyr Ala Ala Phe Leu Ala Ser Gly Tyr Ala Ala
1               5                   10                  15

Lys

<210> SEQ ID NO 334
<211> LENGTH: 12
<212> TYPE: PRT
<213> ORGANISM: Neisseria gonorrhoeae

<400> SEQUENCE: 334

Tyr Ala Ala Phe Leu Ala Ser Gly Tyr Ala Ala Lys
1               5                   10

<210> SEQ ID NO 335
<211> LENGTH: 17
<212> TYPE: PRT
<213> ORGANISM: Neisseria gonorrhoeae

<400> SEQUENCE: 335

Thr Ile Phe Glu Gly Asp Lys Pro Ile Thr Ser Ala Pro Ala Val Ser
1               5                   10                  15

Arg

<210> SEQ ID NO 336
<211> LENGTH: 16
<212> TYPE: PRT
<213> ORGANISM: Neisseria gonorrhoeae

<400> SEQUENCE: 336

Thr Val Cys Pro Asn Gly Tyr Val Tyr Asp Lys Pro Val Asn Val Arg
1               5                   10                  15

<210> SEQ ID NO 337
<211> LENGTH: 15
<212> TYPE: PRT
<213> ORGANISM: Neisseria gonorrhoeae

<400> SEQUENCE: 337

Phe Ser Gln Ala Val Phe His Ser Ala His Glu Ala Ala Val Lys
1               5                   10                  15

<210> SEQ ID NO 338
<211> LENGTH: 13
<212> TYPE: PRT
<213> ORGANISM: Neisseria gonorrhoeae

<400> SEQUENCE: 338

Val Ala Glu Ala Gln Val Tyr Gly Gln Ser Leu Cys Arg
1               5                   10

<210> SEQ ID NO 339
<211> LENGTH: 14
<212> TYPE: PRT
<213> ORGANISM: Neisseria gonorrhoeae

<400> SEQUENCE: 339

Thr Ala Lys Ala Glu Ala Glu Lys Leu Gly Ala His Ala Lys
1               5                   10

<210> SEQ ID NO 340
<211> LENGTH: 15
<212> TYPE: PRT
<213> ORGANISM: Neisseria gonorrhoeae

<400> SEQUENCE: 340

Gly Ala Thr Gly Arg Pro Val Pro Leu Leu Met Asn Tyr Leu Arg
1               5                   10                  15

<210> SEQ ID NO 341
<211> LENGTH: 9
<212> TYPE: PRT
<213> ORGANISM: Neisseria gonorrhoeae

```
<400> SEQUENCE: 341

Gln Asn Ile Thr Thr Leu His Asn Arg
1               5

<210> SEQ ID NO 342
<211> LENGTH: 12
<212> TYPE: PRT
<213> ORGANISM: Neisseria gonorrhoeae

<400> SEQUENCE: 342

Gln Trp Arg Asp Gly Ala Ala Pro Ser Ala Lys Lys
1               5                   10

<210> SEQ ID NO 343
<211> LENGTH: 16
<212> TYPE: PRT
<213> ORGANISM: Neisseria gonorrhoeae

<400> SEQUENCE: 343

Gly Gln Phe Tyr Glu Leu Asn Pro Ala Glu Val Ala Asn Ile Leu Lys
1               5                   10                  15

<210> SEQ ID NO 344
<211> LENGTH: 16
<212> TYPE: PRT
<213> ORGANISM: Neisseria gonorrhoeae

<400> SEQUENCE: 344

Ile Ala Ser Ala Val Ala Gly Gly Ala Asp Glu Ala Met Leu Lys Lys
1               5                   10                  15

<210> SEQ ID NO 345
<211> LENGTH: 13
<212> TYPE: PRT
<213> ORGANISM: Neisseria gonorrhoeae

<400> SEQUENCE: 345

Ile Gln Gly Val Gly Ala Ala Gln Leu Asp Pro Leu Lys
1               5                   10

<210> SEQ ID NO 346
<211> LENGTH: 14
<212> TYPE: PRT
<213> ORGANISM: Neisseria gonorrhoeae

<400> SEQUENCE: 346

Ile Gln Gly Val Gly Ala Ala Gln Leu Asp Pro Leu Lys Arg
1               5                   10

<210> SEQ ID NO 347
<211> LENGTH: 17
<212> TYPE: PRT
<213> ORGANISM: Neisseria gonorrhoeae

<400> SEQUENCE: 347

Asn Tyr Phe Glu Ser Val Leu Ser Thr Pro His Tyr Asn Ala Asp Gln
1               5                   10                  15

Lys

<210> SEQ ID NO 348
<211> LENGTH: 13
<212> TYPE: PRT
<213> ORGANISM: Neisseria gonorrhoeae
```

<400> SEQUENCE: 348

Ile Leu Lys Glu Met Thr Ala Ala Glu Thr Leu Glu Arg
1               5                   10

<210> SEQ ID NO 349
<211> LENGTH: 10
<212> TYPE: PRT
<213> ORGANISM: Neisseria gonorrhoeae

<400> SEQUENCE: 349

Ser Thr Val His Cys Thr Asp Ile Ala Lys
1               5                   10

<210> SEQ ID NO 350
<211> LENGTH: 14
<212> TYPE: PRT
<213> ORGANISM: Neisseria gonorrhoeae

<400> SEQUENCE: 350

Glu Lys Ile Glu Thr Gly Leu Pro Ala Ala Asp Ile Glu Arg
1               5                   10

<210> SEQ ID NO 351
<211> LENGTH: 19
<212> TYPE: PRT
<213> ORGANISM: Neisseria gonorrhoeae

<400> SEQUENCE: 351

Leu Thr Glu Lys Phe Thr Ala Val Pro Glu Gly Phe Ala Leu His Pro
1               5                   10                  15

Thr Ala Lys

<210> SEQ ID NO 352
<211> LENGTH: 15
<212> TYPE: PRT
<213> ORGANISM: Neisseria gonorrhoeae

<400> SEQUENCE: 352

Phe Thr Ala Val Pro Glu Gly Phe Ala Leu His Pro Thr Ala Lys
1               5                   10                  15

<210> SEQ ID NO 353
<211> LENGTH: 19
<212> TYPE: PRT
<213> ORGANISM: Neisseria gonorrhoeae

<400> SEQUENCE: 353

Gln Ala Ile Asp Trp Gly Met Ala Glu Thr Leu Ala Tyr Ala Ser Leu
1               5                   10                  15

Leu Thr Lys

<210> SEQ ID NO 354
<211> LENGTH: 16
<212> TYPE: PRT
<213> ORGANISM: Neisseria gonorrhoeae

<400> SEQUENCE: 354

Val Val Leu Cys Ala Gly Gln Val Tyr Tyr Asp Leu Glu Ala Gly Arg
1               5                   10                  15

<210> SEQ ID NO 355
<211> LENGTH: 18
<212> TYPE: PRT

<213> ORGANISM: Neisseria gonorrhoeae

<400> SEQUENCE: 355

Val Glu Gln Leu Tyr Pro Phe Pro Tyr Asp Glu Val Lys Ala Glu Leu
1               5                   10                  15

Ala Lys

<210> SEQ ID NO 356
<211> LENGTH: 9
<212> TYPE: PRT
<213> ORGANISM: Neisseria gonorrhoeae

<400> SEQUENCE: 356

Asn Gln Gly Ala Phe Tyr Gln Ile Arg
1               5

<210> SEQ ID NO 357
<211> LENGTH: 12
<212> TYPE: PRT
<213> ORGANISM: Neisseria gonorrhoeae

<400> SEQUENCE: 357

His Arg Ile Glu Asp Val Ile Ser Glu Glu Gln Lys
1               5                   10

<210> SEQ ID NO 358
<211> LENGTH: 9
<212> TYPE: PRT
<213> ORGANISM: Neisseria gonorrhoeae

<400> SEQUENCE: 358

Ile Ala Leu Val Thr Gly Ala Ser Arg
1               5

<210> SEQ ID NO 359
<211> LENGTH: 16
<212> TYPE: PRT
<213> ORGANISM: Neisseria gonorrhoeae

<400> SEQUENCE: 359

Gly Ile Gly Ala Ala Ile Ala Asp Thr Leu Ala Ala Ala Gly Ala Lys
1               5                   10                  15

<210> SEQ ID NO 360
<211> LENGTH: 16
<212> TYPE: PRT
<213> ORGANISM: Neisseria gonorrhoeae

<400> SEQUENCE: 360

Ile Ile Gly Thr Ala Thr Gly Glu Ser Gly Ala Ala Ala Ile Ser Lys
1               5                   10                  15

<210> SEQ ID NO 361
<211> LENGTH: 17
<212> TYPE: PRT
<213> ORGANISM: Neisseria gonorrhoeae

<400> SEQUENCE: 361

Ile Ile Gly Thr Ala Thr Gly Glu Ser Gly Ala Ala Ala Ile Ser Lys
1               5                   10                  15

Arg

<210> SEQ ID NO 362

```
<211> LENGTH: 9
<212> TYPE: PRT
<213> ORGANISM: Neisseria gonorrhoeae

<400> SEQUENCE: 362

Leu Ala Gln Trp Gly Gly Glu Gly Arg
1               5

<210> SEQ ID NO 363
<211> LENGTH: 19
<212> TYPE: PRT
<213> ORGANISM: Neisseria gonorrhoeae

<400> SEQUENCE: 363

Val Leu Asn Ser Ala Glu Pro Glu Thr Val Glu Asn Leu Ile Ala Asp
1               5                   10                  15

Ile Glu Lys

<210> SEQ ID NO 364
<211> LENGTH: 16
<212> TYPE: PRT
<213> ORGANISM: Neisseria gonorrhoeae

<400> SEQUENCE: 364

Thr Phe Gly Lys Leu Asp Ile Leu Val Asn Asn Ala Gly Ile Thr Arg
1               5                   10                  15

<210> SEQ ID NO 365
<211> LENGTH: 12
<212> TYPE: PRT
<213> ORGANISM: Neisseria gonorrhoeae

<400> SEQUENCE: 365

Leu Asp Ile Leu Val Asn Asn Ala Gly Ile Thr Arg
1               5                   10

<210> SEQ ID NO 366
<211> LENGTH: 18
<212> TYPE: PRT
<213> ORGANISM: Neisseria gonorrhoeae

<400> SEQUENCE: 366

Ala Leu Pro Glu Glu Thr Arg Gln Thr Phe Thr Ala Gln Thr Ala Leu
1               5                   10                  15

Gly Arg

<210> SEQ ID NO 367
<211> LENGTH: 20
<212> TYPE: PRT
<213> ORGANISM: Neisseria gonorrhoeae

<400> SEQUENCE: 367

Phe Gly Asp Ala Gln Asp Ile Ala Asp Ala Val Leu Phe Leu Ala Ser
1               5                   10                  15

Asp Gln Ala Lys
            20

<210> SEQ ID NO 368
<211> LENGTH: 16
<212> TYPE: PRT
<213> ORGANISM: Neisseria gonorrhoeae

<400> SEQUENCE: 368
```

```
Tyr Ile Thr Gly Gln Thr Leu His Val Asn Gly Gly Met Leu Met Pro
1               5                   10                  15
```

<210> SEQ ID NO 369
<211> LENGTH: 13
<212> TYPE: PRT
<213> ORGANISM: Neisseria gonorrhoeae

<400> SEQUENCE: 369

```
Leu Gly Asn Glu Val Ile Glu Phe Val Asn Val Ser Lys
1               5                   10
```

<210> SEQ ID NO 370
<211> LENGTH: 17
<212> TYPE: PRT
<213> ORGANISM: Neisseria gonorrhoeae

<400> SEQUENCE: 370

```
Val Pro Ala Gly Ala Ile Val Gly Ile Ile Gly Pro Asn Gly Ala Gly
1               5                   10                  15

Lys
```

<210> SEQ ID NO 371
<211> LENGTH: 13
<212> TYPE: PRT
<213> ORGANISM: Neisseria gonorrhoeae

<400> SEQUENCE: 371

```
Asp Ile Leu Gln Val Gly Gln Phe Glu Ile Pro Ala Arg
1               5                   10
```

<210> SEQ ID NO 372
<211> LENGTH: 15
<212> TYPE: PRT
<213> ORGANISM: Neisseria gonorrhoeae

<400> SEQUENCE: 372

```
Lys Gly Glu Val Val Val Val Cys Gly Pro Ser Gly Ser Gly Lys
1               5                   10                  15
```

<210> SEQ ID NO 373
<211> LENGTH: 14
<212> TYPE: PRT
<213> ORGANISM: Neisseria gonorrhoeae

<400> SEQUENCE: 373

```
Asp Ala Phe Pro Ser Gln Leu Ser Gly Gly Gln Gln Gln Arg
1               5                   10
```

<210> SEQ ID NO 374
<211> LENGTH: 11
<212> TYPE: PRT
<213> ORGANISM: Neisseria gonorrhoeae

<400> SEQUENCE: 374

```
Ala Lys Gln Phe Leu Gln Gln Val Met Thr His
1               5                   10
```

<210> SEQ ID NO 375
<211> LENGTH: 26
<212> TYPE: PRT
<213> ORGANISM: Neisseria gonorrhoeae

<400> SEQUENCE: 375

```
Ile Asn Asn Lys Gly Thr Val Thr Val Gly Thr Glu Gly Thr Tyr Ala
1               5                   10                  15

Pro Phe Thr Tyr His Asp Lys Asp Gly Lys
            20                  25
```

<210> SEQ ID NO 376
<211> LENGTH: 36
<212> TYPE: PRT
<213> ORGANISM: Neisseria gonorrhoeae

<400> SEQUENCE: 376

```
Ile Asn Asn Lys Gly Thr Val Thr Val Gly Thr Glu Gly Thr Tyr Ala
1               5                   10                  15

Pro Phe Thr Tyr His Asp Lys Asp Gly Lys Leu Thr Gly Tyr Asp Val
            20                  25                  30

Glu Val Thr Arg
        35
```

<210> SEQ ID NO 377
<211> LENGTH: 16
<212> TYPE: PRT
<213> ORGANISM: Neisseria gonorrhoeae

<400> SEQUENCE: 377

```
Val Glu Phe Lys Glu Thr Gln Trp Asp Ser Met Met Ala Gly Leu Lys
1               5                   10                  15
```

<210> SEQ ID NO 378
<211> LENGTH: 18
<212> TYPE: PRT
<213> ORGANISM: Neisseria gonorrhoeae

<400> SEQUENCE: 378

```
Ala Gly Arg Phe Asp Val Val Ala Asn Gln Val Gly Leu Thr Ser Pro
1               5                   10                  15

Glu Arg
```

<210> SEQ ID NO 379
<211> LENGTH: 15
<212> TYPE: PRT
<213> ORGANISM: Neisseria gonorrhoeae

<400> SEQUENCE: 379

```
Phe Asp Val Val Ala Asn Gln Val Gly Leu Thr Ser Pro Glu Arg
1               5                   10                  15
```

<210> SEQ ID NO 380
<211> LENGTH: 26
<212> TYPE: PRT
<213> ORGANISM: Neisseria gonorrhoeae

<400> SEQUENCE: 380

```
Gln Ala Thr Phe Asp Lys Ser Glu Pro Tyr Ser Trp Ser Gly Ala Val
1               5                   10                  15

Leu Val Ala His Asn Asp Ser Asn Ile Lys
            20                  25
```

<210> SEQ ID NO 381
<211> LENGTH: 20
<212> TYPE: PRT
<213> ORGANISM: Neisseria gonorrhoeae

<400> SEQUENCE: 381

```
Ser Glu Pro Tyr Ser Trp Ser Gly Ala Val Leu Val Ala His Asn Asp
1               5                   10                  15

Ser Asn Ile Lys
            20

<210> SEQ ID NO 382
<211> LENGTH: 12
<212> TYPE: PRT
<213> ORGANISM: Neisseria gonorrhoeae

<400> SEQUENCE: 382

Thr Ala Gln Ser Leu Thr Ser Asn Tyr Gly Glu Lys
1               5                   10

<210> SEQ ID NO 383
<211> LENGTH: 24
<212> TYPE: PRT
<213> ORGANISM: Neisseria gonorrhoeae

<400> SEQUENCE: 383

Ala Lys Ala Ala Gly Ala Gln Leu Val Pro Val Asp Gly Leu Ala Gln
1               5                   10                  15

Ser Leu Thr Leu Ile Glu Gln Lys
            20

<210> SEQ ID NO 384
<211> LENGTH: 22
<212> TYPE: PRT
<213> ORGANISM: Neisseria gonorrhoeae

<400> SEQUENCE: 384

Ala Ala Gly Ala Gln Leu Val Pro Val Asp Gly Leu Ala Gln Ser Leu
1               5                   10                  15

Thr Leu Ile Glu Gln Lys
            20

<210> SEQ ID NO 385
<211> LENGTH: 23
<212> TYPE: PRT
<213> ORGANISM: Neisseria gonorrhoeae

<400> SEQUENCE: 385

Ala Ala Gly Ala Gln Leu Val Pro Val Asp Gly Leu Ala Gln Ser Leu
1               5                   10                  15

Thr Leu Ile Glu Gln Lys Arg
            20

<210> SEQ ID NO 386
<211> LENGTH: 17
<212> TYPE: PRT
<213> ORGANISM: Neisseria gonorrhoeae

<400> SEQUENCE: 386

Arg Ala Asp Ala Thr Leu Asn Asp Glu Leu Ala Val Leu Asp Tyr Leu
1               5                   10                  15

Lys

<210> SEQ ID NO 387
<211> LENGTH: 18
<212> TYPE: PRT
<213> ORGANISM: Neisseria gonorrhoeae
```

<400> SEQUENCE: 387

Arg Ala Asp Ala Thr Leu Asn Asp Glu Leu Ala Val Leu Asp Tyr Leu
1               5                   10                  15

Lys Lys

<210> SEQ ID NO 388
<211> LENGTH: 16
<212> TYPE: PRT
<213> ORGANISM: Neisseria gonorrhoeae

<400> SEQUENCE: 388

Ala Asp Ala Thr Leu Asn Asp Glu Leu Ala Val Leu Asp Tyr Leu Lys
1               5                   10                  15

<210> SEQ ID NO 389
<211> LENGTH: 17
<212> TYPE: PRT
<213> ORGANISM: Neisseria gonorrhoeae

<400> SEQUENCE: 389

Ala Asp Ala Thr Leu Asn Asp Glu Leu Ala Val Leu Asp Tyr Leu Lys
1               5                   10                  15

Lys

<210> SEQ ID NO 390
<211> LENGTH: 19
<212> TYPE: PRT
<213> ORGANISM: Neisseria gonorrhoeae

<400> SEQUENCE: 390

Ile Val Trp Ser Ala Pro Ala Asp Glu Lys Val Gly Ser Gly Leu Ile
1               5                   10                  15

Val Asn Lys

<210> SEQ ID NO 391
<211> LENGTH: 27
<212> TYPE: PRT
<213> ORGANISM: Neisseria gonorrhoeae

<400> SEQUENCE: 391

Ile Val Trp Ser Ala Pro Ala Asp Glu Lys Val Gly Ser Gly Leu Ile
1               5                   10                  15

Val Asn Lys Gly Asn Asp Glu Ala Val Ala Lys
            20                  25

<210> SEQ ID NO 392
<211> LENGTH: 9
<212> TYPE: PRT
<213> ORGANISM: Neisseria gonorrhoeae

<400> SEQUENCE: 392

Val Gly Ser Gly Leu Ile Val Asn Lys
1               5

<210> SEQ ID NO 393
<211> LENGTH: 17
<212> TYPE: PRT
<213> ORGANISM: Neisseria gonorrhoeae

<400> SEQUENCE: 393

Val Gly Ser Gly Leu Ile Val Asn Lys Gly Asn Asp Glu Ala Val Ala
1               5                   10                  15

Lys

<210> SEQ ID NO 394
<211> LENGTH: 9
<212> TYPE: PRT
<213> ORGANISM: Neisseria gonorrhoeae

<400> SEQUENCE: 394

Phe Ser Thr Ala Ile Asn Glu Leu Lys
1               5

<210> SEQ ID NO 395
<211> LENGTH: 15
<212> TYPE: PRT
<213> ORGANISM: Neisseria gonorrhoeae

<400> SEQUENCE: 395

Phe Ser Thr Ala Ile Asn Glu Leu Lys Ala Asp Gly Thr Leu Lys
1               5                   10                  15

<210> SEQ ID NO 396
<211> LENGTH: 16
<212> TYPE: PRT
<213> ORGANISM: Neisseria gonorrhoeae

<400> SEQUENCE: 396

Phe Ser Thr Ala Ile Asn Glu Leu Lys Ala Asp Gly Thr Leu Lys Lys
1               5                   10                  15

<210> SEQ ID NO 397
<211> LENGTH: 14
<212> TYPE: PRT
<213> ORGANISM: Neisseria gonorrhoeae

<400> SEQUENCE: 397

Lys Leu Gly Glu Gln Phe Phe Gly Lys Asp Ile Ser Val Gln
1               5                   10

<210> SEQ ID NO 398
<211> LENGTH: 13
<212> TYPE: PRT
<213> ORGANISM: Neisseria gonorrhoeae

<400> SEQUENCE: 398

Leu Gly Glu Gln Phe Phe Gly Lys Asp Ile Ser Val Gln
1               5                   10

<210> SEQ ID NO 399
<211> LENGTH: 15
<212> TYPE: PRT
<213> ORGANISM: Neisseria gonorrhoeae

<400> SEQUENCE: 399

Ser Gly Tyr Asp Leu Val Val Pro Gly Ile Ala Phe Leu Pro Arg
1               5                   10                  15

<210> SEQ ID NO 400
<211> LENGTH: 18
<212> TYPE: PRT
<213> ORGANISM: Neisseria gonorrhoeae

<400> SEQUENCE: 400

Val Asn Lys Asp Leu Ile Pro Asn Tyr Lys Asn Ile Asp Pro Glu Leu
1               5                   10                  15

Leu Lys

<210> SEQ ID NO 401
<211> LENGTH: 15
<212> TYPE: PRT
<213> ORGANISM: Neisseria gonorrhoeae

<400> SEQUENCE: 401

Gly Ser Asn Pro Glu Asp Leu Lys Ala Ala Ala Glu Val Leu Lys
1               5                   10                  15

<210> SEQ ID NO 402
<211> LENGTH: 12
<212> TYPE: PRT
<213> ORGANISM: Neisseria gonorrhoeae

<400> SEQUENCE: 402

Arg Phe Ser Pro Ser Ile Ile Asp Glu Leu Ala Arg
1               5                   10

<210> SEQ ID NO 403
<211> LENGTH: 11
<212> TYPE: PRT
<213> ORGANISM: Neisseria gonorrhoeae

<400> SEQUENCE: 403

Phe Ser Pro Ser Ile Ile Asp Glu Leu Ala Arg
1               5                   10

<210> SEQ ID NO 404
<211> LENGTH: 18
<212> TYPE: PRT
<213> ORGANISM: Neisseria gonorrhoeae

<400> SEQUENCE: 404

Ala Arg Ser Glu Glu Val Lys Asn Asn Val Gly Ile Glu Val Leu Thr
1               5                   10                  15

Pro Lys

<210> SEQ ID NO 405
<211> LENGTH: 16
<212> TYPE: PRT
<213> ORGANISM: Neisseria gonorrhoeae

<400> SEQUENCE: 405

Ser Glu Glu Val Lys Asn Asn Val Gly Ile Glu Val Leu Thr Pro Lys
1               5                   10                  15

<210> SEQ ID NO 406
<211> LENGTH: 13
<212> TYPE: PRT
<213> ORGANISM: Neisseria gonorrhoeae

<400> SEQUENCE: 406

Tyr Ile Asn Tyr Thr Leu Asp Pro Glu Ile Ala Ala Lys
1               5                   10

<210> SEQ ID NO 407
<211> LENGTH: 15
<212> TYPE: PRT
<213> ORGANISM: Neisseria gonorrhoeae

<400> SEQUENCE: 407

```
Asn Gly Ile Ala Val Thr Phe Ala Pro Ala Ser Lys Pro Ala Arg
1               5                   10                  15

<210> SEQ ID NO 408
<211> LENGTH: 11
<212> TYPE: PRT
<213> ORGANISM: Neisseria gonorrhoeae

<400> SEQUENCE: 408

Glu Lys Met Pro Ala Glu Leu Val Asn Thr Arg
1               5                   10

<210> SEQ ID NO 409
<211> LENGTH: 9
<212> TYPE: PRT
<213> ORGANISM: Neisseria gonorrhoeae

<400> SEQUENCE: 409

Met Pro Ala Glu Leu Val Asn Thr Arg
1               5

<210> SEQ ID NO 410
<211> LENGTH: 15
<212> TYPE: PRT
<213> ORGANISM: Neisseria gonorrhoeae

<400> SEQUENCE: 410

Asn Gly Asn Phe Val Thr Tyr Ala Pro Ser Ser Lys Pro Ala Arg
1               5                   10                  15

<210> SEQ ID NO 411
<211> LENGTH: 15
<212> TYPE: PRT
<213> ORGANISM: Neisseria gonorrhoeae

<400> SEQUENCE: 411

Ser Gly Tyr Asp Leu Thr Ala Pro Ser Ile Ala Asn Val Gly Arg
1               5                   10                  15

<210> SEQ ID NO 412
<211> LENGTH: 15
<212> TYPE: PRT
<213> ORGANISM: Neisseria gonorrhoeae

<400> SEQUENCE: 412

Ala Gln Ile Pro His Tyr Gly Asn Ile Asp Lys Asp Leu Leu Lys
1               5                   10                  15

<210> SEQ ID NO 413
<211> LENGTH: 14
<212> TYPE: PRT
<213> ORGANISM: Neisseria gonorrhoeae

<400> SEQUENCE: 413

Thr Gly Val Gly Val Trp Val Asp Ser Phe Met Ile Pro Arg
1               5                   10

<210> SEQ ID NO 414
<211> LENGTH: 13
<212> TYPE: PRT
<213> ORGANISM: Neisseria gonorrhoeae

<400> SEQUENCE: 414

Tyr Ile Asp Tyr Thr Leu Arg Pro Glu Val Ala Ala Lys
1               5                   10
```

<210> SEQ ID NO 415
<211> LENGTH: 12
<212> TYPE: PRT
<213> ORGANISM: Neisseria gonorrhoeae

<400> SEQUENCE: 415

Phe Ala Glu Tyr Asp Gly Tyr Thr Ala Glu Ala Arg
1               5                   10

<210> SEQ ID NO 416
<211> LENGTH: 10
<212> TYPE: PRT
<213> ORGANISM: Neisseria gonorrhoeae

<400> SEQUENCE: 416

Leu Gln Glu Leu Gln Glu Phe Val Ala Arg
1               5                   10

<210> SEQ ID NO 417
<211> LENGTH: 19
<212> TYPE: PRT
<213> ORGANISM: Neisseria gonorrhoeae

<400> SEQUENCE: 417

Leu Lys Gln Ala Asp Lys Ile Lys Ser Glu Met Val Glu Val Lys Pro
1               5                   10                  15

Ser Thr Arg

<210> SEQ ID NO 418
<211> LENGTH: 11
<212> TYPE: PRT
<213> ORGANISM: Neisseria gonorrhoeae

<400> SEQUENCE: 418

Ser Glu Met Val Glu Val Lys Pro Ser Thr Arg
1               5                   10

<210> SEQ ID NO 419
<211> LENGTH: 11
<212> TYPE: PRT
<213> ORGANISM: Neisseria gonorrhoeae

<400> SEQUENCE: 419

Leu Ala Ile Ile Gly Pro Asn Gly Ala Gly Lys
1               5                   10

<210> SEQ ID NO 420
<211> LENGTH: 13
<212> TYPE: PRT
<213> ORGANISM: Neisseria gonorrhoeae

<400> SEQUENCE: 420

Ser Arg Glu Asp Lys Ile Gln Thr Ala Ser Ala Pro Lys
1               5                   10

<210> SEQ ID NO 421
<211> LENGTH: 12
<212> TYPE: PRT
<213> ORGANISM: Neisseria gonorrhoeae

<400> SEQUENCE: 421

Leu Leu Glu Leu Thr Pro Ala Leu Tyr Val Gly Lys
1               5                   10

<210> SEQ ID NO 422
<211> LENGTH: 18
<212> TYPE: PRT
<213> ORGANISM: Neisseria gonorrhoeae

<400> SEQUENCE: 422

Leu Leu Glu Leu Thr Pro Ala Leu Tyr Val Gly Lys Ala Glu Ala Leu
1               5                   10                  15

Ala Lys

<210> SEQ ID NO 423
<211> LENGTH: 10
<212> TYPE: PRT
<213> ORGANISM: Neisseria gonorrhoeae

<400> SEQUENCE: 423

Met Lys Met Gln Ala Val Val Val Asn Lys
1               5                   10

<210> SEQ ID NO 424
<211> LENGTH: 17
<212> TYPE: PRT
<213> ORGANISM: Neisseria gonorrhoeae

<400> SEQUENCE: 424

Glu Thr Gly Ala Asp Leu Val Val Asn Ala Ala Lys Glu Asp Ala Ala
1               5                   10                  15

Lys

<210> SEQ ID NO 425
<211> LENGTH: 25
<212> TYPE: PRT
<213> ORGANISM: Neisseria gonorrhoeae

<400> SEQUENCE: 425

Thr Gly Gly Ala His Ala Ala Val Val Thr Ala Val Ser Ala Ala Ala
1               5                   10                  15

Phe Asn Ser Ala Val Asn Cys Val Arg
            20                  25

<210> SEQ ID NO 426
<211> LENGTH: 17
<212> TYPE: PRT
<213> ORGANISM: Neisseria gonorrhoeae

<400> SEQUENCE: 426

Val Val Ala Val Gly Leu Pro Pro Glu Ser Met Asp Leu Ser Ile Pro
1               5                   10                  15

Arg

<210> SEQ ID NO 427
<211> LENGTH: 16
<212> TYPE: PRT
<213> ORGANISM: Neisseria gonorrhoeae

<400> SEQUENCE: 427

Leu Val Leu Asp Gly Ile Glu Val Gly Ser Leu Val Gly Thr Arg
1               5                   10                  15

<210> SEQ ID NO 428
<211> LENGTH: 17

```
<212> TYPE: PRT
<213> ORGANISM: Neisseria gonorrhoeae

<400> SEQUENCE: 428

Leu Val Leu Asp Gly Ile Glu Val Val Gly Ser Leu Val Gly Thr Arg
1               5                   10                  15

Lys

<210> SEQ ID NO 429
<211> LENGTH: 13
<212> TYPE: PRT
<213> ORGANISM: Neisseria gonorrhoeae

<400> SEQUENCE: 429

Ala Leu Asp Glu Ala Pro Ala Ile Phe Gln Glu Met Arg
1               5                   10

<210> SEQ ID NO 430
<211> LENGTH: 12
<212> TYPE: PRT
<213> ORGANISM: Neisseria gonorrhoeae

<400> SEQUENCE: 430

Ile Leu Ala Ala His Ala Gly Ala Asn Leu Lys Lys
1               5                   10

<210> SEQ ID NO 431
<211> LENGTH: 14
<212> TYPE: PRT
<213> ORGANISM: Neisseria gonorrhoeae

<400> SEQUENCE: 431

Ile Val Thr Val Gln Thr Leu Gly Gly Ser Gly Ala Leu Lys
1               5                   10

<210> SEQ ID NO 432
<211> LENGTH: 12
<212> TYPE: PRT
<213> ORGANISM: Neisseria gonorrhoeae

<400> SEQUENCE: 432

Leu Ile Glu Gly Ile Asn Pro Ser Thr Phe Phe Lys
1               5                   10

<210> SEQ ID NO 433
<211> LENGTH: 13
<212> TYPE: PRT
<213> ORGANISM: Neisseria gonorrhoeae

<400> SEQUENCE: 433

Val Val Pro Val Gly Thr Pro Thr Ala Glu Gln Lys Arg
1               5                   10

<210> SEQ ID NO 434
<211> LENGTH: 11
<212> TYPE: PRT
<213> ORGANISM: Neisseria gonorrhoeae

<400> SEQUENCE: 434

Arg Leu Glu Pro Leu Thr Glu Gly Ala Ala Lys
1               5                   10

<210> SEQ ID NO 435
<211> LENGTH: 11
```

```
<212> TYPE: PRT
<213> ORGANISM: Neisseria gonorrhoeae

<400> SEQUENCE: 435

Tyr Leu Lys Asp Tyr Gln Thr Pro Ala Tyr Arg
1               5                   10

<210> SEQ ID NO 436
<211> LENGTH: 11
<212> TYPE: PRT
<213> ORGANISM: Neisseria gonorrhoeae

<400> SEQUENCE: 436

Leu Lys Asn Asn Val Phe Glu Leu Thr Ile Lys
1               5                   10

<210> SEQ ID NO 437
<211> LENGTH: 16
<212> TYPE: PRT
<213> ORGANISM: Neisseria gonorrhoeae

<400> SEQUENCE: 437

Arg Ser Asp Thr Leu Gln Gln Val Gln Thr Ala Leu Gln His Pro Lys
1               5                   10                  15

<210> SEQ ID NO 438
<211> LENGTH: 14
<212> TYPE: PRT
<213> ORGANISM: Neisseria gonorrhoeae

<400> SEQUENCE: 438

Asn Val Pro His Phe His Ala Gln Asp Gly Ser Gly Tyr Arg
1               5                   10

<210> SEQ ID NO 439
<211> LENGTH: 13
<212> TYPE: PRT
<213> ORGANISM: Neisseria gonorrhoeae

<400> SEQUENCE: 439

Thr Tyr His Gly Ser Ala Met Ser Ile Pro Val Gln Arg
1               5                   10

<210> SEQ ID NO 440
<211> LENGTH: 9
<212> TYPE: PRT
<213> ORGANISM: Neisseria gonorrhoeae

<400> SEQUENCE: 440

Ala Ala Ile Gln Val Leu Pro Gly Arg
1               5

<210> SEQ ID NO 441
<211> LENGTH: 10
<212> TYPE: PRT
<213> ORGANISM: Neisseria gonorrhoeae

<400> SEQUENCE: 441

Leu Arg Tyr Gln Val Ala Thr Gly Val Arg
1               5                   10

<210> SEQ ID NO 442
<211> LENGTH: 17
<212> TYPE: PRT
<213> ORGANISM: Neisseria gonorrhoeae
```

<400> SEQUENCE: 442

Val His Pro Gly Glu Phe Phe Ala Leu Pro Gln Ser Pro Gln Leu Phe
1               5                   10                  15

Lys

<210> SEQ ID NO 443
<211> LENGTH: 16
<212> TYPE: PRT
<213> ORGANISM: Neisseria gonorrhoeae

<400> SEQUENCE: 443

Gln Val Phe Lys Asp Ala Leu Asn Val Asp Leu Gly Asp Phe Pro Arg
1               5                   10                  15

<210> SEQ ID NO 444
<211> LENGTH: 11
<212> TYPE: PRT
<213> ORGANISM: Neisseria gonorrhoeae

<400> SEQUENCE: 444

Val Val Ala Leu Arg Val Pro Asn Gly Ala Lys
1               5                   10

<210> SEQ ID NO 445
<211> LENGTH: 21
<212> TYPE: PRT
<213> ORGANISM: Neisseria gonorrhoeae

<400> SEQUENCE: 445

Val Asn Asp Ala Gly Asn Leu Ser Asn Gly Glu Asp Ser Gly Leu Gln
1               5                   10                  15

Ser Pro Ile Val Lys
            20

<210> SEQ ID NO 446
<211> LENGTH: 12
<212> TYPE: PRT
<213> ORGANISM: Neisseria gonorrhoeae

<400> SEQUENCE: 446

Tyr Val Ala Val His His Pro Phe Thr Ala Pro Lys
1               5                   10

<210> SEQ ID NO 447
<211> LENGTH: 17
<212> TYPE: PRT
<213> ORGANISM: Neisseria gonorrhoeae

<400> SEQUENCE: 447

Glu Gly His Glu Asp Leu Met Val Ser Asp Pro Ala Asn Cys Leu Ala
1               5                   10                  15

Arg

<210> SEQ ID NO 448
<211> LENGTH: 9
<212> TYPE: PRT
<213> ORGANISM: Neisseria gonorrhoeae

<400> SEQUENCE: 448

Phe Gly Phe Leu Leu Asp Asn Leu Lys
1               5

```
<210> SEQ ID NO 449
<211> LENGTH: 15
<212> TYPE: PRT
<213> ORGANISM: Neisseria gonorrhoeae

<400> SEQUENCE: 449

Phe Gly Ala Pro Pro His Gly Gly Leu Ala Phe Gly Leu Asp Arg
1               5                   10                  15

<210> SEQ ID NO 450
<211> LENGTH: 19
<212> TYPE: PRT
<213> ORGANISM: Neisseria gonorrhoeae

<400> SEQUENCE: 450

Leu Val Thr Leu Met Thr Gly Ala Glu Ser Ile Arg Asp Val Ile Ala
1               5                   10                  15

Phe Pro Lys

<210> SEQ ID NO 451
<211> LENGTH: 15
<212> TYPE: PRT
<213> ORGANISM: Neisseria gonorrhoeae

<400> SEQUENCE: 451

Ala Gln Cys Leu Leu Thr Asp Ala Pro Asn Ser Val Asp Asp Lys
1               5                   10                  15

<210> SEQ ID NO 452
<211> LENGTH: 18
<212> TYPE: PRT
<213> ORGANISM: Neisseria gonorrhoeae

<400> SEQUENCE: 452

Ala Gln Cys Leu Leu Thr Asp Ala Pro Asn Ser Val Asp Asp Lys Gln
1               5                   10                  15

Leu Arg

<210> SEQ ID NO 453
<211> LENGTH: 13
<212> TYPE: PRT
<213> ORGANISM: Neisseria gonorrhoeae

<400> SEQUENCE: 453

Thr Leu Leu Asp Thr Val Ala Val Pro Asn Thr Ala Arg
1               5                   10

<210> SEQ ID NO 454
<211> LENGTH: 16
<212> TYPE: PRT
<213> ORGANISM: Neisseria gonorrhoeae

<400> SEQUENCE: 454

Leu Asn Val Pro Leu Leu Gly Gln Leu Pro Leu Ser Leu Pro Val Arg
1               5                   10                  15

<210> SEQ ID NO 455
<211> LENGTH: 7
<212> TYPE: PRT
<213> ORGANISM: Neisseria gonorrhoeae

<400> SEQUENCE: 455

Gln Lys Lys Val Ile Gly Lys
```

```
1               5
```

<210> SEQ ID NO 456
<211> LENGTH: 17
<212> TYPE: PRT
<213> ORGANISM: Neisseria gonorrhoeae

<400> SEQUENCE: 456

```
Gly Ile Asp Val Pro Thr Ile Thr His Val Ile Asn Tyr Asp Leu Pro
1               5                   10                  15

Lys
```

<210> SEQ ID NO 457
<211> LENGTH: 14
<212> TYPE: PRT
<213> ORGANISM: Neisseria gonorrhoeae

<400> SEQUENCE: 457

```
Arg Gly Asp His Lys Pro Gly Lys Glu Gly Phe Gly Gly Lys
1               5                   10
```

<210> SEQ ID NO 458
<211> LENGTH: 17
<212> TYPE: PRT
<213> ORGANISM: Neisseria gonorrhoeae

<400> SEQUENCE: 458

```
Ala Leu Ala Gly His Asp Leu Leu Ala Ala Ala Gln Thr Gly Thr Gly
1               5                   10                  15

Lys
```

<210> SEQ ID NO 459
<211> LENGTH: 14
<212> TYPE: PRT
<213> ORGANISM: Neisseria gonorrhoeae

<400> SEQUENCE: 459

```
Tyr Ala Thr Ala Ser Thr Ser Pro Ala Met His Pro Val Arg
1               5                   10
```

<210> SEQ ID NO 460
<211> LENGTH: 12
<212> TYPE: PRT
<213> ORGANISM: Neisseria gonorrhoeae

<400> SEQUENCE: 460

```
Ile Val Leu Phe Arg Pro Thr Ala Asn Ile Ala Arg
1               5                   10
```

<210> SEQ ID NO 461
<211> LENGTH: 27
<212> TYPE: PRT
<213> ORGANISM: Neisseria gonorrhoeae

<400> SEQUENCE: 461

```
Ala Ala Asp Glu Ile Pro Asp Ala Pro Ala Ala Leu Tyr Leu Arg Pro
1               5                   10                  15

Thr Leu Ile Gly Thr Asp Pro Val Ile Gly Lys
            20                  25
```

<210> SEQ ID NO 462
<211> LENGTH: 22
<212> TYPE: PRT

<213> ORGANISM: Neisseria gonorrhoeae

<400> SEQUENCE: 462

Ala Gly Ser Pro Ser Glu Thr Ala Leu Leu Tyr Ile Leu Ala Ser Pro
1               5                   10                  15

Val Gly Asp Tyr Phe Lys
            20

<210> SEQ ID NO 463
<211> LENGTH: 8
<212> TYPE: PRT
<213> ORGANISM: Neisseria gonorrhoeae

<400> SEQUENCE: 463

Arg Ser Asp Asn Leu Ile Ala Arg
1               5

<210> SEQ ID NO 464
<211> LENGTH: 11
<212> TYPE: PRT
<213> ORGANISM: Neisseria gonorrhoeae

<400> SEQUENCE: 464

Ala Val Ile Val Gly Thr Gln Ser Phe Gly Lys
1               5                   10

<210> SEQ ID NO 465
<211> LENGTH: 17
<212> TYPE: PRT
<213> ORGANISM: Neisseria gonorrhoeae

<400> SEQUENCE: 465

Ser Pro Asp Val Ser Gln Gly Gln Ser Val Ser Asp Gly Thr Ala Val
1               5                   10                  15

Arg

<210> SEQ ID NO 466
<211> LENGTH: 14
<212> TYPE: PRT
<213> ORGANISM: Neisseria gonorrhoeae

<400> SEQUENCE: 466

Ala Pro His Leu Leu Val Ala Gly Thr Thr Gly Ser Gly Lys
1               5                   10

<210> SEQ ID NO 467
<211> LENGTH: 15
<212> TYPE: PRT
<213> ORGANISM: Neisseria gonorrhoeae

<400> SEQUENCE: 467

Ala Ala Gln Ile Ala Gly Leu Ser Glu Ile Pro Ala Val Ile Lys
1               5                   10                  15

<210> SEQ ID NO 468
<211> LENGTH: 18
<212> TYPE: PRT
<213> ORGANISM: Neisseria gonorrhoeae

<400> SEQUENCE: 468

Thr Ile Ser Asp Glu Thr Ala Leu Ala Met Gly Leu Ile Glu Asn Leu
1               5                   10                  15

Gln Arg

-continued

<210> SEQ ID NO 469
<211> LENGTH: 18
<212> TYPE: PRT
<213> ORGANISM: Neisseria gonorrhoeae

<400> SEQUENCE: 469

Leu Ala Asp Glu Phe Gly Leu Thr His Glu Thr Ile Ala Gln Ala Val
1               5                   10                  15

Gly Lys

<210> SEQ ID NO 470
<211> LENGTH: 15
<212> TYPE: PRT
<213> ORGANISM: Neisseria gonorrhoeae

<400> SEQUENCE: 470

Leu Leu Ser Leu Pro Glu Ser Val Gln Glu Met Leu Tyr Gln Arg
1               5                   10                  15

<210> SEQ ID NO 471
<211> LENGTH: 16
<212> TYPE: PRT
<213> ORGANISM: Neisseria gonorrhoeae

<400> SEQUENCE: 471

Ala Leu Leu Thr Leu Pro Val Val Glu Gln Leu Glu Leu Ala Gln Lys
1               5                   10                  15

<210> SEQ ID NO 472
<211> LENGTH: 13
<212> TYPE: PRT
<213> ORGANISM: Neisseria gonorrhoeae

<400> SEQUENCE: 472

Ser Gln Ala Ala Leu Gln Asn Lys Arg Pro Glu Pro Lys
1               5                   10

<210> SEQ ID NO 473
<211> LENGTH: 12
<212> TYPE: PRT
<213> ORGANISM: Neisseria gonorrhoeae

<400> SEQUENCE: 473

Gln Arg Leu Gln Gln His Leu Asn Ser Leu Pro Lys
1               5                   10

<210> SEQ ID NO 474
<211> LENGTH: 12
<212> TYPE: PRT
<213> ORGANISM: Neisseria gonorrhoeae

<400> SEQUENCE: 474

Val Ser Gly Gln Gly Gly Glu Ile Leu Pro Ser Arg
1               5                   10

<210> SEQ ID NO 475
<211> LENGTH: 17
<212> TYPE: PRT
<213> ORGANISM: Neisseria gonorrhoeae

<400> SEQUENCE: 475

Glu Ala Gly Ala Thr Glu Gln Asn Ile Asn Ala Ala Ile Asp Ala Val
1               5                   10                  15

Arg

<210> SEQ ID NO 476
<211> LENGTH: 15
<212> TYPE: PRT
<213> ORGANISM: Neisseria gonorrhoeae

<400> SEQUENCE: 476

Thr Lys Asn Asn Pro Val Leu Ile Gly Glu Pro Gly Val Gly Lys
1               5                   10                  15

<210> SEQ ID NO 477
<211> LENGTH: 14
<212> TYPE: PRT
<213> ORGANISM: Neisseria gonorrhoeae

<400> SEQUENCE: 477

Leu Leu Val Leu Asp Leu Ala Ala Leu Ile Ala Gly Ala Lys
1               5                   10

<210> SEQ ID NO 478
<211> LENGTH: 16
<212> TYPE: PRT
<213> ORGANISM: Neisseria gonorrhoeae

<400> SEQUENCE: 478

Val Leu Val Gly Glu Pro Ser Val Glu Asp Thr Ile Ala Ile Leu Arg
1               5                   10                  15

<210> SEQ ID NO 479
<211> LENGTH: 16
<212> TYPE: PRT
<213> ORGANISM: Neisseria gonorrhoeae

<400> SEQUENCE: 479

Phe Leu Pro Asp Lys Ala Ile Asp Leu Ile Asp Glu Ala Ala Ser Arg
1               5                   10                  15

<210> SEQ ID NO 480
<211> LENGTH: 11
<212> TYPE: PRT
<213> ORGANISM: Neisseria gonorrhoeae

<400> SEQUENCE: 480

Ala Ile Ser Asp Gly Ala Ala Asn Ile Lys Lys
1               5                   10

<210> SEQ ID NO 481
<211> LENGTH: 8
<212> TYPE: PRT
<213> ORGANISM: Neisseria gonorrhoeae

<400> SEQUENCE: 481

Ile Lys Ile Glu Gln Ala Lys Arg
1               5

<210> SEQ ID NO 482
<211> LENGTH: 14
<212> TYPE: PRT
<213> ORGANISM: Neisseria gonorrhoeae

<400> SEQUENCE: 482

Asn Asn Val Gly Ala Glu Glu Ile Ala Glu Val Val Ser Arg
1               5                   10

<210> SEQ ID NO 483
<211> LENGTH: 23
<212> TYPE: PRT
<213> ORGANISM: Neisseria gonorrhoeae

<400> SEQUENCE: 483

Ser Gly Leu Ala Asp Pro Asn Lys Pro Tyr Gly Ser Phe Leu Phe Leu
1               5                   10                  15

Gly Pro Thr Gly Val Gly Lys
            20

<210> SEQ ID NO 484
<211> LENGTH: 15
<212> TYPE: PRT
<213> ORGANISM: Neisseria gonorrhoeae

<400> SEQUENCE: 484

Ala Leu Ala Gly Phe Leu Phe Asp Ser Glu Asp His Leu Ile Arg
1               5                   10                  15

<210> SEQ ID NO 485
<211> LENGTH: 12
<212> TYPE: PRT
<213> ORGANISM: Neisseria gonorrhoeae

<400> SEQUENCE: 485

Ala Ile Gln Ser Glu Ile Glu Asn Pro Leu Ala Lys
1               5                   10

<210> SEQ ID NO 486
<211> LENGTH: 27
<212> TYPE: PRT
<213> ORGANISM: Neisseria gonorrhoeae

<400> SEQUENCE: 486

Gly Phe Gly Phe Ile Thr Pro Asp Glu Gly Glu Asp Leu Phe Ala
1               5                   10                  15

His Phe Ser Ala Ile Asn Met Glu Gly Phe Lys
            20                  25

<210> SEQ ID NO 487
<211> LENGTH: 30
<212> TYPE: PRT
<213> ORGANISM: Neisseria gonorrhoeae

<400> SEQUENCE: 487

Gly Phe Gly Phe Ile Thr Pro Asp Glu Gly Glu Asp Leu Phe Ala
1               5                   10                  15

His Phe Ser Ala Ile Asn Met Glu Gly Phe Lys Thr Leu Lys
            20                  25                  30

<210> SEQ ID NO 488
<211> LENGTH: 10
<212> TYPE: PRT
<213> ORGANISM: Neisseria gonorrhoeae

<400> SEQUENCE: 488

Val Ser Phe Asp Val Thr Thr Gly Pro Lys
1               5                   10

<210> SEQ ID NO 489
<211> LENGTH: 10

```
<212> TYPE: PRT
<213> ORGANISM: Neisseria gonorrhoeae

<400> SEQUENCE: 489

Gly Lys Gln Ala Ala Asn Ile Gln Ala Ala
1               5                   10

<210> SEQ ID NO 490
<211> LENGTH: 18
<212> TYPE: PRT
<213> ORGANISM: Neisseria gonorrhoeae

<400> SEQUENCE: 490

Ile Gln Pro Val Gly Gln Leu Thr Met Gly Asp Gly Ile Pro Val Gly
1               5                   10                  15

Glu Arg

<210> SEQ ID NO 491
<211> LENGTH: 13
<212> TYPE: PRT
<213> ORGANISM: Neisseria gonorrhoeae

<400> SEQUENCE: 491

Gly Gly Ala Ala Asp Leu Thr Asp Gln Glu Leu Lys Arg
1               5                   10

<210> SEQ ID NO 492
<211> LENGTH: 16
<212> TYPE: PRT
<213> ORGANISM: Neisseria gonorrhoeae

<400> SEQUENCE: 492

Ala Glu Asp Lys Gly Ala Ala Ala Pro Ala Val Gly Val Asp Gly Lys
1               5                   10                  15

<210> SEQ ID NO 493
<211> LENGTH: 17
<212> TYPE: PRT
<213> ORGANISM: Neisseria gonorrhoeae

<400> SEQUENCE: 493

Ala Glu Asp Lys Gly Ala Ala Ala Pro Ala Val Gly Val Asp Gly Lys
1               5                   10                  15

Lys

<210> SEQ ID NO 494
<211> LENGTH: 12
<212> TYPE: PRT
<213> ORGANISM: Neisseria gonorrhoeae

<400> SEQUENCE: 494

His Ala Leu Glu Gly Phe Asn Ala Met Pro Ala Lys
1               5                   10

<210> SEQ ID NO 495
<211> LENGTH: 15
<212> TYPE: PRT
<213> ORGANISM: Neisseria gonorrhoeae

<400> SEQUENCE: 495

Ser Gly Glu Ala Asn Pro Lys Glu Asn Pro Glu Leu Gly Ala Lys
1               5                   10                  15
```

-continued

<210> SEQ ID NO 496
<211> LENGTH: 17
<212> TYPE: PRT
<213> ORGANISM: Neisseria gonorrhoeae

<400> SEQUENCE: 496

Met Ser Glu Glu Asp Leu Lys Ala Val Ala Asn Phe Ile Gln Gly Leu
1               5                   10                  15

Arg

<210> SEQ ID NO 497
<211> LENGTH: 20
<212> TYPE: PRT
<213> ORGANISM: Neisseria gonorrhoeae

<400> SEQUENCE: 497

Ala Ala Thr Gln Pro Ala Pro Gly Val Lys Pro Tyr Asn Ala Leu Gln
1               5                   10                  15

Val Ala Gly Arg
            20

<210> SEQ ID NO 498
<211> LENGTH: 16
<212> TYPE: PRT
<213> ORGANISM: Neisseria gonorrhoeae

<400> SEQUENCE: 498

Asp Val Val Pro Glu Ser Asn Met Pro Ala Phe Pro Trp Leu Ala Arg
1               5                   10                  15

<210> SEQ ID NO 499
<211> LENGTH: 13
<212> TYPE: PRT
<213> ORGANISM: Neisseria gonorrhoeae

<400> SEQUENCE: 499

Asn Lys Val Asp Val Asp Ala Thr Val Ala Asn Met Lys
1               5                   10

<210> SEQ ID NO 500
<211> LENGTH: 12
<212> TYPE: PRT
<213> ORGANISM: Neisseria gonorrhoeae

<400> SEQUENCE: 500

Gly Gly Arg Gly Asp Leu Ser Asp Asp Glu Val Lys
1               5                   10

<210> SEQ ID NO 501
<211> LENGTH: 13
<212> TYPE: PRT
<213> ORGANISM: Neisseria gonorrhoeae

<400> SEQUENCE: 501

Leu Lys Asp Ile Gly Leu Thr Asp Glu Glu Ile Lys Lys
1               5                   10

<210> SEQ ID NO 502
<211> LENGTH: 14
<212> TYPE: PRT
<213> ORGANISM: Neisseria gonorrhoeae

<400> SEQUENCE: 502

Trp Phe Gly Ala Ala Pro Pro Asp Leu Thr Leu Ile Ala Arg

<210> SEQ ID NO 503
<211> LENGTH: 16
<212> TYPE: PRT
<213> ORGANISM: Neisseria gonorrhoeae

<400> SEQUENCE: 503

Gly Gln Pro Val Met Val Lys Asp Glu His Gly Glu Met Lys Pro Lys
1               5                   10                  15

<210> SEQ ID NO 504
<211> LENGTH: 11
<212> TYPE: PRT
<213> ORGANISM: Neisseria gonorrhoeae

<400> SEQUENCE: 504

Leu Tyr Trp Glu Ser Thr Gly Leu His Ser Arg
1               5                   10

<210> SEQ ID NO 505
<211> LENGTH: 10
<212> TYPE: PRT
<213> ORGANISM: Neisseria gonorrhoeae

<400> SEQUENCE: 505

Glu Leu Gly Val Asp Leu Gly Gln Val Lys
1               5                   10

<210> SEQ ID NO 506
<211> LENGTH: 11
<212> TYPE: PRT
<213> ORGANISM: Neisseria gonorrhoeae

<400> SEQUENCE: 506

Phe Gly Asn Val Glu Val Lys Glu Leu Ser Arg
1               5                   10

<210> SEQ ID NO 507
<211> LENGTH: 11
<212> TYPE: PRT
<213> ORGANISM: Neisseria gonorrhoeae

<400> SEQUENCE: 507

Ile Lys Lys Ile Ser Gly Gln Asn Leu Ser Arg
1               5                   10

<210> SEQ ID NO 508
<211> LENGTH: 8
<212> TYPE: PRT
<213> ORGANISM: Neisseria gonorrhoeae

<400> SEQUENCE: 508

Ile Ser Gly Gln Asn Leu Ser Arg
1               5

<210> SEQ ID NO 509
<211> LENGTH: 9
<212> TYPE: PRT
<213> ORGANISM: Neisseria gonorrhoeae

<400> SEQUENCE: 509

Leu Ser Pro Leu Ala Phe Ile Ile Lys
1               5

<210> SEQ ID NO 510
<211> LENGTH: 17
<212> TYPE: PRT
<213> ORGANISM: Neisseria gonorrhoeae

<400> SEQUENCE: 510

Ala Phe Pro Glu Phe Asn Ala Ser Leu Asp Gly Asp Asn Leu Val Leu
1               5                   10                  15

Lys

<210> SEQ ID NO 511
<211> LENGTH: 21
<212> TYPE: PRT
<213> ORGANISM: Neisseria gonorrhoeae

<400> SEQUENCE: 511

Asn Tyr Phe Asn Ile Gly Phe Ala Ala Asp Thr Pro Asn Gly Leu Val
1               5                   10                  15

Val Pro Val Ile Lys
            20

<210> SEQ ID NO 512
<211> LENGTH: 26
<212> TYPE: PRT
<213> ORGANISM: Neisseria gonorrhoeae

<400> SEQUENCE: 512

Asn Tyr Phe Asn Ile Gly Phe Ala Ala Asp Thr Pro Asn Gly Leu Val
1               5                   10                  15

Val Pro Val Ile Lys Asp Val Asp Gln Lys
            20                  25

<210> SEQ ID NO 513
<211> LENGTH: 11
<212> TYPE: PRT
<213> ORGANISM: Neisseria gonorrhoeae

<400> SEQUENCE: 513

Gln Ile Ser Gln Glu Leu Thr Glu Leu Ser Lys
1               5                   10

<210> SEQ ID NO 514
<211> LENGTH: 12
<212> TYPE: PRT
<213> ORGANISM: Neisseria gonorrhoeae

<400> SEQUENCE: 514

Gln Ile Ser Gln Glu Leu Thr Glu Leu Ser Lys Lys
1               5                   10

<210> SEQ ID NO 515
<211> LENGTH: 15
<212> TYPE: PRT
<213> ORGANISM: Neisseria gonorrhoeae

<400> SEQUENCE: 515

Ser Gln Ile Lys Pro Val Trp Asn Gly Lys Glu Phe Ala Pro Arg
1               5                   10                  15

<210> SEQ ID NO 516
<211> LENGTH: 9
<212> TYPE: PRT
<213> ORGANISM: Neisseria gonorrhoeae

<400> SEQUENCE: 516

Val Ile Asp Gly Ala Ala Gly Met Arg
1               5

<210> SEQ ID NO 517
<211> LENGTH: 10
<212> TYPE: PRT
<213> ORGANISM: Neisseria gonorrhoeae

<400> SEQUENCE: 517

Phe Thr Val Phe Leu Ala Asn Leu Leu Lys
1               5                   10

<210> SEQ ID NO 518
<211> LENGTH: 9
<212> TYPE: PRT
<213> ORGANISM: Neisseria gonorrhoeae

<400> SEQUENCE: 518

Leu Leu Ile Ala Ala Ala Glu Ala Arg
1               5

<210> SEQ ID NO 519
<211> LENGTH: 38
<212> TYPE: PRT
<213> ORGANISM: Neisseria gonorrhoeae

<400> SEQUENCE: 519

Gly Val Pro Val Ala Asp Pro Leu Thr Met Gln Thr Ser Ile Pro His
1               5                   10                  15

Ile Phe Ile Ala Gly Asp Ala Ser Asn Gln Leu Pro Leu Leu His Glu
            20                  25                  30

Ala Ala Asp Gln Gly Lys
        35

<210> SEQ ID NO 520
<211> LENGTH: 13
<212> TYPE: PRT
<213> ORGANISM: Neisseria gonorrhoeae

<400> SEQUENCE: 520

Ala Glu Ala Ala Ala Ala Pro Ala Gln Glu Ala Pro Lys
1               5                   10

<210> SEQ ID NO 521
<211> LENGTH: 15
<212> TYPE: PRT
<213> ORGANISM: Neisseria gonorrhoeae

<400> SEQUENCE: 521

Thr Leu Gly Gly Val Cys Leu Asn Val Gly Cys Ile Pro Ser Lys
1               5                   10                  15

<210> SEQ ID NO 522
<211> LENGTH: 13
<212> TYPE: PRT
<213> ORGANISM: Neisseria gonorrhoeae

<400> SEQUENCE: 522

Ala Leu Leu His Asn Ala Ala Val Ile Asp Glu Val Arg
1               5                   10

```
<210> SEQ ID NO 523
<211> LENGTH: 9
<212> TYPE: PRT
<213> ORGANISM: Neisseria gonorrhoeae

<400> SEQUENCE: 523

Ala Tyr Lys Asp Gly Val Val Ser Arg
1               5

<210> SEQ ID NO 524
<211> LENGTH: 10
<212> TYPE: PRT
<213> ORGANISM: Neisseria gonorrhoeae

<400> SEQUENCE: 524

Leu Thr Gly Gly Leu Ala Gly Met Ala Lys
1               5                   10

<210> SEQ ID NO 525
<211> LENGTH: 9
<212> TYPE: PRT
<213> ORGANISM: Neisseria gonorrhoeae

<400> SEQUENCE: 525

Asn Cys Ile Ile Ala Ala Gly Ser Arg
1               5

<210> SEQ ID NO 526
<211> LENGTH: 16
<212> TYPE: PRT
<213> ORGANISM: Neisseria gonorrhoeae

<400> SEQUENCE: 526

Ile Ile Asp Ser Ser Gly Ala Leu Ala Leu Lys Glu Val Pro Gly Lys
1               5                   10                  15

<210> SEQ ID NO 527
<211> LENGTH: 14
<212> TYPE: PRT
<213> ORGANISM: Neisseria gonorrhoeae

<400> SEQUENCE: 527

Glu Pro Gln Arg Tyr Asp Ala Val Leu Val Ala Ala Gly Arg
1               5                   10

<210> SEQ ID NO 528
<211> LENGTH: 11
<212> TYPE: PRT
<213> ORGANISM: Neisseria gonorrhoeae

<400> SEQUENCE: 528

Ala Pro Asn Gly Lys Leu Ile Ser Ala Glu Lys
1               5                   10

<210> SEQ ID NO 529
<211> LENGTH: 21
<212> TYPE: PRT
<213> ORGANISM: Neisseria gonorrhoeae

<400> SEQUENCE: 529

Thr Asn Val Pro His Ile Tyr Ala Ile Gly Asp Ile Val Gly Gln Pro
1               5                   10                  15

Met Leu Ala His Lys
            20
```

<210> SEQ ID NO 530
<211> LENGTH: 16
<212> TYPE: PRT
<213> ORGANISM: Neisseria gonorrhoeae

<400> SEQUENCE: 530

Ala Val His Glu Gly His Val Ala Ala Glu Asn Cys Ala Gly His Lys
1               5                   10                  15

<210> SEQ ID NO 531
<211> LENGTH: 23
<212> TYPE: PRT
<213> ORGANISM: Neisseria gonorrhoeae

<400> SEQUENCE: 531

Val Ile Pro Gly Val Ala Tyr Thr Ser Pro Glu Val Ala Trp Val Gly
1               5                   10                  15

Glu Thr Glu Leu Ser Ala Lys
            20

<210> SEQ ID NO 532
<211> LENGTH: 12
<212> TYPE: PRT
<213> ORGANISM: Neisseria gonorrhoeae

<400> SEQUENCE: 532

Ala Ile Ala Asn Gly Cys Asp Asn Gly Phe Thr Lys
1               5                   10

<210> SEQ ID NO 533
<211> LENGTH: 39
<212> TYPE: PRT
<213> ORGANISM: Neisseria gonorrhoeae

<400> SEQUENCE: 533

Ile Asp Thr Ala Ala Thr Val Ala Ala Glu Ala Pro Ala Ala Ala Pro
1               5                   10                  15

Ala Glu Ala Ala Pro Ala Ala Val Pro Ala Ala Ala Gln Asn Asn Ala
            20                  25                  30

Ala Met Pro Ala Ala Ala Lys
            35

<210> SEQ ID NO 534
<211> LENGTH: 17
<212> TYPE: PRT
<213> ORGANISM: Neisseria gonorrhoeae

<400> SEQUENCE: 534

Leu Ala Ala Glu Thr Gly Val Asp Val Asn Val Leu Gln Gly Ser Gly
1               5                   10                  15

Arg

<210> SEQ ID NO 535
<211> LENGTH: 32
<212> TYPE: PRT
<213> ORGANISM: Neisseria gonorrhoeae

<400> SEQUENCE: 535

Val Leu Lys Glu Asp Val Gln Asn Ala Ala Ala Lys Pro Ala Ala Ala
1               5                   10                  15

Val Ala Pro Ala Val Ala Leu Pro Ala Gly Ala Arg Pro Glu Glu Arg
            20                  25                  30

<210> SEQ ID NO 536
<211> LENGTH: 37
<212> TYPE: PRT
<213> ORGANISM: Neisseria gonorrhoeae

<400> SEQUENCE: 536

Val Leu Lys Glu Asp Val Gln Asn Ala Ala Ala Lys Pro Ala Ala Ala
1               5                   10                  15

Val Ala Pro Ala Val Ala Leu Pro Ala Gly Ala Arg Pro Glu Glu Arg
            20                  25                  30

Val Pro Met Ser Arg
        35

<210> SEQ ID NO 537
<211> LENGTH: 26
<212> TYPE: PRT
<213> ORGANISM: Neisseria gonorrhoeae

<400> SEQUENCE: 537

Leu Leu Ala Ser Gln Gln Glu Asn Ala Ile Leu Thr Thr Phe Asn Glu
1               5                   10                  15

Val Asn Met Lys Pro Ile Met Asp Leu Arg
            20                  25

<210> SEQ ID NO 538
<211> LENGTH: 18
<212> TYPE: PRT
<213> ORGANISM: Neisseria gonorrhoeae

<400> SEQUENCE: 538

Glu Ala Val Leu Thr Leu Val Ala Ile Lys Asp Ala Leu Glu Asp Pro
1               5                   10                  15

Val Arg

<210> SEQ ID NO 539
<211> LENGTH: 18
<212> TYPE: PRT
<213> ORGANISM: Neisseria gonorrhoeae

<400> SEQUENCE: 539

Ala Ala Leu Gly Glu Phe Glu Ser Leu Pro Val Ser Gly Glu Tyr Ile
1               5                   10                  15

His Arg

<210> SEQ ID NO 540
<211> LENGTH: 8
<212> TYPE: PRT
<213> ORGANISM: Neisseria gonorrhoeae

<400> SEQUENCE: 540

Phe Gly Thr His Gln Leu Pro Lys
1               5

<210> SEQ ID NO 541
<211> LENGTH: 8
<212> TYPE: PRT
<213> ORGANISM: Neisseria gonorrhoeae

<400> SEQUENCE: 541

Phe Leu Pro Asp His Leu Pro Lys
1               5

<210> SEQ ID NO 542
<211> LENGTH: 9
<212> TYPE: PRT
<213> ORGANISM: Neisseria gonorrhoeae

<400> SEQUENCE: 542

Phe Ala Val Ala Ser Ala Ala Ile Arg
1               5

<210> SEQ ID NO 543
<211> LENGTH: 21
<212> TYPE: PRT
<213> ORGANISM: Neisseria gonorrhoeae

<400> SEQUENCE: 543

Gly Ala Gln Tyr Pro Ala Glu His Asn Val Gly His Leu Tyr Glu Ala
1               5                   10                  15

Lys Pro Ala Leu Lys
            20

<210> SEQ ID NO 544
<211> LENGTH: 14
<212> TYPE: PRT
<213> ORGANISM: Neisseria gonorrhoeae

<400> SEQUENCE: 544

Lys Leu Asp Pro Thr Asn Ser Phe Asn Pro Gly Ile Gly Lys
1               5                   10

<210> SEQ ID NO 545
<211> LENGTH: 21
<212> TYPE: PRT
<213> ORGANISM: Neisseria gonorrhoeae

<400> SEQUENCE: 545

Gly Gly Ile Ser Thr Asn Glu Ala Val Leu Glu Gln Leu Ala Pro Asp
1               5                   10                  15

Tyr Pro Leu Pro Lys
            20

<210> SEQ ID NO 546
<211> LENGTH: 14
<212> TYPE: PRT
<213> ORGANISM: Neisseria gonorrhoeae

<400> SEQUENCE: 546

Leu Ala Ser Asn Asn Pro Asn Leu Gln Asn Ile Pro Ile Arg
1               5                   10

<210> SEQ ID NO 547
<211> LENGTH: 17
<212> TYPE: PRT
<213> ORGANISM: Neisseria gonorrhoeae

<400> SEQUENCE: 547

Ala Ala Ile Asn Ala Pro Met Gln Gly Thr Ala Ser Asp Leu Ile Lys
1               5                   10                  15

Arg

<210> SEQ ID NO 548
<211> LENGTH: 18
<212> TYPE: PRT

<213> ORGANISM: Neisseria gonorrhoeae

<400> SEQUENCE: 548

Met Asn Lys Ser Glu Leu Ile Glu Ala Ile Ala Gln Glu Ala Asp Ile
1               5                   10                  15

Ser Lys

<210> SEQ ID NO 549
<211> LENGTH: 23
<212> TYPE: PRT
<213> ORGANISM: Neisseria gonorrhoeae

<400> SEQUENCE: 549

Met Asn Lys Ser Glu Leu Ile Glu Ala Ile Ala Gln Glu Ala Asp Ile
1               5                   10                  15

Ser Lys Ala Ala Ala Gln Lys
            20

<210> SEQ ID NO 550
<211> LENGTH: 14
<212> TYPE: PRT
<213> ORGANISM: Neisseria gonorrhoeae

<400> SEQUENCE: 550

Ala Leu Asp Ala Thr Thr Asn Ala Val Thr Asn Ala Leu Lys
1               5                   10

<210> SEQ ID NO 551
<211> LENGTH: 11
<212> TYPE: PRT
<213> ORGANISM: Neisseria gonorrhoeae

<400> SEQUENCE: 551

Thr Gly Glu Pro Leu Thr Ile Ala Ala Ala Lys
1               5                   10

<210> SEQ ID NO 552
<211> LENGTH: 14
<212> TYPE: PRT
<213> ORGANISM: Neisseria gonorrhoeae

<400> SEQUENCE: 552

Gln Leu Ser His Ser Asp Arg Pro Glu Leu Thr Gln Ala Lys
1               5                   10

<210> SEQ ID NO 553
<211> LENGTH: 15
<212> TYPE: PRT
<213> ORGANISM: Neisseria gonorrhoeae

<400> SEQUENCE: 553

Ala Val Ala Asp Lys Glu Asn Pro Gln Ile Phe Phe Leu Gly Lys
1               5                   10                  15

<210> SEQ ID NO 554
<211> LENGTH: 19
<212> TYPE: PRT
<213> ORGANISM: Neisseria gonorrhoeae

<400> SEQUENCE: 554

Lys Lys Pro Leu Glu Lys Leu Asp Ser Ala Asp Leu Ala Thr Asp Ile
1               5                   10                  15

Ser Pro Arg

```
<210> SEQ ID NO 555
<211> LENGTH: 13
<212> TYPE: PRT
<213> ORGANISM: Neisseria gonorrhoeae

<400> SEQUENCE: 555

Leu Asp Ser Ala Asp Leu Ala Thr Asp Ile Ser Pro Arg
1               5                   10

<210> SEQ ID NO 556
<211> LENGTH: 10
<212> TYPE: PRT
<213> ORGANISM: Neisseria gonorrhoeae

<400> SEQUENCE: 556

Val Ala Ser Val Ala Glu Leu Val Glu Lys
1               5                   10

<210> SEQ ID NO 557
<211> LENGTH: 8
<212> TYPE: PRT
<213> ORGANISM: Neisseria gonorrhoeae

<400> SEQUENCE: 557

Ile Ile Leu Val His Gly Val Arg
1               5

<210> SEQ ID NO 558
<211> LENGTH: 11
<212> TYPE: PRT
<213> ORGANISM: Neisseria gonorrhoeae

<400> SEQUENCE: 558

Thr Gly Val Arg Gly Asp Tyr Leu Ile Glu Arg
1               5                   10

<210> SEQ ID NO 559
<211> LENGTH: 25
<212> TYPE: PRT
<213> ORGANISM: Neisseria gonorrhoeae

<400> SEQUENCE: 559

Gln Leu Leu Asp His Ala Ala Glu Asn Ser Tyr Gly Leu Pro Ala Phe
1               5                   10                  15

Asn Val Asn Asn Leu Glu Gln Met Arg
            20                  25

<210> SEQ ID NO 560
<211> LENGTH: 22
<212> TYPE: PRT
<213> ORGANISM: Neisseria gonorrhoeae

<400> SEQUENCE: 560

Ala Ile Met Glu Ala Ala Asp Gln Val Asn Ala Pro Val Ile Val Gln
1               5                   10                  15

Ala Ser Ala Gly Ala Arg
            20

<210> SEQ ID NO 561
<211> LENGTH: 9
<212> TYPE: PRT
<213> ORGANISM: Neisseria gonorrhoeae
```

```
<400> SEQUENCE: 561

Lys Tyr Ala Gly Ala Pro Phe Leu Arg
1               5

<210> SEQ ID NO 562
<211> LENGTH: 15
<212> TYPE: PRT
<213> ORGANISM: Neisseria gonorrhoeae

<400> SEQUENCE: 562

Leu Ser His Asp Gln Met Leu Thr Ser Val Glu Asp Ala Val Arg
1               5                   10                  15

<210> SEQ ID NO 563
<211> LENGTH: 11
<212> TYPE: PRT
<213> ORGANISM: Neisseria gonorrhoeae

<400> SEQUENCE: 563

Phe Thr Arg Pro Pro Thr Gly Asp Val Leu Arg
1               5                   10

<210> SEQ ID NO 564
<211> LENGTH: 25
<212> TYPE: PRT
<213> ORGANISM: Neisseria gonorrhoeae

<400> SEQUENCE: 564

Val Ile Asn Glu Tyr Gly Gly Asn Ile Gly Glu Thr Tyr Gly Val Pro
1               5                   10                  15

Val Glu Glu Ile Val Glu Gly Ile Lys
            20                  25

<210> SEQ ID NO 565
<211> LENGTH: 9
<212> TYPE: PRT
<213> ORGANISM: Neisseria gonorrhoeae

<400> SEQUENCE: 565

Lys Val Asn Ile Asp Thr Asp Leu Arg
1               5

<210> SEQ ID NO 566
<211> LENGTH: 9
<212> TYPE: PRT
<213> ORGANISM: Neisseria gonorrhoeae

<400> SEQUENCE: 566

Leu Ala Ser Thr Gly Ala Val Arg Arg
1               5

<210> SEQ ID NO 567
<211> LENGTH: 17
<212> TYPE: PRT
<213> ORGANISM: Neisseria gonorrhoeae

<400> SEQUENCE: 567

Phe Gln Gly Thr Ala Glu Leu Lys Asp Asp Ala Ile Val Val Asn Gly
1               5                   10                  15

Arg

<210> SEQ ID NO 568
<211> LENGTH: 13
```

```
<212> TYPE: PRT
<213> ORGANISM: Neisseria gonorrhoeae

<400> SEQUENCE: 568

Lys Val Val Ile Ser Ala Pro Gly Gly Asn Asp Val Lys
1               5                   10

<210> SEQ ID NO 569
<211> LENGTH: 15
<212> TYPE: PRT
<213> ORGANISM: Neisseria gonorrhoeae

<400> SEQUENCE: 569

Ala Ala Ala Leu Asn Ile Val Pro Asn Ser Thr Gly Ala Ala Lys
1               5                   10                  15

<210> SEQ ID NO 570
<211> LENGTH: 12
<212> TYPE: PRT
<213> ORGANISM: Neisseria gonorrhoeae

<400> SEQUENCE: 570

Ala Ile Gly Leu Val Ile Pro Glu Leu Asn Gly Lys
1               5                   10

<210> SEQ ID NO 571
<211> LENGTH: 19
<212> TYPE: PRT
<213> ORGANISM: Neisseria gonorrhoeae

<400> SEQUENCE: 571

Ala Ile Gly Leu Val Ile Pro Glu Leu Asn Gly Lys Leu Asp Gly Ser
1               5                   10                  15

Ala Gln Arg

<210> SEQ ID NO 572
<211> LENGTH: 21
<212> TYPE: PRT
<213> ORGANISM: Neisseria gonorrhoeae

<400> SEQUENCE: 572

Val Pro Val Ala Thr Gly Ser Leu Thr Glu Leu Val Ser Val Leu Glu
1               5                   10                  15

Arg Pro Ala Thr Lys
            20

<210> SEQ ID NO 573
<211> LENGTH: 29
<212> TYPE: PRT
<213> ORGANISM: Neisseria gonorrhoeae

<400> SEQUENCE: 573

Val Pro Val Ala Thr Gly Ser Leu Thr Glu Leu Val Ser Val Leu Glu
1               5                   10                  15

Arg Pro Ala Thr Lys Glu Glu Ile Asn Ala Ala Met Lys
            20                  25

<210> SEQ ID NO 574
<211> LENGTH: 9
<212> TYPE: PRT
<213> ORGANISM: Neisseria gonorrhoeae

<400> SEQUENCE: 574
```

-continued

```
Thr Leu Glu Tyr Phe Ala Gly Lys Ile
1               5

<210> SEQ ID NO 575
<211> LENGTH: 12
<212> TYPE: PRT
<213> ORGANISM: Neisseria gonorrhoeae

<400> SEQUENCE: 575

Asn Ile Ala Ile Ile Ala His Val Asp His Gly Lys
1               5                   10

<210> SEQ ID NO 576
<211> LENGTH: 11
<212> TYPE: PRT
<213> ORGANISM: Neisseria gonorrhoeae

<400> SEQUENCE: 576

Val Met Asp Ser Asn Asp Leu Glu Lys Glu Arg
1               5                   10

<210> SEQ ID NO 577
<211> LENGTH: 14
<212> TYPE: PRT
<213> ORGANISM: Neisseria gonorrhoeae

<400> SEQUENCE: 577

Ala Leu Ala Leu Gly Leu Lys Pro Ile Val Val Ile Asn Lys
1               5                   10

<210> SEQ ID NO 578
<211> LENGTH: 19
<212> TYPE: PRT
<213> ORGANISM: Neisseria gonorrhoeae

<400> SEQUENCE: 578

Leu Glu Glu Thr Asp Glu Ser Ser Asp Met Arg Pro Leu Phe Asp Thr
1               5                   10                  15

Ile Leu Lys

<210> SEQ ID NO 579
<211> LENGTH: 20
<212> TYPE: PRT
<213> ORGANISM: Neisseria gonorrhoeae

<400> SEQUENCE: 579

Ile Lys Pro Gly Gln Thr Val Ala Val Met Asn His Glu Gln Gln Ile
1               5                   10                  15

Ala Gln Gly Arg
            20

<210> SEQ ID NO 580
<211> LENGTH: 8
<212> TYPE: PRT
<213> ORGANISM: Neisseria gonorrhoeae

<400> SEQUENCE: 580

Ile Asn Gln Leu Leu Gly Phe Lys
1               5

<210> SEQ ID NO 581
<211> LENGTH: 11
<212> TYPE: PRT
<213> ORGANISM: Neisseria gonorrhoeae
```

```
<400> SEQUENCE: 581

Glu Gly Tyr Glu Leu Ala Val Gly Lys Pro Arg
1               5                   10

<210> SEQ ID NO 582
<211> LENGTH: 10
<212> TYPE: PRT
<213> ORGANISM: Neisseria gonorrhoeae

<400> SEQUENCE: 582

Thr Arg Leu Glu Tyr His Ile Pro Ala Arg
1               5                   10

<210> SEQ ID NO 583
<211> LENGTH: 8
<212> TYPE: PRT
<213> ORGANISM: Neisseria gonorrhoeae

<400> SEQUENCE: 583

Leu Glu Tyr His Ile Pro Ala Arg
1               5

<210> SEQ ID NO 584
<211> LENGTH: 20
<212> TYPE: PRT
<213> ORGANISM: Neisseria gonorrhoeae

<400> SEQUENCE: 584

Met Gln Pro Ala Ile Val Glu Phe Val Asp Ile Ala Gly Leu Val Ala
1               5                   10                  15

Gly Ala Ser Lys
            20

<210> SEQ ID NO 585
<211> LENGTH: 13
<212> TYPE: PRT
<213> ORGANISM: Neisseria gonorrhoeae

<400> SEQUENCE: 585

Lys Leu Leu Pro His Leu Asp Glu Gly Lys Pro Val Arg
1               5                   10

<210> SEQ ID NO 586
<211> LENGTH: 28
<212> TYPE: PRT
<213> ORGANISM: Neisseria gonorrhoeae

<400> SEQUENCE: 586

Ser Thr Ile Val Tyr Thr His Thr Asp Glu Ala Pro Ala Leu Ala Thr
1               5                   10                  15

Gln Ser Leu Leu Pro Ile Val Gln Ala Phe Ala Arg
            20                  25

<210> SEQ ID NO 587
<211> LENGTH: 14
<212> TYPE: PRT
<213> ORGANISM: Neisseria gonorrhoeae

<400> SEQUENCE: 587

Ile Leu Ala Ala Phe Pro Glu Tyr Leu Thr Glu Ala Gln Arg
1               5                   10
```

<210> SEQ ID NO 588
<211> LENGTH: 16
<212> TYPE: PRT
<213> ORGANISM: Neisseria gonorrhoeae

<400> SEQUENCE: 588

Leu Pro Asn Ile Ser Ala Ser Val Pro Gln Leu Thr Ala Ala Ile Lys
1               5                   10                  15

<210> SEQ ID NO 589
<211> LENGTH: 11
<212> TYPE: PRT
<213> ORGANISM: Neisseria gonorrhoeae

<400> SEQUENCE: 589

Ile Lys Gly Ser Ala Val Asn Pro Val Leu Arg
1               5                   10

<210> SEQ ID NO 590
<211> LENGTH: 9
<212> TYPE: PRT
<213> ORGANISM: Neisseria gonorrhoeae

<400> SEQUENCE: 590

Gly Ser Ala Val Asn Pro Val Leu Arg
1               5

<210> SEQ ID NO 591
<211> LENGTH: 14
<212> TYPE: PRT
<213> ORGANISM: Neisseria gonorrhoeae

<400> SEQUENCE: 591

Asp Ala Pro Val Lys Asp Trp Val Gln Leu Ala Val Asn Arg
1               5                   10

<210> SEQ ID NO 592
<211> LENGTH: 18
<212> TYPE: PRT
<213> ORGANISM: Neisseria gonorrhoeae

<400> SEQUENCE: 592

Leu Ser Asn Thr Pro Ala Val Phe Trp Leu Asp Glu Asn Arg Pro His
1               5                   10                  15

Asp Lys

<210> SEQ ID NO 593
<211> LENGTH: 16
<212> TYPE: PRT
<213> ORGANISM: Neisseria gonorrhoeae

<400> SEQUENCE: 593

Leu Lys Asn Gly Glu Asp Thr Ile Ser Val Thr Gly Asn Val Leu Arg
1               5                   10                  15

<210> SEQ ID NO 594
<211> LENGTH: 17
<212> TYPE: PRT
<213> ORGANISM: Neisseria gonorrhoeae

<400> SEQUENCE: 594

Asp Tyr Leu Thr Asp Leu Phe Pro Ile Leu Glu Leu Gly Thr Ser Ala
1               5                   10                  15

Lys

<210> SEQ ID NO 595
<211> LENGTH: 12
<212> TYPE: PRT
<213> ORGANISM: Neisseria gonorrhoeae

<400> SEQUENCE: 595

His Val Gln Gln Phe Leu Glu Glu Asn His Leu Arg
1               5                   10

<210> SEQ ID NO 596
<211> LENGTH: 14
<212> TYPE: PRT
<213> ORGANISM: Neisseria gonorrhoeae

<400> SEQUENCE: 596

Ala Gln Val Leu Ala Asp Thr Leu Asp Ala Ala Thr Glu Lys
1               5                   10

<210> SEQ ID NO 597
<211> LENGTH: 16
<212> TYPE: PRT
<213> ORGANISM: Neisseria gonorrhoeae

<400> SEQUENCE: 597

Ala Ala Phe Ala Pro Leu Ala Ala Ala Leu Thr Ala Asp Glu Ala Lys
1               5                   10                  15

<210> SEQ ID NO 598
<211> LENGTH: 27
<212> TYPE: PRT
<213> ORGANISM: Neisseria gonorrhoeae

<400> SEQUENCE: 598

Ala Ala Phe Ala Pro Leu Ala Ala Ala Leu Thr Ala Asp Glu Ala Lys
1               5                   10                  15

Ile Val Glu Glu Leu Ser Ala Val Gln Gly Lys
            20                  25

<210> SEQ ID NO 599
<211> LENGTH: 18
<212> TYPE: PRT
<213> ORGANISM: Neisseria gonorrhoeae

<400> SEQUENCE: 599

Ala Ala Gln Ala Met Arg Pro Ser Ala Thr Phe Asn Gln Val Leu Asn
1               5                   10                  15

Ala Leu

<210> SEQ ID NO 600
<211> LENGTH: 9
<212> TYPE: PRT
<213> ORGANISM: Neisseria gonorrhoeae

<400> SEQUENCE: 600

Thr Pro Val Gly Leu Glu Ala Ile Arg
1               5

<210> SEQ ID NO 601
<211> LENGTH: 21
<212> TYPE: PRT
<213> ORGANISM: Neisseria gonorrhoeae

<400> SEQUENCE: 601

```
Ala Val Glu Asp Ala Gly Ala Val Phe Ala Ile Ser Pro Gly Leu His
1               5                   10                  15

Glu Ser Leu Ala Arg
            20

<210> SEQ ID NO 602
<211> LENGTH: 19
<212> TYPE: PRT
<213> ORGANISM: Neisseria gonorrhoeae

<400> SEQUENCE: 602

Asn Val Gly Asp Leu Ser Ser Leu Ser Ser Trp Thr Ala Glu Gln Phe
1               5                   10                  15

Asp Pro Arg

<210> SEQ ID NO 603
<211> LENGTH: 14
<212> TYPE: PRT
<213> ORGANISM: Neisseria gonorrhoeae

<400> SEQUENCE: 603

Ser Gly Ala Asp Ala Leu Val Val Ser Asn His Gly Gly Arg
1               5                   10

<210> SEQ ID NO 604
<211> LENGTH: 9
<212> TYPE: PRT
<213> ORGANISM: Neisseria gonorrhoeae

<400> SEQUENCE: 604

Phe His Glu Leu Pro Val Pro Gly Lys
1               5

<210> SEQ ID NO 605
<211> LENGTH: 12
<212> TYPE: PRT
<213> ORGANISM: Neisseria gonorrhoeae

<400> SEQUENCE: 605

Glu Thr Arg Pro Asp Val Val Ile Gly Thr Gly Arg
1               5                   10

<210> SEQ ID NO 606
<211> LENGTH: 16
<212> TYPE: PRT
<213> ORGANISM: Neisseria gonorrhoeae

<400> SEQUENCE: 606

Gly Ala Leu Asp Val Gly Ala Thr Thr Ile Asn Glu Glu Met Lys Arg
1               5                   10                  15

<210> SEQ ID NO 607
<211> LENGTH: 21
<212> TYPE: PRT
<213> ORGANISM: Neisseria gonorrhoeae

<400> SEQUENCE: 607

Ala Ala Met Glu Ser Gly Val Ala Thr Arg Pro Ile Ala Asp Leu Glu
1               5                   10                  15

Ala Tyr Ala Ala Lys
            20
```

```
<210> SEQ ID NO 608
<211> LENGTH: 20
<212> TYPE: PRT
<213> ORGANISM: Neisseria gonorrhoeae

<400> SEQUENCE: 608

Glu Gln Asn Leu Asn Glu Phe Leu Ala Val Lys Glu Asp Ile Val Ser
1               5                   10                  15

Gly Thr Val Lys
            20

<210> SEQ ID NO 609
<211> LENGTH: 11
<212> TYPE: PRT
<213> ORGANISM: Neisseria gonorrhoeae

<400> SEQUENCE: 609

His Gly Ile Ile Val Glu Val Val Ala Gly Lys
1               5                   10

<210> SEQ ID NO 610
<211> LENGTH: 11
<212> TYPE: PRT
<213> ORGANISM: Neisseria gonorrhoeae

<400> SEQUENCE: 610

Ile Asp Pro Gln Gly Thr Cys Ile Gly Val Arg
1               5                   10

<210> SEQ ID NO 611
<211> LENGTH: 12
<212> TYPE: PRT
<213> ORGANISM: Neisseria gonorrhoeae

<400> SEQUENCE: 611

Val Asn Ala Val Ser Asn Glu Leu Ser Gly Glu Arg
1               5                   10

<210> SEQ ID NO 612
<211> LENGTH: 9
<212> TYPE: PRT
<213> ORGANISM: Neisseria gonorrhoeae

<400> SEQUENCE: 612

Leu Gly Glu Val Ser Asp Asp Met Arg
1               5

<210> SEQ ID NO 613
<211> LENGTH: 21
<212> TYPE: PRT
<213> ORGANISM: Neisseria gonorrhoeae

<400> SEQUENCE: 613

Asn Leu Glu Gly Val Asp Ala Asp Met Leu Leu Ser Leu Ala Glu Ala
1               5                   10                  15

Gly Ile Thr Thr Arg
            20

<210> SEQ ID NO 614
<211> LENGTH: 16
<212> TYPE: PRT
<213> ORGANISM: Neisseria gonorrhoeae

<400> SEQUENCE: 614
```

-continued

Ser Ala Pro Leu Gln Glu Thr Ser His Ala Ala Val Pro Ala Ala Arg
1               5                   10                  15

<210> SEQ ID NO 615
<211> LENGTH: 12
<212> TYPE: PRT
<213> ORGANISM: Neisseria gonorrhoeae

<400> SEQUENCE: 615

Leu Gly Leu Gln Asp Gly Gln Thr Ala Val Ala Lys
1               5                   10

<210> SEQ ID NO 616
<211> LENGTH: 16
<212> TYPE: PRT
<213> ORGANISM: Neisseria gonorrhoeae

<400> SEQUENCE: 616

Ile Gly Asp Gly Lys Ile Phe Val Leu Pro Val Glu Glu Ala Ile Arg
1               5                   10                  15

<210> SEQ ID NO 617
<211> LENGTH: 11
<212> TYPE: PRT
<213> ORGANISM: Neisseria gonorrhoeae

<400> SEQUENCE: 617

Ile Phe Val Leu Pro Val Glu Glu Ala Ile Arg
1               5                   10

<210> SEQ ID NO 618
<211> LENGTH: 14
<212> TYPE: PRT
<213> ORGANISM: Neisseria gonorrhoeae

<400> SEQUENCE: 618

Leu Pro Ala His Glu Ala Lys Pro Ser Phe Glu Gln Glu Lys
1               5                   10

<210> SEQ ID NO 619
<211> LENGTH: 12
<212> TYPE: PRT
<213> ORGANISM: Neisseria gonorrhoeae

<400> SEQUENCE: 619

Ala Lys Pro Ala Asn Gly Lys Pro Ala Tyr Val Arg
1               5                   10

<210> SEQ ID NO 620
<211> LENGTH: 17
<212> TYPE: PRT
<213> ORGANISM: Neisseria gonorrhoeae

<400> SEQUENCE: 620

Gln Ala Leu Ala Gln Gln Gln Ser Ala Asn Thr Phe Asp Leu Leu Ile
1               5                   10                  15

Arg

<210> SEQ ID NO 621
<211> LENGTH: 16
<212> TYPE: PRT
<213> ORGANISM: Neisseria gonorrhoeae

<400> SEQUENCE: 621

```
Ala Leu Gln Asp Arg Thr Gly Gln Lys Val Pro Ser Val Val Phe Arg
1               5                   10                  15

<210> SEQ ID NO 622
<211> LENGTH: 11
<212> TYPE: PRT
<213> ORGANISM: Neisseria gonorrhoeae

<400> SEQUENCE: 622

Thr Gly Gln Lys Val Pro Ser Val Val Phe Arg
1               5                   10

<210> SEQ ID NO 623
<211> LENGTH: 7
<212> TYPE: PRT
<213> ORGANISM: Neisseria gonorrhoeae

<400> SEQUENCE: 623

Val Pro Ser Val Val Phe Arg
1               5

<210> SEQ ID NO 624
<211> LENGTH: 17
<212> TYPE: PRT
<213> ORGANISM: Neisseria gonorrhoeae

<400> SEQUENCE: 624

Thr Arg Val Gly Asp Thr Trp Lys Asp Val Ser Thr Asp Asp Leu Phe
1               5                   10                  15

Lys

<210> SEQ ID NO 625
<211> LENGTH: 15
<212> TYPE: PRT
<213> ORGANISM: Neisseria gonorrhoeae

<400> SEQUENCE: 625

Val Gly Asp Thr Trp Lys Asp Val Ser Thr Asp Asp Leu Phe Lys
1               5                   10                  15

<210> SEQ ID NO 626
<211> LENGTH: 22
<212> TYPE: PRT
<213> ORGANISM: Neisseria gonorrhoeae

<400> SEQUENCE: 626

Lys Val Val Val Phe Ser Leu Pro Gly Ala Phe Thr Pro Thr Cys Ser
1               5                   10                  15

Ser Ser His Leu Pro Arg
            20

<210> SEQ ID NO 627
<211> LENGTH: 21
<212> TYPE: PRT
<213> ORGANISM: Neisseria gonorrhoeae

<400> SEQUENCE: 627

Val Val Val Phe Ser Leu Pro Gly Ala Phe Thr Pro Thr Cys Ser Ser
1               5                   10                  15

Ser His Leu Pro Arg
            20

<210> SEQ ID NO 628
```

```
<211> LENGTH: 8
<212> TYPE: PRT
<213> ORGANISM: Neisseria gonorrhoeae

<400> SEQUENCE: 628

Glu Asp Leu Gly Phe Gly Lys Arg
1               5

<210> SEQ ID NO 629
<211> LENGTH: 12
<212> TYPE: PRT
<213> ORGANISM: Neisseria gonorrhoeae

<400> SEQUENCE: 629

Tyr Ser Met Leu Val Asn Asp Gly Val Val Glu Lys
1               5                   10

<210> SEQ ID NO 630
<211> LENGTH: 13
<212> TYPE: PRT
<213> ORGANISM: Neisseria gonorrhoeae

<400> SEQUENCE: 630

Met Phe Ile Glu Pro Glu Glu Pro Gly Asp Pro Phe Lys
1               5                   10

<210> SEQ ID NO 631
<211> LENGTH: 22
<212> TYPE: PRT
<213> ORGANISM: Neisseria gonorrhoeae

<400> SEQUENCE: 631

Met Phe Ile Glu Pro Glu Glu Pro Gly Asp Pro Phe Lys Val Ser Asp
1               5                   10                  15

Ala Asp Thr Met Leu Lys
            20

<210> SEQ ID NO 632
<211> LENGTH: 9
<212> TYPE: PRT
<213> ORGANISM: Neisseria gonorrhoeae

<400> SEQUENCE: 632

Val Ser Asp Ala Asp Thr Met Leu Lys
1               5

<210> SEQ ID NO 633
<211> LENGTH: 7
<212> TYPE: PRT
<213> ORGANISM: Neisseria gonorrhoeae

<400> SEQUENCE: 633

Phe Val Ala Pro Asp Trp Lys
1               5

<210> SEQ ID NO 634
<211> LENGTH: 25
<212> TYPE: PRT
<213> ORGANISM: Neisseria gonorrhoeae

<400> SEQUENCE: 634

Phe Val Ala Pro Asp Trp Lys Ala Gln Glu Ser Val Ala Ile Phe Thr
1               5                   10                  15

Lys Pro Gly Cys Gln Phe Cys Ala Lys
```

```
                    20                  25

<210> SEQ ID NO 635
<211> LENGTH: 18
<212> TYPE: PRT
<213> ORGANISM: Neisseria gonorrhoeae

<400> SEQUENCE: 635

Ala Gln Glu Ser Val Ala Ile Phe Thr Lys Pro Gly Cys Gln Phe Cys
1               5                   10                  15

Ala Lys

<210> SEQ ID NO 636
<211> LENGTH: 8
<212> TYPE: PRT
<213> ORGANISM: Neisseria gonorrhoeae

<400> SEQUENCE: 636

Val Lys Gln Ala Leu Gln Asp Lys
1               5

<210> SEQ ID NO 637
<211> LENGTH: 19
<212> TYPE: PRT
<213> ORGANISM: Neisseria gonorrhoeae

<400> SEQUENCE: 637

Val Lys Gln Ala Leu Gln Asp Lys Gly Leu Ser Tyr Glu Glu Ile Val
1               5                   10                  15

Leu Gly Lys

<210> SEQ ID NO 638
<211> LENGTH: 27
<212> TYPE: PRT
<213> ORGANISM: Neisseria gonorrhoeae

<400> SEQUENCE: 638

Val Lys Gln Ala Leu Gln Asp Lys Gly Leu Ser Tyr Glu Glu Ile Val
1               5                   10                  15

Leu Gly Lys Asp Ala Thr Val Thr Ser Val Arg
                    20                  25

<210> SEQ ID NO 639
<211> LENGTH: 17
<212> TYPE: PRT
<213> ORGANISM: Neisseria gonorrhoeae

<400> SEQUENCE: 639

Gln Ala Leu Gln Asp Lys Gly Leu Ser Tyr Glu Glu Ile Val Leu Gly
1               5                   10                  15

Lys

<210> SEQ ID NO 640
<211> LENGTH: 25
<212> TYPE: PRT
<213> ORGANISM: Neisseria gonorrhoeae

<400> SEQUENCE: 640

Gln Ala Leu Gln Asp Lys Gly Leu Ser Tyr Glu Glu Ile Val Leu Gly
1               5                   10                  15

Lys Asp Ala Thr Val Thr Ser Val Arg
                20                  25
```

<210> SEQ ID NO 641
<211> LENGTH: 19
<212> TYPE: PRT
<213> ORGANISM: Neisseria gonorrhoeae

<400> SEQUENCE: 641

Gly Leu Ser Tyr Glu Glu Ile Val Leu Gly Lys Asp Ala Thr Val Thr
1               5                   10                  15

Ser Val Arg

<210> SEQ ID NO 642
<211> LENGTH: 16
<212> TYPE: PRT
<213> ORGANISM: Neisseria gonorrhoeae

<400> SEQUENCE: 642

Ala Ile Thr Gly Lys Met Thr Ala Pro Gln Val Phe Ile Gly Gly Lys
1               5                   10                  15

<210> SEQ ID NO 643
<211> LENGTH: 11
<212> TYPE: PRT
<213> ORGANISM: Neisseria gonorrhoeae

<400> SEQUENCE: 643

Met Thr Ala Pro Gln Val Phe Ile Gly Gly Lys
1               5                   10

<210> SEQ ID NO 644
<211> LENGTH: 14
<212> TYPE: PRT
<213> ORGANISM: Neisseria gonorrhoeae

<400> SEQUENCE: 644

Tyr Ile Gly Gly Ser Glu Asp Leu Glu Ala Tyr Leu Ala Lys
1               5                   10

<210> SEQ ID NO 645
<211> LENGTH: 15
<212> TYPE: PRT
<213> ORGANISM: Neisseria gonorrhoeae

<400> SEQUENCE: 645

Tyr Ile Gly Gly Ser Glu Asp Leu Glu Ala Tyr Leu Ala Lys Asn
1               5                   10                  15

<210> SEQ ID NO 646
<211> LENGTH: 17
<212> TYPE: PRT
<213> ORGANISM: Neisseria gonorrhoeae

<400> SEQUENCE: 646

Asn Gln Leu Gly Cys Ser Asn Leu Ala His Gly Tyr Ala Ala Met Pro
1               5                   10                  15

Lys

<210> SEQ ID NO 647
<211> LENGTH: 8
<212> TYPE: PRT
<213> ORGANISM: Neisseria gonorrhoeae

<400> SEQUENCE: 647

```
Tyr Ala Ala Gly His Leu Ala Arg
1               5
```

<210> SEQ ID NO 648
<211> LENGTH: 17
<212> TYPE: PRT
<213> ORGANISM: Neisseria gonorrhoeae

<400> SEQUENCE: 648

```
Ala Asp Val Asn His Phe Thr Ala Ala Gly Gly Leu Pro Phe Val Ile
1               5                   10                  15

Arg
```

<210> SEQ ID NO 649
<211> LENGTH: 13
<212> TYPE: PRT
<213> ORGANISM: Neisseria gonorrhoeae

<400> SEQUENCE: 649

```
Lys Ala Asp Asn Pro Phe Ser Pro Asp Gly Gly Leu Arg
1               5                   10
```

<210> SEQ ID NO 650
<211> LENGTH: 11
<212> TYPE: PRT
<213> ORGANISM: Neisseria gonorrhoeae

<400> SEQUENCE: 650

```
Leu Thr Pro Pro Leu Gly Ile Leu Gln Asp Arg
1               5                   10
```

<210> SEQ ID NO 651
<211> LENGTH: 19
<212> TYPE: PRT
<213> ORGANISM: Neisseria gonorrhoeae

<400> SEQUENCE: 651

```
Val Pro Ala Ser Ile His Met Thr Pro Glu Ala Leu Met Gly Gly Asn
1               5                   10                  15

Ile Ala Lys
```

<210> SEQ ID NO 652
<211> LENGTH: 21
<212> TYPE: PRT
<213> ORGANISM: Neisseria gonorrhoeae

<400> SEQUENCE: 652

```
Val Leu Val Val Pro Val Ser Ala Gly Leu Asn Thr Ser Ala Ala Ala
1               5                   10                  15

Gln Ala Phe Ala Lys
            20
```

<210> SEQ ID NO 653
<211> LENGTH: 26
<212> TYPE: PRT
<213> ORGANISM: Neisseria gonorrhoeae

<400> SEQUENCE: 653

```
Val Ala Ala Leu Asp Ala Ala Asn Leu Val Ile Glu Gly Ile Ala Pro
1               5                   10                  15

Asp Ala Asp Lys Ile Tyr Leu Ala Gly Lys
            20                  25
```

```
<210> SEQ ID NO 654
<211> LENGTH: 21
<212> TYPE: PRT
<213> ORGANISM: Neisseria gonorrhoeae

<400> SEQUENCE: 654

Thr Gly Leu Thr Phe Phe Gly Ser Ser Asp Ala Leu Lys Asp Val Ser
1               5                   10                  15

Val Leu Ala Gly Arg
            20

<210> SEQ ID NO 655
<211> LENGTH: 8
<212> TYPE: PRT
<213> ORGANISM: Neisseria gonorrhoeae

<400> SEQUENCE: 655

Asp Val Ser Val Leu Ala Gly Arg
1               5

<210> SEQ ID NO 656
<211> LENGTH: 8
<212> TYPE: PRT
<213> ORGANISM: Neisseria gonorrhoeae

<400> SEQUENCE: 656

Arg Leu Ser Pro Ala Gln Phe Arg
1               5

<210> SEQ ID NO 657
<211> LENGTH: 10
<212> TYPE: PRT
<213> ORGANISM: Neisseria gonorrhoeae

<400> SEQUENCE: 657

Ile Val Leu Pro Glu Gly Ala Glu Pro Arg
1               5                   10

<210> SEQ ID NO 658
<211> LENGTH: 11
<212> TYPE: PRT
<213> ORGANISM: Neisseria gonorrhoeae

<400> SEQUENCE: 658

Thr Val Gln Ala Ala Ala Ile Cys His Glu Lys
1               5                   10

<210> SEQ ID NO 659
<211> LENGTH: 15
<212> TYPE: PRT
<213> ORGANISM: Neisseria gonorrhoeae

<400> SEQUENCE: 659

Thr Val Gln Ala Ala Ala Ile Cys His Glu Lys Gly Ile Ala Arg
1               5                   10                  15

<210> SEQ ID NO 660
<211> LENGTH: 11
<212> TYPE: PRT
<213> ORGANISM: Neisseria gonorrhoeae

<400> SEQUENCE: 660

Arg Glu Glu Val Glu Ala Val Ala Lys Glu Arg
1               5                   10
```

-continued

<210> SEQ ID NO 661
<211> LENGTH: 24
<212> TYPE: PRT
<213> ORGANISM: Neisseria gonorrhoeae

<400> SEQUENCE: 661

Glu Lys Arg Pro Asp Leu Ala Ile Asp Gly Pro Leu Gln Tyr Asp Ala
1               5                   10                  15

Ala Thr Val Pro Gly Val Gly Lys
            20

<210> SEQ ID NO 662
<211> LENGTH: 28
<212> TYPE: PRT
<213> ORGANISM: Neisseria gonorrhoeae

<400> SEQUENCE: 662

Ser Lys Ala Pro Gly Ser Pro Val Ala Gly Gln Ala Thr Val Leu Val
1               5                   10                  15

Phe Pro Asp Leu Asn Thr Gly Asn Cys Thr Tyr Lys
            20                  25

<210> SEQ ID NO 663
<211> LENGTH: 15
<212> TYPE: PRT
<213> ORGANISM: Neisseria gonorrhoeae

<400> SEQUENCE: 663

Ser Ala Asn Val Leu Ser Val Gly Pro Leu Leu Gln Gly Leu Arg
1               5                   10                  15

<210> SEQ ID NO 664
<211> LENGTH: 8
<212> TYPE: PRT
<213> ORGANISM: Neisseria gonorrhoeae

<400> SEQUENCE: 664

Lys Thr Asp Ala Lys Leu Pro Lys
1               5

<210> SEQ ID NO 665
<211> LENGTH: 8
<212> TYPE: PRT
<213> ORGANISM: Neisseria gonorrhoeae

<400> SEQUENCE: 665

Tyr Val Ile Ala Lys Leu Pro Lys
1               5

<210> SEQ ID NO 666
<211> LENGTH: 21
<212> TYPE: PRT
<213> ORGANISM: Neisseria gonorrhoeae

<400> SEQUENCE: 666

Asn Ile Val Ala Ser Val Pro Gln Asn Leu Ala Thr Ile Glu Gln Leu
1               5                   10                  15

Thr Tyr Thr Ala Lys
            20

<210> SEQ ID NO 667
<211> LENGTH: 21

<212> TYPE: PRT
<213> ORGANISM: Neisseria gonorrhoeae

<400> SEQUENCE: 667

Gly Ile Ala Gln Thr Val Ala Ser Gln Thr Asn Ala Asp Val Gln Cys
1               5                   10                  15
Val His Pro Ala Arg
            20

<210> SEQ ID NO 668
<211> LENGTH: 22
<212> TYPE: PRT
<213> ORGANISM: Neisseria gonorrhoeae

<400> SEQUENCE: 668

Tyr Phe Ala Asn Asp Leu Lys Thr Asp Glu Gln Gln Phe Glu Leu Asp
1               5                   10                  15
Ala Pro Thr Leu Thr Lys
            20

<210> SEQ ID NO 669
<211> LENGTH: 27
<212> TYPE: PRT
<213> ORGANISM: Neisseria gonorrhoeae

<400> SEQUENCE: 669

Ile Leu Asp Ser Leu Asn Glu Ala Val Pro Gly Ser Thr Tyr Leu Thr
1               5                   10                  15
Ser Leu Asp Ala Val Thr Ala Asp Ser Tyr Arg
            20                  25

<210> SEQ ID NO 670
<211> LENGTH: 17
<212> TYPE: PRT
<213> ORGANISM: Neisseria gonorrhoeae

<400> SEQUENCE: 670

Ala Ala Glu Ser Lys Glu Asn Pro Ala Ser Gly Asn Ala Gln Glu Ala
1               5                   10                  15
Asn

<210> SEQ ID NO 671
<211> LENGTH: 13
<212> TYPE: PRT
<213> ORGANISM: Neisseria gonorrhoeae

<400> SEQUENCE: 671

Phe Gln Ile Glu His Gln Ile Glu Ser Ala Phe Ser Arg
1               5                   10

<210> SEQ ID NO 672
<211> LENGTH: 15
<212> TYPE: PRT
<213> ORGANISM: Neisseria gonorrhoeae

<400> SEQUENCE: 672

Leu Lys Pro Ala Leu Gly Glu Ser Ser His Ala Ala Cys Pro Arg
1               5                   10                  15

<210> SEQ ID NO 673
<211> LENGTH: 11
<212> TYPE: PRT
<213> ORGANISM: Neisseria gonorrhoeae

<400> SEQUENCE: 673

Gly Ile Glu Ser Thr Ala Leu His Val Leu Arg
1               5                   10

<210> SEQ ID NO 674
<211> LENGTH: 15
<212> TYPE: PRT
<213> ORGANISM: Neisseria gonorrhoeae

<400> SEQUENCE: 674

Ala Gln Val Pro Val Asp Val Ala Thr Phe Leu Leu Asn Glu Lys
1               5                   10                  15

<210> SEQ ID NO 675
<211> LENGTH: 16
<212> TYPE: PRT
<213> ORGANISM: Neisseria gonorrhoeae

<400> SEQUENCE: 675

Ala Gln Val Pro Val Asp Val Ala Thr Phe Leu Leu Asn Glu Lys Arg
1               5                   10                  15

<210> SEQ ID NO 676
<211> LENGTH: 16
<212> TYPE: PRT
<213> ORGANISM: Neisseria gonorrhoeae

<400> SEQUENCE: 676

Ile Arg Thr Asp Asp Val Glu Glu Asp Gly Glu Pro Ser Tyr Lys Arg
1               5                   10                  15

<210> SEQ ID NO 677
<211> LENGTH: 17
<212> TYPE: PRT
<213> ORGANISM: Neisseria gonorrhoeae

<400> SEQUENCE: 677

Val Ala Glu Pro Glu Glu Asp Glu Ser Ala Lys Pro Phe Gly Gly Glu
1               5                   10                  15

Lys

<210> SEQ ID NO 678
<211> LENGTH: 9
<212> TYPE: PRT
<213> ORGANISM: Neisseria gonorrhoeae

<400> SEQUENCE: 678

Ala Ala Arg Pro Glu Pro Ala Val Lys
1               5

<210> SEQ ID NO 679
<211> LENGTH: 12
<212> TYPE: PRT
<213> ORGANISM: Neisseria gonorrhoeae

<400> SEQUENCE: 679

His Thr Ser Pro Ala Pro Thr Ala Ala Pro Glu Lys
1               5                   10

<210> SEQ ID NO 680
<211> LENGTH: 19
<212> TYPE: PRT
<213> ORGANISM: Neisseria gonorrhoeae

<400> SEQUENCE: 680

Ile Phe Gly Gly Ser Glu Thr Gln Ala Val Pro Ala Ala Glu Thr Ser
1               5                   10                  15

Glu Lys Arg

<210> SEQ ID NO 681
<211> LENGTH: 23
<212> TYPE: PRT
<213> ORGANISM: Neisseria gonorrhoeae

<400> SEQUENCE: 681

Asn Val Gln Pro Ala Ala Pro Val Ala Asp Ala Ala Pro Pro Glu Thr
1               5                   10                  15

Glu Gly Gln Thr Gly Lys Arg
            20

<210> SEQ ID NO 682
<211> LENGTH: 15
<212> TYPE: PRT
<213> ORGANISM: Neisseria gonorrhoeae

<400> SEQUENCE: 682

Ile Glu Gln Tyr Leu Asn Ile His Asp Thr Ala Asp Lys Val Arg
1               5                   10                  15

<210> SEQ ID NO 683
<211> LENGTH: 12
<212> TYPE: PRT
<213> ORGANISM: Neisseria gonorrhoeae

<400> SEQUENCE: 683

Ala Trp Ala Ala Gln Pro Glu Val Gln Ala Gly Arg
1               5                   10

<210> SEQ ID NO 684
<211> LENGTH: 15
<212> TYPE: PRT
<213> ORGANISM: Neisseria gonorrhoeae

<400> SEQUENCE: 684

Ile Tyr Gln Arg Pro Phe Gly Gly His Thr Ala Glu His Gly Lys
1               5                   10                  15

<210> SEQ ID NO 685
<211> LENGTH: 8
<212> TYPE: PRT
<213> ORGANISM: Neisseria gonorrhoeae

<400> SEQUENCE: 685

Ile Asp His Ile Gly Ala Glu Lys
1               5

<210> SEQ ID NO 686
<211> LENGTH: 10
<212> TYPE: PRT
<213> ORGANISM: Neisseria gonorrhoeae

<400> SEQUENCE: 686

Ser Val Gln Leu His Ala Gly Val Phe Arg
1               5                   10

<210> SEQ ID NO 687

```
<211> LENGTH: 8
<212> TYPE: PRT
<213> ORGANISM: Neisseria gonorrhoeae

<400> SEQUENCE: 687

Thr Glu His Val Val Trp Gln Lys
1               5

<210> SEQ ID NO 688
<211> LENGTH: 13
<212> TYPE: PRT
<213> ORGANISM: Neisseria gonorrhoeae

<400> SEQUENCE: 688

Leu Ala Ala Ala Val Asp Met Ala Ala Ala Glu Ser Lys
1               5                   10

<210> SEQ ID NO 689
<211> LENGTH: 28
<212> TYPE: PRT
<213> ORGANISM: Neisseria gonorrhoeae

<400> SEQUENCE: 689

Leu Ala Ala Ala Val Asp Met Ala Ala Ala Glu Ser Lys Asp Val Ala
1               5                   10                  15

Asn Ser His Ile Phe Asp Ala Met Val Asn Gln Lys
            20                  25

<210> SEQ ID NO 690
<211> LENGTH: 15
<212> TYPE: PRT
<213> ORGANISM: Neisseria gonorrhoeae

<400> SEQUENCE: 690

Asp Val Ala Asn Ser His Ile Phe Asp Ala Met Val Asn Gln Lys
1               5                   10                  15

<210> SEQ ID NO 691
<211> LENGTH: 11
<212> TYPE: PRT
<213> ORGANISM: Neisseria gonorrhoeae

<400> SEQUENCE: 691

Ile Lys Leu Gln Glu Pro Glu Val Leu Lys Lys
1               5                   10

<210> SEQ ID NO 692
<211> LENGTH: 13
<212> TYPE: PRT
<213> ORGANISM: Neisseria gonorrhoeae

<400> SEQUENCE: 692

Val Leu Ala Ala Tyr Glu Ser Pro Glu Ser Gln Ala Arg
1               5                   10

<210> SEQ ID NO 693
<211> LENGTH: 17
<212> TYPE: PRT
<213> ORGANISM: Neisseria gonorrhoeae

<400> SEQUENCE: 693

Ala Gln Met Tyr Ser Leu Gln Asp Gly Asn Ile His Asn Ile Ala Val
1               5                   10                  15

Lys
```

<210> SEQ ID NO 694
<211> LENGTH: 17
<212> TYPE: PRT
<213> ORGANISM: Neisseria gonorrhoeae

<400> SEQUENCE: 694

Asn Ser Ala His Thr Tyr Val Thr Ser Ser Pro Ser Met Asp Ile Ser
1               5                   10                  15

Lys

<210> SEQ ID NO 695
<211> LENGTH: 10
<212> TYPE: PRT
<213> ORGANISM: Neisseria gonorrhoeae

<400> SEQUENCE: 695

Phe Leu Asn His Asn Pro Ala Asn Pro Lys
1               5                   10

<210> SEQ ID NO 696
<211> LENGTH: 12
<212> TYPE: PRT
<213> ORGANISM: Neisseria gonorrhoeae

<400> SEQUENCE: 696

Ala Glu Thr Gly Lys Pro Ser Ile Ile Cys Cys Lys
1               5                   10

<210> SEQ ID NO 697
<211> LENGTH: 16
<212> TYPE: PRT
<213> ORGANISM: Neisseria gonorrhoeae

<400> SEQUENCE: 697

Thr His Gly Ala Pro Leu Gly Ala Asp Glu Ile Glu Ala Thr Arg Lys
1               5                   10                  15

<210> SEQ ID NO 698
<211> LENGTH: 15
<212> TYPE: PRT
<213> ORGANISM: Neisseria gonorrhoeae

<400> SEQUENCE: 698

Leu Glu Ala Gly Trp Asn Glu Leu Phe Ala Gln Tyr Gln Ala Lys
1               5                   10                  15

<210> SEQ ID NO 699
<211> LENGTH: 10
<212> TYPE: PRT
<213> ORGANISM: Neisseria gonorrhoeae

<400> SEQUENCE: 699

Tyr Pro Ala Glu Ala Ala Glu Phe Val Arg
1               5                   10

<210> SEQ ID NO 700
<211> LENGTH: 15
<212> TYPE: PRT
<213> ORGANISM: Neisseria gonorrhoeae

<400> SEQUENCE: 700

Lys Leu Pro Glu Asn Phe Asp Glu Tyr Val Gln Thr Ala Leu Lys
1               5                   10                  15

<210> SEQ ID NO 701
<211> LENGTH: 12
<212> TYPE: PRT
<213> ORGANISM: Neisseria gonorrhoeae

<400> SEQUENCE: 701

Lys Ala Ser Gln Asn Ser Ile Glu Ile Leu Ala Lys
1               5                   10

<210> SEQ ID NO 702
<211> LENGTH: 12
<212> TYPE: PRT
<213> ORGANISM: Neisseria gonorrhoeae

<400> SEQUENCE: 702

Asp Lys Gly Gly Asn Tyr Ile His Tyr Gly Val Arg
1               5                   10

<210> SEQ ID NO 703
<211> LENGTH: 10
<212> TYPE: PRT
<213> ORGANISM: Neisseria gonorrhoeae

<400> SEQUENCE: 703

Val Leu Ala Gly Gln Gly Ile Ala Val Arg
1               5                   10

<210> SEQ ID NO 704
<211> LENGTH: 13
<212> TYPE: PRT
<213> ORGANISM: Neisseria gonorrhoeae

<400> SEQUENCE: 704

Tyr Val Gly Leu Asn Gly Ala Val Val Gly Ile Asn Arg
1               5                   10

<210> SEQ ID NO 705
<211> LENGTH: 14
<212> TYPE: PRT
<213> ORGANISM: Neisseria gonorrhoeae

<400> SEQUENCE: 705

Ala Phe Gly Phe Thr Val Asp Asn Val Val Asp Thr Val Lys
1               5                   10

<210> SEQ ID NO 706
<211> LENGTH: 11
<212> TYPE: PRT
<213> ORGANISM: Neisseria gonorrhoeae

<400> SEQUENCE: 706

Ile Asn Ser Ala Leu Thr Pro Gln Pro Gln Lys
1               5                   10

<210> SEQ ID NO 707
<211> LENGTH: 16
<212> TYPE: PRT
<213> ORGANISM: Neisseria gonorrhoeae

<400> SEQUENCE: 707

Glu Leu Gly Leu Pro Glu Lys Leu Lys Asp Leu Ala Val Ala Pro Arg
1               5                   10                  15

```
<210> SEQ ID NO 708
<211> LENGTH: 15
<212> TYPE: PRT
<213> ORGANISM: Neisseria gonorrhoeae

<400> SEQUENCE: 708

Gly Ser Asp Leu Phe Val Thr Thr His Phe Pro Pro Ala Met Lys
1               5                   10                  15

<210> SEQ ID NO 709
<211> LENGTH: 7
<212> TYPE: PRT
<213> ORGANISM: Neisseria gonorrhoeae

<400> SEQUENCE: 709

Leu Asp Gly Lys Ile Thr Arg
1               5

<210> SEQ ID NO 710
<211> LENGTH: 10
<212> TYPE: PRT
<213> ORGANISM: Neisseria gonorrhoeae

<400> SEQUENCE: 710

Ile Thr Asp Glu Pro Leu Thr Ala Glu Lys
1               5                   10

<210> SEQ ID NO 711
<211> LENGTH: 15
<212> TYPE: PRT
<213> ORGANISM: Neisseria gonorrhoeae

<400> SEQUENCE: 711

Ile Gly Ala Ile Asp Phe Leu Glu Lys Pro Ile Ser Leu Gln Lys
1               5                   10                  15

<210> SEQ ID NO 712
<211> LENGTH: 11
<212> TYPE: PRT
<213> ORGANISM: Neisseria gonorrhoeae

<400> SEQUENCE: 712

Ser Thr Val Pro Ile Ile Met Leu Thr Ala Lys
1               5                   10

<210> SEQ ID NO 713
<211> LENGTH: 7
<212> TYPE: PRT
<213> ORGANISM: Neisseria gonorrhoeae

<400> SEQUENCE: 713

Ile Asn Ala Ile Leu Arg Arg
1               5

<210> SEQ ID NO 714
<211> LENGTH: 26
<212> TYPE: PRT
<213> ORGANISM: Neisseria gonorrhoeae

<400> SEQUENCE: 714

Ala Gln His Ser Gly Glu Gln Asn Asn Ala Pro Asn Ser Ile Ser Val
1               5                   10                  15

Ser Asp Val Val Leu Tyr Pro Ala Lys Arg
            20                  25
```

```
<210> SEQ ID NO 715
<211> LENGTH: 11
<212> TYPE: PRT
<213> ORGANISM: Neisseria gonorrhoeae

<400> SEQUENCE: 715

Leu Gly Asp Ala Ser Leu Ile Gln Thr Val Arg
1               5                   10

<210> SEQ ID NO 716
<211> LENGTH: 12
<212> TYPE: PRT
<213> ORGANISM: Neisseria gonorrhoeae

<400> SEQUENCE: 716

Val Gln Trp Leu Asp Pro Val Pro Glu Val Leu Arg
1               5                   10

<210> SEQ ID NO 717
<211> LENGTH: 22
<212> TYPE: PRT
<213> ORGANISM: Neisseria gonorrhoeae

<400> SEQUENCE: 717

Phe Gly Val Ile Gln Thr Gly Leu Gln Leu Gln Gly Lys Pro Gln Ser
1               5                   10                  15

Ala Pro Pro Thr Gln Lys
            20

<210> SEQ ID NO 718
<211> LENGTH: 14
<212> TYPE: PRT
<213> ORGANISM: Neisseria gonorrhoeae

<400> SEQUENCE: 718

Ala Ala Ala Glu His Pro Leu Ser Val Gln Asn Glu Glu Arg
1               5                   10

<210> SEQ ID NO 719
<211> LENGTH: 11
<212> TYPE: PRT
<213> ORGANISM: Neisseria gonorrhoeae

<400> SEQUENCE: 719

Lys Val Asn Ile Asn Ile Pro Phe Pro Gln Arg
1               5                   10

<210> SEQ ID NO 720
<211> LENGTH: 15
<212> TYPE: PRT
<213> ORGANISM: Neisseria gonorrhoeae

<400> SEQUENCE: 720

Ile Val Ile Met Ala Ala Leu Asn Val Val His Asp Leu Leu Lys
1               5                   10                  15

<210> SEQ ID NO 721
<211> LENGTH: 19
<212> TYPE: PRT
<213> ORGANISM: Neisseria gonorrhoeae

<400> SEQUENCE: 721

Ser Glu Gln Ala Ala Glu Gly Val Tyr Asn Tyr Ile Thr Val Ala Ser
1               5                   10                  15
```

Leu Pro Arg

<210> SEQ ID NO 722
<211> LENGTH: 11
<212> TYPE: PRT
<213> ORGANISM: Neisseria gonorrhoeae

<400> SEQUENCE: 722

Gln Gly Asp Thr Leu Trp Gly Ile Ser Gly Lys
1               5                   10

<210> SEQ ID NO 723
<211> LENGTH: 10
<212> TYPE: PRT
<213> ORGANISM: Neisseria gonorrhoeae

<400> SEQUENCE: 723

Tyr Leu Tyr Ser Pro Trp Gln Trp Cys Arg
1               5                   10

<210> SEQ ID NO 724
<211> LENGTH: 24
<212> TYPE: PRT
<213> ORGANISM: Neisseria gonorrhoeae

<400> SEQUENCE: 724

Leu Trp Gly Ala Asn Arg Asp Gln Ile His Asn Pro Asp Leu Ile Tyr
1               5                   10                  15

Pro Gly Gln Val Leu Val Leu Arg
            20

<210> SEQ ID NO 725
<211> LENGTH: 18
<212> TYPE: PRT
<213> ORGANISM: Neisseria gonorrhoeae

<400> SEQUENCE: 725

Asp Gln Ile His Asn Pro Asp Leu Ile Tyr Pro Gly Gln Val Leu Val
1               5                   10                  15

Leu Arg

<210> SEQ ID NO 726
<211> LENGTH: 21
<212> TYPE: PRT
<213> ORGANISM: Neisseria gonorrhoeae

<400> SEQUENCE: 726

Ile Ser Pro Asp Lys Glu Val Ser Gly Tyr Gly Ile Pro Ala Ile Asp
1               5                   10                  15

Val Asn Phe Tyr Arg
            20

<210> SEQ ID NO 727
<211> LENGTH: 11
<212> TYPE: PRT
<213> ORGANISM: Neisseria gonorrhoeae

<400> SEQUENCE: 727

Val Phe Met Gln His Pro Gln Ile Val Ser Arg
1               5                   10

<210> SEQ ID NO 728

```
<211> LENGTH: 12
<212> TYPE: PRT
<213> ORGANISM: Neisseria gonorrhoeae

<400> SEQUENCE: 728

Val Phe Met Gln His Pro Gln Ile Val Ser Arg Lys
1               5                   10

<210> SEQ ID NO 729
<211> LENGTH: 19
<212> TYPE: PRT
<213> ORGANISM: Neisseria gonorrhoeae

<400> SEQUENCE: 729

Val Phe Met Gln His Pro Gln Ile Val Ser Arg Lys Glu Thr Ala Ala
1               5                   10                  15

Ala Pro Arg

<210> SEQ ID NO 730
<211> LENGTH: 8
<212> TYPE: PRT
<213> ORGANISM: Neisseria gonorrhoeae

<400> SEQUENCE: 730

Leu Leu Ser Gly Pro Glu Gly Arg
1               5

<210> SEQ ID NO 731
<211> LENGTH: 25
<212> TYPE: PRT
<213> ORGANISM: Neisseria gonorrhoeae

<400> SEQUENCE: 731

Ile Asn Lys Asn Ile Thr Asp Pro Asp Thr Gly Lys Phe Leu Gly Gln
1               5                   10                  15

Glu Val Ala Phe Ser Gly Ile Val Arg
            20                  25

<210> SEQ ID NO 732
<211> LENGTH: 22
<212> TYPE: PRT
<213> ORGANISM: Neisseria gonorrhoeae

<400> SEQUENCE: 732

Asn Ile Thr Asp Pro Asp Thr Gly Lys Phe Leu Gly Gln Glu Val Ala
1               5                   10                  15

Phe Ser Gly Ile Val Arg
            20

<210> SEQ ID NO 733
<211> LENGTH: 13
<212> TYPE: PRT
<213> ORGANISM: Neisseria gonorrhoeae

<400> SEQUENCE: 733

Phe Leu Gly Gln Glu Val Ala Phe Ser Gly Ile Val Arg
1               5                   10

<210> SEQ ID NO 734
<211> LENGTH: 12
<212> TYPE: PRT
<213> ORGANISM: Neisseria gonorrhoeae

<400> SEQUENCE: 734
```

```
Ser Leu Asp Tyr Thr Asp Ser Ala Leu Glu Gln Arg
1               5                   10
```

<210> SEQ ID NO 735
<211> LENGTH: 9
<212> TYPE: PRT
<213> ORGANISM: Neisseria gonorrhoeae

<400> SEQUENCE: 735

```
Leu Lys Asp Asn Glu Tyr Tyr Thr Arg
1               5
```

<210> SEQ ID NO 736
<211> LENGTH: 22
<212> TYPE: PRT
<213> ORGANISM: Neisseria gonorrhoeae

<400> SEQUENCE: 736

```
Ser Ile Gln Pro Leu Val Val Glu Thr Ala Ile Ser Glu Ile Gln Gln
1               5                   10                  15

Gly Asp Tyr Leu Met Lys
            20
```

<210> SEQ ID NO 737
<211> LENGTH: 15
<212> TYPE: PRT
<213> ORGANISM: Neisseria gonorrhoeae

<400> SEQUENCE: 737

```
Ile Val Ser Val Phe Glu Gly Val Gly Val Gly Gly Gln Phe Lys
1               5                   10                  15
```

<210> SEQ ID NO 738
<211> LENGTH: 23
<212> TYPE: PRT
<213> ORGANISM: Neisseria gonorrhoeae

<400> SEQUENCE: 738

```
Thr Ile Thr Ile Asp Lys Gly Gly Asp Gly Leu Asp Lys Gly Ala
1               5                   10                  15

Val Leu Ser Leu Tyr Lys Arg
            20
```

<210> SEQ ID NO 739
<211> LENGTH: 17
<212> TYPE: PRT
<213> ORGANISM: Neisseria gonorrhoeae

<400> SEQUENCE: 739

```
Lys Lys Thr Met Gln Val Asn Leu Ser Asn Asn Leu Thr Glu Glu Pro
1               5                   10                  15

Lys
```

<210> SEQ ID NO 740
<211> LENGTH: 15
<212> TYPE: PRT
<213> ORGANISM: Neisseria gonorrhoeae

<400> SEQUENCE: 740

```
Thr Met Gln Val Asn Leu Ser Asn Asn Leu Thr Glu Glu Pro Lys
1               5                   10                  15
```

<210> SEQ ID NO 741
<211> LENGTH: 26
<212> TYPE: PRT
<213> ORGANISM: Neisseria gonorrhoeae

<400> SEQUENCE: 741

Ser Arg Asp Thr Val Glu Leu Ile Ser Thr Pro Ala Glu Glu Val Gly
1               5                   10                  15

Leu Ala Met Val Tyr His Thr Ala Pro Lys
            20                  25

<210> SEQ ID NO 742
<211> LENGTH: 24
<212> TYPE: PRT
<213> ORGANISM: Neisseria gonorrhoeae

<400> SEQUENCE: 742

Asp Thr Val Glu Leu Ile Ser Thr Pro Ala Glu Glu Val Gly Leu Ala
1               5                   10                  15

Met Val Tyr His Thr Ala Pro Lys
            20

<210> SEQ ID NO 743
<211> LENGTH: 10
<212> TYPE: PRT
<213> ORGANISM: Neisseria gonorrhoeae

<400> SEQUENCE: 743

Asp Leu Asp Asn Met Pro Asp Gln Gly Arg
1               5                   10

<210> SEQ ID NO 744
<211> LENGTH: 13
<212> TYPE: PRT
<213> ORGANISM: Neisseria gonorrhoeae

<400> SEQUENCE: 744

Ile Tyr Leu Glu Ser Lys Gln Ala Arg Asn Ile Gln Lys
1               5                   10

<210> SEQ ID NO 745
<211> LENGTH: 14
<212> TYPE: PRT
<213> ORGANISM: Neisseria gonorrhoeae

<400> SEQUENCE: 745

Thr Ile Leu His Ala Pro Asp Lys Gln Ser Leu Thr Tyr Lys
1               5                   10

<210> SEQ ID NO 746
<211> LENGTH: 15
<212> TYPE: PRT
<213> ORGANISM: Neisseria gonorrhoeae

<400> SEQUENCE: 746

Leu Leu Thr Ala Gly Pro Asn Leu Leu Pro Asp Asn Pro Glu Arg
1               5                   10                  15

<210> SEQ ID NO 747
<211> LENGTH: 14
<212> TYPE: PRT
<213> ORGANISM: Neisseria gonorrhoeae

<400> SEQUENCE: 747

-continued

Ile Asp Ser Ser Val Ile Asp Ala Gln Val Ala Ala Phe Arg
1               5                   10

<210> SEQ ID NO 748
<211> LENGTH: 8
<212> TYPE: PRT
<213> ORGANISM: Neisseria gonorrhoeae

<400> SEQUENCE: 748

Ala Glu Asp Thr Pro Gln Leu Arg
1               5

<210> SEQ ID NO 749
<211> LENGTH: 19
<212> TYPE: PRT
<213> ORGANISM: Neisseria gonorrhoeae

<400> SEQUENCE: 749

Gln Ser Leu Leu Glu Asn Glu Val Val Asn Thr Val Val Ala Gln Glu
1               5                   10                  15

Val Lys Arg

<210> SEQ ID NO 750
<211> LENGTH: 10
<212> TYPE: PRT
<213> ORGANISM: Neisseria gonorrhoeae

<400> SEQUENCE: 750

Ser Ala Glu Phe Lys Asp Ala Leu Ala Lys
1               5                   10

<210> SEQ ID NO 751
<211> LENGTH: 11
<212> TYPE: PRT
<213> ORGANISM: Neisseria gonorrhoeae

<400> SEQUENCE: 751

Lys Ser Gly Asp Asp Lys Lys Pro Ser Phe Lys
1               5                   10

<210> SEQ ID NO 752
<211> LENGTH: 18
<212> TYPE: PRT
<213> ORGANISM: Neisseria gonorrhoeae

<400> SEQUENCE: 752

Val Ala Pro Lys Pro Thr Pro Glu Gln Ile Leu Asn Ser Gly Ser Ile
1               5                   10                  15

Glu Lys

<210> SEQ ID NO 753
<211> LENGTH: 15
<212> TYPE: PRT
<213> ORGANISM: Neisseria gonorrhoeae

<400> SEQUENCE: 753

Ala Ala Thr Pro Gly Pro Tyr Thr Phe Ile Leu Gln Ala Thr Lys
1               5                   10                  15

<210> SEQ ID NO 754
<211> LENGTH: 10
<212> TYPE: PRT
<213> ORGANISM: Neisseria gonorrhoeae

<400> SEQUENCE: 754

Ser Ala Lys Asn Asn Gly Asn Val Gln Arg
1               5                   10

<210> SEQ ID NO 755
<211> LENGTH: 8
<212> TYPE: PRT
<213> ORGANISM: Neisseria gonorrhoeae

<400> SEQUENCE: 755

Arg Ile Met Val Gly Lys Asn Lys
1               5

<210> SEQ ID NO 756
<211> LENGTH: 26
<212> TYPE: PRT
<213> ORGANISM: Neisseria gonorrhoeae

<400> SEQUENCE: 756

Phe Lys Pro Leu Ala Leu Gly Ile Asp Gln Asp Leu Ile Ala Ala Leu
1               5                   10                  15

Pro Gln Tyr Asp Ser Ala Leu Ile Ala Arg
            20                  25

<210> SEQ ID NO 757
<211> LENGTH: 29
<212> TYPE: PRT
<213> ORGANISM: Neisseria gonorrhoeae

<400> SEQUENCE: 757

Ala Gly Ala Thr Asp Ser Glu Ile Ala Gly Ala Leu Ala Thr Ala Ile
1               5                   10                  15

Ala Leu Asn Ala Gly Ala Ala Tyr Thr Tyr Ala Leu Arg
            20                  25

<210> SEQ ID NO 758
<211> LENGTH: 9
<212> TYPE: PRT
<213> ORGANISM: Neisseria gonorrhoeae

<400> SEQUENCE: 758

Ala Leu Glu Ala Val Glu Thr Gln Lys
1               5

<210> SEQ ID NO 759
<211> LENGTH: 13
<212> TYPE: PRT
<213> ORGANISM: Neisseria gonorrhoeae

<400> SEQUENCE: 759

Thr Glu Gln Glu Thr Leu Gln Thr Ile Pro Ser Pro Lys
1               5                   10

<210> SEQ ID NO 760
<211> LENGTH: 18
<212> TYPE: PRT
<213> ORGANISM: Neisseria gonorrhoeae

<400> SEQUENCE: 760

Val Val Phe Val Ser Ile Asp Pro Glu Arg Asp Thr Pro Glu Ile Ile
1               5                   10                  15

Gly Lys

```
<210> SEQ ID NO 761
<211> LENGTH: 21
<212> TYPE: PRT
<213> ORGANISM: Neisseria gonorrhoeae

<400> SEQUENCE: 761

Gln Phe Asn Pro Asp Phe Ile Gly Leu Thr Ala Thr Gly Gly Gln Asn
1               5                   10                  15

Leu Pro Val Ile Lys
            20

<210> SEQ ID NO 762
<211> LENGTH: 24
<212> TYPE: PRT
<213> ORGANISM: Neisseria gonorrhoeae

<400> SEQUENCE: 762

Ile Val Ala Leu Val Thr Val Lys Pro Glu Tyr Thr Glu Thr Leu Ala
1               5                   10                  15

Ala Gln Phe Lys Glu Leu Val Lys
            20

<210> SEQ ID NO 763
<211> LENGTH: 11
<212> TYPE: PRT
<213> ORGANISM: Neisseria gonorrhoeae

<400> SEQUENCE: 763

Ser Val Gln Ile Asn Gly Gln Ala Ala Lys Pro
1               5                   10

<210> SEQ ID NO 764
<211> LENGTH: 10
<212> TYPE: PRT
<213> ORGANISM: Neisseria gonorrhoeae

<400> SEQUENCE: 764

Val Lys Pro Ala Gly Tyr Ala Ala Pro Lys
1               5                   10

<210> SEQ ID NO 765
<211> LENGTH: 40
<212> TYPE: PRT
<213> ORGANISM: Neisseria gonorrhoeae

<400> SEQUENCE: 765

Thr Ala Ala Val Glu Ser Arg Pro Ala Val Pro Ala Ala Ala Gln Thr
1               5                   10                  15

Pro Val Lys Pro Ala Ala Gln Pro Pro Val Gln Ser Ala Pro Gln Pro
            20                  25                  30

Ala Ala Pro Ala Ala Glu Asn Lys
        35                  40

<210> SEQ ID NO 766
<211> LENGTH: 20
<212> TYPE: PRT
<213> ORGANISM: Neisseria gonorrhoeae

<400> SEQUENCE: 766

Ala Val Pro Ala Pro Ala Pro Ala Pro Gln Ser Pro Ala Ala Ser Pro
1               5                   10                  15

Ser Gly Thr Arg
```

-continued

```
                20

<210> SEQ ID NO 767
<211> LENGTH: 14
<212> TYPE: PRT
<213> ORGANISM: Neisseria gonorrhoeae

<400> SEQUENCE: 767

Ser Val Gly Gly Ile Val Trp Gln Arg Pro Thr Gln Gly Lys
1               5                   10

<210> SEQ ID NO 768
<211> LENGTH: 11
<212> TYPE: PRT
<213> ORGANISM: Neisseria gonorrhoeae

<400> SEQUENCE: 768

Ala Ser Ala Glu Glu Ala Val Thr Glu Ala Lys
1               5                   10

<210> SEQ ID NO 769
<211> LENGTH: 18
<212> TYPE: PRT
<213> ORGANISM: Neisseria gonorrhoeae

<400> SEQUENCE: 769

Ala Ser Ala Glu Glu Ala Val Thr Glu Ala Lys Asp Ala Ala Ala Glu
1               5                   10                  15

Thr Lys

<210> SEQ ID NO 770
<211> LENGTH: 31
<212> TYPE: PRT
<213> ORGANISM: Neisseria gonorrhoeae

<400> SEQUENCE: 770

Ala Ser Ala Glu Glu Ala Val Thr Glu Ala Lys Asp Ala Ala Ala Glu
1               5                   10                  15

Thr Lys Glu Ala Val Ser Glu Ala Ala Lys Asp Thr Leu Asn Lys
            20                  25                  30

<210> SEQ ID NO 771
<211> LENGTH: 13
<212> TYPE: PRT
<213> ORGANISM: Neisseria gonorrhoeae

<400> SEQUENCE: 771

Glu Ala Val Ser Glu Ala Ala Lys Asp Thr Leu Asn Lys
1               5                   10

<210> SEQ ID NO 772
<211> LENGTH: 30
<212> TYPE: PRT
<213> ORGANISM: Neisseria gonorrhoeae

<400> SEQUENCE: 772

Glu Ala Val Ser Glu Ala Ala Lys Asp Thr Leu Asn Lys Ala Ala Asp
1               5                   10                  15

Ala Ala Gln Glu Ala Ala Asp Lys Met Lys Asp Ala Ala Lys
            20                  25                  30

<210> SEQ ID NO 773
<211> LENGTH: 13
```

<212> TYPE: PRT
<213> ORGANISM: Neisseria gonorrhoeae

<400> SEQUENCE: 773

Ala Ala Asp Ala Ala Gln Glu Ala Ala Asp Lys Met Lys
1               5                   10

<210> SEQ ID NO 774
<211> LENGTH: 17
<212> TYPE: PRT
<213> ORGANISM: Neisseria gonorrhoeae

<400> SEQUENCE: 774

Ala Ala Asp Ala Ala Gln Glu Ala Ala Asp Lys Met Lys Asp Ala Ala
1               5                   10                  15

Lys

<210> SEQ ID NO 775
<211> LENGTH: 17
<212> TYPE: PRT
<213> ORGANISM: Neisseria gonorrhoeae

<400> SEQUENCE: 775

His Leu Val Val Ala Val Asp Gly Ser Glu Thr Ser Ile Asn Ala Leu
1               5                   10                  15

Lys

<210> SEQ ID NO 776
<211> LENGTH: 12
<212> TYPE: PRT
<213> ORGANISM: Neisseria gonorrhoeae

<400> SEQUENCE: 776

His Ala Ala Glu Leu Ala Gly Val Asn Gly Ala Arg
1               5                   10

<210> SEQ ID NO 777
<211> LENGTH: 42
<212> TYPE: PRT
<213> ORGANISM: Neisseria gonorrhoeae

<400> SEQUENCE: 777

Leu Thr Leu Val His Val Ala Asn Pro Ala Glu Tyr Met Ala Leu Ala
1               5                   10                  15

Pro Glu Phe Leu Gln His Glu Ser Tyr Glu Ala Ala Ala Val Ala Gln
            20                  25                  30

Gly Asn Glu Val Leu Asp Ala Ala Glu Arg
        35                  40

<210> SEQ ID NO 778
<211> LENGTH: 14
<212> TYPE: PRT
<213> ORGANISM: Neisseria gonorrhoeae

<400> SEQUENCE: 778

Thr Pro Ala Val Gln Gln Pro Ala Asp Ala Glu Val Leu Lys
1               5                   10

<210> SEQ ID NO 779
<211> LENGTH: 12
<212> TYPE: PRT
<213> ORGANISM: Neisseria gonorrhoeae

```
<400> SEQUENCE: 779

Lys Pro Thr Leu Pro Ala Ala Asn Glu Met Ala Arg
1               5                   10

<210> SEQ ID NO 780
<211> LENGTH: 18
<212> TYPE: PRT
<213> ORGANISM: Neisseria gonorrhoeae

<400> SEQUENCE: 780

Ala Pro Asn Glu Ser Asn Ala Val Thr Glu Gln Lys Pro Gly Leu Phe
1               5                   10                  15

Lys Arg

<210> SEQ ID NO 781
<211> LENGTH: 7
<212> TYPE: PRT
<213> ORGANISM: Neisseria gonorrhoeae

<400> SEQUENCE: 781

Leu Arg Val Glu Ala Gln Arg
1               5

<210> SEQ ID NO 782
<211> LENGTH: 15
<212> TYPE: PRT
<213> ORGANISM: Neisseria gonorrhoeae

<400> SEQUENCE: 782

Asn Ile Leu Leu Pro Leu Ala Thr Glu His Gly Gln Ile Ala Arg
1               5                   10                  15

<210> SEQ ID NO 783
<211> LENGTH: 15
<212> TYPE: PRT
<213> ORGANISM: Neisseria gonorrhoeae

<400> SEQUENCE: 783

Ala Ala Leu Ala Gly Ser Asn Ile Asp Pro Ile Ala Phe Glu Arg
1               5                   10                  15

<210> SEQ ID NO 784
<211> LENGTH: 12
<212> TYPE: PRT
<213> ORGANISM: Neisseria gonorrhoeae

<400> SEQUENCE: 784

Ile Ala Lys Asp Glu Pro Asp Met Pro Arg Pro Lys
1               5                   10

<210> SEQ ID NO 785
<211> LENGTH: 32
<212> TYPE: PRT
<213> ORGANISM: Neisseria gonorrhoeae

<400> SEQUENCE: 785

Leu Phe Asp Glu His Asn Glu Leu Asp Asp Lys Ile Thr Gly Leu Ala
1               5                   10                  15

Asn Asn Pro Val Thr Ser Gly Ala Glu Thr Ile Asp Glu Leu Lys Lys
                20                  25                  30

<210> SEQ ID NO 786
<211> LENGTH: 13
```

```
<212> TYPE: PRT
<213> ORGANISM: Neisseria gonorrhoeae

<400> SEQUENCE: 786

Leu Lys Leu Lys Asp Glu Leu Tyr Ala Ile Leu Gln Lys
1               5                   10

<210> SEQ ID NO 787
<211> LENGTH: 12
<212> TYPE: PRT
<213> ORGANISM: Neisseria gonorrhoeae

<400> SEQUENCE: 787

Ala Asn Glu Asn Ser Pro Asn Ile Tyr Phe Ile Arg
1               5                   10

<210> SEQ ID NO 788
<211> LENGTH: 11
<212> TYPE: PRT
<213> ORGANISM: Neisseria gonorrhoeae

<400> SEQUENCE: 788

Ile Asp Asp Leu Gly Ser Thr Val Gln Gly Arg
1               5                   10

<210> SEQ ID NO 789
<211> LENGTH: 10
<212> TYPE: PRT
<213> ORGANISM: Neisseria gonorrhoeae

<400> SEQUENCE: 789

Leu Leu Asp Ser Gln Asp Pro Thr Ala Arg
1               5                   10

<210> SEQ ID NO 790
<211> LENGTH: 20
<212> TYPE: PRT
<213> ORGANISM: Neisseria gonorrhoeae

<400> SEQUENCE: 790

Ala Thr Phe Tyr Ile Val Pro Asn Met Asn Pro Asp Gly Ser Ala Leu
1               5                   10                  15

Gly Asn Leu Arg
            20

<210> SEQ ID NO 791
<211> LENGTH: 12
<212> TYPE: PRT
<213> ORGANISM: Neisseria gonorrhoeae

<400> SEQUENCE: 791

Ser Pro Ile Ala Phe Phe Asn Ala Leu Ser Gln Lys
1               5                   10

<210> SEQ ID NO 792
<211> LENGTH: 15
<212> TYPE: PRT
<213> ORGANISM: Neisseria gonorrhoeae

<400> SEQUENCE: 792

Ile Val Pro Thr Asn His Ala Asp Ser Asn Thr Gly Leu Val Arg
1               5                   10                  15

<210> SEQ ID NO 793
```

```
<211> LENGTH: 11
<212> TYPE: PRT
<213> ORGANISM: Neisseria gonorrhoeae

<400> SEQUENCE: 793

Asn Leu Asp Lys Thr Gln Ala Ala Ala Glu Arg
1               5                   10

<210> SEQ ID NO 794
<211> LENGTH: 15
<212> TYPE: PRT
<213> ORGANISM: Neisseria gonorrhoeae

<400> SEQUENCE: 794

Ala Ala Glu Gln Thr Gly Asn Ala Val Glu Lys Gly Trp Asp Lys
1               5                   10                  15

<210> SEQ ID NO 795
<211> LENGTH: 17
<212> TYPE: PRT
<213> ORGANISM: Neisseria gonorrhoeae

<400> SEQUENCE: 795

Ala Ala Glu Gln Thr Gly Asn Ala Val Glu Lys Gly Trp Asp Lys Thr
1               5                   10                  15

Lys

<210> SEQ ID NO 796
<211> LENGTH: 21
<212> TYPE: PRT
<213> ORGANISM: Neisseria gonorrhoeae

<400> SEQUENCE: 796

Ala Ala Glu Gln Thr Gly Asn Ala Val Glu Lys Gly Trp Asp Lys Thr
1               5                   10                  15

Lys Glu Ala Val Lys
            20

<210> SEQ ID NO 797
<211> LENGTH: 22
<212> TYPE: PRT
<213> ORGANISM: Neisseria gonorrhoeae

<400> SEQUENCE: 797

Ala Ala Glu Gln Thr Gly Asn Ala Val Glu Lys Gly Trp Asp Lys Thr
1               5                   10                  15

Lys Glu Ala Val Lys Lys
            20

<210> SEQ ID NO 798
<211> LENGTH: 14
<212> TYPE: PRT
<213> ORGANISM: Neisseria gonorrhoeae

<400> SEQUENCE: 798

Ala Ala Val Ala Ala Ala Thr Asn Asp Val Glu Asn Lys Lys
1               5                   10

<210> SEQ ID NO 799
<211> LENGTH: 14
<212> TYPE: PRT
<213> ORGANISM: Neisseria gonorrhoeae

<400> SEQUENCE: 799
```

```
Lys Gln Gly Val Thr Asp Ala Ala Glu Gln Thr Glu Ser Arg
1               5                   10
```

<210> SEQ ID NO 800
<211> LENGTH: 13
<212> TYPE: PRT
<213> ORGANISM: Neisseria gonorrhoeae

<400> SEQUENCE: 800

```
Gln Gly Val Thr Asp Ala Ala Glu Gln Thr Glu Ser Arg
1               5                   10
```

<210> SEQ ID NO 801
<211> LENGTH: 7
<212> TYPE: PRT
<213> ORGANISM: Neisseria gonorrhoeae

<400> SEQUENCE: 801

```
Leu Lys Gln Pro Arg Arg Arg
1               5
```

<210> SEQ ID NO 802
<211> LENGTH: 19
<212> TYPE: PRT
<213> ORGANISM: Neisseria gonorrhoeae

<400> SEQUENCE: 802

```
Gly Val Ala Val Ile Asn His Pro Asn Pro Leu Gln Gly Gly Thr Asn
1               5                   10                  15

Thr Asn Lys
```

<210> SEQ ID NO 803
<211> LENGTH: 17
<212> TYPE: PRT
<213> ORGANISM: Neisseria gonorrhoeae

<400> SEQUENCE: 803

```
Leu Asn Phe Gly Gln Ile Gly Ser His Ile Ala Gly Asp Gly Ala Val
1               5                   10                  15

Arg
```

<210> SEQ ID NO 804
<211> LENGTH: 11
<212> TYPE: PRT
<213> ORGANISM: Neisseria gonorrhoeae

<400> SEQUENCE: 804

```
Leu Gly Ser Leu Gln Glu Gln Arg Ala Pro Arg
1               5                   10
```

<210> SEQ ID NO 805
<211> LENGTH: 16
<212> TYPE: PRT
<213> ORGANISM: Neisseria gonorrhoeae

<400> SEQUENCE: 805

```
Asn Ala Val Asp Ile Gly Ser Lys Pro Asn Ala Asp Val Ala Trp Lys
1               5                   10                  15
```

<210> SEQ ID NO 806
<211> LENGTH: 13
<212> TYPE: PRT
<213> ORGANISM: Neisseria gonorrhoeae

```
<400> SEQUENCE: 806

Asn Lys Pro Ala Gly Ile Ile Ser His Ser Val Gly Lys
1               5                   10

<210> SEQ ID NO 807
<211> LENGTH: 28
<212> TYPE: PRT
<213> ORGANISM: Neisseria gonorrhoeae

<400> SEQUENCE: 807

Val Gly Gln His Val Val Glu Pro Tyr Ile Ile Arg Asp Asp Val
1               5                   10                  15

Pro Thr Gly Glu Gly Ser Asn Tyr His Leu Ser Lys
            20                  25

<210> SEQ ID NO 808
<211> LENGTH: 17
<212> TYPE: PRT
<213> ORGANISM: Neisseria gonorrhoeae

<400> SEQUENCE: 808

Asp Met Asn Phe Ile Gly Leu Gly Gly Cys Gly Gly Gly Leu Ser Glu
1               5                   10                  15

Lys

<210> SEQ ID NO 809
<211> LENGTH: 22
<212> TYPE: PRT
<213> ORGANISM: Neisseria gonorrhoeae

<400> SEQUENCE: 809

Ala Gly Asp Val Ala Leu Val Gly Gly Ala Gly Pro Ile Gly Leu Leu
1               5                   10                  15

Leu Ala Ala Val Leu Lys
            20

<210> SEQ ID NO 810
<211> LENGTH: 13
<212> TYPE: PRT
<213> ORGANISM: Neisseria gonorrhoeae

<400> SEQUENCE: 810

Ile Lys Leu Asp Lys Leu Val Ser Glu Gly Phe Glu Arg
1               5                   10

<210> SEQ ID NO 811
<211> LENGTH: 10
<212> TYPE: PRT
<213> ORGANISM: Neisseria gonorrhoeae

<400> SEQUENCE: 811

Leu Ile His Asn Asn Glu Ser Ala Val Lys
1               5                   10

<210> SEQ ID NO 812
<211> LENGTH: 10
<212> TYPE: PRT
<213> ORGANISM: Neisseria gonorrhoeae

<400> SEQUENCE: 812

Ala Gln Tyr Leu Leu Glu Asn Leu Leu Lys
1               5                   10
```

<210> SEQ ID NO 813
<211> LENGTH: 19
<212> TYPE: PRT
<213> ORGANISM: Neisseria gonorrhoeae

<400> SEQUENCE: 813

Met Pro His Gly Thr Thr Thr Pro Tyr Leu Asn Thr Val Ser Val Glu
1               5                   10                  15

Asn Glu Lys

<210> SEQ ID NO 814
<211> LENGTH: 10
<212> TYPE: PRT
<213> ORGANISM: Neisseria gonorrhoeae

<400> SEQUENCE: 814

Leu Thr Glu Asp Gln Leu Asn Asn Phe Arg
1               5                   10

<210> SEQ ID NO 815
<211> LENGTH: 16
<212> TYPE: PRT
<213> ORGANISM: Neisseria gonorrhoeae

<400> SEQUENCE: 815

Glu Gly Leu Asp Asn Leu Ile Phe Val Ile Asn Cys Asn Leu Gln Arg
1               5                   10                  15

<210> SEQ ID NO 816
<211> LENGTH: 18
<212> TYPE: PRT
<213> ORGANISM: Neisseria gonorrhoeae

<400> SEQUENCE: 816

Ile Ile Gln Glu Leu Glu Gly Asn Phe Ala Gly Ala Gly Trp Asn Val
1               5                   10                  15

Val Lys

<210> SEQ ID NO 817
<211> LENGTH: 11
<212> TYPE: PRT
<213> ORGANISM: Neisseria gonorrhoeae

<400> SEQUENCE: 817

Leu Leu Ala Lys Asp Lys Asp Gly Ile Leu Arg
1               5                   10

<210> SEQ ID NO 818
<211> LENGTH: 16
<212> TYPE: PRT
<213> ORGANISM: Neisseria gonorrhoeae

<400> SEQUENCE: 818

Asp Gly Ala Tyr Val Arg Glu His Phe Phe Asn Thr Pro Glu Leu Lys
1               5                   10                  15

<210> SEQ ID NO 819
<211> LENGTH: 16
<212> TYPE: PRT
<213> ORGANISM: Neisseria gonorrhoeae

<400> SEQUENCE: 819

Ala Leu Val Ala Asp Met Thr Asp Glu Gln Leu Trp Ala Leu Asn Arg
1               5                   10                  15

<210> SEQ ID NO 820
<211> LENGTH: 14
<212> TYPE: PRT
<213> ORGANISM: Neisseria gonorrhoeae

<400> SEQUENCE: 820

Gly Gly His Asp Pro Gln Lys Val Tyr Asn Ala Tyr Asp Arg
1               5                   10

<210> SEQ ID NO 821
<211> LENGTH: 15
<212> TYPE: PRT
<213> ORGANISM: Neisseria gonorrhoeae

<400> SEQUENCE: 821

Ala Ala Asn His Ala Asp Gly Lys Pro Thr Val Ile Leu Ala Lys
1               5                   10                  15

<210> SEQ ID NO 822
<211> LENGTH: 21
<212> TYPE: PRT
<213> ORGANISM: Neisseria gonorrhoeae

<400> SEQUENCE: 822

Thr Ile Lys Gly Tyr Gly Met Gly Ala Ser Gly Glu Gly Gln Asn Val
1               5                   10                  15

Ala His Gln Ala Lys
            20

<210> SEQ ID NO 823
<211> LENGTH: 18
<212> TYPE: PRT
<213> ORGANISM: Neisseria gonorrhoeae

<400> SEQUENCE: 823

Gly Tyr Gly Met Gly Ala Ser Gly Glu Gly Gln Asn Val Ala His Gln
1               5                   10                  15

Ala Lys

<210> SEQ ID NO 824
<211> LENGTH: 7
<212> TYPE: PRT
<213> ORGANISM: Neisseria gonorrhoeae

<400> SEQUENCE: 824

Ala Ser Leu Lys Gln Phe Arg
1               5

<210> SEQ ID NO 825
<211> LENGTH: 11
<212> TYPE: PRT
<213> ORGANISM: Neisseria gonorrhoeae

<400> SEQUENCE: 825

Arg Asp Ala Leu Gly Gly Tyr Leu Pro Gln Arg
1               5                   10

<210> SEQ ID NO 826
<211> LENGTH: 10
<212> TYPE: PRT
<213> ORGANISM: Neisseria gonorrhoeae

<400> SEQUENCE: 826

Asp Ala Leu Gly Gly Tyr Leu Pro Gln Arg
1               5                   10

<210> SEQ ID NO 827
<211> LENGTH: 20
<212> TYPE: PRT
<213> ORGANISM: Neisseria gonorrhoeae

<400> SEQUENCE: 827

Lys Pro Thr Gln Glu Val Leu Glu Val Pro Glu Leu Ser Ala Phe Asp
1               5                   10                  15

Ala Gln Leu Lys
            20

<210> SEQ ID NO 828
<211> LENGTH: 15
<212> TYPE: PRT
<213> ORGANISM: Neisseria gonorrhoeae

<400> SEQUENCE: 828

Ser Ser Gly Glu Arg Glu Phe Ser Thr Thr Met Ala Phe Val Arg
1               5                   10                  15

<210> SEQ ID NO 829
<211> LENGTH: 10
<212> TYPE: PRT
<213> ORGANISM: Neisseria gonorrhoeae

<400> SEQUENCE: 829

Ile Leu Ser Thr Leu Leu Lys Asp Lys Lys
1               5                   10

<210> SEQ ID NO 830
<211> LENGTH: 9
<212> TYPE: PRT
<213> ORGANISM: Neisseria gonorrhoeae

<400> SEQUENCE: 830

Thr Phe Gly Met Glu Gly Met Phe Arg
1               5

<210> SEQ ID NO 831
<211> LENGTH: 16
<212> TYPE: PRT
<213> ORGANISM: Neisseria gonorrhoeae

<400> SEQUENCE: 831

Gly Gln Gln Tyr Thr Pro Gln Asp Lys Asp Gln Leu Met Phe Tyr Lys
1               5                   10                  15

<210> SEQ ID NO 832
<211> LENGTH: 14
<212> TYPE: PRT
<213> ORGANISM: Neisseria gonorrhoeae

<400> SEQUENCE: 832

Ile Gly Asp Leu Ala Trp Ala Ala Gly Asp Met His Ala Arg
1               5                   10

<210> SEQ ID NO 833
<211> LENGTH: 22
<212> TYPE: PRT

<213> ORGANISM: Neisseria gonorrhoeae

<400> SEQUENCE: 833

Lys Val Gln Leu Met Gly Ser Gly Thr Ile Leu Gln Glu Val Ile Ala
1               5                   10                  15
Gly Ala Glu Leu Leu Lys
            20

<210> SEQ ID NO 834
<211> LENGTH: 21
<212> TYPE: PRT
<213> ORGANISM: Neisseria gonorrhoeae

<400> SEQUENCE: 834

Val Gln Leu Met Gly Ser Gly Thr Ile Leu Gln Glu Val Ile Ala Gly
1               5                   10                  15
Ala Glu Leu Leu Lys
            20

<210> SEQ ID NO 835
<211> LENGTH: 20
<212> TYPE: PRT
<213> ORGANISM: Neisseria gonorrhoeae

<400> SEQUENCE: 835

Ala Asp Phe Gly Val Glu Ala Asp Ile Trp Ser Cys Pro Ser Phe Asn
1               5                   10                  15
Leu Leu His Arg
            20

<210> SEQ ID NO 836
<211> LENGTH: 31
<212> TYPE: PRT
<213> ORGANISM: Neisseria gonorrhoeae

<400> SEQUENCE: 836

Leu His Pro Leu Glu Ala Glu Lys Val Pro Phe Val Thr Ser Gln Leu
1               5                   10                  15
Gln Gly His Asp Gly Pro Val Ile Ala Ala Thr Asp Tyr Ile Arg
            20                  25                  30

<210> SEQ ID NO 837
<211> LENGTH: 23
<212> TYPE: PRT
<213> ORGANISM: Neisseria gonorrhoeae

<400> SEQUENCE: 837

Val Pro Phe Val Thr Ser Gln Leu Gln Gly His Asp Gly Pro Val Ile
1               5                   10                  15
Ala Ala Thr Asp Tyr Ile Arg
            20

<210> SEQ ID NO 838
<211> LENGTH: 17
<212> TYPE: PRT
<213> ORGANISM: Neisseria gonorrhoeae

<400> SEQUENCE: 838

Ala Tyr Ile Pro Asn Asp Tyr His Val Leu Gly Thr Asp Gly Phe Gly
1               5                   10                  15
Arg

<210> SEQ ID NO 839
<211> LENGTH: 22
<212> TYPE: PRT
<213> ORGANISM: Neisseria gonorrhoeae

<400> SEQUENCE: 839

Phe Phe Glu Val Asp Arg Tyr Asn Val Ala Val Ala Ala Leu Ala Ala
1               5                   10                  15

Leu Ala Glu Gln Gly Lys
            20

<210> SEQ ID NO 840
<211> LENGTH: 16
<212> TYPE: PRT
<213> ORGANISM: Neisseria gonorrhoeae

<400> SEQUENCE: 840

Tyr Asn Val Ala Val Ala Ala Leu Ala Ala Leu Ala Glu Gln Gly Lys
1               5                   10                  15

<210> SEQ ID NO 841
<211> LENGTH: 19
<212> TYPE: PRT
<213> ORGANISM: Neisseria gonorrhoeae

<400> SEQUENCE: 841

Tyr Asn Val Ala Val Ala Ala Leu Ala Ala Leu Ala Glu Gln Gly Lys
1               5                   10                  15

Val Ser Lys

<210> SEQ ID NO 842
<211> LENGTH: 12
<212> TYPE: PRT
<213> ORGANISM: Neisseria gonorrhoeae

<400> SEQUENCE: 842

Val Ser Lys Glu Thr Val Gln Gln Ala Ile Glu Lys
1               5                   10

<210> SEQ ID NO 843
<211> LENGTH: 12
<212> TYPE: PRT
<213> ORGANISM: Neisseria gonorrhoeae

<400> SEQUENCE: 843

Tyr Gly Ile Lys Ala Asp Ser Ala Pro Ser Trp Lys
1               5                   10

<210> SEQ ID NO 844
<211> LENGTH: 13
<212> TYPE: PRT
<213> ORGANISM: Neisseria gonorrhoeae

<400> SEQUENCE: 844

Tyr Gly Ile Lys Ala Asp Ser Ala Pro Ser Trp Lys Arg
1               5                   10

<210> SEQ ID NO 845
<211> LENGTH: 9
<212> TYPE: PRT
<213> ORGANISM: Neisseria gonorrhoeae

<400> SEQUENCE: 845

```
Ala Asp Ser Ala Pro Ser Trp Lys Arg
1               5

<210> SEQ ID NO 846
<211> LENGTH: 20
<212> TYPE: PRT
<213> ORGANISM: Neisseria gonorrhoeae

<400> SEQUENCE: 846

Ile Val Ala Thr Leu Gly Pro Gly Ser Asn Asn Val Glu Leu Leu Glu
1               5                   10                  15

Asp Met Ile Arg
            20

<210> SEQ ID NO 847
<211> LENGTH: 8
<212> TYPE: PRT
<213> ORGANISM: Neisseria gonorrhoeae

<400> SEQUENCE: 847

Val Gly Gly Leu Asn Val Val Arg
1               5

<210> SEQ ID NO 848
<211> LENGTH: 16
<212> TYPE: PRT
<213> ORGANISM: Neisseria gonorrhoeae

<400> SEQUENCE: 848

Phe Asn Phe Ser His Gly Thr Pro Glu Phe His Gln Glu Asn Ala Arg
1               5                   10                  15

<210> SEQ ID NO 849
<211> LENGTH: 15
<212> TYPE: PRT
<213> ORGANISM: Neisseria gonorrhoeae

<400> SEQUENCE: 849

Gly Gly Gly Leu Ser Ala Gly Ala Leu Thr Glu Lys Asp Phe Arg
1               5                   10                  15

<210> SEQ ID NO 850
<211> LENGTH: 12
<212> TYPE: PRT
<213> ORGANISM: Neisseria gonorrhoeae

<400> SEQUENCE: 850

Gly Ser Thr Ala Val Arg Pro Gly Leu Val Ser Lys
1               5                   10

<210> SEQ ID NO 851
<211> LENGTH: 17
<212> TYPE: PRT
<213> ORGANISM: Neisseria gonorrhoeae

<400> SEQUENCE: 851

Gly Asp Leu Ala Val Glu Val Gly His Ala Ala Val Pro Ala Leu Gln
1               5                   10                  15

Lys

<210> SEQ ID NO 852
<211> LENGTH: 18
<212> TYPE: PRT
<213> ORGANISM: Neisseria gonorrhoeae
```

```
<400> SEQUENCE: 852

His Asn Ile Thr Leu Pro Ile Phe Ala Leu Thr Pro Ser Val Ser Ala
1               5                   10                  15

Gln Arg

<210> SEQ ID NO 853
<211> LENGTH: 15
<212> TYPE: PRT
<213> ORGANISM: Neisseria gonorrhoeae

<400> SEQUENCE: 853

Phe Ser Asp Gly Glu Val Ala Val Glu Leu Leu Glu Asn Val Arg
1               5                   10                  15

<210> SEQ ID NO 854
<211> LENGTH: 9
<212> TYPE: PRT
<213> ORGANISM: Neisseria gonorrhoeae

<400> SEQUENCE: 854

Ser Val Arg Val Pro Ile Ser Ala Lys
1               5

<210> SEQ ID NO 855
<211> LENGTH: 13
<212> TYPE: PRT
<213> ORGANISM: Neisseria gonorrhoeae

<400> SEQUENCE: 855

Leu Val Ala Asn Met Leu Tyr Ser Ala Gly Ile Asp Arg
1               5                   10

<210> SEQ ID NO 856
<211> LENGTH: 16
<212> TYPE: PRT
<213> ORGANISM: Neisseria gonorrhoeae

<400> SEQUENCE: 856

Ala Asn Val Ala Glu Val Met Asn Ile Ile Gly Asp Ile Gln Gly Lys
1               5                   10                  15

<210> SEQ ID NO 857
<211> LENGTH: 22
<212> TYPE: PRT
<213> ORGANISM: Neisseria gonorrhoeae

<400> SEQUENCE: 857

Ile Ala Ser Ser Glu Ile Asp Gln Val Val Val Thr Asp Thr Ile Pro
1               5                   10                  15

Leu Ser Glu Ala Ala Lys
            20

<210> SEQ ID NO 858
<211> LENGTH: 13
<212> TYPE: PRT
<213> ORGANISM: Neisseria gonorrhoeae

<400> SEQUENCE: 858

Gln Val Thr Ile Ala Gly Leu Leu Ala Glu Thr Val Arg
1               5                   10

<210> SEQ ID NO 859
```

```
<211> LENGTH: 16
<212> TYPE: PRT
<213> ORGANISM: Neisseria gonorrhoeae

<400> SEQUENCE: 859

Ile Leu Gly Met Gly Asp Val Leu Thr Leu Ile Glu Asp Val Gln Lys
1               5                   10                  15

<210> SEQ ID NO 860
<211> LENGTH: 14
<212> TYPE: PRT
<213> ORGANISM: Neisseria gonorrhoeae

<400> SEQUENCE: 860

Ile Ala Met Gly Ala Gly Thr Thr Val Gln Glu Val Asn Lys
1               5                   10

<210> SEQ ID NO 861
<211> LENGTH: 17
<212> TYPE: PRT
<213> ORGANISM: Neisseria gonorrhoeae

<400> SEQUENCE: 861

Ile Ala Met Gly Ala Gly Thr Thr Val Gln Glu Val Asn Lys Leu Leu
1               5                   10                  15

Lys

<210> SEQ ID NO 862
<211> LENGTH: 28
<212> TYPE: PRT
<213> ORGANISM: Neisseria gonorrhoeae

<400> SEQUENCE: 862

Asn Glu Asn Ser Gly Gly Ala Pro Tyr Asp Glu Gly Tyr Gly Gln Ser
1               5                   10                  15

Gln Glu Ala Tyr Gln Arg Pro Ala Gln Gln Ser Arg
            20                  25

<210> SEQ ID NO 863
<211> LENGTH: 18
<212> TYPE: PRT
<213> ORGANISM: Neisseria gonorrhoeae

<400> SEQUENCE: 863

Gln Pro Ala Pro Asp Ala Pro Ser His Pro Gln Glu Ala Pro Ala Ala
1               5                   10                  15

Pro Arg

<210> SEQ ID NO 864
<211> LENGTH: 9
<212> TYPE: PRT
<213> ORGANISM: Neisseria gonorrhoeae

<400> SEQUENCE: 864

Ser Val Leu Ile Asn Lys Asp Thr Lys
1               5

<210> SEQ ID NO 865
<211> LENGTH: 15
<212> TYPE: PRT
<213> ORGANISM: Neisseria gonorrhoeae

<400> SEQUENCE: 865
```

```
Asn Gly Thr Phe His Ser Glu Gln Ala Leu Ala Tyr Gly Thr Lys
1               5                   10                  15

<210> SEQ ID NO 866
<211> LENGTH: 16
<212> TYPE: PRT
<213> ORGANISM: Neisseria gonorrhoeae

<400> SEQUENCE: 866

Leu Val Gly Pro Asn Cys Pro Gly Val Ile Thr Pro Gly Glu Cys Lys
1               5                   10                  15

<210> SEQ ID NO 867
<211> LENGTH: 13
<212> TYPE: PRT
<213> ORGANISM: Neisseria gonorrhoeae

<400> SEQUENCE: 867

Ile Gly Ile Met Pro Gly His Ile His Thr Pro Gly Arg
1               5                   10

<210> SEQ ID NO 868
<211> LENGTH: 12
<212> TYPE: PRT
<213> ORGANISM: Neisseria gonorrhoeae

<400> SEQUENCE: 868

Met Gly His Ala Gly Ala Ile Ile Ser Gly Gly Lys
1               5                   10

<210> SEQ ID NO 869
<211> LENGTH: 14
<212> TYPE: PRT
<213> ORGANISM: Neisseria gonorrhoeae

<400> SEQUENCE: 869

Ser Pro Ala Glu Leu Gly Thr Thr Met Leu Glu Val Leu Lys
1               5                   10

<210> SEQ ID NO 870
<211> LENGTH: 10
<212> TYPE: PRT
<213> ORGANISM: Neisseria gonorrhoeae

<400> SEQUENCE: 870

Ala Asn Arg Pro Thr Pro Ile Ser Gln Arg
1               5                   10

<210> SEQ ID NO 871
<211> LENGTH: 11
<212> TYPE: PRT
<213> ORGANISM: Neisseria gonorrhoeae

<400> SEQUENCE: 871

Asp Leu Lys Ser Glu Glu Asn Leu Thr Gly Arg
1               5                   10

<210> SEQ ID NO 872
<211> LENGTH: 11
<212> TYPE: PRT
<213> ORGANISM: Neisseria gonorrhoeae

<400> SEQUENCE: 872

Ala Tyr Asn Thr Val Val Pro Ala Ser Gly Lys
1               5                   10
```

<210> SEQ ID NO 873
<211> LENGTH: 15
<212> TYPE: PRT
<213> ORGANISM: Neisseria gonorrhoeae

<400> SEQUENCE: 873

Ile Leu Thr Gly Gly Val Asp Ala Asn Ala Leu His Arg Pro Lys
1               5                   10                  15

<210> SEQ ID NO 874
<211> LENGTH: 25
<212> TYPE: PRT
<213> ORGANISM: Neisseria gonorrhoeae

<400> SEQUENCE: 874

Val Leu Thr Gly Val Thr Thr Thr Gly Thr Pro His Leu Gly Asn Tyr
1               5                   10                  15

Val Gly Ala Ile Arg Pro Ala Val Arg
            20                  25

<210> SEQ ID NO 875
<211> LENGTH: 21
<212> TYPE: PRT
<213> ORGANISM: Neisseria gonorrhoeae

<400> SEQUENCE: 875

Tyr Asn Ala Leu Thr Ser Asn Pro Ser Gln Ile Glu Glu Ile Leu Gln
1               5                   10                  15

Ala Gly Ala Gln Lys
            20

<210> SEQ ID NO 876
<211> LENGTH: 12
<212> TYPE: PRT
<213> ORGANISM: Neisseria gonorrhoeae

<400> SEQUENCE: 876

Met Gln Ile Thr Asp Leu Leu Ala Phe Gly Ala Lys
1               5                   10

<210> SEQ ID NO 877
<211> LENGTH: 17
<212> TYPE: PRT
<213> ORGANISM: Neisseria gonorrhoeae

<400> SEQUENCE: 877

Asn Lys Ala Ser Asp Leu His Leu Ser Ser Gly Ile Ser Pro Met Ile
1               5                   10                  15

Arg

<210> SEQ ID NO 878
<211> LENGTH: 15
<212> TYPE: PRT
<213> ORGANISM: Neisseria gonorrhoeae

<400> SEQUENCE: 878

Ala Ser Asp Leu His Leu Ser Ser Gly Ile Ser Pro Met Ile Arg
1               5                   10                  15

<210> SEQ ID NO 879
<211> LENGTH: 10
<212> TYPE: PRT

```
<213> ORGANISM: Neisseria gonorrhoeae

<400> SEQUENCE: 879

Phe Arg Val Asn Ala Phe Asn Thr Gly Arg
1               5                   10

<210> SEQ ID NO 880
<211> LENGTH: 20
<212> TYPE: PRT
<213> ORGANISM: Neisseria gonorrhoeae

<400> SEQUENCE: 880

Thr Ile Pro Ser Thr Val Leu Ser Leu Glu Glu Leu Lys Ala Pro Ser
1               5                   10                  15

Ile Phe Gln Lys
            20

<210> SEQ ID NO 881
<211> LENGTH: 7
<212> TYPE: PRT
<213> ORGANISM: Neisseria gonorrhoeae

<400> SEQUENCE: 881

Lys Ser Leu Ile Asn Gln Arg
1               5

<210> SEQ ID NO 882
<211> LENGTH: 17
<212> TYPE: PRT
<213> ORGANISM: Neisseria gonorrhoeae

<400> SEQUENCE: 882

Ser Met Leu Ser Glu Ser Leu Thr Ala Val Ile Ser Gln Asn Leu Leu
1               5                   10                  15

Lys

<210> SEQ ID NO 883
<211> LENGTH: 14
<212> TYPE: PRT
<213> ORGANISM: Neisseria gonorrhoeae

<400> SEQUENCE: 883

Val Ala Ser His Glu Ile Leu Ile Ala Asn Pro Ala Val Arg
1               5                   10
```